(12) United States Patent
Schuijers et al.

(10) Patent No.: US 12,234,453 B2
(45) Date of Patent: Feb. 25, 2025

(54) REGULATION OF TRANSCRIPTION THROUGH CTCF LOOP ANCHORS

(71) Applicant: Whitehead Institute for Biomedical Research, Cambridge, MA (US)

(72) Inventors: Jurian Schuijers, Somerville, MA (US); Abraham S. Weintraub, Cambridge, MA (US); John C. Manteiga, Boston, MA (US); Richard A. Young, Boston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 18/329,541

(22) Filed: Jun. 5, 2023

(65) Prior Publication Data
US 2024/0141335 A1    May 2, 2024

Related U.S. Application Data

(62) Division of application No. 16/469,131, filed as application No. PCT/US2017/065918 on Dec. 12, 2017, now abandoned.

(60) Provisional application No. 62/433,234, filed on Dec. 12, 2016.

(51) Int. Cl.
| | | |
|---|---|---|
| C12N 15/11 | (2006.01) | |
| A61K 38/00 | (2006.01) | |
| C12N 9/22 | (2006.01) | |
| C12N 15/90 | (2006.01) | |
| C12Q 1/6886 | (2018.01) | |

(52) U.S. Cl.
CPC ............. *C12N 15/11* (2013.01); *C12N 9/22* (2013.01); *C12N 15/907* (2013.01); *C12Q 1/6886* (2013.01); *A61K 38/00* (2013.01); *C12N 2310/20* (2017.05); *C12N 2800/80* (2013.01); *C12Q 2600/106* (2013.01); *C12Q 2600/154* (2013.01)

(58) Field of Classification Search
CPC ........ C12N 15/11; C12N 9/22; C12N 15/907; C12N 2310/20; C12N 2800/80; C12Q 1/6886; C12Q 2600/106; C12Q 2600/154; A61K 38/00
See application file for complete search history.

(56) References Cited

U.S. PATENT DOCUMENTS

| | | |
|---|---|---|
| 6,780,986 B1 | 8/2004 | Heintz et al. |
| 8,513,207 B2 | 8/2013 | Brown |
| 9,801,877 B2 | 10/2017 | Yao et al. |
| 10,378,027 B2 | 8/2019 | Joung et al. |
| 11,312,955 B2 | 4/2022 | Berry et al. |
| 11,434,476 B2 | 9/2022 | Jaenisch et al. |
| 11,873,496 B2 | 1/2024 | Young et al. |
| 2008/0311039 A1 | 12/2008 | Bonavida et al. |
| 2009/0082470 A1 | 3/2009 | Farjo |
| 2012/0115227 A1 | 5/2012 | Cohen-Haguenauer et al. |
| 2014/0273226 A1 | 9/2014 | Wu |
| 2014/0322707 A1 | 10/2014 | He et al. |
| 2015/0071906 A1 | 3/2015 | Liu et al. |
| 2015/0353885 A1 | 12/2015 | Sourdive |
| 2015/0376612 A1 | 12/2015 | Lee et al. |
| 2016/0010076 A1 | 1/2016 | Joung et al. |
| 2016/0024474 A1 | 1/2016 | Conway et al. |
| 2016/0186208 A1 | 6/2016 | Jaenisch et al. |
| 2016/0215280 A1 | 7/2016 | Fanucchi et al. |
| 2016/0340749 A1 | 11/2016 | Stelzer et al. |
| 2017/0014449 A1 | 1/2017 | Bangera et al. |
| 2017/0130247 A1 | 5/2017 | Dowen et al. |
| 2017/0362649 A1 | 12/2017 | Lieberman-Aiden et al. |
| 2018/0245079 A1 | 8/2018 | Lieberman Aiden et al. |
| 2019/0024086 A1 | 1/2019 | Lande et al. |
| 2019/0127713 A1 | 5/2019 | Gersbach |
| 2019/0241964 A1 | 8/2019 | Hunter et al. |
| 2019/0309291 A1 | 10/2019 | Lee et al. |
| 2019/0352648 A1 | 11/2019 | Young et al. |
| 2019/0359959 A1 | 11/2019 | Jaenisch et al. |
| 2020/0002558 A1 | 1/2020 | Iwasaki et al. |
| 2020/0149039 A1 | 5/2020 | Schuijers et al. |
| 2020/0224274 A1 | 7/2020 | Bernstein et al. |
| 2023/0096554 A1 | 3/2023 | Jaenisch et al. |
| 2024/0263184 A1 | 8/2024 | Young et al. |

FOREIGN PATENT DOCUMENTS

| | | |
|---|---|---|
| EP | 3382018 A1 | 10/2018 |
| WO | WO-2006/025802 A1 | 3/2006 |
| WO | WO-2009/146033 A2 | 12/2009 |

(Continued)

OTHER PUBLICATIONS

Amabile, et al., "Inheritable Silencing of Endogenous Genes by Hit-and-Run Targeted Epigenetic Editing," Cell, 167:219-232 (2016).

(Continued)

*Primary Examiner* — Paul J Holland

(74) *Attorney, Agent, or Firm* — Morse, Barnes-Brown & Pendleton, P.C.; Lisa M. Warren, Esq.; Erin E. Bryan, Esq.

(57) ABSTRACT

Disclosed are methods of altering expression of a gene with a promoter region CTCF binding site. Also disclosed are compositions and methods useful for treating a disease or condition involving over-expression or under-expression of a gene with a promoter region CTCF binding site. Further disclosed are cells and non-human animals with modified a promoter region CTCF binding site, as well as methods for screening for compounds that can modify the expression of a gene with a promoter region CTCF binding site.

20 Claims, 12 Drawing Sheets

Specification includes a Sequence Listing.

(56) References Cited

FOREIGN PATENT DOCUMENTS

| WO | WO-2012/019168 A3 | 7/2012 |
|----|----|----|
| WO | WO-2013/176772 A1 | 11/2013 |
| WO | WO-2014/071247 A1 | 5/2014 |
| WO | WO-2014/172470 A2 | 10/2014 |
| WO | WO-2015/033293 A1 | 3/2015 |
| WO | WO-2015/038892 A1 | 3/2015 |
| WO | WO-2015/191780 A2 | 12/2015 |
| WO | WO-2015/196128 A2 | 12/2015 |
| WO | WO-2016/063264 A1 | 4/2016 |
| WO | WO-2016/022363 A3 | 5/2016 |
| WO | WO-2016/081798 A1 | 5/2016 |
| WO | WO-2016/070037 A3 | 6/2016 |
| WO | WO-2016/103233 A2 | 6/2016 |
| WO | WO-2016/115326 A1 | 7/2016 |
| WO | WO-2016/073990 A3 | 8/2016 |
| WO | WO-2016130600 A2 | 8/2016 |
| WO | WO-2016/154330 A1 | 9/2016 |
| WO | WO-2016/164356 A1 | 10/2016 |
| WO | WO-2016/174250 A1 | 11/2016 |
| WO | WO-2016/130600 A9 | 12/2016 |
| WO | WO-2017/031370 A1 | 2/2017 |
| WO | WO-2017/040793 A1 | 3/2017 |
| WO | WO-2017/011710 A3 | 4/2017 |
| WO | WO-2017/064546 A1 | 4/2017 |
| WO | WO-2017/106290 A1 | 6/2017 |
| WO | WO-2017/143042 A3 | 10/2017 |
| WO | WO-2017/208247 A1 | 12/2017 |
| WO | WO-2018/035495 A1 | 2/2018 |
| WO | WO-2018/049073 A1 | 3/2018 |
| WO | WO-2018/049075 A1 | 3/2018 |
| WO | WO-2018/049077 A1 | 3/2018 |
| WO | WO-2018/049079 A1 | 3/2018 |
| WO | WO-2018/111944 A1 | 6/2018 |
| WO | WO-2018/129544 A1 | 7/2018 |
| WO | WO-2018/204764 A1 | 11/2018 |
| WO | WO-2019/036430 A1 | 2/2019 |
| WO | WO-2019/071054 A1 | 4/2019 |

OTHER PUBLICATIONS

Banani et al., "Biomolecular condensates: organizers of cellular biochemistry," Nature Reviews Molecular Cell Biology, vol. 18, No. 5, pp. 285-298 (2017).
Barrera, L. et al., "Survey of variation in human transcription factors reveals prevalent DNA binding changes," Science, 351 (6280):1450-1454 (2016).
Beagan JA, et al., "YY1 and CTCF orchestrate a 3D chromatin looping switch during early neural lineage commitment," *Genome Res*, 27(7):1139-1152 (2017).
Bell, A.C., et al., "Methylation of a CTCF-dependent boundary controls imprinted expression of the Igf2 gene," Nature 405, 482-485 (2000).
Bonavida, "Therapeutic YY1 inhibitors in cancer: ALL in ONE," *Critical Reviews™ in Oncogenesis* 22.1-2 (2017).
Brunk, et al., "Regulated demethylation of the myoddistal enhancer during skeletal myogenesis," Developmental biology, 177.2: 490-503 (1996).
Chen, W.G., et al., "Derepression of BDNF transcription involves calcium-dependent phosphorylation of MeCP2," Science 302, 885-889 (2003).
Cho, et al., "Antisense Transcription and Short Article Heterochromatin at the DM1 CTG Repeats Are Constrained by CTCF," Molecular Cell, vol. 20, pp. 483-489 (2005).
Choudhury, et al., "CRISPR-dCas9 mediated TET1 targeting for selective DNA demethylation at BRCA1 promoter," Oncotarget, vol. 7, No. 29, pp. 46545-46556 (published Jun. 23, 2016).
Cong, et al., "Multiplex Genome Engineering Using CRISPR/Cas Systems" Science, vol. 339, pp. 819-823 (2013).
De Groote, et al. "Epigenetic Editing: targeted rewriting of epigenetic marks to modulate expression of selected target genes," Nucleic Acids Res, vol. 40, No. 21, pp. 10596-10613 (2012).

De Souza, et al., "DNA methylation profiling in human Huntington's disease brain," Human Molecular Genetics, vol. 25, No. 10, pp. 2013-2030 (2016).
De Wit, et al., "CTCF Binding Polarity Determines Chromatin Looping," Molecular Cell, vol. 60. No. 4, pp. 676-684 (2015).
Deng, et al., "Controlling Long-Range Genomic Interactions at a Native Locus by Targeted Tethering of a Looping Factor," Cell, vol. 149, pp. 1233-1244 (2012).
Dowen, J. et al., "Control of Cell Identity Genes Occurs in Insulated Neighborhoods in Mammalian Chromosomes," Cell, 159:374-387 (2014).
Dávalos-Salas, et al., "Gain of DNA methylation is enhanced in the absence of CTCF at the human retinoblastoma gene promoter," BMC cancer, 11.1, 1-11 (2011).
Ecker, et al., "Genomics: ENCODE explained," Nature, Sep. 6; vol. 489 (7414) pp. 52-55 (2012).
Extended European Search Report for Application No. 17849560.2 dated Mar. 31, 2020.
Filippova, et al., "Tumor-associated Zinc Finger Mutations in the CTCF Transcription Factor Selectively Alter Its DNA-binding Specificity," Cancer Research, 62, 48-52 (2002).
Final Office Action for U.S. Appl. No. 16/469,131 dated Feb. 3, 2023.
Final Office Action for U.S. Appl. No. 16/476,868 dated Feb. 6, 2023.
Flavahan, et al., "Insulator dysfunction and oncogene activation in IDH mutant gliomas," Nature, vol. 529, No. 7584, pp. 110-114 (2015).
Guo et al., "YY1 Target DB: an integral information resource for Yin Yang 1 target loci," Database, vol. pp. 1-10 (2013).
Guo, C. et al., "CTCF Binding Elements Mediate Control of V(D)J Recombination," Nature, 477(7365):424-430 (2011).
Herold, M. et al., "CTCF: insights into insulator function during development," Development, 139:1045-1057 (2012).
Hnisz, D. et al., "Activation of proto-oncogenes by disruption of chromosome neighborhoods," Science, 351(6280):1454-1458 (2016).
Hnisz, D. et al., "Convergence of Developmental and Oncogenic Signaling Pathways at Transcriptional Super-Enhancers," Molecular Cell, 58:362-370 (2015).
Hnisz, D. et al., "Super-Enhancers in the Control of Cell Identity and Disease," Cell, 155:934-947 (2013).
Hsu, "Completion of a Programmable DNA-Binding Small Molecule Library," Thesis, California Institute of Technology, retrieved from thesis.library.caltech.edu/4398, 153 pages (2008).
Hsu, Carey Frank, "Completion of a Programmable DNA-Binding Small Molecule Library," Thesis, California Institute of Technology [retrieved Nov. 22, 2017], from the internet: https://thesis.library.caltech.edu/4398/ (Oct. 30, 2008).
International Preliminary Report on Patentability for International Application No. PCT/US2017/047674, issued Feb. 19, 2019.
International Preliminary Report on Patentability for International Application No. PCT/US2017/050553, issued Mar. 12, 2019.
International Preliminary Report on Patentability for International Application No. PCT/US2017/065918, issued Jun. 18, 2019.
International Search Report and Written Opinion issued in PCT/US2017/050553, dated Jan. 30, 2018.
International Search Report for International Application No. PCT/US2017/47674, dated Jan. 4, 2018.
International Search Report for International Application No. PCT/US2017/065918, dated Apr. 30, 2018.
International Search Report for PCT/US2017/50553 (Methods and Compositions for Modulating Gene Expression, filed Sep. 7, 2017), issued by ISA/US, 6 pages (Jan. 30, 2018).
International Search Report for PCT/US2017/50556 (Methods and Compositions for Modulating Gene Expression, filed Sep. 7, 2017), issued by ISA/US, 5 pages (Dec. 26, 2017).
International Search Report for PCT/US2017/50558 (Methods and Compositions for Modulating Gene Expression, filed Sep. 7, 2017), issued by ISA/US, 5 pages (Dec. 18, 2017).
International Search Report for PCT/US2017/50561 (Methods and Compositions for Modulating Gene Expression, filed Sep. 7, 2017), issued by ISA/US, 5 pages (Dec. 18, 2017).

(56) References Cited

OTHER PUBLICATIONS

International Search Report issued in PCT/US2018/013003 dated Jun. 1, 2018.
Ishimaru, Naoki, et al., "Differential epigenetic regulation of BDNF and NT-3 genes by trichostatin A and 5-aza-2'-deoxycytidine in Neuro-2a cells," Biochemical and biophysical research communications, 394.1: 173-177 (2010).
Issad, et al., "O-GlcNAc modification of transcription factors, glucose sensing and glucotoxicity," Trends in Endocrinology and Metabolism, 19, 10, 380-389 (2008).
Ji, X. et al., "3D Chromosome Regulatory Landscape of Human Pluripotent Cells," Cell Stem Cell, 18:262-275 (2016).
Ji, X. et al., "Chromatin proteomic profiling reveals novel proteins associated with histone-marked genomic regions," PNAS, 112(12):3841-3846 (2015).
Jinek, et al., "A Programmable Dual-RNA-Guided DNA Endonuclease in Adaptive Bacterial Immunity," Science, vol. 337, pp. 816-821 (2012).
Kang, J.Y., et al., "Disruption of CTCF/cohesin-mediated high-order chromatin structures by DNA methylation downregulates PTGS2 expression," Oncogene 34, 5677-5684 (2015).
Kearns, et al., "Functional annotation of native enhancers with a Cas9-histone demethylase fusion" Nature Methods, vol. 12, No. 5, pp. 401-403 (2015).
Kim, et al., "Genome-wide target specificities of CRISPR RNA-guided programmable deaminases," Nat Biotechnol, vol. 35, pp. 475-480 (2017).
Kim, S., et al., "CTCF as a multifunctional protein in genome regulation and gene expression," *Experimental & Molecular Medicine*, 47, e166 (2015).
Koferle, et al., "Brave new epigenomes: the dawn of epigenetic engineering," Genome Medicine, vol. 7, No. 59, pp. 1-3 (2015).
Komor, et al., "Programmable editing of a target base in genomic DNA without double-stranded DNA cleavage," Nature, vol. 533, pp. 420-424, Supplement (2016).
Krylov, et al., "A general method to design dominant negatives to B-HLHZip proteins that abolish DNA binding," PNAS, vol. 94, No. 23, pp. 12274-12279 (1997).
Kungulovski, et al., "Epigenome editing: state of the art, concepts, and perspectives," Trends in Genetics, 32.2: 101-113 (2015).
Lee, et al., "Evidence for physical interaction between the zinc-finger transcription factors YY1 and Sp1," *Proceedings of the National Academy of Sciences*, 90.13: 6145-6149 (1993).
Lei, et al., "Targeted DNA methylation in vivo using an engineered dCas9-MQ1 fusion protein," Nature Communications, 8, Article No. 16026 (2017).
Li, et al., "An alternative CTCF isoform antagonizes canonical CTCF occupancy and changes chromatin architecture to promote apoptosis," Nature Communications, article No. 1535; pp. 1-13 (2019).
Lin, et al., "Formation and Maturation of Phase-Separated Liquid Droplets by RNA-Binding Proteins" Molecular Cell, vol. 60, pp. 208-219 (2015).
Ling, J Q, et al., "Long-range DNA interactions are specifically altered by locked nucleic acid-targeting of a CTFC binding site," Biochimica et Biophysica Acta. Gene Regulatory Mechanisms, vol. 1809, No. 1. pp. 24-33 (2011).
Liu, et al., "Editing DNA Methylation in the Mammalian Genome," Cell, 167(1):233-247 (2016).
Lo, et al., "Genetic and epigenetic control of gene expression by CRISPR-Cas systems," F1000Research, 6: 747 (2017).
Lopez-Bertoni, et al., "DNMT-dependent suppression of microRNA regulates the induction of GBM tumor-propagating phenotype by Oct4 and Sox2," Oncogene, 34, 3994-4004 (2017).
Ma, et al. "Targeted Gene Suppression by Inducing De Novo DNA Methylation in the Gene Promotor," Epigenetics & Chromatin, vol. 7:20, pp. 1-11 (2014).
Mansour, M. et al., "An oncogenic super-enhancer formed through somatic mutation of a noncoding intergenic element," Science, 346(6215):1373-7 (Nov. 13, 2014).

Martinowich, K., "DNA methylation-related chromatin remodeling in activity-dependent BDNF gene regulation," Science 302, 890-893 (2003).
McClellan, Michael J., et al., "Modulation of enhancer looping and differential gene targeting by Epstein-Barr virus transcription factors directs cellular reprogramming," *PLoS Pathog* 9.9: e1003636 (2013).
McDonald, et al., "Reprogrammable CRISPR/Cas9-based system for inducing site-specific DNA methylation," Biology open, 5.6: 866-874 (2016).
Morgan, et al., "Manipulation of nuclear architecture through CRISPR-mediated chromosomal looping," Nature Communications, vol. 8, Article 15993, 9 pages (2017).
Morita, et al., "Targeted DNA demethylation in vivo using dCas9-peptide repeat and scFv-TET1 catalytic domain fusions," Nature biotechnology, 34.10:1060-1065 (2016).
Narenda, et al. "CTCF establishes discrete functional chromatin domains at the Hox clusters during differentiation," Science, vol. 347, No. 6225, pp. 1017-1021 (2015).
Narlikar, et al., "Identifying regulatory elements in eukaryotic genomes," *Briefings in functional genomics and proteomics* 8.4,: 215-230 (2009).
Non-Final Office Action for U.S. Appl. No. 16/326,700 dated Dec. 7, 2021.
Non-Final Office Action for U.S. Appl. No. 16/469,131 dated Jun. 20, 2022.
Non-Final Office Action for U.S. Appl. No. 16/476,868 dated Jul. 6, 2022.
Notice of Allowance for U.S. Appl. No. 16/476,868, mailed Jun. 1, 2023.
Notice of Allowance for U.S. Appl. No. 16/476,868 dated Sep. 19, 2023.
Patterson, et al., "DNA Methylation: Bisulphite Modification and Analysis" J Vis Exp., vol. 56, e3170, pp. 1-9 (2011).
Phillips, J.E., et al., "CTCF: master weaver of the genome," Cell 137, 1194-1211 (2009).
Rada-Iglesias, et al., "Whole-genome maps of USF1 and USF2 binding and histone H3 acetylation reveal new aspects of promoter structure and candidate genes for common human disorders," Genome Research, vol. 18(3), pp. 380-392 (2008).
Ran, et al., "Genome engineering using the CRISPR-Cas9 system," Nature Protocols, vol. 8, No. 11, pp. 2281-2308, (2013).
Rodriguez, et al., "CTCF is a DNA methylation-sensitive positive regulator of the INK/ARF locus," Biochem. Biophys. Res. Commun., 392(2):129-34, (2010).
Rudolph Jaenish, In Vitro Reprogramming of Somatic Cells Into Pluripotent ES-Like Cells, HD045022 (Funding date: Jun. 15, 2008).
Rudolph Jaenish, Nuclear Cloning and the Reprogramming of the Genome, HD045022 (Funding date: Jul. 28, 2003).
Sabari, et al., "Coactivator condensation at super-enhancers links phase separation and gene control," Science, 361(6400): eaar3958, pp. 1-16 (2018).
Schultz, M.D., et al., "Human body epigenome maps reveal noncanonical DNA methylation variation." Nature 523, 212-216 (2015).
Shin, et al., "Spatiotemporal control of intracellular phase transitions using light-activated optoDroplets," Cell, vol. 168, No. 1-2, pp. 159-171, (2017).
Singh, et al., "Protein Engineering Approaches in the Post-Genomic Era," Current Protein and Peptide Science, 18, 1-11 (2017).
Spencer, R. et al., "A Boundary Element Between Tsix and Xist Binds the Chromatin Insulator Ctcf and Contributes to Initiation of X-Chromosome Inactivation," Genetics, 189:441-454 (2011).
Stelzer, Y., et al., "Tracing dynamic changes of DNA methylation at single-cell resolution," Cell 163, 218-229 (2015).
Stepper, et al., "Efficient targeted DNA methylation with chimeric dCas9-Dnmt3a-Dnmt3L methyltransferase," Nucleic acids research, 45.4: 1703-1713 (2016).
Subramaniam, et al., "DNA methyltransferases: a novel target for prevention and therapy," Frontiers in Oncology, 4 (May 1, 2014).
Supplementary Partial European Search Report in Application No. EP 17 88 1835, dated Jul. 30, 2020.

(56) References Cited

OTHER PUBLICATIONS

Sweatt, J.D., "The emerging field of neuroepigenetics," Neuron 80, 624-632 (2013).
Szabó, P. et al., "Role of CTCF Binding Sites in the Igf2/H19 Imprinting Control Region," Molecular and Cellular Biology, 24(11):4791-4800 (2004).
Tang, Z. et al., "CTCF-Mediated Human 3D Genome Architecture Reveals Chromatin Topology for Transcription," Cell, 163:1-17 (2015).
Thakore, et al., "Highly Specific Epigenome Editing by CRISPR/Cas9 Repressors for Silencing of Distal Regulatory Elements," Nat Methods, vol. 12, No. 12, pp. 1143-1149, (2015).
The ENCODE Project Consortium, "An Integrated Encyclopedia of DNA Elements in the Human Genome" Nature, vol. 6; 489 (7414):57-74 (2012).
Torres, A. et al., "Potent and sustained cellular inhibition of miR-122 by lysine-derivatized peptide nucleic acids (PNA) and phosphorothioate locked nucleic acid (LNA)/2'-O-methyl (OMe) mixmer anti-miRs in the absence of transfection agents," Artificial DNA: PNA & XNA, 2(3):71-78 (2011).
Viscidi, et al., "Novel Chemical Method for the Preparation of Nucleic Acids for Nonisotopic Hybridization," J Clin Microbiol, vol. 23, No. 2, pp. 311-317 (1986).
Votja, et al., "Repurposing the CRISPR-Cas9 system for targeted DNA methylation," Nucleic Acids Research, 2016, vol. 44, No. 12 5615-5628 (published on Mar. 11, 2016).
Wang, H., et al., "Widespread plasticity in CTCF occupancy linked to DNA methylation," Genome Res 22, 1680-1688 (2012).
Weintraub, Abraham S., et al., "YY1 is a structural regulator of enhancer-promoter loops." Cell 171.7: 1573-1588 (2017).
Woloszynska-Read, et al., "DNA Methylation-dependent Regulation of BORIS/CTCFL Expression in Ovarian Cancer," Cancer Immunity, vol. 7, 1 pp. 1-10 (2007).
Written Opinion for PCT/US2017/50553 (Methods and Compositions for Modulating Gene Expression, filed Sep. 7, 2017), issued by ISA/US, 12 pages (dated Jan. 30, 2018).
Written Opinion for PCT/US2017/50556 (Methods and Compositions for Modulating Gene Expression, filed Sep. 7, 2017), issued by ISA/US, 8 pages (dated Dec. 26, 2017).
Written Opinion for PCT/US2017/50558 (Methods and Compositions for Modulating Gene Expression, filed Sep. 7, 2017), issued by ISA/US, 6 pages (dated Dec. 18, 2017).
Written Opinion for PCT/US2017/50561 (Methods and Compositions for Modulating Gene Expression, filed Sep. 7, 2017), issued by ISA/US, 6 pages (dated Dec. 18, 2017).
Wu, et al., "MicroRNAs direct rapid deadenylation of mRNA" Proc Natl Acad Sci, vol. 103, pp. 4034-4039 (2006).
Wu, H., et al., "Reversing DNA methylation: mechanisms, genomics, and biological functions," Cell 156, 45-68 (2014).
Xiong, et al. "Targeted DNA methylation in human cells using engineered dCas9-methyltransferases," Scientific reports, 7.1: 1-14 (2017).
Xu, et al., "A CRISPR-based approach for targeted DNA demethylation," Cell discovery, 2.1: 1-12 (2016).
Yan, et al., "DNA methylation reactivates GAD1 expression in cancer by preventing CTCF-mediated polycomb repressive complex 2 recruitment," Oncogene, 35(30):3995-4008 (2016).
Young, et al., Abstract, "Epigenomic Changes in Normal T-cell Development and Leukemogenesis," National Institutes of Health Grant No. CA109901 (Funding Date: Apr. 15, 2010).
Young, et al., Abstract, "Transcriptional Ragulatory Network in Living Cells," National Institutes of Health Grant No. HG002668 (Funding Date: May 2, 2003).
Zhang, et al., "Propagated Perturbations from a Peripheral Mutation Show Interactions Supporting WW Domain Thermostability," Structure, 26, 1474-1485 (2018).
Zhao, et al., "CTCF cooperates with noncoding RNA MYCNOS to promote neuroblastoma progression through facilitating MYCN expression," Oncogene, 35, 3565-3576 (2016).
Ziebarth, et al., "CTCFBSDB 2.0: a database for CTCF-binding sites and genome organization," Nucleic Acid Research, vol. 41; D188-94 (2013).
Corrected Notice of Allowability for U.S. Appl. No. 17/858,758 mailed May 23, 2024.
Notice of Allowance for U.S. Appl. No. 17/858,758 mailed Dec. 8, 2023.
Notice of Allowance for U.S. Appl. No. 17/858,758 mailed Jul. 23, 2024.
Stepper, Peter, et al. "Efficient targeted DNA methylation with chimeric dCas9-Dnmt3a-Dnmt3L methyltransferase." Nucleic acids research, 45.4 (2016): 1703-1713.
Young et al., Abstract "Transcriptional Regulatory Networks in Living Cells," National Institutes of Health Grant No. HG002668 (Funding Start Date: Apr. 17, 2007).
Young et al., Abstract "Transcriptional Regulatory Networks in Living Cells," National Institutes of Health Grant No. HG002668 (Funding Start Date: Jul. 1, 2015).
Young et al., Abstract "Transcriptional Regulatory Networks in Living Cells," National Institutes of Health Grant No. HG002668 (Funding Start Date: May 26, 2010).
Zheng, "Cellular and Molecular Biology of Tumors," Military Medical Press, pp. 265-273, 2014.

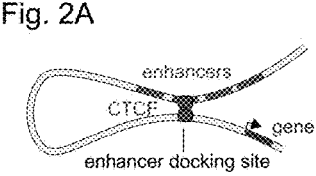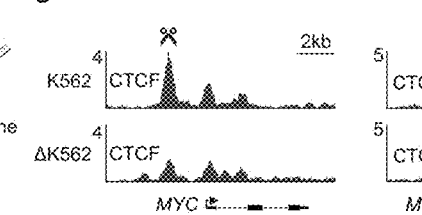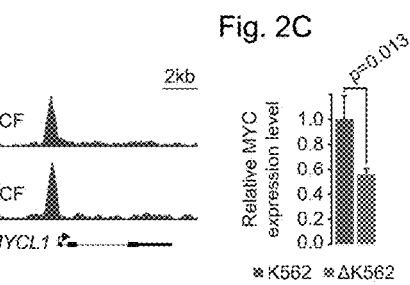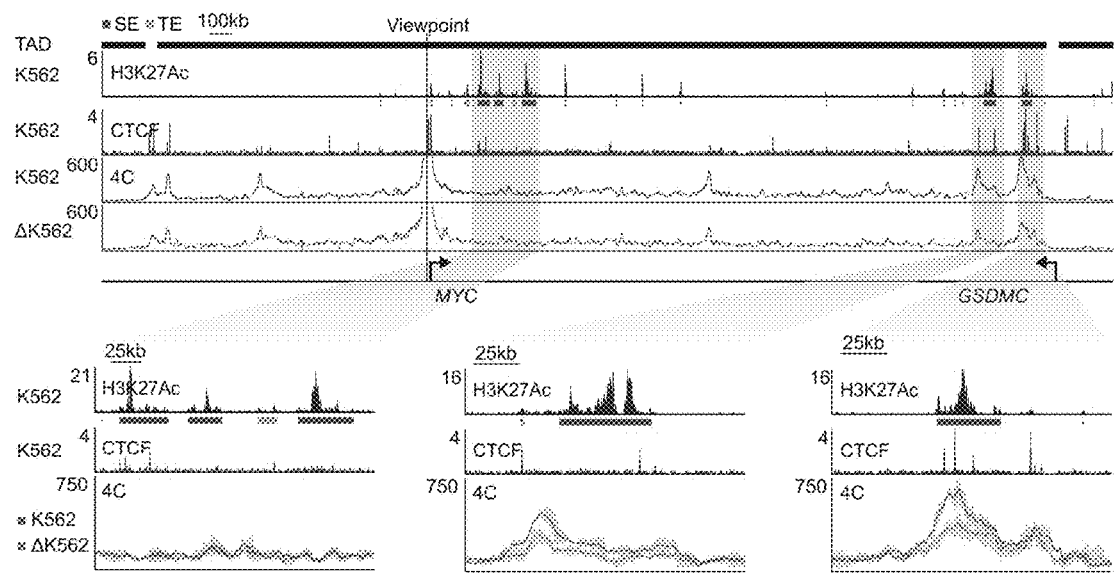

Fig. 3A

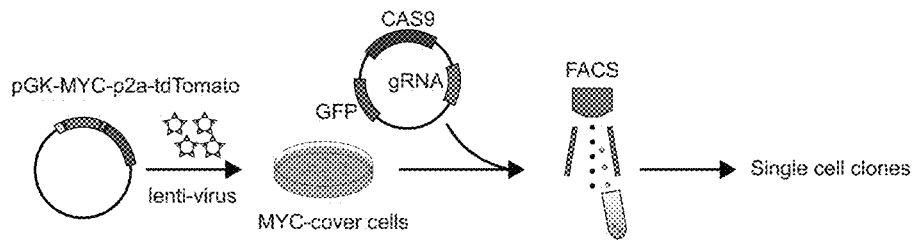

Fig. 3B

```
                CTCF consensus motif
WT   TGACATCCAGGCGCGATGATCTCTGCTGCC................CACACTTACTTTACTTT    SEQ ID NO: 22
         gRNA
WT   TGACATCCAGGCGCG................................AGGGCACACTTACTTTACTTT    SEQ ID NO: 27
K562
Allele 1   TGACATCCAGGCGCGATGATCTCTGCTGCC----------------CTTACTTTACTTT    SEQ ID NO: 25
Allele 2   TGACATCCAGGCGCGATGATCTCTGCTGCC----------------CTTACTTTACTTT    SEQ ID NO: 26
HCT-116
Allele 1   TGACATCCAGGCGCGATGATCTCTGCT-----------GCACACTTACTTTACTTT    SEQ ID NO: 23
Allele 2   TGACATCCAGGCGCGATGAT-------------AGAGGGCACACTTACTTTACTTT    SEQ ID NO: 24
Jurkat
Allele 1   TGACATCCAGGCGCGATGATCTCTGCTGC-AGTA-----TCACACTTACTTTACTTT    SEQ ID NO: 28
Allele 2   TGACATCCAGGCGCGATGATCTCTGCTGCCAGTAGAGGGCACACTTACTTTACTTT    SEQ ID NO: 29
                          (insertion)  AGGTGACT
MCF7
Allele 1   TGACATCCAGGCGCGATGATCTCTGCTGCCAGTAGAGGGCACACTTACTTTACTTT    SEQ ID NO: 31
           (insertion)   AGGAAAGTAAAGTGTACCTAAAAGAAAGTGTACCTCTA   SEQ ID NO: 30
Allele 2   TGACATCCAGGCGCGATGATCTCTGCTGC-AGTAGAGGGCACACTTACTTTACTTT    SEQ ID NO: 32
                          (insertion)  ................TTA  SEQ ID NO: 33
```

Fig. 3C

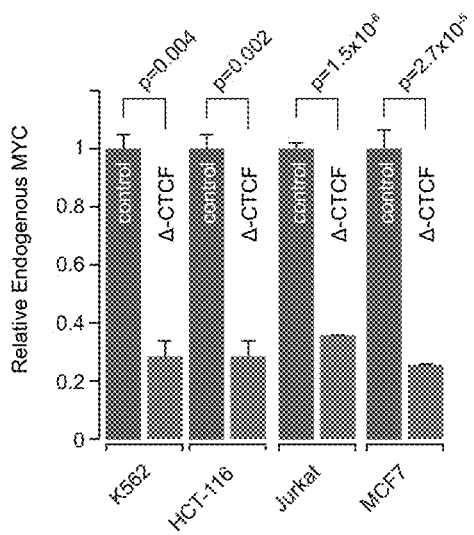

Targeted methylation of the MYC CTCF enhancer loop anchor using dCas9-DNMT3A-3L without the 5'NLS in HEK293T

REGULATION OF TRANSCRIPTION THROUGH CTCF LOOP ANCHORS

RELATED APPLICATION

This application is a divisional of U.S. application Ser. No. 16/469,131, filed Jun. 12, 2019, which is a national stage filing under 35 U.S.C. 371 of International Application No. PCT/US2017/065918, filed Dec. 12, 2017, which claims the benefit of U.S. Provisional Application Ser. No. 62/433,234, filed Dec. 12, 2016, the contents of which are hereby incorporated by reference in their entirety. International Application No. PCT/US2017/065918 was published under PCT Article 21(2) in English.

GOVERNMENT SUPPORT

This invention was made with government support under Grant Nos. HG002668 and CA109901 awarded by the National Institutes of Health. The government has certain rights in the invention.

SEQUENCE LISTING

The Sequence Listing associated with this application is provided in .xml format in lieu of a paper copy and is hereby incorporated by reference into the specification. The name of the .xml file containing the Sequence Listing is WIBR-159-102. The xml file is 47,703 bytes, was created on Jun. 27, 2023, and is being submitted electronically via Patent Center.

BACKGROUND OF THE INVENTION

The ability to activate transcription of specific genes is fundamental to the establishment of gene expression programs that define cell identity. To accomplish this, transcription factors (TFs) bind enhancer elements and regulate transcription from the promoters of nearby or distant genes through physical contacts that involve looping of DNA between enhancers and promoters (Bonev and Cavalli, 2016; Buecker and Wysocka, 2012; Bulger and Groudine, 2011; Fraser et al., 2015; Heard and Bickmore, 2007; de Laat and Duboule, 2013; Müller et al., 1989; Pombo and Dillon, 2015; Spitz, 2016; Tolhuis et al., 2002). However, the mechanisms that ensure that specific enhancers interact with specific promoters are not well understood. Most study of eukaryotic enhancer-promoter interactions has focused on cofactors that lack DNA binding capabilities and bridge enhancer-bound transcription factors and the promoter-bound transcription apparatus (Allen and Taatjes, 2015; Deng et al., 2012; Jeronimo et al., 2016; Kagey et al., 2010; Malik and Roeder, 2010, 2016; Petrenko et al., 2016; Phillips-Cremins et al., 2013). Some enhancer-promoter interactions are likely determined by the nature of transcription factors bound at the two sites (Muerdter and Stark, 2016), but there is little understanding of the rules that govern these interactions.

Recent studies have revealed that specific chromosome structures play important roles in gene control. Enhancer-promoter interactions generally occur within larger chromosomal loop structures formed by the interaction of CTCF proteins bound to each of the loop anchors (Dekker and Mirny, 2016; Fraser et al., 2015; Gibcus and Dekker, 2013; Gorkin et al., 2014; Hnisz et al., 2016; Merkenschlager and Nora, 2016). These loop structures, variously called TADs, loop domains, CTCF contact domains and insulated neighborhoods, tend to insulate enhancers and genes within the CTCF-CTCF loops from elements outside those loops (Dixon et al., 2012, 2016; Dowen et al., 2014; Franke et al., 2016; Hnisz et al., 2016; Ji et al., 2016; Lupiailez et al., 2015; Narendra et al., 2015; Nora et al., 2012; Phillips-Cremins et al., 2013; Rao et al., 2014; Tang et al., 2015). Constraining DNA interactions within CTCF-CTCF loop structures in this manner may facilitate proper enhancer-promoter contacts.

SUMMARY OF THE INVENTION

CTCF does not generally occupy enhancer and promoter elements (Cuddapah et al., 2009; Dixon et al., 2012; Handoko et al., 2011; Ji et al., 2016; Kim et al., 2007; Parelho et al., 2008; Phillips-Cremins et al., 2013; Rao et al., 2014; Rubio et al., 2008; Tang et al., 2015; Wendt et al., 2008), but where CTCF does bind these elements, it may engender enhancer-promoter interactions (Guo et al., 2015; Lee et al., 2017; Splinter et al., 2006; de Wit et al., 2015). This consideration led us to further investigate the class of human genes that contain CTCF-bound sites at promoters to learn whether these are utilized to facilitate contacts with enhancers via CTCF-CTCF interactions. We report here that ~2000 human genes have highly conserved promoter-proximal sites that are bound by CTCF regardless of the cell type examined and that these sites can form contacts with diverse cell-type specific enhancers. These genes appear to have evolved CTCF enhancer-docking sites in order to facilitate contacts with the diverse CTCF-bound enhancers formed by cell-type specific transcription factors during development, and thus experience activation in a broad range of cell types. Interestingly, this set of genes with CTCF-bound enhancer-docking sites includes many important cancer-associated genes, and the enhancer-docking site of one of these, MYC, was studied in detail.

Elevated expression of the c-MYC transcription factor occurs frequently in human cancers and is associated with tumor aggression and poor clinical outcome (Berns et al., 2013; Grotzer et al, 2001; Nesbit et al., 1999; Rao et al., 1998; Dang, 2012). There has been considerable interest in understanding the mechanisms responsible for aberrant transcriptional regulation of MYC in tumor cells. Promoter-proximal regulatory sequences were identified in early studies, but these were not sufficient to recapitulate endogenous patterns of MYC expression (Lavenu et al., 1994; Wierstra, 2008). Subsequent reports noted putative regulatory elements that occur over 1 megabase (Mb) away from MYC, suggesting that distal elements might be involved in MYC regulation (Ahmadiyeh et al., 2010; Hallikas et al., 2006; Pomerantz et al., 2009; Sotelo et al., 2010; Tuupanen et al., 2009; Wright et al., 2010; Yochum et al., 2008). Recent studies have described large tumor-specific super-enhancers in the 3 Mb region surrounding the MYC gene (Chapuy et al, 2013; Herranz et al., 2014; Hnisz et al., 2013; Lin et al., 2016; Wang et al., 2015; Xiang et al., 2014; Zhang et al, 2015). It is not clear how these large enhancer clusters, which differ in size, composition and distance from MYC, all accomplish the same task of stimulating MYC overexpression in a broad spectrum of tumors. Molecular features common to these regulatory elements might prove to be valuable for therapeutic targeting in cancer.

Genetic and epigenetic perturbation of the MYC enhancer-docking site reduces CTCF binding, super-enhancer interaction, MYC gene expression and tumor cell proliferation. These observations reveal a mechanism for enhancer-promoter interaction that is employed during development to allow genes to have cell-specific contacts with diverse enhancers and is exploited by cancer cells to facilitate oncogenic expression of genes driven by diverse super-enhancers.

We show here that diverse tumor-specific super-enhancers acquired throughout the 3 Mb MYC insulated neighborhood functionally interact with a single conserved site containing densely clustered CTCF motifs in the MYC promoter. CRISPR-mediated deletion analysis shows that this common CTCF site is required for super-enhancer looping to the MYC promoter, high MYC expression and rapid cell proliferation in multiple cancers. Targeted methylation of the MYC enhancer anchor by dCAS9-DNMT3A-3L fusion proteins abrogate CTCF binding with consequent loss of MYC expression, suggesting a common vulnerability and a novel approach for therapeutic targeting. Disruption of CTCF protein binding with the MYC promoter CTCF binding site by compounds including targeted nucleic acid derivatives are predicted to have a similar effect.

Disclosed herein are methods of altering expression of a gene with a promoter region (i.e., within or proximal (e.g., within 2.5 kilobases of the transcription start site) to the promoter) CTCF binding site (e.g., an oncogene, MYC, TGIF1, VEGFAI, RUNX1, CDK6, BCL2L1, PIM1, CSNK1A1 or a gene listed in Table 51) by altering the interaction or binding between CTCF protein and CTCF binding site(s) to a promoter region of the gene. In some aspects, the gene is MYC. Generally said alteration will comprise inhibiting or reducing the binding of CTCF protein and CTCF binding site in the promoter region of the gene (e.g., an oncogene, MYC, TGIF1, VEGFAI, RUNX1, CDK6, BCL2L1, PIM1, CSNK1A1 or a gene listed in Table 51), thereby reducing or eliminating expression of the gene. However said alteration may alternatively comprise enhancing the binding of CTCF protein to CTCF binding site in the promoter region of the gene (e.g., an oncogene, MYC, TGIF1, VEGFAI, RUNX1, CDK6, BCL2L1, PIM1, CSNK1A1 or a gene listed in Table 51), thereby enhancing expression. Methods of therapy corresponding to alteration of expression of the gene (e.g., an oncogene, MYC, TGIF1, VEGFAI, RUNX1, CDK6, BCL2L1, PIM1, CSNK1A1 or a gene listed in Table 51) are also encompassed.

Disclosed herein are compositions useful for treating a disease or condition involving over-expression or under-expression of a gene with a promoter region CTCF binding site (e.g., an oncogene, MYC, TGIF1, VEGFAI, RUNX1, CDK6, BCL2L1, PIM1, CSNK1A1 or a gene listed in Table 51), comprising a catalytically inactive site specific nuclease fused to an effector domain having methylation or demethylation activity; and one or more guide sequences homologous or complementary to at least a portion of the promoter region CTCF binding site and/or a portion within 200-300 nucleotides of either side of the promoter region CTCF binding site. In some aspects, the disease or condition is cancer.

Also disclosed herein are compositions useful for treating a disease or condition involving over-expression or under-expression of a gene with a promoter region CTCF binding site (e.g., an oncogene, MYC, TGIF1, VEGFAI, RUNX1, CDK6, BCL2L1, PIM1, CSNK1A1 or a gene listed in Table 51). In some embodiments, the composition comprises a mixture of proteins (e.g., a fusion protein comprising a catalytically inactive site specific nuclease fused to an effector domain having methylation activity) and nucleic acid sequences (e.g., one or more guide RNAs, one or more sequences encoding guide RNA). In some embodiments, the composition comprises one or more guide sequences and one or more nucleic acids encoding a fusion protein comprising a catalytically inactive site specific nuclease fused to an effector domain having methylation activity. In some embodiments, the composition comprises one or more nucleic acids encoding a catalytically inactive site specific nuclease fused to an effector domain having methylation or demethylation activity and one or more nucleic acids encoding guide sequences. In some embodiments, the guide sequences are homologous or complementary to at least a portion of the MYC promoter region CTCF binding site and/or a portion within 200-300 nucleotides upstream or downstream of the MYC promoter region CTCF binding site. In some embodiments, the guide sequences are homologous or complementary to at least a portion of a promoter region CTCF binding site listed in Table 51 and/or a portion within 200-300 nucleotides upstream or downstream of the promoter region CTCF binding site listed in Table 51. In some embodiments, the guide sequences are homologous or complementary to at least a portion of a promoter region CTCF binding site for TGIF1, VEGFAI, RUNX1, CDK6, BCL2L1, PIM1, or CSNK1A1 and/or a portion within 200-300 nucleotides upstream or downstream of the promoter region CTCF binding site for TGIF1, VEGFAI, RUNX1, CDK6, BCL2L1, PIM1, or CSNK1A1. In some aspects, the disease or condition is cancer.

In some aspects, the effector domain comprises DNMT3A-3L or DNMT3A-3L lacking the 5' nuclear localization signal (NLS) domain. In some aspects, the catalytically inactive site specific nuclease is a catalytically inactive Cas (e.g., Cas9); in other aspects the catalytically inactive site specific nuclease is a catalytically inactive Cpf1. In some aspects, the catalytically inactive site specific nuclease fused to an effector domain having methylation activity is dCas9-DNMT3A-3L or dCas9-DNMT3A-3L lacking the 5' NLS.

Also disclosed herein are methods for modulating methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51) in a cell comprising introducing into the cell a catalytically inactive site specific nuclease fused to an effector domain having methylation or demethylation activity; and one or more guide sequences homologous or complementary to at least a portion of the promoter region CTCF binding site, thereby methylating or demethylating the promoter region CTCF binding site. In some aspects, methylation of the promoter region CTCF binding site of the gene (e.g., an oncogene, MYC, TGIF1, VEGFAI, RUNX1, CDK6, BCL2L1, PIM1, CSNK1A1 or a gene listed in Table 51) is increased or decreased by about 2-fold, 2.5-fold, 2.7-fold, 3.0 fold, or 4.0 fold or more. In some aspects, methylation of the promoter region CTCF binding site of a gene (e.g., an oncogene, MYC, TGIF1, VEGFAI, RUNX1, CDK6, BCL2L1, PIM1, CSNK1A1 or a gene listed in Table 51) is increased or decreased by at least one site, at least two sites, at least three sites, at least five sites, at least ten sites, at least fifteen sites, at least twenty sites, at least twenty-five sites, or more. In some aspects, methylation of CpG in the promoter region CTCF binding site of a gene (e.g., an oncogene, MYC, TGIF1, VEGFAI, RUNX1, CDK6, BCL2L1, PIM1, CSNK1A1 or a gene listed in Table 51) is increased or decreased by at least one site, at least two sites, at least three sites, at least five sites, at least ten sites, at least fifteen sites, at least twenty sites, at least twenty-five sites, or more.

Also disclosed herein are methods of modulating the expression of a gene with a promoter region CTCF binding site (e.g., an oncogene, MYC, TGIF1, VEGFAI, RUNX1, CDK6, BCL2L1, PIM1, CSNK1A1 or a gene listed in Table 51) in a subject in need thereof comprising introducing into the subject a catalytically inactive site specific nuclease fused to an effector domain having methylation or demethylation activity; and one or more guide sequences homologous or complementary to at least a portion of the promoter region CTCF binding site, thereby modulating the expression of mRNA of the gene in cells of the subject. In some aspects, expression of the gene (e.g., an oncogene, MYC, TGIF1, VEGFAI, RUNX1, CDK6, BCL2L1, PIM1, CSNK1A1 or a gene listed in Table 51) is increased or decreased by about 10%, 20%, 30%, 40%, 50%, 60%, 70%, 80%, or 90%. In some aspects, protein expression is increased or decreased by about 10%, 20%, 30%, 40%, 50%, 60%, 70%, 80%, or 90%.

In some aspects, the effector domain comprises DNMT3A-3L. In some aspects, the catalytically inactive site specific nuclease is a catalytically inactive Cas (e.g., Cas9). In some aspects, the catalytically inactive site specific nuclease fused to an effector domain having methylation activity is dCas9-DNMT3A-3L or dCas9-DNMT3A-3L without the 5' NLS.

In some embodiments, 2, 3, 4, 5, 6, 7, 8, 9, 10, 11, 12, 13, 14, 15, 16, 17, 18, 19, 20, or 21 genomic sequences (e.g., regions of the MYC, TGIF1, VEGFAI, RUNX1, CDK6, BCL2L1, PIM1, CSNK1A1 or a gene listed in Table S1 promoter region CTCF binding site) are modified in the cell. In some embodiments, the genomic sequences to be modified are CTCF binding motifs. The cell may be a stem cell, a neuron, a post-mitotic cell, or a fibroblast. In some aspects, the cell is a human cell or a mouse cell. In some aspects, the cell is a cancer cell.

In certain embodiments, the methods further comprise introducing the cell into a non-human mammal. The non-human mammal may be a mouse.

Also disclosed are isolated modified cells produced by the methods described herein.

Also disclosed herein are methods of treating a subject in need thereof, comprising administering to the subject a composition that suppresses, reduces or eliminates the binding of CTCF to a promoter region CTCF binding site of a gene (e.g., an oncogene, MYC, TGIF1, VEGFAI, RUNX1, CDK6, BCL2L1, PIM1, CSNK1A1 or a gene listed in Table 51). In some aspects the subject is human. In some aspects, the subject has cancer. In some aspects the cancer is colorectal cancer, leukemia or breast cancer.

Also disclosed herein are methods of screening for a compound that modulates expression of a gene having a promoter region CTCF binding site (e.g., an oncogene, MYC, TGIF1, VEGFAI, RUNX1, CDK6, BCL2L1, PIM1, CSNK1A1 or a gene listed in Table 51) comprising contacting a cell with a test agent; and measuring methylation in the promoter region CTCF binding site, wherein the test agent is identified as a compound that modulates expression if the level of methylation of the promoter region CTCF binding site in the cell contacted with the test agent differs from the level of methylation of said promoter region CTCF binding site in a control cell not contacted with the test agent.

Also disclosed herein are methods of screening for a compound that modulates expression of a gene having a promoter region CTCF binding site (e.g., an oncogene, MYC, TGIF1, VEGFAI, RUNX1, CDK6, BCL2L1, PIM1, CSNK1A1 or a gene listed in Table 51) comprising contacting a cell with a test agent; and measuring binding between CTCF protein and CTCF binding site(s) within the promoter region, wherein the test agent is identified as a compound that modulates expression of the gene if the level of binding between CTCF protein and CTCF binding site(s) within the promoter region in the cell contacted with the test agent differs from the level of binding in a control cell not contacted with the test agent.

In some aspects, the test agent comprises a small molecule. In some aspects, the test agent comprises a nucleic acid. In some aspects, the compound is identified as an anti-cancer agent.

The above discussed, and many other features and attendant advantages of the present inventions will become better understood by reference to the following detailed description of the invention.

BRIEF DESCRIPTION OF THE DRAWINGS

(FIG. 1A) The number of genes with a constitutive CTCF site near the promoter that occur within a constitutive insulated neighborhood and have differential enhancers within that insulated neighborhood. A neighborhood was considered constitutive if it was identified in at least two out of three datasets and a CTCF site was considered constitutive if it was present in all three cell types. Genome interaction data from this study, (Heidari et al., 2014; Hnisz et al., 2016). H3K27ac and CTCF ChIP-seq data from this study, (Encode Consortium, 2012; Frietze et al., 2012; Gertz et al., 2013; Hnisz et al., 2016) (FIG. 1B) The 4.5 Mb region surrounding the MYC gene. The 2.8 Mb TAD containing MYC and part of the two adjacent TADs are indicated with thick black horizontal lines. Super-enhancers (data from (Becket et al., 2016; Frietze et al., 2012; Lin et al., 2012; Pope et al., 2014; Wang et al., 2011)) are shown in colored boxes for a panel of tumor cell lines that express MYC. (FIG. 1C) Chromosome interaction data at the MYC locus. HCT-116 SMC1 HiChIP interactions with an ORIGAMI score of at least 0.9 and a minimum PET count of 9 are shown as purple arcs. The insulated neighborhood spanning interaction is shown in blue. MCF7 CTCF and PolII ChIA-PET: interactions from the PolII ChIA-PET are shown as purple arcs and the insulated neighborhood spanning interactions from the CTCF ChIA-PET are shown in blue. Data from ENCODE and (Li et al., 2012). K562 RAD21 ChIA-PET interactions with an ORIGAMI score of at least 0.9 are shown as purple arcs. The insulated neighborhood spanning interaction is shown in blue and has an ORIGAMI score of 0.44. Data from (Heidari et al., 2014). Jurkat SMC1 ChIA-PET interactions with an ORIGAMI score of at least 0.99 are shown as purple arcs and the insulated neighborhood spanning interactions are shown in blue. Data from (Hnisz et al., 2016). CTCF ChIP-seq peaks are depicted as purple, super-enhancers are depicted as red and typical enhancers as grey rectangles. Data from this study, (Hnisz et al., 2016; Pope et al., 2014). (FIG. 1D) CTCF ChIP-seq and SMC1 ChIA-PET read pileup at the MYC promoter. Purple tracks display CTCF ChIP-seq signal in the four cell lines from panels C. Light blue track displays the read counts from read pileup of Jurkat SMC1 ChIA-PET data showing that the majority of the ChIA-PET reads are found at the enhancer docking site. Blue bars indicate CpG islands. ChIP-seq read counts are shown in reads per million sequenced reads per basepair. ChIA-PET reads are shown as read counts per basepair. (FIG. 1E) The top panel depicts all putative CTCF binding motifs as blue arrows indicating the orientation of the motif. 100 vertebrate conservation from UCSC genome browser is depicted in the bottom panel. The motif depicted in dark blue occurs in the most conserved region and shows the best match with consensus CTCF motif (e.g., CCGCGNGGNGGCAG; SEQ ID NO: 21).

FIGS. 2A-2D. Perturbation of common MYC enhancer docking site reduces CTCF occupancy, and looping to super-enhancers. (FIG. 2A) Schematic representation of the proposed model for an enhancer-docking site upstream of the MYC gene. (FIG. 2B) CTCF ChIP-seq data for the MYC locus in wild type (K562) and enhancer loop-anchor deletion (AK562) cells (left panel). A 210 bp segment in the middle of the CTCF binding site was deleted through CRISPR/Cas9 genome editing. The MYCL locus is shown as a control (right panel). Read counts are shown in reads per million sequenced reads per basepair. (FIG. 2C) qPCR showing the MYC mRNA levels after deletion of the enhancer anchor site in K562 cells. p-value was generated with a Students T-test. Error bars represent the standard deviation of the mean from three biological replicates. (FIG. 2D) 4C analysis showing reduced looping of common loop-anchor to super-enhancers in 210 bp deletion cells (AK562) versus parental cells (K562). Blowup shows the 4C interactions for five K562 specific super-enhancers. The 4C viewpoint is situated 112 basepairs up-stream of the deleted loop-anchor region. Shading represents the 90% confidence interval based on three biological replicates. Reads are shown in reads per million sequenced reads per basepair.

FIGS. 3A-3C. Homozygous deletion of the core CTCF motif reduces MYC expression. (FIG. 3A) Schematic representation of the experiment. HCT-116, K562, Jurkat and MCF7 cells were transduced with a construct expressing MYC under a pGK promoter and selected for successful integration. These cells were then transiently transfected with plasmid carrying Cas9 and a gRNA targeting the CTCF binding motif. Positive cells were identified and selected using fluorescence assisted cell sorting (FACS). These cells were multiplied and clonal populations were characterized. (FIG. 3B) Top panel, shows the position weight matrix for the CTCF motif. Bottom panel shows sequences from the selected K562, HCT-116, Jurkat and MCF7 cell lines. For the aneuploid MCF7 cell line the two most common mutations are depicted. Sequence highlighted in blue is complementary to the gRNA sequence targeting the most prominent motif which is shown here in bold sequence. (FIG. 3C) qPCR showing endogenous MYC mRNA levels in K562, HCT-116, Jurkat and MCF7 cells that express exogenous MYC together with the A-CTCF deletion counterparts. p-value was generated with a Students T-test. Error bars represent the standard deviation of the mean from three biological replicates.

(FIG. 4A) Top panel shows CTCF ChIP-seq at the MYC gene region in HCT-116 cells. ChIP-seq reads are shown in reads per million sequenced reads per basepair. Bottom panels shows a blowup of the −700 bp region underneath the CTCF peak depicting the CTCF motifs (blue arrows) and the gRNAs (red rectangles) used to target dCas9-DNMT3A-3L to the enhancer-docking site. Lollipop symbols indicate the location of CpGs that are assayed for methylation levels in C. (FIG. 4B) Schematic representation of the experiment. HCT-116 or HEK293T cells were transfected with plasmids encoding the dCAS9-DNMT3A-3L, green fluorescent protein (GFP) and a gRNA together with a plasmid encoding 2 additional gRNAs. HCT-116 cells were isolated by FACS after two days and DNA and RNA were isolated. HEK293T cells did not require sorting due to high (~80%) transfection efficiencies. (FIG. 4C) Methylation at MYC promoter loop-anchor site in untreated cells, cells transfected with dCas9-DNMT3A-3L alone or with dCas9-DNMT3A-3L in conjunction with the 5 indicated gRNAs. (FIG. 4D) qPCR analysis of MYC mRNA levels and fraction of methylated CpGs for untreated, transfected and control transfected cells. Error bars represent the standard deviation of the mean for three biological replicates.

(FIG. 5A) Promoter Hi-C interaction data and H3K27Ac ChIP-seq at the MYC TAD for cell types that represent different stages in hematopoietic development. The 2.9 Mb TAD containing MYC and part of the two adjacent TADs are indicated with thick black horizontal lines. Promoter Hi-C interactions are shown as purple colored arcs; the intensity of purple color reflects the confidence score from (Javierre et al., 2016). H3K27Ac ChIP-seq signal is shown, measured in reads per million sequenced reads per basepair (data from (Bernstein et al., 2010; Encode Consortium, 2012; Schmidt et al., 2016; Xu et al., 2012)). Super-enhancers are depicted as red rectangles and typical enhancers as grey rectangles. The relative level of MYC transcripts in the corresponding cell types are shown as boxplots in fragments per kilobase of exon per million sequenced reads (FPKM), expression data from the BLUEPRINT consortium, fetal thymus expression data from the ENCODE consortium. (FIG. 5B) CTCF ChIP-seq at the MYC gene region in HCT-116 cells and the average signal of whole genome bisulfite sequencing data for a panel of five cell types. Average percent methylation of each CpG in the region is represented as a blue bar. ChIP-seq reads are shown in reads per million sequenced reads per basepair.

(FIG. 6A) Examples of genes with enhancer docking sites (EDS) from the different cell types analyzed. CTCF ChIP-seq peaks are shown as purple rectangles, typical enhancer are shown as grey rectangles and super-enhancers are shown as red rectangles. HCT-116 HiChIP interactions are shown in purple for the TGIF1 locus. The insulated neighborhood interactions are shown in blue. K562 RAD21 ChIA-PET interactions with an ORIGAMI score of at least 0.9 and a minimum PET count of 30 are shown as purple arcs for the VEGFA locus. The insulated neighborhood spanning interaction is shown in blue. Data from (Heidari et al., 2014). Jurkat SMC1 ChIA-PET interactions with an ORIGAMI score of at least 0.97 are shown as purple arcs and the insulated neighborhood spanning interactions are shown in blue for the RUNX1 locus. Data from (Hnisz et al., 2016a). (FIG. 6B) Conservation analysis of the CTCF motifs in the constitutive CTCF bound elements in enhancer-docking sites. The mean 46-way PhastCons score of the highest JASPAR scoring motifs in constitutive CTCF peaks within EDS s and their flanking regions are shown.

(FIG. 7A) The 4.5 Mb region surrounding the MYC gene. The 2.8 Mb TAD containing MYC and part of the two adjacent TADs are indicated with thick black horizontal lines. The TAD-spanning CTCF-CTCF loop is indicated in light blue. H3K27Ac ChIP-seq signal (reads per million sequenced reads per basepair, data from (Becket et al., 2016; Frietze et al., 2012; Lin et al., 2012; Pope et al., 2014; Wang et al., 2011)) is shown in dark blue for a panel of tumor cell lines that express MYC. Tumor super-enhancers in the MYC TAD are depicted as red and typical enhancers are depicted as grey rectangles. (FIG. 7B) Heatmap of the ORIGAMI processed HiChIP, unfiltered data showing the MYC TAD with flanking regions (chr8:

127100000-131525000) and Heatmaps of Hi-C interaction data showing the MYC TAD with flanking regions (chr8: 127100000-131525000) across seven different cell types (data from (Rao et al., 2014)). No effort was made so smooth the HiChIP data as opposed to the smoothened HiC data. Scale bars represent the contrast settings used, numbers indicate the maximum intensity cutoff. The color intensity represents the PET count and the cutoff is represented in PET numbers for the HiChIP data. (FIG. 7C) CTCF ChIP-seq across a panel of tumor cell lines (data from (Anders et al., 2014; Encode Consortium, 2012; Hnisz et al., 2016; Pope et al., 2014; Wang et al., 2012; Yan et al., 2013)), and from mouse T-helper cells and Opossum, Dog, and Rhesus macaque liver (data from (Schmidt et al., 2012; Stadler et al., 2011)). Read counts are shown in reads per million sequenced reads per basepair. (FIG. 7D) ChIA-PET read pileups at the MYC promoter and quantification of the reads in the three CTCF peaks indicated. Light blue tracks display the read counts from read pileups of MCF7 CTCF, K562 RAD21 and Jurkat SMC1 ChIA-PET data showing that the majority of the ChIA-PET reads are found at the enhancer-docking site. Reads are shown as read counts per basepair. (FIG. 7E) The top panel depicts all putative CTCF binding motifs as blue arrows indicating the orientation of the motif. 100 vertebrate conservation from UCSC genome browser is depicted in the middle panel. The motif depicted in dark blue occurs in the most conserved region and shows the best match with consensus CTCF motif. The bottom panel shows the JASPAR score for the corresponding putative CTCF motifs in the middle panel. Below is the sequence of the motifs with the highest JASPAR score compared to the CTCF motif position weight matrix. Matching sequence is displayed in the same color as the corresponding base in the position weight matrix.

(FIG. 8A) Heat map of fragment lengths after genotyping PCR of wild type K562 and ΔK562 cells. PCR product was analyzed with a Fragment Analyzer and fragments of different lengths were quantified. (FIG. 8B) 4C analysis of the contacts in the MYC insulated neighborhood in wild type and 210-Δ K562 cells. Three replicate experiments for each condition shown. Black bars indicate the TAD calls, red rectangles indicate super enhancers and grey rectangles indicate typical enhancers. Top track shows H3K27Ac ChIP-seq from wild type K562 cells. (FIG. 8C) Perturbation of common MYC enhancer docking site reduces MYC expression and proliferation rate across cancers. Schematic representation of the experiment. Cells were transduced with one virus carrying Cas9 and two viruses each carrying one guide RNA (gRNA) under a doxycycline inducible promoter. After selection for all three components, cells were induced with doxycycline for 3 days prior to harvest and testing. (FIG. 8D) qPCR showing the MYC mRNA levels after deletion of the enhancer anchor site in K562, HCT-116, Jurkat and MCF7 cells. p-values were generated with a Students T-test. Error bars represent the standard deviation of the mean from three biological replicates. (FIG. 8E) Proliferation of parental (grey) and loop-anchor deleted (blue) K562, HCT-116, Jurkat and MCF7 cells. Error bars represent the standard deviation of the mean from six biological replicates FIGS. 9A-9B. Generation of cells with exogenous MYC expression (MYC-cover cells).

(FIG. 12A) Methylation at MYC promoter loop-anchor site in untreated cells, cells transfected with dCas9-DNMT3A-3L without the 5' NLS alone or with dCas9-DNMT3A-3L without the 5' NLS in conjunction with 4 gRNAs. (FIG. 12B) qPCR analysis of MYC mRNA levels and fraction of methylated CpGs for untreated, transfected and control transfected cells. dCas9-DNMT3A-3L without the 5' NLS has reduced methlylation and a reduced effect on control transfected cells (transfected with dCas9-DNMT3A-3L without the 5' NLS but not gRNA) as compared to dCas9-DNMT3A-3L (See FIGS. 4C and D above).

DETAILED DESCRIPTION OF THE INVENTION

Figure 1A:
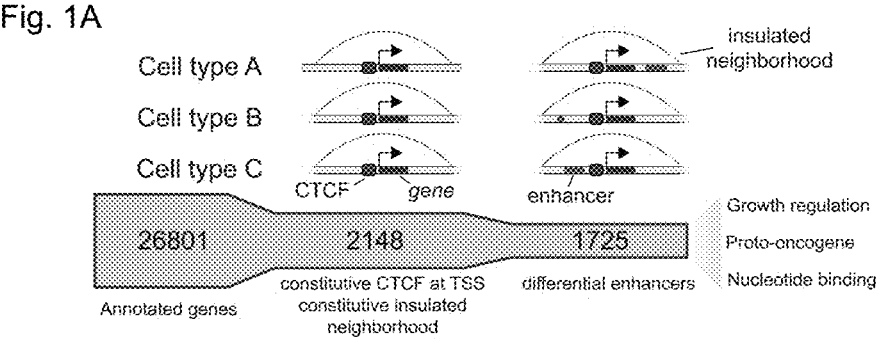
FIGS. 1A-1E. Constitutive CTCF sites at promoters loop to differential enhancers.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N J, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, ncbi.nlm.nih.gov/omim/and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In some aspects, the invention is directed to compositions for treating a disease or condition involving over-expression or under-expression of a gene with a promoter region CTCF binding site (e.g., an oncogene, MYC, TGIF1, VEGFAI, RUNX1, CDK6, BCL2L1, PIM1, CSNK1A1 or a gene listed in Table 51), comprising a catalytically inactive site specific nuclease fused to an effector domain having methylation activity; and one or more guide sequences homologous or complementary to at least a portion of the promoter region CTCF binding site. In one aspect, the invention is directed to compositions for treating a disease or condition involving over-expression of MYC, comprising a catalytically inactive site specific nuclease fused to an effector domain having methylation activity; and one or more guide sequences homologous or complementary to at least a portion of the MYC promoter CTCF binding site.

In some aspects, the invention is directed to compositions for treating a disease or condition involving over-expression or under-expression of a gene with a promoter region CTCF binding site (e.g., an oncogene, MYC, TGIF1, VEGFAI, RUNX1, CDK6, BCL2L1, PIM1, CSNK1A1 or a gene listed in Table 51), comprising one or more nucleic acids encoding a catalytically inactive site specific nuclease fused to an effector domain having methylation activity and one or more guide sequences homologous or complementary to at least a portion of the promoter region CTCF binding site. In some aspects, the invention is directed to compositions for treating a disease or condition involving over-expression of MYC comprising one or more nucleic acids encoding a catalytically inactive site specific nuclease fused to an effector domain having methylation activity and one or more guide sequences homologous or complementary to at least a portion of the MYC promoter CTCF binding site.

In some aspects, the composition is capable of modulating the expression (e.g., increasing or decreasing the expression) of a gene with a promoter region CTCF binding site (e.g., an oncogene, MYC, TGIF1, VEGFAI, RUNX1, CDK6, BCL2L1, PIM1, CSNK1A1 or a gene listed in Table 51) by changing the degree of methylation of the promoter region CTCF binding site. In some embodiments, the composition is capable of increasing methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51). In some embodiments, the composition is capable of decreasing methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51). In some embodiments, the composition is capable of modulating expression of a gene having a promoter region CTCF binding site (e.g., an oncogene, MYC, TGIF1, VEGFAI, RUNX1, CDK6, BCL2L1, PIM1, CSNK1A1 or a gene listed in Table 51) by modulating the binding of CTCF to the promoter region CTCF binding site. In some embodiments, the composition is capable of decreasing binding of CTCF to the promoter region CTCF binding site. In some embodiments, the composition is capable of increasing binding of CTCF to the promoter region CTCF binding site.

In some aspects, the composition is capable of modulating the expression of MYC by changing the degree of methylation of the MYC promoter CTCF binding site. In some aspects, the composition is capable of modulating the expression of MYC by changing the degree of methylation of the MYC promoter CTCF binding site. In some embodiments, the composition is capable of increasing methylation of the MYC promoter CTCF binding site. In some embodiments, the composition is capable of decreasing methylation of the MYC promoter CTCF binding site. In some embodiments, the composition is capable of modulating MYC expression by modulating the binding of CTCF to the MYC promoter CTCF binding site. In some embodiments, the composition is capable of decreasing binding of CTCF to the MYC promoter CTCF binding site. In some embodiments, the composition is capable of increasing binding of CTCF to the MYC promoter CTCF binding site.

Without being limited to theory, it is believed based on the results shown herein that CTCF associates with the MYC promoter region and homodimerizes with a CTCF associated with a MYC enhancer region. The homodimerization forms a promoter-enhancer DNA loop, bringing enhancers into physical proximity with the MYC promoter region and increasing expression of MYC. The degree of methylation of the MYC promoter region modulates CTCF binding and modulates MYC expression.

Some aspects of the invention are directed towards a method of contacting a cell with a composition described herein and modulating promoter region CTCF binding site methylation of a gene (e.g., an oncogene, MYC, TGIF1, VEGFAI, RUNX1, CDK6, BCL2L1, PIM1, CSNK1A1 or a gene listed in Table 51). Some aspects of the invention are directed towards a method of contacting a cell with a composition described herein and modulating expression of a gene having a promoter region CTCF binding site. Some aspects of the invention are directed towards a method of treating a patient with a disease or condition involving over-expression or under-expression of a gene having a promoter region CTCF binding site by administering a composition described herein and modulating expression of the gene. In some embodiments, the disease or condition is cancer.

In some embodiments, a CTCF binding site as used herein refers to a domain comprising one or more (e.g., 2, 3, 4, 5, 6 or more) CTCF binding motifs. In some embodiments, the CTCF binding site comprises a nucleotide sequence proximate to (e.g, within about 50 nucleotides, 75 nucleotides, 100 nucleotides, 125 nucleotides, 150 nucleotides, 200 nucleotides, 250 nucleotides, 300 nucleotides, 500 nucleotides, 1000 nucleotides, 1500 nucleotides, 2000 nucleotides, 3000 nucleotides, or 5000 nucleotides) either or both ends of a CTCF binding motif. In some embodiments, the CTCF binding site comprises a domain with one or more (e.g., 2, 3, 4, 5, 6 or more) CTCF binding motifs and a nucleotide sequence proximate to (e.g, within about 50 nucleotides, 75 nucleotides, 100 nucleotides, 125 nucleotides, 150 nucleotides, 200 nucleotides, 250 nucleotides, 300 nucleotides, 500 nucleotides, 1000 nucleotides, 1500 nucleotides, 2000 nucleotides, 3000 nucleotides, or 5000 nucleotides) either or both ends of the one or more CTCF binding motifs. It is understood by a person of skill in the art that not every nucleotide in a promoter region CTCF binding site may interact with CTCF.

Some aspects of the invention are directed towards a method of contacting a cell with a composition described herein and modulating MYC promoter CTCF binding site methylation. Some aspects of the invention are directed towards a method of contacting a cell with a composition described herein and modulating MYC expression. Some aspects of the invention are directed towards a method of treating a patient with a disease or condition involving MYC over-expression or under-expression by administering a composition described herein and modulating MYC expression. In some embodiments, the disease or condition is cancer and administration of the composition reduces MYC expression.

The MYC promoter CTCF binding site as used herein refers to a domain of the MYC promoter comprising multiple (e.g., 2, 3, 4, 5, 6 or more) CTCF binding motifs. It is understood by a person of skill in the art that not every nucleotide in the MYC promoter CTCF binding site may interact with CTCF.

The terms "disease," "disorder" or "condition" are used interchangeably and may refer to any alteration from a state of health and/or normal functioning of an organism, e.g., an abnormality of the body or mind that causes pain, discomfort, dysfunction, distress, degeneration, or death to the individual afflicted. Diseases include any disease known to those of ordinary skill in the art. In some embodiments a disease is a chronic disease, e.g., it typically lasts or has lasted for at least 3-6 months, or more, e.g., 1, 2, 3, 5, 10 or more years, or indefinitely. Disease may have a characteristic set of symptoms and/or signs that occur commonly in individuals suffering from the disease. Diseases and methods of diagnosis and treatment thereof are described in standard medical textbooks such as Longo, D., et al. (eds.), Harrison's Principles of Internal Medicine, 18th Edition; McGraw-Hill Professional, 2011 and/or Goldman's Cecil Medicine, Saunders; 24 edition (Aug. 5, 2011). In certain embodiments a disease is a multigenic disorder (also referred to as complex, multifactorial, or polygenic disorder). Such diseases may be associated with the effects of multiple genes, sometimes in combination with environmental factors (e.g., exposure to particular physical or chemical agents or biological agents such as viruses, lifestyle factors such as diet, smoking, etc.). A multigenic disorder may be any disease for which it is known or suspected that multiple genes (e.g., particular alleles of such genes, particular polymorphisms in such genes) may contribute to risk of developing the disease and/or may contribute to the way the disease manifests (e.g., its severity, age of onset, rate of progression, etc.) In some embodiments a multigenic disease is a disease that has a genetic component as shown by familial aggregation (occurs more commonly in certain families than in the general population) but does not follow Mendelian laws of inheritance, e.g., the disease does not clearly follow a dominant, recessive, X-linked, or Y-linked inheritance pattern. In some embodiments a multigenic disease is one that is not typically controlled by variants of large effect in a single gene (as is the case with Mendelian disorders). In some embodiments a multigenic disease may occur in familial form and sporadically. Examples include, e.g., Parkinson's disease, Alzheimer's disease, and various types of cancer. Examples of multigenic diseases include many common diseases such as hypertension, diabetes mellitus (e.g., type II diabetes mellitus), cardiovascular disease, cancer, and stroke (ischemic, hemorrhagic). In some embodiments a disease, e.g., a multigenic disease is a psychiatric, neurological, neurodevelopmental disease, neurodegenerative disease, cardiovascular disease, autoimmune disease, cancer, metabolic disease, or respiratory disease. In some embodiments the disease or condition involves over-expression of MYC. In some embodiments the disease or condition involves aberrant expression of TGIF1, VEGFAI, RUNX1, CDK6, BCL2L1, PIM1, CSNK1A1 or a gene listed in Table 51.

In some embodiments, the disease or condition involving over-expression of MYC, or aberrant expression of TGIF1, VEGFAI, RUNX1, CDK6, BCL2L1, PIM1, CSNK1A1 or a gene listed in Table 51, is cancer which term is generally used interchangeably to refer to a disease characterized by one or more tumors, e.g., one or more malignant or potentially malignant tumors. The term "tumor" as used herein encompasses abnormal growths comprising aberrantly proliferating cells. As known in the art, tumors are typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclear to cytoplasmic ratio, atypical mitoses, etc.); invasion of adjacent tissues (e.g., breaching a basement membrane); and/or metastasis. Malignant tumors have a tendency for sustained growth and an ability to spread, e.g., to invade locally and/or metastasize regionally and/or to distant locations, whereas benign tumors often remain localized at the site of origin and are often self-limiting in terms of growth. The term "tumor" includes malignant solid tumors, e.g., carcinomas (cancers arising from epithelial cells), sarcomas (cancers arising from cells of mesenchymal origin), and malignant growths in which there may be no detectable solid tumor mass (e.g., certain hematologic malignancies). Cancer includes, but is not limited to: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma; oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma. It will be appreciated that a variety of different tumor types can arise in certain organs, which may differ with regard to, e.g., clinical and/or pathological features and/or molecular markers. Tumors arising in a variety of different organs are discussed, e.g., the WHO Classification of Tumours series, $4^{th}$ ed, or $3^{rd}$ ed (Pathology and Genetics of Tumours series), by the International Agency for Research on Cancer (IARC), WHO Press, Geneva, Switzerland, all volumes of which are incorporated herein by reference. In some embodiments, the cancer is lung cancer, breast cancer, cervical cancer, colon cancer, gastric cancer, kidney cancer, leukemia, liver cancer, lymphoma, (e.g., a Non-Hodgkin lymphoma, e.g., diffuse large B-cell lymphoma, Burkitts lymphoma) ovarian cancer, pancreatic cancer, prostate cancer, rectal cancer, sarcoma, skin cancer, testicular cancer, or uterine cancer. The type of cancer is not limited as long as over-expression of MYC, or aberrant expression of aberrant expression of TGIF1, VEGFAI, RUNX1, CDK6, BCL2L1, PIM1, CSNK1A1 or a gene listed in Table 51, is exhibited. In some embodiments, the cancer is colorectal cancer, leukemia (e.g., acute T-cell leukemia, Chronic Myeloid Leukemia), or breast cancer. In some embodiments the cancer is neuroblastoma and administering the composition increases methylation of the CTCF binding site within the N-MYC promoter, thereby decreasing expression of N-MYC. In some embodiments the cancer is lung cancer and administering the composition increases methylation of the CTCF binding site within the L-MYC promoter, thereby decreasing expression of L-MYC.

In some embodiments, a method of treating a subject in need of treatment for cancer comprises measuring expression and/or activity of TGIF1, VEGFAI, RUNX1, CDK6, BCL2L1, PIM1, CSNK1A1 or a gene listed in Table 51 in a cancer (e.g., in a sample obtained from a cancer (e.g., a biopsy sample, circulating cancer cells, etc.)); determining that the cancer comprises cells with aberrant expression of TGIF1, VEGFAI, RUNX1, CDK6, BCL2L1, PIM1, CSNK1A1 or a gene listed in Table 51 relative to a reference value; and administering a composition disclosed herein that modulates expression of TGIF1, VEGFAI, RUNX1, CDK6, BCL2L1, PIM1, CSNK1A1 or a gene listed in Table 51 to the subject. Measuring expression may comprise measuring mRNA or protein. Measuring activity may comprise measuring expression of one or more target genes of TGIF1, VEGFAI, RUNX1, CDK6, BCL2L1, PIM1, CSNK1A1 or a gene listed in Table 51. In some embodiments a reference value may be a value for a normal, non-cancer cell, e.g., of the same cell type as the cancer cell. In some aspects, a method of treating cancer may further comprise administering a second ant-cancer agent (e.g., a conventional chemotherapy agent, a molecularly targeted therapy, a cancer immunotherapy agent, radiotherapy, or a combination thereof).

In some embodiments a method of treating a subject in need of treatment for cancer comprises measuring expression and/or activity of MYC in a cancer (e.g., in a sample obtained from a cancer (e.g., a biopsy sample, circulating cancer cells, etc.)); determining that the cancer comprises cells that over-express MYC relative to a reference value; and administering a composition disclosed herein that reduces MYC expression to the subject. Measuring expression may comprise measuring MYC mRNA or protein. Measuring MYC activity may comprise measuring expression of one or more MYC target genes. In some embodiments a reference value may be a value for a normal, non-cancer cell, e.g., of the same cell type as the cancer cell. In some embodiments a method comprises determining that the cancer comprises cells that harbor three or more copies of MYC (MYC amplification) or a MYC translocation; and administering a composition disclosed herein that reduces MYC expression to the subject. In some aspects, a method of treating cancer may further comprise administering a second ant-cancer agent (e.g., a conventional chemotherapy agent, a molecularly targeted therapy, a cancer immunotherapy agent, radiotherapy, or a combination thereof).

In some embodiments, the disease or condition involving over-expression of the MYC gene is a proliferative disease such as restenosis or polycystic kidney disease.

By "MYC" as used herein refers to nucleic acid sequences encoding any MYC protein, peptide, or polypeptide having MYC activity. The term "MYC" is also meant to include other MYC encoding sequence, such as MYC isoforms (e.g., N-MYC, L-MYC, etc.), mutant MYC genes, splice variants of MYC genes, and MYC gene polymorphisms. In some embodiments, MYC is NCBI Gene ID 4609

In some embodiments, the MYC promoter CTCF binding site is located 2 kb upstream of the major transcript start site (E. M. Klenova et al., ref (32), incorporated by reference in its entirety). In some embodiments, the MYC promoter CTCF binding site is located at Chr8:128746041-128746751 (Genome build GR37/HG19). In some embodiments, the MYC is N-MYC. In some embodiments, the N-MYC promoter CTCF binding site is located at Chr2: 16079556-16080469 (Genome build GR37/HG19). In some embodiments, the MYC is L-MYC. In some embodiments, the L-MYC promoter binding site is located at chr1: 40367702-40368974 (Genome build GR37/HG19).

As used herein, the terms "site specific nuclease" and "a targetable nuclease" are used interchangeably. Site specific nucleases and targetable nucleases are known in the art. See U.S. Pat. Pub. Nos. 20140068797, 20140186919, 20140170753 and WO/2014/172470, incorporated herein by reference in their entireties. In some embodiments, a site specific nuclease is a targetable nuclease. In some embodiments, a targetable nuclease is a site specific nuclease. In some embodiments, the site-specific nuclease is a Cas protein. In some embodiments, the site-specific nuclease is catalytically inactive. In some embodiments, the catalytically inactive site specific nuclease is a catalytically inactive Cas protein. A variety of CRISPR associated (Cas) genes or proteins which are known in the art can be used in the compositions and methods of the invention and the choice of Cas protein will depend upon the particular situation (e.g., www.ncbi.nlm.nih.gov/gene/?term=cas9). Specific examples of Cas proteins include Cas1, Cas2, Cas3, Cas4, Cas5, Cas6, Cas7, Cas8, Cas9 and Cas10. In a particular aspect, the Cas nucleic acid or protein used in the compositions is Cas9. In some embodiments a Cas protein, e.g., a Cas9 protein, may be from any of a variety of prokaryotic species. In some embodiments a particular Cas protein, e.g., a particular Cas9 protein, may be selected to recognize a particular protospacer-adjacent motif (PAM) sequence. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a Streptococcus, (e.g., a S. pyogenes, a S. thermophilus) a Cryptococcus, a Corynebacterium, a Haemophilus, a Eubacterium, a Pasteurella, a Prevotella, a Veillonella, or a Marinobacter. In some embodiments nucleic acids encoding two or more different Cas proteins, or two or more Cas proteins, may be present in the composition, e.g., to allow for recognition and modification of sites comprising the same, similar or different PAM motifs.

In some embodiments, the Cas protein is Cpf1 protein or a functional portion thereof. In some embodiments, the Cas protein is Cpf1 from any bacterial species or functional portion thereof. In certain embodiments, a Cpf1 protein is a *Francisella novicida* U112 protein or a functional portion thereof, a Acidaminococcus sp. BV3L6 protein or a functional portion thereof, or a Lachnospiraceae bacterium ND2006 protein or a functional portion thereof. Cpf1 protein is a member of the type V CRISPR systems. Cpf1 protein is a polypeptide comprising about 1300 amino acids. Cpf1 contains a RuvC-like endonuclease domain. Catalytically inactive Cpf1 is known in the art. See US Pat. Pub. No. 20160208243, incorporated by reference in its entirety.

In some embodiments, the Cas protein is a variant polypeptide with at least about 50%, 60%. 70%, 80%, 90%, 95%, or 99% sequence identity to a naturally occurring Cas protein.

In some embodiments a Cas9 nickase may be generated by inactivating one or more of the Cas9 nuclease domains. In some embodiments, an amino acid substitution at residue 10 in the RuvC I domain of Cas9 converts the nuclease into a DNA nickase. For example, the aspartate at amino acid residue 10 can be substituted for alanine (Cong et al, Science, 339:819-823). Other amino acids mutations that create a catalytically inactive Cas9 protein include mutating at residue 10 and/or residue 840. Mutations at both residue 10 and residue 840 can create a catalytically inactive Cas9 protein, sometimes referred herein as dCas9. In some embodiments, dCas9 is a D10A and a H840A Cas9 mutant that is catalytically inactive.

In some embodiments, the catalytically inactive site specific nuclease is a catalytically inactive Cas9 protein. In some embodiments, the catalytically inactive site specific nuclease is a catalytically inactive Cpf1 protein.

As used herein an "effector domain" is a molecule (e.g., protein) that modulates the expression and/or activation of a genomic sequence (e.g., gene). The effector domain may have methylation activity (e.g., DNA methylation activity). In some aspects, the effector domain targets one or both alleles of a gene. The effector domain can be introduced as a nucleic acid sequence and/or as a protein. In some aspects, the effector domain can be a constitutive or an inducible effector domain. In some aspects, a Cas (e.g., dCas) nucleic acid sequence or variant thereof and an effector domain nucleic acid sequence are introduced into the cell as a chimeric sequence. In some aspects, the effector domain is fused to a molecule that associates with (e.g., binds to) Cas protein (e.g., the effector molecule is fused to an antibody or antigen binding fragment thereof that binds to Cas protein). In some aspects, a Cas (e.g., dCas) protein or variant thereof and an effector domain are fused or tethered creating a chimeric protein and are introduced into the cell as the chimeric protein. In some aspects, the Cas (e.g., dCas) protein and effector domain bind as a protein-protein interaction. In some aspects, the Cas (e.g., dCas) protein and effector domain are covalently linked. In some aspects, the effector domain associates non-covalently with the Cas (e.g., dCas) protein. In some aspects, a Cas (e.g., dCas) nucleic acid sequence and an effector domain nucleic acid sequence are introduced as separate sequences and/or proteins. In some aspects, the Cas (e.g., dCas) protein and effector domain are not fused or tethered.

As shown herein, fusions of a catalytically inactive (D10A; H840A) Cas9 protein (dCas9) tethered with all or a portion of (e.g., biologically active portion of) an (one or more) effector domain create chimeric proteins that can be guided to specific DNA sites by one or more RNA sequences (sgRNA) to modulate activity and/or expression of MYC. In specific aspects, fusions of a dCas9 tethered with all or a portion of an effector domain create chimeric proteins that can be guided to specific DNA sites by one or more RNA sequences to modulate or modify methylation of MYC. As used herein, a "biologically active portion of an effector domain" is a portion that maintains the function (e.g. completely, partially, minimally) of an effector domain (e.g., a "minimal" or "core" domain). The fusion of the Cas9 (e.g., dCas9) with all or a portion of one or more effector domains created a chimeric protein.

Examples of effector domains include a transcription(al) activating domain, a coactivator domain, a transcription factor, a transcriptional pause release factor domain, a negative regulator of transcriptional elongation domain, a transcriptional repressor domain, a chromatin organizer domain, a remodeler domain, a histone modifier domain, a DNA modification domain, a RNA binding domain, a protein interaction input device domain (Grunberg and Serrano, Nucleic Acids Research, 38 (8): 2663-2675 (2010), and a protein interaction output device domain (Grunberg and Serrano, Nucleic Acids Research, 38 (8): 2663-2675 (2010). As used herein a "protein interaction input device" and a "protein interaction output device" refers to a protein-protein interaction (PPI). In some aspect, binding partners are targeted to different sites in the genome using the catalytically inactive Cas protein. The binding partners interact, thereby bringing the targeted loci into proximity.

In some aspects, the effector domain is a DNA modifier. Specific examples of DNA modifiers include 5hmc conversion from 5 mC such as Tetl (Tet1CD); DNA demethylation by Tetl, ACID A, MBD4, Apobec1, Apobec2, Apobec3, Tdg, Gadd45a, Gadd45b, ROS1; DNA methylation by Dnmtl, DNMT3A, Dnmt3b, CpG Methyltransferase M.SssI, and/or M.EcoHK31I. In specific aspects, an effector domain is DNMT3A. In some aspects, the effector domain is the C-terminal domain of DNMT3A (i.e., DNMT3A-C). In some aspects, the DNMT3A-C effector domain is complexed with the C-terminal portion of DNMT3L (DNMT3L-C). In some aspects, a chimeric protein comprising DNMT3A-C and DNMT3L-C (sometimes referred to herein as DNMT3A-3L) is used for the effector domain. In some aspects, DNMT3A-3L is a single chain fusion protein as provided in Siddique, et al. (2013) incorporated herein by reference in its entirety. In some embodiments, the effector domain is DNMT3A-3L without the 5' NLS. In some embodiments, dCas9 is fused to DNMT3A-3L or DNMT3A-3L without the 5' NLS.

DNA methylation is established by two de novo DNA methyltransferases (DNMT3A/B), and is maintained by DNMT1 (Smith and Meissner, (2013). DNA methylation: roles in mammalian development. Nature reviews Genetics 14, 204-220). Gene activation during development is associated with demethylation of promoter and enhancer sequences. In addition, demethylation can be achieved through oxidation of the methyl group by TET (ten-eleven translocation) dioxygenases to form 5-hydroxymethylcytosine (5-hmC), and then restoration into unmodified cytosines by either DNA replication-dependent dilution or DNA glycosylase-initiated base excision repair (BER), a process termed as active demethylation and proposed to operate during specific developmental stages such as preimplantation embryos or in post-mitotic neurons.

In one aspect of the invention, fusion of the dCas9 to an effector domain can be to that of a single copy or multiple/tandem copies of full-length or partial-length effectors. Other fusions can be with split (functionally complementary) versions of the effector domains. In some embodiments, the effector domain can include full-length or partial-length effectors from more than one effector (e.g., DNMT3A and DNMT3L). Effector domains for use in the methods include any one of the following classes of proteins: proteins that mediate drug inducible looping of DNA and/or contacts of genomic loci, proteins that aid in the three-dimensional proximity of genomic loci bound by dCas9 with different sgRNA.

Other examples of effector domains are described in PCT Application No. PCT/US2014/034387 and U.S. application Ser. No. 14/785,031, which are incorporated herein by reference in their entirety.

In some embodiments, the catalytically inactive site specific nuclease fused to an effector domain having DNA methylation activity is dCas9-DNMT3A-3L or dCas9-DNMT3A-3L without the 5' NLS.

In some aspects the invention is directed to (e.g., a composition comprising, consisting essentially of, consisting of) a nucleic acid sequence that encodes a fusion protein (chimeric protein) comprising all or a portion of a Cas (e.g., dCas) protein fused to all or a portion of one or more effector domains. In some aspects, the invention is directed to (e.g., a composition comprising, consisting essentially of, consisting of) a fusion protein comprising all or a portion of a Cas (e.g., dCas) protein fused to all or a portion of one or more effector domains. In some aspects all or a portion of the Cas (e.g., dCas) protein targets but does not cleave a nucleic acid sequence. In some aspects, the Cas (e.g., dCas) protein can be fused to the N-terminus or C-terminus of one or more effector domains. In some aspects, the portion of the effector domain modulates the methylation of the genomic sequence (e.g., demethylates or methylates the genomic sequence). In some aspects, the effector domain comprises the c-terminal portions of DNMT3A and DNMT3L. In some aspects, the invention is directed to (e.g., a composition comprising, consisting essentially of, consisting of) a fusion protein comprising dCas9-DNMT3A-3L or dCas9-DNMT3A-3L without the 5' NLS.

In some aspects, the invention is directed to (e.g., a composition comprising, consisting essentially of, consisting of) a catalytically inactive nuclease (e.g., dCas9), an effector domain (e.g., DNMT3a, DNMT3A-C, DNMT3A-3L, DNMT3A-3L without the 5' NLS) and one or more guide sequences. In some aspects, the invention is directed to (e.g., a composition comprising, consisting essentially of, consisting of) nucleic acids encoding a catalytically inactive nuclease (e.g., dCas9), an effector domain (e.g., DNMT3a, DNMT3A-C, DNMT3A-3L, DNMT3A-3L without the 5' NLS) and one or more guide sequences.

In some aspects, the invention is directed to (e.g., a composition comprising, consisting essentially of, consisting of) a mixture of nucleic acids and polypeptides. In some embodiments, the invention is directed to (e.g., a composition comprising, consisting essentially of, consisting of) a catalytically inactive nuclease (e.g., dCas9), an effector domain (e.g., DNMT3a, DNMT3A-C, DNMT3A-3L, DNMT3A-3L without the 5' NLS) and one or more nucleic acids encoding one or more guide sequences. In some embodiments, the invention is directed to (e.g., a composition comprising, consisting essentially of, consisting of) a catalytically inactive nuclease (e.g., dCas9) and effector (e.g., DNMT3a, DNMT3A-C, DNMT3A-3L, DNMT3A-3L without the 5' NLS) fusion protein and one or more nucleic acids encoding one or more guide sequences. In some embodiments, the invention is directed to (e.g., a composition comprising, consisting essentially of, consisting of) one or more nucleic acids encoding a catalytically inactive nuclease (e.g., dCas9) and an effector domain (e.g., DNMT3a, DNMT3A-C, DNMT3A-3L, DNMT3A-3L without the 5' NLS) and one or more nucleic acids encoding one or more guide sequences. In some embodiments, the invention is directed to (e.g., a composition comprising, consisting essentially of, consisting of) a catalytically inactive nuclease (e.g., dCas9) and effector (e.g., DNMT3a, DNMT3A-C, DNMT3A-3L, DNMT3A-3L without the 5' NLS) fusion protein and one or more nucleic acids encoding one or more guide sequences. Every combination of encoding nucleic acids (e.g., encoding a catalytically inactive site specific nuclease, effector, catalytically inactive nuclease-effector fusion protein, and/or guide sequence) with or without non-encoded components (e.g., a catalytically inactive site specific nuclease, effector, catalytically inactive nuclease-effector fusion protein, and/or guide sequence) having the capability to modulate MYC expression are contemplated herein.

In some aspects, the nucleic acid sequence encoding the fusion protein and/or the one or more guide sequences are isolated. An "isolated," "substantially pure," or "substantially pure and isolated" nucleic acid sequence, as used herein, is one that is separated from nucleic acids that normally flank the gene or nucleotide sequence (as in genomic sequences) and/or has been completely or partially purified from other transcribed sequences (e.g., as in an RNA or cDNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. An "isolated," "substantially pure," or "substantially pure and isolated" protein (e.g., chimeric protein; fusion protein), as used herein, is one that is separated from or substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50%, 80%, 90%, 95%, 98% or 99% (on a molar basis) of all macromolecular species present.

In one aspect, fusion of catalytically inactive site specific nuclease (e.g, a catalytically inactive Cas protein) with all or a portion of one or more effector domains comprise one or more linkers. As used herein, a "linker" is something that connects or fuses two or more moieties (e.g see Hermanson, Bioconjugate Techniques, 2n d Edition, which is hereby incorporated by reference in its entirety). As will be appreciated by one of ordinary skill in the art, a variety of linkers can be used. In one aspect, a linker comprises one or more amino acids. In some aspects, a linker comprises two or more amino acids. In one aspect, a linker comprises the amino acid sequence GS. In some aspects, fusion of Cas9

(e.g., dCas9) with two or more effector domains comprises one or more interspersed linkers (e.g., GS linkers) between the domains. In some aspects, one or more nuclear localization sequences may be located between the catalytically inactive nuclease (e.g., dCas9) and the effector domain. For example, a fusion protein may include dCas9-NLS-DNMT3A or dCas9-NLS-DNMT3A-3L. In some embodiments, the one or more nuclear localization sequences may be located anywhere in the fusion protein. In some embodiments, the fusion protein does not comprise a NLS, or does not comprise an NLS located between the catalytically inactive nuclease (e.g., dCas9) and the effector domain.

In some aspects, one or more guide sequences include sequences that recognize DNA in a site-specific manner. For example, guide sequences can include guide ribonucleic acid (RNA) sequences utilized by a CRISPR system or sequences within a TALEN or zinc finger system that recognize DNA in a site-specific manner. In some embodiments, the guide sequences comprise a portion that is complementary or homologous to a portion of each of the one or more genomic sequences and comprise a binding site for the catalytically inactive site specific nuclease. In some embodiments, one or more guide sequences do not comprise a binding site for the catalytically inactive site specific nuclease. In some embodiments, one or more guide sequences comprise a moity that blocks (e.g., sterically blocks) CTCF binding when the one or more guide sequences is bound to genomic sequences. In some embodiments, the guide sequence is referred to as guide RNA (gRNA) or single guide RNA (sgRNA).

In some aspects, a single guide sequence can be complementary or homologous to one or more (e.g., all) of the genomic sequences that are being modulated or modified. In one aspect, a single guide is complementary or homologous to a single target genomic sequence. In a particular aspect in which two or more target genomic sequences are to be modulated or modified, multiple (e.g., 2, 3, 4, 5, 6, 7, 8, 9, 10, or more) guide sequences are introduced wherein each guide sequence is complementary or homologous to (specific for) one target genomic sequence. In some aspects, two or more, three or more, four or more, five or more, or six or more guide sequences are complementary or homologous to (specific for) different parts of the same target sequence. In one aspect, two or more guide sequences bind to different sequences of the same region of DNA. In some aspects, a single guide sequence is complementary or homologous to at least two target or more (e.g., all) of the genomic sequences. It will also be apparent to those of skill in the art that the portion of the guide sequence that is complementary or homologous to one or more of the genomic sequences and the portion of the guide sequence that binds to the catalytically inactive site specific nuclease can be introduced as a single sequence or as 2 (or more) separate sequences into a cell. In some embodiments the sequence that binds to the catalytically inactive site specific nuclease comprises a stem-loop.

In some embodiments, one or more guide sequences comprise a sequence homologous or complementary to a portion of a promoter region CTCF binding site of a gene (e.g., an oncogene, MYC, TGIF1, VEGFAI, RUNX1, CDK6, BCL2L1, PIM1, CSNK1A1 or a gene listed in Table 51). In some embodiments, one or more guide sequences comprise a sequence homologous or complementary to a nucleotide sequence of a promoter region CTCF binding site of a gene (e.g., an oncogene, MYC, TGIF1, VEGFAI, RUNX1, CDK6, BCL2L1, PIM1, CSNK1A1 or a gene listed in Table 51) and/or a sequence within 100, 200, 300, 400, 500, 600, 700, 800, 900 or 1000 nt of the promoter region CTCF binding site. The portion of the guide sequence homologous or complementary to the promoter region CTCF binding site or adjacent sequence (e.g., within 100, 200, 300, 400, 500, 600, 700, 800, 900 or 1000 nt of the promoter region CTCF binding site) can comprise 15 nt or more, 18 nt or more, or 20 nt or more.

In some embodiments, one or more guide sequences comprise a sequence homologous or complementary to a portion of the MYC promoter CTCF binding site. In some embodiments, one or more guide sequences comprise a sequence homologous or complementary to a nucleotide sequence of the MYC promoter CTCF binding site and/or a sequence within 100, 200, 300, 400, 500, 600, 700, 800, 900 or 1000 nt of the MYC promoter CTCF binding site. The portion of the guide sequence homologous or complementary to the MYC promoter CTCF binding site or adjacent sequence (e.g., within 100, 200, 300, 400, 500, 600, 700, 800, 900 or 1000 nt of the MYC promoter CTCF binding site) can comprise 15 nt or more, 18 nt or more, or 20 nt or more.

In some embodiments, guide sequence used to modify gene expression (e.g., MYC, TGIF1, VEGFAI, RUNX1, CDK6, BCL2L1, PIM1, CSNK1A1 or a gene listed in Table 51 gene expression) is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications (e.g., RNA comprising one or more non-standard and/or non-naturally occurring bases and/or modifications to the backbone, internucleoside linkage(s) and/or sugar). Methods of modifying bases of RNA are well known in the art. Examples of such modified bases include those contained in the nucleosides 5-methylcytidine (5 mC), pseudouridine (T), 5-methyluridine, 2'O-methyluridine, 2-thiouridine, N-6 methyladenosine, hypoxanthine, dihydrouridine (D), inosine (I), and 7-methylguanosine (m7G). It should be noted that any number of bases, sugars, or backbone linkages in a RNA sequence can be modified in various embodiments. It should further be understood that combinations of different modifications may be used. In some embodiments an RNA comprises one or more modifications selected from: phosphorothioate, 2'-OMe, 2'-F, 2'-constrained ethyl (2'-cEt), 2'-OMe 3' phosphorothioate (MS), and 2'-OMe 3-thioPACE (MSP) modifications. In some embodiments a modification may stabilize the RNA and/or increase its binding affinity to a complementary sequence.

In some embodiments, the one or more guide sequences comprise at least one locked nucleic acid (LNA) unit, such as 1, 2, 3, 4, 5, 6, 7, or 8 LNA units, such as from about 3-7 or 4-8 LNA units, or 3, 4, 5, 6 or 7 LNA units. In some embodiments, all the nucleotides of the one or more guide sequences are LNA. In some embodiments, the one or more guide sequences may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-cytosine.

In some aspects, the RNA sequence is a morpholino. Morpholinos are typically synthetic molecules, of about 25 bases in length and bind to complementary sequences of RNA by standard nucleic acid base-pairing. Morpholinos have standard nucleic acid bases, but those bases are bound to morpholine rings instead of deoxyribose rings and are linked through phosphorodiamidate groups instead of phosphates. Morpholinos do not degrade their target RNA molecules, unlike many antisense structural types (e.g., phosphorothioates, siRNA). Instead, morpholinos act by steric blocking and bind to a target sequence within a RNA and block molecules that might otherwise interact with the RNA.

In some embodiments, an RNA sequence can vary in length from about 8 base pairs (bp) to about 200 bp. In some embodiments, each of the one or more guide sequences can be about 9 to about 190 bp; about 10 to about 150 bp; about 15 to about 120 bp; about 20 to about 100 bp; about 30 to about 90 bp; about 40 to about 80 bp; about 50 to about 70 bp in length.

Chemical modifications and methods of synthesizing guide RNAs (guide sequences) are known in the art. See WO/2016/164356, herein incorporated by reference in its entirety.

The portion of each genomic sequence (e.g., MYC, TGIF1, VEGFAI, RUNX1, CDK6, BCL2L1, PIM1, CSNK1A1 or a gene listed in Table 51 promoter region CTCT binding sequence) to which each guide sequence is complementary or homologous to can also vary in size. In particular aspects, the portion of each genomic sequence to which the guide sequence is complementary or homologous to can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each guide sequence can be at least about 70%, 75%, 80%, 85%, 90%, 95%, 100%, etc. identical, complementary or similar to the portion of each genomic sequence. In some embodiments, each guide sequence is completely or partially identical, complementary or similar to each genomic sequence. For example, each guide sequence can differ from perfect complementarity or homology to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more guide sequences are perfectly complementary or homologous (100%) across at least about 10 to about 25 (e.g., about 20) nucleotides of the genomic sequence.

As will be apparent to those of ordinary skill in the art, the one or more RNA sequences can further comprise one or more expression control elements. For example, in some embodiments the RNA sequences comprises a promoter, suitable to direct expression in cells, wherein the portion of the RNA sequence is operably linked to the expression control element(s). The promoter can be a viral promoter (e.g., a CMV promoter) or a mammalian promoter (e.g., a PGK promoter). The RNA sequence can comprise other genetic elements, e.g., to enhance expression or stability of a transcript. In some embodiments the additional coding region encodes a selectable marker (e.g., a reporter gene such as green fluorescent protein (GFP)).

As described herein, the one or more guide sequences also comprise a (one or more) binding site for a (one or more) catalytically inactive site specific nuclease. The catalytically inactive site specific nuclease may be a catalytically inactive CRISPR associated (Cas) protein. In a particular aspect, upon hybridization of the one or more guide sequences to the one or more genomic sequences, the catalytically inactive site specific nuclease binds to the one or more guide sequences.

In some aspects, the guide sequences are ribonucleic acid guide sequences. In some aspects, each guide sequence is from about 10 base pairs to about 150 base pairs in length.

In some aspects, the composition comprises at least two guide sequences. In some aspects, the compositions and methods disclosed herein can comprise 1, 2, 3, 4, 5, 6, 7, 8, 9, 10 or more guide sequences. In some embodiments, the compositions and methods disclosed herein can comprise 1, 2 or 5 guide sequences.

In some aspects, the one or more guide sequences comprise a sequence homologous to a sequence selected from the group consisting of SEQ ID NOS. 1-8.

| | |
|---|---|
| GCCTGGATGTCAACGAGGGC | SEQ ID NO: 1 |
| GCGGGTGCTGCCCAGAGAGG | SEQ ID NO: 2 |
| GCAAAATCCAGCATAGCGAT | SEQ ID NO: 3 |
| CTATTCAACCGCATAAGAGA | SEQ ID NO: 4 |
| CGCTGAGCTGCAAACTCAAC | SEQ ID NO: 5 |
| ACCGCCTGTCCTTCCCCCGC | SEQ ID NO: 6 |
| TTGGTTGCTCCCCGCGTTTG | SEQ ID NO: 7 |
| ATGATCTCTGCTGCCAGTAG | SEQ ID NO: 8 |

There are various ways that a polypeptide comprising a catalytically inactive site specific nuclease fused to an effector domain having methylation activity can be delivered to a cell or subject, e.g., by administering a nucleic acid that encodes the polypeptide, which nucleic acid may be, e.g., a viral vector or may be a translatable nucleic acid (e.g, synthetic modified mRNA. In some embodiments a nucleic acid sequence encoding a polypeptide is codon optimized for expression in mammalian cells, e.g., human cells. Examples of modified mRNA are described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624). Additional examples are found in numerous PCT and US applications and issued patents to Moderna Therapeutics, e.g., PCT/US2011/046861; PCT/US2011/054636, PCT/US2011/054617, U.S. Ser. No. 14/390,100 (and additional patents and patent applications mentioned in these.) In some embodiments the guide sequence can be delivered as a nucleic acid that encodes the guide sequence. In some embodiments a nucleic acid comprises a first portion that encodes a polypeptide comprising a catalytically inactive site-specific nuclease fused to an effector domain and a second portion that encodes a guide RNA. One of ordinary skill in the art will appreciate that a nucleic acid that encodes a polypeptide or RNA may be operably linked to a promoter capable of directing expression in a cell or subject, e.g., a mammalian cell or subject.

Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. In some embodiments administration may be performed by direct administration to a tissue or organ (e.g., skin, heart, liver, lung, kidney, brain, eye, muscle, bone, nerve) or tumor. The nucleic acid(s) or protein(s) may be physically associated with, e.g., encapsulated, e.g., in lipid-containing particles, e.g., solid lipid nanoparticles, liposomes, polymeric particles (e.g., PLGA particles). In some embodiments one or more nucleic acids may be administered using a vector (e.g., a viral vector such as an adenoviral vector, lentiviral vector, or adeno-associated virus vector). In some embodiments one or more nucleic acids, proteins, and/or vectors may be combined with a pharmaceutically acceptable carrier to produce a pharmaceutical composition, which may be administered to a subject.

In some embodiments a nucleic acid, polypeptide, or particle may be targeted to cells of a particular type, e.g., cancer cells of a particular type or expressing a particular cell surface marker. For example, a nucleic acid, protein, or a particle comprising a nucleic acid or vector may comprise or be conjugated to a targeting moiety that binds to a marker expressed at the surface of a target cell (e.g., binds to a tumor antigen or a receptor expressed by the target cell). A targeting moiety may comprise, e.g., an antibody or antigen-binding portion thereof, an engineered protein capable of specific binding, a nucleic acid aptamer, a ligand, etc.

In some embodiments, nucleic acids encoding one or more components (e.g., catalytically inactive site specific nuclease, effector domain, catalytically inactive site specific nuclease-effector domain fusion protein, one or more guide sequences) are delivered by one or more viral vectors e.g., a retroviral vector such as a lentiviral vector or gamma retroviral vector, or an adenoviral or AAV vector. In some embodiments, the nucleic acids encoding a catalytically inactive site specific nuclease, effector domain, and/or catalytically inactive site specific nuclease-effector domain fusion protein are codon-optimized for expression in a subject (e.g., human).

In some aspects, the invention is directed towards a composition that inhibits binding of CTCF to a promoter region CTCF binding site of a gene (e.g., an oncogene, MYC, TGIF1, VEGFAI, RUNX1, CDK6, BCL2L1, PIM1, CSNK1A1 or a gene listed in Table 51). In some embodiments, the composition comprises a small molecule or a nucleic acid derivative. In some embodiments, the composition binds to CTCF. In some embodiments, the composition binds to a promoter region CTCF binding site of a gene (e.g., an oncogene, MYC, TGIF1, VEGFAI, RUNX1, CDK6, BCL2L1, PIM1, CSNK1A1 or a gene listed in Table 51).

Also disclosed herein are methods for methylating a promoter region CTCF binding site of a gene (e.g., an oncogene, MYC, TGIF1, VEGFAI, RUNX1, CDK6, BCL2L1, PIM1, CSNK1A1 or a gene listed in Table 51) in a cell comprising introducing into the cell a catalytically inactive site specific nuclease fused to an effector domain having methylation activity; and one or more guide sequences homologous or complementary to at least a portion of the promoter region CTCF binding site, thereby methylating the promoter region CTCF binding site.

In some embodiments, the catalytically inactive site specific nuclease is a catalytically inactive Cas protein as described herein. In some embodiments, the catalytically inactive site specific nuclease is a catalytically inactive Cas9 protein as described herein. In some embodiments, the catalytically inactive site specific nuclease is a catalytically inactive Cpf1 protein as described herein. In some embodiments, the effector domain having methylation activity is DNMT3A-3L or DNMT3A-3L without a 5' NLS as described herein. In some embodiments, the catalytically inactive site specific nuclease fused to an effector domain having methylation activity is dCas9-DNMT3A-3L or dCas9-DNMT3A-3L without a 5' NLS as described herein. In some aspects, expression of a gene with a promoter region CTCF binding site is modulated. In some aspects, expression of a gene with a promoter region CTCF binding site is decreased. In some aspects, expression of a gene with a promoter region CTCF binding site is increased.

In some aspects, the invention is directed towards a composition that inhibits binding of CTCF to the MYC promoter CTCF binding site. In some embodiments, the composition comprises a small molecule or a nucleic acid derivative. In some embodiments, the composition binds to CTCF. In some embodiments, the composition binds to the MYC promoter CTCF binding site.

Also disclosed herein are methods for methylating a MYC promoter CTCF binding site in a cell comprising introducing into the cell a catalytically inactive site specific nuclease fused to an effector domain having methylation activity; and one or more guide sequences homologous or complementary to at least a portion of the MYC promoter CTCF binding site, thereby methylating the MYC promoter CTCF binding site.

In some embodiments, the catalytically inactive site specific nuclease is a catalytically inactive Cas protein as described herein. In some embodiments, the catalytically inactive site specific nuclease is a catalytically inactive Cas9 protein as described herein. In some embodiments, the catalytically inactive site specific nuclease is a catalytically inactive Cpf1 protein as described herein. In some embodiments, the effector domain having methylation activity is DNMT3A-3L as described herein. In some embodiments, the catalytically inactive site specific nuclease fused to an effector domain having methylation activity is dCas9-DNMT3A-3L as described herein. In some aspects, MYC expression is modulated. In some aspects, MYC expression is decreased. In some aspects, MYC expression is increased.

In some embodiments, the guide sequences are ribonucleic acid guide sequences as described herein. In some embodiments, the guide sequence is from about 10 base pairs to about 150 base pairs in length. In some embodiments, the one or more guide sequences comprise two or more guide sequences. In some embodiments, the one or more guide sequences comprise a sequence encoded by a nucleic acid sequence selected from the group consisting of SEQ ID NOS. 1-8.

The methods described herein can be used to modify or modulate one or more genomic sequences (e.g., MYC, TGIF1, VEGFAI, RUNX1, CDK6, BCL2L1, PIM1, CSNK1A1 or a gene listed in Table 51 promoter region CTCF binding site) in a variety of cells, which includes somatic cells, stem cells, mitotic or post-mitotic cells, neurons, fibroblasts, or zygotes. A cell, zygote, embryo, or post-natal mammal can be of vertebrate (e.g., mammalian) origin. In some aspects, the vertebrates are mammals or avians. Particular examples include primate (e.g., human), rodent (e.g., mouse, rat), canine, feline, bovine, equine, caprine, porcine, or avian (e.g., chickens, ducks, geese, turkeys) cells, zygotes, embryos, or post-natal mammals. In some embodiments, the cell, zygote, embryo, or post-natal mammal is isolated (e.g., an isolated cell; an isolated zygote; an isolated embryo). In some embodiments, a mouse cell, mouse zygote, mouse embryo, or mouse post-natal mammal is used. In some embodiments, a rat cell, rat zygote, rat embryo, or rat post-natal mammal is used. In some embodiments, a human cell, human zygote or human embryo is used. The methods described herein can be used to modify or modulate one or more genomic sequences (e.g., methylate or demethylate a promoter region CTCF binding site) in a mammal (e.g., a mouse, a human) in vivo.

Stem cells may include totipotent, pluripotent, multipotent, oligopotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc.

In some embodiments, the cell is a mammalian cell. In some embodiments, the cell is a human cell. In some embodiments, the cell is a mouse cell. In some embodiments, the cell is a cancer cell as disclosed herein.

In some aspects, methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51) is increased by about 2-fold, 2.5-fold, 2.7-fold, 3.0 fold, 3.5-fold, 4.0 fold or more. In some aspects, methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51) is increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some aspects, methylation of a promoter region CTCF binding site of a gene (e.g., an oncogene, MYC, TGIF1, VEGFAI, RUNX1, CDK6, BCL2L1, PIM1, CSNK1A1 or a gene listed in Table 51) is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, methylation of the promoter region CTCF binding site of a gene (e.g., an oncogene, MYC, TGIF1, VEGFAI, RUNX1, CDK6, BCL2L1, PIM1, CSNK1A1 or a gene listed in Table 51) is increased or decreased by at least one site, at least two sites, at least three sites, at least five sites, at least ten sites, at least fifteen sites, at least twenty sites, at least twenty-five sites, or more. In some aspects, methylation of CpGs in the promoter region CTCF binding site of a gene (e.g., an oncogene, MYC, TGIF1, VEGFAI, RUNX1, CDK6, BCL2L1, PIM1, CSNK1A1 or a gene listed in Table 51) is increased or decreased by at least one site, at least two sites, at least three sites, at least five sites, at least ten sites, at least fifteen sites, at least twenty sites, at least twenty-five sites, or more. Reporters of genomic methylation are described in U.S. application Ser. No. 15/078,851, which is incorporated herein by reference in its entirety. Any method known in the art may be used to measure genomic methylation and is not limited.

In some aspects, expression of a gene having a promoter region CTCF binding site is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, expression of a gene having a promoter region CTCF binding site is increased by about 10%, 15%, 20%, 25%, 30%, 35%, 40%, 45%, 50%, 55%, 60%, 65%, 70%, 75%, 80%, 85%, 90%, 100%, 150%, 200% or more. Methods of measuring gene expression are known in the art. Any method known in the art may be used to measure gene expression and is not limited.

In some aspects, methylation of the MYC promoter CTCF binding site is increased by about 2-fold, 2.5-fold, 2.7-fold, 3.0 fold, 3.5-fold, 4.0 fold or more. In some aspects, methylation of the MYC promoter CTCF binding site is increased by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some aspects, methylation of the MYC promoter CTCF binding site is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, methylation of the MYC promoter region CTCF binding site is increased or decreased by at least one site, at least two sites, at least three sites, at least five sites, at least ten sites, at least fifteen sites, at least twenty sites, at least twenty-five sites, or more. In some aspects, methylation of CpGs in the MYC promoter region CTCF binding site is increased or decreased by at least one site, at least two sites, at least three sites, at least five sites, at least ten sites, at least fifteen sites, at least twenty sites, at least twenty-five sites, or more.

In some aspects, MYC expression is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, MYC expression is increased by about 10%, 15%, 20%, 25%, 30%, 35%, 40%, 45%, 50%, 55%, 60%, 65%, 70%, 75%, 80%, 85%, 90%, 100%, 150%, 200% or more. Methods of measuring MYC expression are known in the art. Any method known in the art may be used to measure MYC expression and is not limited.

In some aspects, the invention is directed to a method of producing a nonhuman mammal carrying modifications in a promoter region CTCF binding site of a gene (e.g., an oncogene, MYC, TGIF1, VEGFAI, RUNX1, CDK6, BCL2L1, PIM1, CSNK1A1 or a gene listed in Table 51) comprising introducing into a zygote or an embryo a catalytically inactive site specific nuclease fused to an effector domain having methylation or demethylation activity, and one or more guide sequences. The zygote or the embryo is maintained under conditions in which the guide sequence hybridizes to a portion of each of the one or more genomic sequences, and the catalytically inactive site specific nuclease fused to an effector domain either methylates or demethylates the genomic sequence, thereby producing an embryo having one or more modified genomic sequences. The embryo having one or more modified genomic sequences may be transferred into a foster nonhuman mammalian mother. The foster nonhuman mammalian mother is maintained under conditions in which one or more offspring carrying the one or more modified genomic sequences are produced, thereby producing a nonhuman mammal carrying modifications in one or more genomic sequences.

In some aspects, the invention is directed to a method of producing a nonhuman mammal carrying modifications in a MYC promoter CTCF binding site comprising introducing into a zygote or an embryo a catalytically inactive site specific nuclease fused to an effector domain having methylation or demethylation activity, and one or more guide sequences. The zygote or the embryo is maintained under conditions in which the guide sequence hybridizes to a portion of each of the one or more genomic sequences (e.g., MYC promoter CTCF binding site), and the catalytically inactive site specific nuclease fused to an effector domain either methylates or demethylates the genomic sequence (e.g., MYC promoter CTCF binding site), thereby producing an embryo having one or more modified genomic sequences. The embryo having one or more modified genomic sequences (e.g., MYC promoter CTCF binding site) may be transferred into a foster nonhuman mammalian mother. The foster nonhuman mammalian mother is maintained under conditions in which one or more offspring carrying the one or more modified genomic sequences (e.g., MYC promoter CTCF binding site) are produced, thereby producing a nonhuman mammal carrying modifications in one or more genomic sequences (e.g., MYC promoter CTCF binding site).

As will be apparent to those of skill in the art, the nonhuman mammals can also be produced using methods described herein and/or with conventional methods, see for example, U.S. Published Application No. 2011/0302665. A method of producing a non-human mammalian embryo can comprise injecting non-human mammalian ES cells (e.g., iPSCs) into non-human tetraploid blastocysts and maintaining said resulting tetraploid blastocysts under conditions that result in formation of embryos, thereby producing a non-human mammalian embryo. In some embodiments, said non-human mammalian cells are mouse cells and said non-human mammalian embryo is a mouse. In some embodiments, said mouse cells are mutant mouse cells and are injected into said non-human tetraploid blastocysts by microinjection. In some embodiments laser-assisted micromanipulation or piezo injection is used. In some embodiments, a non-human mammalian embryo comprises a mouse embryo.

Another example of such conventional techniques is two step cloning which involves introducing embryonic stem (ES) and/or induced pluripotent stem (iPS) cells into a blastocyst (e.g., a tetraploid blastocyst) and maintaining the blastocyst under conditions that result in development of an embryo. The embryo is then transferred into an appropriate foster mother, such as a pseudopregnant female (e.g., of the same species as the embryo). The foster mother is then maintained under conditions that result in development of live offspring.

Another example is the use of the tetraploid complementation assay in which cells of two mammalian embryos are combined to form a new embryo (Tarn and Rossant, Develop, 750:6156-6163 (2003)). The assay involves producing a tetraploid cell in which every chromosome exists fourfold. This is done by taking an embryo at the two-cell stage and fusing the two cells by applying an electrical current. The resulting tetraploid cell continues to divide, and all daughter cells will also be tetraploid. Such a tetraploid embryo develops normally to the blastocyst stage and will implant in the wall of the uterus. In the tetraploid complementation assay, a tetraploid embryo (either at the morula or blastocyst stage) is combined with normal diploid embryonic stem cells (ES) from a different organism. The embryo develops normally; the fetus is exclusively derived from the ES cell, while the extraembryonic tissues are exclusively derived from the tetraploid cells.

Another conventional method used to produce nonhuman mammals includes pronuclear microinjection. DNA is introduced directly into the male pronucleus of a nonhuman mammal egg just after fertilization. Similar to the two-step cloning described above, the egg is implanted into a pseudopregnant female. Offspring are screened for the integrated transgene. Heterozygous offspring can be subsequently mated to generate homozygous animals.

A variety of nonhuman mammals can be used in the methods described herein. For example, the nonhuman mammal can be a rodent (e.g., mouse, rat, guinea pig, hamster), a nonhuman primate, a canine, a feline, a bovine, an equine, a porcine or a caprine.

In some aspects, various mouse strains and mouse models of human disease are used in conjunction with the methods of producing a nonhuman mammal carrying mutations or other modifications (e.g., altered methylation) in one or more target nucleic acid sequences described herein (e.g., an oncogene, MYC, TGIF1, VEGFAI, RUNX1, CDK6, BCL2L1, PIM1, CSNK1A1 or a gene listed in Table 51 promoter region CTCF binding site). One of ordinary skill in the art appreciates the thousands of commercially and non-commercially available strains of laboratory mice for modeling human disease. Mice models exist for diseases such as cancer, cardiovascular disease, autoimmune diseases and disorders, inflammatory diseases, diabetes (type 1 and 2), neurological diseases, and other diseases. Examples of commercially available research strains include, and is not limited to, 11BHSD2 Mouse, GSK3B Mouse, 129-E Mouse HSD1 1B1 Mouse, AK Mouse Immortomouse®, Athymic Nude Mouse, LCAT Mouse, B6 Albino Mouse, Lox-1 Mouse, B6C3F1 Mouse, Ly5 Mouse, B6D2F1 (BDF1) Mouse, MMP9 Mouse, BALB/c Mouse, NIH-III Nude Mouse, BALB/c Nude Mouse, NOD Mouse, NOD SCID Mouse, Black Swiss Mouse, NSE-p25 Mouse, C3H Mouse, NU/NU Nude Mouse, C57BL/6-E Mouse, PCSK9 Mouse, C57BL/6N Mouse, PGP Mouse (P-glycoprotein Deficient), CB6F1 Mouse, repTOP™ ERE-Luc Mouse, CD-I® Mouse, repTOP™ mitolRE Mouse, CD-I® Nude Mouse, repTOP™ PPRE-Luc Mouse, CD1-E Mouse, Rip-HAT Mouse, CD2F1 (CDF1) Mouse, SCID Hairless Congenic (SHC™) Mouse, CF-1™ Mouse, SCID Hairless Outbred (SHO™) Mouse, DBA/2 Mouse, SJL-E Mouse, Fox Chase CB 17™ Mouse, SKH1-E Mouse, Fox Chase SCID® Beige Mouse, Swiss Webster (CFW®) Mouse, Fox Chase SCID® Mouse, TARGATT™ Mouse, FVB Mouse, THE POUND MOUSE™, and GLUT 4 Mouse. Other mouse strains include BALB/c, C57BL/6, C57BL/10, C3H, ICR, CBA, A/J, NOD, DBA/1, DBA/2, MOLD, 129, HRS, MRL, NZB, NIH, AKR, SJL, NZW, CAST, KK, SENCAR, C57L, SAMR1, SAMP1, C57BR, and NZO.

In some aspects, the method of producing a nonhuman mammal carrying modifications in one or more genomic sequences (e.g., an oncogene, MYC, TGIF1, VEGFAI, RUNX1, CDK6, BCL2L1, PIM1, CSNK1A1 or a gene listed in Table 51 promoter region CTCF binding site) further comprises mating one or more commercially and/or non-commercially available nonhuman mammal with the nonhuman mammal carrying modifications in one or more genomic sequences (e.g., an oncogene, MYC, TGIF1, VEGFAI, RUNX1, CDK6, BCL2L1, PIM1, CSNK1A1 or a gene listed in Table 51 promoter region CTCF binding site) produced by the methods described herein. The invention is also directed to nonhuman mammals produced by the methods described herein.

As will be apparent to those of skill in the art, a variety of methods can be used to introduce nucleic acid and/or protein into a cell, zygote, embryo, and or mammal. Suitable methods include calcium phosphate or lipid-mediated transfection, electroporation, injection, and transduction or infection using a vector (e.g., a viral vector such as an adenoviral vector, lentiviral vector, or adeno-associated viral vector). In some aspects, the nucleic acid and/or protein is complexed with a vehicle, e.g., a cationic vehicle, that facilitates uptake of the nucleic acid and/or protein, e.g., via endocytosis.

The method described herein can further comprise isolating the cell or zygote produced by the methods. Thus, in some aspects, the invention is directed to a cell or zygote (an isolated cell or zygote) produced by the methods described herein. In some aspects, the disclosure provides a clonal population of cells harboring the modification(s), replicating cultures comprising cells harboring the modification(s) and cells isolated from the generated animals.

The methods described herein can further comprise crossing the generated animals with other animals harboring genetic modifications (optionally in same strain background) and/or having one or more phenotypes of interest (e.g., disease susceptibility—such as NOD mice). In addition, the methods may comprise modifying a cell, zygote, and/or animal from a strain that harbors one or more genetic modifications and/or has one or more phenotypes of interest (e.g., disease susceptibility). In some aspects, the genetic modifications are epigenetic modifications.

The methods described herein can further comprise assessing whether the one or more target nucleic acids have been modified and/or modulated using a variety of known methods.

In some embodiments methods described herein are used to produce multiple genetic modifications in a cell, zygote, embryo, or animal, wherein at least one of the genetic modifications methylates or demethylates a CTCF region binding site of a gene (e.g., an oncogene, MYC, TGIF1, VEGFAI, RUNX1, CDK6, BCL2L1, PIM1, CSNK1A1 or a gene listed in Table 51) promoter region CTCF binding site, and at least one of the genetic modifications is in a different gene or genomic location. In some embodiments, a genetic modification includes epigenetic modifications. The resulting cell, zygote, embryo, or animal, or a cell, zygote, embryo, or animal generated therefrom, is analyzed. In some embodiments at least one of the genetic modifications may be conditional (e.g., the effect of the modification, such as gene methylation or demethylation, only becomes manifest under certain conditions, which are typically under control of the artisan). In some embodiments animals are permitted to develop at least to post-natal stage, e.g., to adult stage. The appropriate conditions for the modification to produce an effect (sometimes termed "inducing conditions") are imposed, and the phenotype of the animal is subsequently analyzed. A phenotype may be compared to that of an unmodified animal or to the phenotype prior to the imposition of the inducing conditions.

Analysis may comprise any type of phenotypic analysis known in the art, e.g., examination of the structure, size, development, weight, or function, of any tissue, organ, or organ system (or the entire organism), analysis of behavior, activity of any biological pathway or process, level of any particular substance or gene product, etc. In some embodiments analysis comprises gene expression analysis, e.g., at the level of mRNA or protein. In some embodiments such analysis may comprise, e.g., use of microarrays (e.g., oligonucleotide microarrays, sometimes termed "chips"), high throughput sequencing (e.g., RNASeq), ChIP on Chip analysis, ChIPSeq analysis, etc. In some embodiments high content screening may be used, in which elements of high throughput screening may be applied to the analysis of individual cells through the use of automated microscopy and image analysis (see, e.g., Zanella et al, (2010). High content screening: seeing is believing. Trends Biotechnol. 28:237-245). In some embodiments analysis comprises quantitative analyses of components of cells such as spatiotemporal distributions of individual proteins, cytoskeletal structures, vesicles, and organelles, e.g., when contacted with test agents, e.g., chemical compounds. In some embodiments activation or inhibition of individual proteins and protein-protein interactions and/or changes in biological processes and cell functions may be assessed. A range of fluorescent probes for biological processes, functions, and cell components are available and may be used, e.g., with fluorescence microscopy. In some embodiments cells or animals generated according to methods herein may comprise a reporter, e.g., a fluorescent reporter or enzyme (e.g., a luciferase such as *Gaussia, Renilla*, or firefly luciferase) that, for example, reports on the expression or activity of particular genes. Such reporter may be fused to a protein, so that the protein or its activity is rendered detectable, optionally using a non-invasive detection means, e.g., an imaging or detection means such as PET imaging, MRI, fluorescence detection. Multiplexed genome editing according to the invention may allow installation of reporters for detection of multiple proteins, e.g., 2-20 different proteins, e.g., in a cell, tissue, organ, or animal, e.g., in a living animal.

Multiplexed genome editing or modification according to the present invention may be useful to determine or examine the biological role(s) and/or roles in disease of genes of unknown function. For example, discovery of synthetic effects caused by modifications in first and second genes (e.g., wherein one of the modifications comprises altered methylation of a CTCF region binding site of a gene) may pinpoint a genetic or biochemical pathway in which such gene(s) or encoded gene product(s) is involved.

In some embodiments it is contemplated to use, in methods described herein, cells or zygotes generated in or derived from animals produced in projects such as the International Knockout Mouse Consortium (IKMC), the website of which is http://www.knockoutmouse.org). In some embodiments it is contemplated to cross animals generated as described herein with animals generated by or available through the IKMC. For example, in some embodiments a mouse gene to be modified according to methods described herein is any gene from the Mouse Genome Informatics (MG1) database for which sequences and genome coordinates are available, e.g., any gene predicted by the NCBI, Ensembl, and Vega (Vertebrate Genome Annotation) pipelines for mouse Genome Build 37 (NCBI) or Genome Reference Consortium GRCm38.

In some embodiments, a gene or genomic location to the modified is included in a genome of a species for which a fully sequenced genome exists. Genome sequences may be obtained, e.g., from the UCSC Genome Browser (http://genome.ucsc.edu/index.html). For example, in some embodiments a human gene or sequence to be modified according to methods described herein may be found in Human Genome Build hg19 (Genome Reference Consortium). In some embodiments a gene is any gene for which a Gene ID has been assigned in the Gene Database of the NCBI (http://www.ncbi.nlm.nih.gov/gene). In some embodiments a gene is any gene for which a genomic, cDNA, mRNA, or encoded gene product (e.g., protein) sequence is available in a. database such as any of those available at the National Center for Biotechnology Information (www.ncbi.nih.gov) or Universal Protein Resource (www.uniprot.org). Databases include, e.g., GenBank, RefSeq, Gene, Uni.ProtKR/SwissProt, UniProtKB/Trembl, and the like.

In some embodiments animals generated according to methods described herein may be useful in the identification of candidate agents for treatment of disease and/or for testing agents for potential toxicity or side effects. In some embodiments any method described herein may comprise contacting an animal generated according to methods described herein, e.g., any genetically modified animal generated as described herein, with a test agent (e.g., a small molecule, nucleic acid, polypeptide, lipid, etc.). In some embodiments contacting comprises administering the test agent. Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. In some embodiments a method may further comprise analyzing the animal. Such analysis may, for example assess the effect of the test agent in an animal having a genetic modification(s) introduced according to the methods. In some embodiments a test agent that reduces or enhances an effect of one or more genetic modification(s) may be identified. In some embodiments if a test agent reduces or inhibits development of a disease associated with or produced by the genetic modification(s), (or reduces or inhibits one or more symptoms or signs of such a disease) the test agent may be identified as a candidate agent for treatment of a disease associated with or produced by the genetic modification(s) or associated with or produced by naturally occurring mutations in a gene or genomic location harboring the genetic modification.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than abou t 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments a small molecule is an artificial (non-naturally occurring) molecule. In some embodiments, a small molecule is non-polymeric. In some embodiments, a small molecule is not an amino acid. In some embodiments, a small molecule is not a nucleotide. In some embodiments, a small molecule is not a saccharide. In some embodiments, the term "small molecule" excludes molecules that are ingredients found in standard tissue culture medium.

In some embodiments a cell may be a diseased cell or may originate from a subject suffering from a disease, e.g., a disease affecting the cell or organ from which the cell was obtained. In some embodiments a mutation is introduced into a genomic region of the cell that is associated with a disease (e.g., any disease of interest, such as diseases mentioned herein). For example, in some embodiments it is of interest to methylate or demethylate a gene or genomic location (e.g., a Promoter region CTCF binding site of a gene, a MYC Promoter CTCF binding site) that is known or suspected to be involved in disease pathogenesis and/or known or suspected to be associated with increased or decreased risk of developing a disease or particular manifestation(s) of a disease. In some embodiments it is of interest to methylate or demethylate a gene or genomic location (e.g., a Promoter region CTCF binding site of a gene, a MYC Promoter CTCF binding site) and determine whether such modification alters the risk of developing a disease or one or more manifestations of a disease, alters progression of the disease, or alters the response of a subject to therapy or candidate therapy for a disease. In some embodiments it is of interest to modify an abnormal or disease-associated nucleotide or sequence (e.g., a Promoter region CTCF binding site of a gene, a MYC Promoter CTCF binding site) to one that is normal or not associated with disease. In some embodiments this may allow production of genetically matched cells or cell lines (e.g., iPS cells or cell lines) that differ only at one or more selected sites of genetic modification (e.g., a Promoter region CTCF binding site of a gene, a MYC Promoter CTCF binding site). Multiplexed genome editing as described herein may allow for production of cells or cell lines that are isogenic except with regard to, e.g., between 2 and 20 selected sites of genetic alterations (e.g., within a Promoter region CTCF binding site of a gene, within a MYC Promoter CTCF binding site). This may allow for the study of the combined effect of multiple modifications that are suspected of or known to play a role in disease risk, development or progression.

Also disclosed herein are methods of modulating the expression of a gene with a promoter region CTCF binding site (e.g., an oncogene, MYC, TGIF1, VEGFAI, RUNX1, CDK6, BCL2L1, PIM1, CSNK1A1 or a gene listed in Table 51) in a subject in need thereof comprising introducing into the subject a catalytically inactive site specific nuclease fused to an effector domain having methylation or demethylation activity; and one or more guide sequences homologous or complementary to at least a portion of the promoter region CTCF binding site, thereby modulating the expression of the gene in cells of the subject. In some embodiments, the effector domain has methylation activity and the expression of a gene with a promoter region CTCF binding site is decreased. In some embodiments, the effector domain has methylation activity and the expression of a gene with a promoter region CTCF binding site is increased. In some embodiments, the effector domain has demethylation activity and the expression of a gene with a promoter region CTCF binding site is increased. In some embodiments, the effector domain has methylation activity and the expression of a gene with a promoter region CTCF binding site is decreased. In some embodiments, the effector domain has demethylation activity and the expression of a gene with a promoter region CTCF binding site is decreased. In some embodiments, the effector domain has methylation activity and MYC expression is decreased. In some embodiments, the effector domain has demethylation activity and MYC expression is increased.

In some embodiments, the catalytically inactive site specific nuclease is a catalytically inactive Cas protein as described herein. In some embodiments, the catalytically inactive site specific nuclease is a catalytically inactive Cas9 protein as described herein. In some embodiments, the catalytically inactive site specific nuclease is a catalytically inactive Cpf1 protein as described herein. In some embodiments, the effector domain having methylation activity is DNMT3A-3L as described herein.

In some embodiments, the catalytically inactive site specific nuclease fused to an effector domain having methylation activity is dCas9-DNMT3A-3L or dCas9-DNMT3A-3L without a 5' NLS as described herein.

In some embodiments, the guide sequences are ribonucleic acid guide sequences as described herein. In some embodiments, the guide sequence is from about 10 base pairs to about 150 base pairs in length. In some embodiments, the one or more guide sequences comprise two or more guide sequences.

In some embodiments, the one or more guide sequences comprise a sequence encoded by a nucleic acid sequence selected from the group consisting of SEQ ID NOS. 1-8.

In some aspects, expression of a gene having a promoter region CTCF binding site is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, expression of a gene having a promoter region CTCF binding site is increased by about 10%, 15%, 20%, 25%, 30%, 35%, 40%, 45%, 50%, 55%, 60%, 65%, 70%, 75%, 80%, 85%, 90%, 100%, 150%, 200% or more. In some aspects, MYC expression is decreased by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, MYC expression is increased by about 10%, 15%, 20%, 25%, 30%, 35%, 40%, 45%, 50%, 55%, 60%, 65%, 70%, 75%, 80%, 85%, 90%, 100%, 150%, 200% or more.

In some aspects, the effector domain comprises DNMT3A-3L. In some aspects, the catalytically inactive site specific nuclease is a catalytically inactive Cas (e.g., Cas9). In some aspects, the catalytically inactive site specific nuclease fused to an effector domain having methylation activity is dCas9-DNMT3A-3L or dCas9-DNMT3A-3L without a 5' NLS.

Some aspects of the disclosure are related to methods of treating a subject in need thereof, comprising administering to the subject a composition that enhances, suppresses, reduces or eliminates the binding of CTCF to a promoter region CTCF binding site of a gene (e.g., an oncogene, MYC, TGIF1, VEGFAI, RUNX1, CDK6, BCL2L1, PIM1, CSNK1A1 or a gene listed in Table 51). Also disclosed herein are methods of treating a disease or condition involving aberrant MYC expression in a subject, comprising administering to the subject a composition that modulates the binding of CTCF to a MYC promoter CTCF binding site. In some aspects, aberrant MYC expression is over-expression. In some aspects, aberrant MYC expression is under-expression. In some aspects, the subject has cancer.

In some aspects, the composition is a composition described herein. In some aspects, the composition comprises a nucleic acid sequence, protein, organic molecule, inorganic molecule, or small molecule. In some aspects, the composition reduces binding of CTCF to a promoter region CTCF binding site of a gene (e.g., an oncogene, MYC, TGIF1, VEGFAI, RUNX1, CDK6, BCL2L1, PIM1, CSNK1A1 or a gene listed in Table 51) by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In some aspects, composition increases binding of CTCF to a promoter region CTCF binding site of a gene (e.g., an oncogene, MYC, TGIF1, VEGFAI, RUNX1, CDK6, BCL2L1, PIM1, CSNK1A1 or a gene listed in Table 51) by about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 500%, 600% or more. In some aspects the subject is human. The disease or condition involving aberrant gene (e.g., an oncogene, MYC, TGIF1, VEGFAI, RUNX1, CDK6, BCL2L1, PIM1, CSNK1A1 or a gene listed in Table 51) expression in a subject is any disease or condition described herein. In some aspects the disease or condition is cancer as described herein. In some aspects, the cancer is colorectal cancer, leukemia or breast cancer.

Also disclosed herein are methods of screening for a compound that modulates expression of a gene having a promoter region CTCF binding site (e.g., an oncogene, MYC, TGIF1, VEGFAI, RUNX1, CDK6, BCL2L1, PIM1, CSNK1A1 or a gene listed in Table 51) comprising, contacting a cell with a test agent; and measuring methylation in the promoter region CTCF binding site, wherein the test agent is identified as a compound that modulates expression of the gene if the level of methylation of the promoter region CTCF binding site in the cell contacted with the test agent differs from the level of methylation of said promoter region CTCF binding site in a control cell not contacted with the test agent. In some aspects, the test agent is identified as an anti-cancer compound if the level of methylation of the promoter region CTCF binding site in the cell contacted with the test agent is higher than the level of methylation of said promoter region CTCF binding site in a control cell not contacted with the test agent.

Also disclosed herein are methods of screening for a compound that modulates MYC expression comprising, contacting a cell with a test agent; and measuring methylation in a MYC promoter CTCF binding site, wherein the test agent is identified as a compound that modulates MYC expression if the level of methylation of the MYC promoter CTCF binding site in the cell contacted with the test agent differs from the level of methylation of said MYC promoter CTCF binding site in a control cell not contacted with the test agent. In some aspects, the test agent is identified as an anti-cancer compound if the level of methylation of the MYC promoter CTCF binding site in the cell contacted with the test agent is higher than the level of methylation of said MYC promoter CTCF binding site in a control cell not contacted with the test agent.

Methods of measuring methylation are known in the art and are not limited. In some embodiments the cells used in the method comprise cancer cells.

Also disclosed herein are methods of screening for a compound that modulates expression of a gene having a promoter region CTCF binding site (e.g., an oncogene, MYC, TGIF1, VEGFAI, RUNX1, CDK6, BCL2L1, PIM1, CSNK1A1 or a gene listed in Table 51) comprising contacting a cell with a test agent; and measuring binding between CTCF protein and CTCF binding site(s) within the promoter region, wherein the test agent is identified as a compound that modulates expression of the gene if the level of binding between CTCF protein and CTCF binding site(s)

within the promoter region in the cell contacted with the test agent differs from the level of binding in a control cell not contacted with the test agent.

Also disclosed herein are methods of screening for a compound that modulates MYC expression comprising contacting a cell with a test agent; and measuring binding between CTCF protein and CTCF binding site(s) within the MYC promoter, wherein the test agent is identified as a compound that modulates MYC expression if the level of binding between CTCF protein and CTCF binding site(s) within the MYC promoter in the cell contacted with the test agent differs from the level of binding in a control cell not contacted with the test agent.

Also disclosed herein are methods of screening for a compound that modulates MYC expression comprising, contacting a cell with a test agent; and measuring binding of CTCF to the MYC promoter CTCF binding site, wherein the test agent is identified as a compound that modulates MYC expression if the level of binding of CTCF to the MYC promoter CTCF binding site in the cell contacted with the test agent differs from the level of binding of CTCF to the MYC promoter CTCF binding site in a control cell not contacted with the test agent. In some aspects, the test agent is identified as an anti-cancer compound if the level of binding of CTCF to the MYC promoter CTCF binding site in the cell contacted with the test agent is lower than the level of binding of CTCF to the MYC promoter CTCF binding site in a control cell not contacted with the test agent. Methods of measuring binding of CTCF to a DNA site of interest are known in the art and are not limited. For example, one could use ChIP-Seq. In some embodiments the cells used in the method comprise cancer cells.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated."

Specific examples of these methods are set forth below in the Examples.

EXAMPLES

Proper regulation of gene expression is dependent on specific interactions between enhancers and promoters, but the mechanisms responsible for this specificity are not well-understood. We have identified a class of human genes that utilize CTCF-CTCF interactions to connect different cell-type specific enhancers with a single promoter-proximal element that functions as a docking site for those enhancers. At these genes, the enhancers are often bound by CTCF in a cell-type specific fashion whereas the promoter-proximal enhancer-docking sites are constitutively bound by CTCF. The proto-oncogene MYC, which is controlled by different cell-type specific enhancers during development, is a prominent example of a gene regulated in this fashion. We find that many human cancer cells acquire super-enhancers at the MYC locus and exploit this CTCF-mediated enhancer-docking mechanism to express MYC at oncogenic levels. Genetic and epigenetic perturbation of the MYC enhancer-docking site in tumor cells reduces CTCF binding, super-enhancer interaction, MYC gene expression and cell proliferation. Additional genes with roles in cancer employ a CTCF-bound enhancer-docking site to engender interactions with tumor specific CTCF-bound enhancers. Thus, a CTCF-dependent enhancer-docking mechanism, which facilitates interaction with cell-specific enhancers during development, is exploited by cancer cells to dysregulate expression of prominent oncogenes. Oncogene enhancer-docking sites can be repressed by dCas9-DNMT-mediated DNA methylation and may thus represent a common vulnerability in multiple human cancers.

CTCF does not generally occupy enhancer and promoter elements (Cuddapah et al., 2009; Dixon et al., 2012; Handoko et al., 2011; Ji et al., 2016; Kim et al., 2007; Parelho et al., 2008; Phillips-Cremins et al., 2013; Rao et al., 2014; Rubio et al., 2008; Tang et al., 2015; Wendt et al., 2008), but where CTCF does bind these elements, it may engender enhancer-promoter interactions (Guo et al., 2015; Lee et al., 2017; Splinter et al., 2006; de Wit et al., 2015). This consideration led us to further investigate the class of human genes that contain CTCF-bound sites at promoters to learn whether these are utilized to facilitate contacts with enhancers via CTCF-CTCF interactions. We report here that ~2000 human genes have highly conserved promoter-proximal sites that are bound by CTCF regardless of the cell type examined and that these sites can form contacts with diverse cell-type specific enhancers. These genes appear to have evolved CTCF enhancer-docking sites in order to facilitate contacts with the diverse CTCF-bound enhancers formed by cell-type specific transcription factors during development, and thus experience activation in a broad range of cell types. Interestingly, this set of genes with CTCF-bound enhancer-docking sites includes many important cancer-associated genes, and the enhancer-docking site of one of these, MYC, was studied in detail. Genetic and epigenetic perturbation of the MYC enhancer-docking site reduces CTCF binding, super-enhancer interaction, MYC gene expression and tumor cell proliferation. These observations reveal a mechanism for enhancer-promoter interaction that is employed during development to allow genes to have cell-specific contacts with diverse enhancers and is exploited by cancer cells to facilitate oncogenic expression of genes driven by diverse super-enhancers.

Example 1—Promoter-Proximal CTCF-Bound Sites are Putative Enhancer-Docking Sites To gain insights into the interactions between genes and their regulatory elements that may be mediated by CTCF, we focused our study on genes that have CTCF-bound sites at their promoters and are expressed in multiple cell types through the activity of different cell-specific enhancers (FIG. 1A). Because genes and their regulatory elements generally interact within the context of large CTCF-mediated DNA loops (insulated neighborhoods) that encompass them and facilitate accurate assessment of enhancer-promoter interactions (Ji et al., 2016; Hnisz et al., 2016a), we selected for further analysis the 2148 genes that have promoter-proximal CTCF-bound sites and occur within constitutive insulated neighborhoods (CTCF-CTCF loops shared by all at least two out of three cells examined). These genes shared two prominent features. They tend to be expressed in multiple cell types, apparently through the action of different cell-specific enhancers (1725/2148 have evidence for cell-type specific enhancers within their neighborhoods and, where DNA interaction data is available, there is evidence for cell-type specific interactions between those enhancers and the promoter-proximal CTCF-bound sites). As a class, they include many genes with cancer-associated functions, including proto-oncogenes and genes involved in growth control (FIG. 1A, Table 51). Prominent among these was the MYC oncogene, which because of its role in a broad spectrum of cancer cells, we chose for further study of promoter-proximal CTCF sites that may play a role in enhancer-promoter looping.

TABLE S1

Constitutive CTCF peaks within a constitutive IN across HCT116, Jurkat, K562 within 2.5 kb of TSS

| chr | start | stop | gene | loops to differential enhancers |
|---|---|---|---|---|
| chr9 | 116161118 | 116166118 | NM_000031 | yes |
| chr19 | 45406506 | 45411506 | NM_000041 | yes |
| chr11 | 108091059 | 108096059 | NM_000051 | yes |
| chr1 | 57429313 | 57434313 | NM_000066 | yes |
| chr1 | 201079194 | 201084194 | NM_000069 | yes |
| chr11 | 2904495 | 2909495 | NM_000076 | yes |
| chr10 | 104594790 | 104599790 | NM_000102 | yes |
| chr5 | 149337800 | 149342800 | NM_000112 | yes |
| chr19 | 11492518 | 11497518 | NM_000121 | yes |
| chr1 | 169553269 | 169558269 | NM_000130 | yes |
| chr1 | 24192359 | 24197359 | NM_000147 | yes |
| chr17 | 73758780 | 73763780 | NM_000154 | yes |
| chr3 | 50226543 | 50231543 | NM_000172 | yes |
| chr5 | 142780754 | 142785754 | NM_000176 | yes |
| chr20 | 33541120 | 33546120 | NM_000178 | yes |
| chr19 | 10379017 | 10384017 | NM_000201 | yes |
| chr21 | 35882073 | 35887073 | NM_000219 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr2 | 27307111 | 27312111 | NM_000221 | yes |
| chr16 | 67975515 | 67980515 | NM_000229 | yes |
| chr11 | 47371753 | 47376753 | NM_000256 | yes |
| chr1 | 171619273 | 171624273 | NM_000261 | yes |
| chr17 | 49228420 | 49233420 | NM_000269 | yes |
| chr18 | 21164081 | 21169081 | NM_000271 | yes |
| chr10 | 102502968 | 102507968 | NM_000278 | yes |
| chr1 | 161133681 | 161138681 | NM_000309 | yes |
| chr11 | 62377713 | 62382713 | NM_000327 | yes |
| chr6 | 16759221 | 16764221 | NM_000332 | yes |
| chr1 | 201344328 | 201349328 | NM_000364 | yes |
| chr1 | 45475305 | 45480305 | NM_000374 | yes |
| chr6 | 36643956 | 36648956 | NM_000389 | yes |
| chr17 | 40702076 | 40707076 | NM_000413 | yes |
| chr7 | 142657003 | 142662003 | NM_000420 | yes |
| chr1 | 26322148 | 26327148 | NM_000437 | yes |
| chr19 | 17980282 | 17985282 | NM_000453 | yes |
| chr12 | 56388543 | 56393543 | NM_000456 | yes |
| chr1 | 173884016 | 173889016 | NM_000488 | yes |
| chr5 | 37837282 | 37842282 | NM_000514 | yes |
| chr17 | 61993712 | 61998712 | NM_000515 | yes |
| chr11 | 17407706 | 17412706 | NM_000525 | yes |
| chr3 | 135966667 | 135971667 | NM_000532 | yes |
| chr17 | 7588368 | 7593368 | NM_000546 | yes |
| chr20 | 34023470 | 34028470 | NM_000557 | yes |
| chr1 | 154375169 | 154380169 | NM_000565 | yes |
| chr1 | 207492317 | 207497317 | NM_000574 | yes |
| chr5 | 131393847 | 131398847 | NM_000588 | yes |
| chr5 | 140010535 | 140015535 | NM_000591 | yes |
| chr7 | 22764261 | 22769261 | NM_000600 | yes |
| chr7 | 150685644 | 150690644 | NM_000603 | yes |
| chr11 | 6459754 | 6464754 | NM_000613 | yes |
| chr1 | 169678343 | 169683343 | NM_000655 | yes |
| chr7 | 100491092 | 100496092 | NM_000665 | yes |
| chr3 | 52014800 | 52019800 | NM_000666 | yes |
| chr15 | 78911137 | 78916137 | NM_000743 | yes |
| chr15 | 78931087 | 78936087 | NM_000750 | yes |
| chr8 | 67088380 | 67093380 | NM_000756 | yes |
| chr17 | 38169114 | 38174114 | NM_000759 | yes |
| chr7 | 91761340 | 91766340 | NM_000786 | yes |
| chr17 | 61551922 | 61556922 | NM_000789 | yes |
| chr2 | 171670700 | 171675700 | NM_000817 | yes |
| chr17 | 72853507 | 72858507 | NM_000835 | yes |
| chr6 | 2997550 | 3002550 | NM_000904 | yes |
| chr1 | 153648664 | 153653664 | NM_000906 | yes |
| chr12 | 120763092 | 120768092 | NM_000928 | yes |
| chr11 | 64016495 | 64021495 | NM_000932 | yes |
| chr2 | 68477151 | 68482151 | NM_000945 | yes |
| chr6 | 57179915 | 57184915 | NM_000947 | yes |
| chr19 | 14583674 | 14588674 | NM_000955 | yes |
| chr1 | 93295094 | 93300094 | NM_000969 | yes |
| chr1 | 24015769 | 24020769 | NM_000975 | yes |
| chr19 | 17968187 | 17973187 | NM_000980 | yes |
| chr19 | 11543578 | 11548578 | NM_001001329 | yes |
| chr5 | 156770229 | 156775229 | NM_001001343 | yes |
| chr17 | 40167094 | 40172094 | NM_001001349 | yes |
| chr22 | 31029302 | 31034302 | NM_001001479 | yes |
| chr11 | 19136192 | 19141192 | NM_001001483 | yes |
| chr12 | 109528793 | 109533793 | NM_001001655 | yes |
| chr21 | 36258487 | 36263487 | NM_001001890 | yes |
| chr19 | 1239249 | 1244249 | NM_001001975 | yes |
| chr12 | 54068012 | 54073012 | NM_001002031 | yes |
| chr2 | 64748939 | 64753939 | NM_001002243 | yes |
| chr5 | 115174803 | 115179803 | NM_001002924 | yes |
| chr1 | 29447921 | 29452921 | NM_001003682 | yes |
| chr22 | 30819111 | 30824111 | NM_001003704 | yes |
| chr3 | 51973821 | 51978821 | NM_001003931 | yes |
| chr9 | 113097664 | 113102664 | NM_001003936 | yes |
| chr15 | 40395787 | 40400787 | NM_001003942 | yes |
| chr1 | 206806381 | 206811381 | NM_001004023 | yes |
| chr1 | 57282869 | 57287869 | NM_001004303 | yes |
| chr7 | 100059394 | 100064394 | NM_001004323 | yes |
| chr1 | 113260689 | 113265689 | NM_001004440 | yes |
| chr2 | 220406228 | 220411228 | NM_001005209 | yes |
| chr1 | 204795282 | 204800282 | NM_001005388 | yes |
| chr1 | 149821681 | 149826681 | NM_001005464 | yes |
| chr1 | 149810265 | 149815265 | NM_001005464_2 | yes |
| chr2 | 159310892 | 159315892 | NM_001005476 | yes |
| chr1 | 119908899 | 119913899 | NM_001005783 | yes |
| chr1 | 154295536 | 154300536 | NM_001005855 | yes |
| chr12 | 56471392 | 56476392 | NM_001005915 | yes |
| chr1 | 93424579 | 93429579 | NM_001006605 | yes |
| chr17 | 72730856 | 72735856 | NM_001006638 | yes |
| chr1 | 207625145 | 207630145 | NM_001006658 | yes |
| chr3 | 183964813 | 183969813 | NM_001006941 | yes |
| chr11 | 64124125 | 64129125 | NM_001006944 | yes |
| chr11 | 2168333 | 2173333 | NM_001007139 | yes |
| chr1 | 174966071 | 174971071 | NM_001007214 | yes |
| chr1 | 161065681 | 161070681 | NM_001007255 | yes |
| chr1 | 115298171 | 115303171 | NM_001007553 | yes |
| chr12 | 49728471 | 49733471 | NM_001008223 | yes |
| chr7 | 135192375 | 135197375 | NM_001008225 | yes |
| chr18 | 43751488 | 43756488 | NM_001008239 | yes |
| chr6 | 34214385 | 34219385 | NM_001008703 | yes |
| chr20 | 5091233 | 5096233 | NM_001009923 | yes |
| chr1 | 109100471 | 109105471 | NM_001010883 | yes |
| chr1 | 110690636 | 110695636 | NM_001010898 | yes |
| chr3 | 195619932 | 195624932 | NM_001010938 | yes |
| chr20 | 49408931 | 49413931 | NM_001010974 | yes |
| chr8 | 71579100 | 71584100 | NM_001011720 | yes |
| chr1 | 156828171 | 156833171 | NM_001012331 | yes |
| chr9 | 35826244 | 35831244 | NM_001012446 | yes |
| chr19 | 56162916 | 56167916 | NM_001012478 | yes |
| chr10 | 27147516 | 27152516 | NM_001012750 | yes |
| chr19 | 12073369 | 12078369 | NM_001012753 | yes |
| chr1 | 145586935 | 145591935 | NM_001012758 | yes |
| chr16 | 67698217 | 67703217 | NM_001012984 | yes |
| chr2 | 25013751 | 25018751 | NM_001013663 | yes |
| chr12 | 31942675 | 31947675 | NM_001013699 | yes |
| chr16 | 67676530 | 67681530 | NM_001013838 | yes |
| chr5 | 43037947 | 43042947 | NM_001014279 | yes |
| chr2 | 71556385 | 71561385 | NM_001014972 | yes |
| chr17 | 4689754 | 4694754 | NM_001014985 | yes |
| chr17 | 73519283 | 73524283 | NM_001015002 | yes |
| chrX | 106957211 | 106962211 | NM_001015881 | yes |
| chr1 | 202160618 | 202165618 | NM_001017403 | yes |
| chr6 | 117921205 | 117926205 | NM_001017408 | yes |
| chr1 | 249197942 | 249202942 | NM_001017434 | yes |
| chr17 | 61521045 | 61526045 | NM_001017916 | yes |
| chr22 | 21981894 | 21986840 | NM_001017964 | yes |
| chr1 | 91867926 | 91872926 | NM_001017975 | yes |
| chr22 | 30780802 | 30785802 | NM_001017981 | yes |
| chr1 | 155160206 | 155165206 | NM_001018016 | yes |
| chr22 | 21316918 | 21321918 | NM_001018060 | yes |
| chr5 | 142781545 | 142786545 | NM_001018076 | yes |
| chr9 | 130562960 | 130567960 | NM_001018078 | yes |
| chr17 | 49228397 | 49233397 | NM_001018136 | yes |
| chr17 | 49240296 | 49245296 | NM_001018137 | yes |
| chr17 | 49241583 | 49246583 | NM_001018138 | yes |
| chr17 | 49241362 | 49246362 | NM_001018139 | yes |
| chr1 | 154242539 | 154247539 | NM_001018837 | yes |
| chr3 | 183733248 | 183738248 | NM_001023587 | yes |
| chr1 | 153597617 | 153602617 | NM_001024211 | yes |
| chr1 | 153597244 | 153602244 | NM_001024212 | yes |
| chr1 | 153597024 | 153602024 | NM_001024213 | yes |
| chr5 | 148928615 | 148933615 | NM_001025105 | yes |
| chr21 | 44525188 | 44530188 | NM_001025203 | yes |
| chr6 | 43735446 | 43740446 | NM_001025366 | yes |
| chr1 | 161037260 | 161042260 | NM_001025598 | yes |
| chr19 | 18109441 | 18114441 | NM_001025604 | yes |
| chr12 | 56433186 | 56438186 | NM_001029 | yes |
| chr8 | 101155599 | 101160599 | NM_001029860 | yes |
| chr1 | 27927505 | 27932505 | NM_001029882 | yes |
| chr5 | 176825137 | 176830137 | NM_001029886 | yes |
| chr12 | 51661702 | 51666702 | NM_001031628 | yes |
| chr5 | 176728245 | 176733245 | NM_001031677 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr3 | 47552699 | 47557699 | NM_001031703 | yes |
| chr19 | 30203463 | 30208463 | NM_001031726 | yes |
| chr1 | 168145583 | 168150583 | NM_001031800 | yes |
| chr8 | 103663692 | 103668692 | NM_001032282 | yes |
| chr12 | 98906851 | 98911851 | NM_001032283 | yes |
| chr20 | 48727235 | 48732235 | NM_001032288 | yes |
| chr1 | 40365187 | 40370187 | NM_001033081 | yes |
| chr17 | 27276008 | 27281008 | NM_001033561 | yes |
| chr12 | 121075922 | 121080922 | NM_001033677 | yes |
| chr12 | 51661494 | 51666494 | NM_001033873 | yes |
| chr12 | 56507874 | 56512874 | NM_001035267 | yes |
| chr12 | 120905160 | 120910160 | NM_001037494 | yes |
| chr22 | 30683116 | 30688116 | NM_001037666 | yes |
| chr1 | 151029625 | 151034625 | NM_001038707 | yes |
| chr7 | 37022217 | 37027217 | NM_001039459 | yes |
| chr11 | 63603900 | 63608900 | NM_001039469 | yes |
| chr11 | 64065363 | 64070363 | NM_001039496 | yes |
| chr1 | 155291438 | 155296438 | NM_001039517 | yes |
| chr1 | 110750836 | 110755836 | NM_001039574 | yes |
| chr14 | 23396294 | 23401294 | NM_001039619 | yes |
| chr15 | 91470910 | 91475910 | NM_001039675 | yes |
| chr14 | 24896231 | 24901231 | NM_001039771 | yes |
| chr15 | 90317089 | 90322089 | NM_001039958 | yes |
| chr7 | 1123943 | 1128943 | NM_001039966 | yes |
| chr17 | 7530912 | 7535912 | NM_001040 | yes |
| chr5 | 140010786 | 140015786 | NM_001040021 | yes |
| chr12 | 32906387 | 32911387 | NM_001040436 | yes |
| chr5 | 159623548 | 159628548 | NM_001040442 | yes |
| chr8 | 80677598 | 80682598 | NM_001040708 | yes |
| chr17 | 7182554 | 7187554 | NM_001042 | yes |
| chr19 | 7743207 | 7748207 | NM_001042461 | yes |
| chrX | 14045535 | 14050535 | NM_001042479 | yes |
| chr16 | 29815358 | 29820358 | NM_001042539 | yes |
| chr3 | 196666964 | 196671964 | NM_001042540 | yes |
| chr9 | 35826722 | 35831722 | NM_001042589 | yes |
| chr1 | 113247525 | 113252525 | NM_001042678 | yes |
| chr1 | 113247178 | 113252178 | NM_001042679 | yes |
| chr4 | 110352371 | 110357371 | NM_001042734 | yes |
| chr9 | 127613196 | 127618196 | NM_001045476 | yes |
| chr1 | 28842245 | 28847245 | NM_001048194 | yes |
| chr19 | 4906942 | 4911942 | NM_001048201 | yes |
| chr17 | 38571702 | 38576702 | NM_001067 | yes |
| chr6 | 3155283 | 3160283 | NM_001069 | yes |
| chr20 | 33461828 | 33466828 | NM_001076552 | yes |
| chr17 | 26217909 | 26222909 | NM_001076680 | yes |
| chr17 | 42295750 | 42300750 | NM_001076683 | yes |
| chr17 | 42294541 | 42299541 | NM_001076684 | yes |
| chr16 | 68295919 | 68300919 | NM_001076785 | yes |
| chr9 | 99326703 | 99331703 | NM_001077181 | yes |
| chr2 | 178970566 | 178975566 | NM_001077197 | yes |
| chr11 | 65147645 | 65152645 | NM_001077241 | yes |
| chr10 | 104151835 | 104156835 | NM_001077494 | yes |
| chr7 | 73079674 | 73084674 | NM_001077621 | yes |
| chr6 | 44188741 | 44193741 | NM_001078175 | yes |
| chr6 | 44188863 | 44193863 | NM_001078177 | yes |
| chr11 | 67234248 | 67239248 | NM_001078650 | yes |
| chr5 | 140996122 | 141001122 | NM_001079812 | yes |
| chr2 | 202095666 | 202100666 | NM_001080124 | yes |
| chr17 | 73778420 | 73783420 | NM_001080419 | yes |
| chr19 | 6735133 | 6740133 | NM_001080452 | yes |
| chr2 | 176946190 | 176951190 | NM_001080458 | yes |
| chr17 | 72355458 | 72360458 | NM_001080466 | yes |
| chr1 | 156861023 | 156866023 | NM_001080471 | yes |
| chr20 | 42937392 | 42942392 | NM_001080472 | yes |
| chr7 | 134231349 | 134236349 | NM_001080538 | yes |
| chr9 | 139255763 | 139260763 | NM_001080849 | yes |
| chr12 | 120701074 | 120706074 | NM_001080855 | yes |
| chr19 | 12938730 | 12943730 | NM_001080997 | yes |
| chr19 | 46281361 | 46286361 | NM_001081563 | yes |
| chr17 | 63130956 | 63135956 | NM_001081955 | yes |
| chr20 | 62336294 | 62341294 | NM_001083113 | yes |
| chr9 | 130495128 | 130500128 | NM_001085347 | yes |
| chr17 | 27914110 | 27919110 | NM_001085454 | yes |
| chr16 | 2388247 | 2393247 | NM_001089 | yes |
| chr10 | 81368195 | 81373195 | NM_001093770 | yes |
| chr12 | 50448920 | 50453920 | NM_001095 | yes |
| chr7 | 1125223 | 1130223 | NM_001098201 | yes |
| chr17 | 1957104 | 1962104 | NM_001098202 | yes |
| chr10 | 43902196 | 43907196 | NM_001098204 | yes |
| chr10 | 43901832 | 43906832 | NM_001098205 | yes |
| chr10 | 43900799 | 43905799 | NM_001098206 | yes |
| chr12 | 48150389 | 48155389 | NM_001098531 | yes |
| chr12 | 48149681 | 48154681 | NM_001098532 | yes |
| chr12 | 50133092 | 50138092 | NM_001098576 | yes |
| chr11 | 10671348 | 10676348 | NM_001098579 | yes |
| chr12 | 53843386 | 53848386 | NM_001098620 | yes |
| chr10 | 81317717 | 81322717 | NM_001098668 | yes |
| chr12 | 52461258 | 52466258 | NM_001098673 | yes |
| chr11 | 65337320 | 65342320 | NM_001098784 | yes |
| chr14 | 24709380 | 24714380 | NM_001099274 | yes |
| chr8 | 145200419 | 145205419 | NM_001099280 | yes |
| chr2 | 232570735 | 232575735 | NM_001099285 | yes |
| chr12 | 56658567 | 56663567 | NM_001099337 | yes |
| chr11 | 65341009 | 65346009 | NM_001099409 | yes |
| chr15 | 75133052 | 75138052 | NM_001099436 | yes |
| chr8 | 86130151 | 86135151 | NM_001099670 | yes |
| chr20 | 43989240 | 43994240 | NM_001099791 | yes |
| chr19 | 12883934 | 12888934 | NM_001100176 | yes |
| chr4 | 39977076 | 39982076 | NM_001100399 | yes |
| chr7 | 5567732 | 5572732 | NM_001101 | yes |
| chr2 | 101765409 | 101770409 | NM_001102426 | yes |
| chr14 | 21570363 | 21575363 | NM_001102454 | yes |
| chr1 | 155288140 | 155293140 | NM_001105203 | yes |
| chr1 | 155291228 | 155296228 | NM_001105205 | yes |
| chr16 | 31467817 | 31472817 | NM_001105247 | yes |
| chr1 | 10090541 | 10095541 | NM_001105562 | yes |
| chr10 | 124893067 | 124898067 | NM_001105574 | yes |
| chr1 | 156548657 | 156553657 | NM_001105669 | yes |
| chr16 | 30032155 | 30037155 | NM_001109659 | yes |
| chr8 | 146124346 | 146129346 | NM_001109689 | yes |
| chr22 | 42333723 | 42338723 | NM_001110215 | yes |
| chr1 | 55269236 | 55274236 | NM_001110533 | yes |
| chr2 | 158482899 | 158487899 | NM_001111032 | yes |
| chr4 | 39697164 | 39702164 | NM_001111112 | yes |
| chr1 | 161006274 | 161011274 | NM_001113205 | yes |
| chr1 | 163039195 | 163044195 | NM_001113380 | yes |
| chr1 | 163036544 | 163041544 | NM_001113381 | yes |
| chr1 | 201977190 | 201982190 | NM_001114309 | yes |
| chr6 | 126109409 | 126114409 | NM_001122842 | yes |
| chr16 | 31117115 | 31122115 | NM_001122957 | yes |
| chr1 | 109653979 | 109658979 | NM_001122961 | yes |
| chr9 | 127949718 | 127954718 | NM_001123355 | yes |
| chr1 | 71510991 | 71515991 | NM_001126044 | yes |
| chr19 | 35998891 | 36003891 | NM_001126059 | yes |
| chr14 | 23282607 | 23287607 | NM_001126105 | yes |
| chr14 | 23286520 | 23291520 | NM_001126106 | yes |
| chr17 | 7576311 | 7581311 | NM_001126115 | yes |
| chr18 | 710162 | 715162 | NM_001126123 | yes |
| chr1 | 92946856 | 92951856 | NM_001127215 | yes |
| chr1 | 92949128 | 92954128 | NM_001127216 | yes |
| chr19 | 47733523 | 47738523 | NM_001127240 | yes |
| chr14 | 50997300 | 51002300 | NM_001127713 | yes |
| chr16 | 89677216 | 89682216 | NM_001128141 | yes |
| chr1 | 95697211 | 95702211 | NM_001128142 | yes |
| chr18 | 43301592 | 43306592 | NM_001128588 | yes |
| chr15 | 42064132 | 42069132 | NM_001128608 | yes |
| chr18 | 12655412 | 12660412 | NM_001128626 | yes |
| chr15 | 40507129 | 40512129 | NM_001128628 | yes |
| chr10 | 105236497 | 105241497 | NM_001129742 | yes |
| chr8 | 145688531 | 145693531 | NM_001129888 | yes |
| chr19 | 34285251 | 34290251 | NM_001129994 | yes |
| chr5 | 141014017 | 141019017 | NM_001130029 | yes |
| chr1 | 75196592 | 75201592 | NM_001130042 | yes |
| chr11 | 47276968 | 47281968 | NM_001130101 | yes |
| chr15 | 74419215 | 74424215 | NM_001130136 | yes |
| chr15 | 74419496 | 74424496 | NM_001130137 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr15 | 74420090 | 74425090 | NM_001130138 | yes |
| chr6 | 135499953 | 135504953 | NM_001130172 | yes |
| chr12 | 56580858 | 56585858 | NM_001130420 | yes |
| chr1 | 225963015 | 225968015 | NM_001130440 | yes |
| chr4 | 141346315 | 141351315 | NM_001130675 | yes |
| chr3 | 187451785 | 187456785 | NM_001130845 | yes |
| chr11 | 67270343 | 67275343 | NM_001130848 | yes |
| chr17 | 46891969 | 46896969 | NM_001130918 | yes |
| chr1 | 110034201 | 110039201 | NM_001134400 | yes |
| chr1 | 110034158 | 110039158 | NM_001134402 | yes |
| chr1 | 86041546 | 86046546 | NM_001134445 | yes |
| chr6 | 41752681 | 41757681 | NM_001134493 | yes |
| chr20 | 62336865 | 62341865 | NM_001134758 | yes |
| chr1 | 159912886 | 159917886 | NM_001135050 | yes |
| chr22 | 19935960 | 19940960 | NM_001135161 | yes |
| chr11 | 72430903 | 72435903 | NM_001135190 | yes |
| chr1 | 151168521 | 151173521 | NM_001135636 | yes |
| chr17 | 1417682 | 1422682 | NM_001135642 | yes |
| chr1 | 40040021 | 40045021 | NM_001135653 | yes |
| chr17 | 43210514 | 43215514 | NM_001135705 | yes |
| chr19 | 35604232 | 35609232 | NM_001136007 | yes |
| chr1 | 225995276 | 226000276 | NM_001136018 | yes |
| chr1 | 249150625 | 249155625 | NM_001136036 | yes |
| chr14 | 24766539 | 24771539 | NM_001136050 | yes |
| chr19 | 18041324 | 18046324 | NM_001136203 | yes |
| chr1 | 44396492 | 44401492 | NM_001136215 | yes |
| chr6 | 44235980 | 44240980 | NM_001137560 | yes |
| chr16 | 67515216 | 67520216 | NM_001138 | yes |
| chr11 | 61714856 | 61719856 | NM_001139443 | yes |
| chr6 | 109701515 | 109706515 | NM_001142401 | yes |
| chr19 | 45907107 | 45912107 | NM_001142502 | yes |
| chr9 | 130522219 | 130527219 | NM_001142531 | yes |
| chr9 | 130522197 | 130527197 | NM_001142532 | yes |
| chr11 | 63271024 | 63276024 | NM_001142535 | yes |
| chr11 | 63272959 | 63277959 | NM_001142537 | yes |
| chr1 | 46710867 | 46715867 | NM_001142548 | yes |
| chr1 | 156695763 | 156700763 | NM_001142560 | yes |
| chr17 | 33444388 | 33449388 | NM_001142571 | yes |
| chr17 | 74378190 | 74383190 | NM_001142601 | yes |
| chr17 | 74378789 | 74383789 | NM_001142602 | yes |
| chr7 | 86686514 | 86691514 | NM_001142749 | yes |
| chr16 | 30994019 | 30999019 | NM_001142777 | yes |
| chr17 | 6915556 | 6920556 | NM_001142798 | yes |
| chr5 | 176736792 | 176741792 | NM_001142935 | yes |
| chr6 | 134496510 | 134501510 | NM_001143677 | yes |
| chr6 | 134494570 | 134499570 | NM_001143678 | yes |
| chr15 | 91425776 | 91430776 | NM_001143783 | yes |
| chr15 | 91425165 | 91430165 | NM_001143785 | yes |
| chr12 | 56318409 | 56323409 | NM_001143853 | yes |
| chr10 | 105003144 | 105008144 | NM_001143909 | yes |
| chr1 | 28049990 | 28054990 | NM_001143912 | yes |
| chr1 | 245131131 | 245136131 | NM_001143943 | yes |
| chr17 | 37319914 | 37324914 | NM_001143968 | yes |
| chr17 | 7586889 | 7591889 | NM_001143990 | yes |
| chr17 | 7588258 | 7593258 | NM_001143991 | yes |
| chr17 | 7589167 | 7594167 | NM_001143992 | yes |
| chr15 | 89087434 | 89092434 | NM_001144074 | yes |
| chr11 | 118475806 | 118480806 | NM_001144758 | yes |
| chr17 | 40166683 | 40171683 | NM_001144766 | yes |
| chr6 | 56816926 | 56821926 | NM_001144769 | yes |
| chr1 | 117111215 | 117116215 | NM_001144822 | yes |
| chr9 | 127903338 | 127908338 | NM_001144877 | yes |
| chr17 | 40169587 | 40174587 | NM_001144927 | yes |
| chr12 | 3859866 | 3864866 | NM_001144958 | yes |
| chr11 | 119064084 | 119069084 | NM_001145018 | yes |
| chr17 | 45916199 | 45921199 | NM_001145023 | yes |
| chr20 | 33732661 | 33737661 | NM_001145025 | yes |
| chr19 | 14167471 | 14172471 | NM_001145028 | yes |
| chr17 | 28254374 | 28259374 | NM_001145053 | yes |
| chr11 | 61273772 | 61278772 | NM_001145077 | yes |
| chr5 | 157096061 | 157101061 | NM_001145132 | yes |
| chr19 | 16175817 | 16180817 | NM_001145160 | yes |
| chr2 | 175197321 | 175202321 | NM_001145250 | yes |
| chr1 | 156022017 | 156027017 | NM_001145264 | yes |
| chr17 | 38471973 | 38476973 | NM_001145301 | yes |
| chr2 | 178126359 | 178131359 | NM_001145412 | yes |
| chr3 | 38535263 | 38540263 | NM_001145464 | yes |
| chr1 | 117661911 | 117666911 | NM_001145635 | yes |
| chr1 | 45137894 | 45142894 | NM_001145636 | yes |
| chr5 | 54466505 | 54471505 | NM_001145734 | yes |
| chr5 | 150223585 | 150228585 | NM_001145805 | yes |
| chr11 | 1858219 | 1863219 | NM_001145829 | yes |
| chr11 | 1858932 | 1863932 | NM_001145841 | yes |
| chr7 | 91761559 | 91766559 | NM_001146152 | yes |
| chr1 | 43230255 | 43235255 | NM_001146289 | yes |
| chr3 | 52006146 | 52011146 | NM_001146314 | yes |
| chr12 | 6979799 | 6984949 | NM_001146316 | yes |
| chr17 | 8645654 | 8650654 | NM_001158261 | yes |
| chr1 | 120351703 | 120356703 | NM_001159352 | yes |
| chr1 | 204910854 | 204915854 | NM_001160331 | yes |
| chr17 | 27051449 | 27056449 | NM_001160407 | yes |
| chr20 | 56193132 | 56198132 | NM_001160417 | yes |
| chr20 | 32897108 | 32902108 | NM_001161766 | yes |
| chr1 | 75196336 | 75201336 | NM_001162916 | yes |
| chr17 | 73627014 | 73632014 | NM_001162995 | yes |
| chr19 | 46193241 | 46198241 | NM_001163377 | yes |
| chr9 | 115093444 | 115098444 | NM_001163788 | yes |
| chr17 | 72730459 | 72735459 | NM_001163989 | yes |
| chr1 | 186342390 | 186347390 | NM_001164245 | yes |
| chr3 | 57991627 | 57996627 | NM_001164317 | yes |
| chr12 | 110904026 | 110909026 | NM_001164372 | yes |
| chr12 | 110903589 | 110908589 | NM_001164373 | yes |
| chr7 | 150752552 | 150757552 | NM_001164410 | yes |
| chr7 | 100610404 | 100615404 | NM_001164462 | yes |
| chr19 | 35643345 | 35648345 | NM_001164605 | yes |
| chr8 | 141643146 | 141648146 | NM_001164623 | yes |
| chr12 | 53815139 | 53820139 | NM_001164690 | yes |
| chr14 | 23538279 | 23543279 | NM_001164816 | yes |
| chr1 | 35322146 | 35327146 | NM_001164824 | yes |
| chr1 | 35322838 | 35327838 | NM_001164825 | yes |
| chr17 | 37790833 | 37795833 | NM_001165937 | yes |
| chr17 | 8019734 | 8024734 | NM_001165960 | yes |
| chr17 | 8024910 | 8029910 | NM_001165967 | yes |
| chr17 | 57295328 | 57300328 | NM_001165993 | yes |
| chr11 | 102215413 | 102220413 | NM_001166 | yes |
| chr11 | 67139148 | 67144148 | NM_001166212 | yes |
| chr11 | 17408378 | 17413378 | NM_001166290 | yes |
| chr3 | 50281826 | 50286826 | NM_001166425 | yes |
| chr11 | 116660636 | 116665636 | NM_001166598 | yes |
| chr4 | 87853654 | 87858654 | NM_001166693 | yes |
| chr6 | 41701497 | 41706497 | NM_001167827 | yes |
| chr12 | 123847256 | 123852256 | NM_001167856 | yes |
| chr22 | 50962368 | 50967368 | NM_001169109 | yes |
| chr22 | 50962074 | 50967074 | NM_001169110 | yes |
| chr22 | 50961533 | 50966533 | NM_001169111 | yes |
| chr9 | 33400180 | 33405180 | NM_001170 | yes |
| chr1 | 86171616 | 86176616 | NM_001170670 | yes |
| chr11 | 61246085 | 61251085 | NM_001170753 | yes |
| chr10 | 98589517 | 98594517 | NM_001170765 | yes |
| chr12 | 53642870 | 53647870 | NM_001170790 | yes |
| chrX | 70313499 | 70318499 | NM_001170931 | yes |
| chr3 | 50605958 | 50610958 | NM_001171741 | yes |
| chr6 | 35307835 | 35312835 | NM_001171818 | yes |
| chr1 | 29446513 | 29451513 | NM_001171868 | yes |
| chr1 | 33333914 | 33338914 | NM_001171940 | yes |
| chr1 | 33335593 | 33340593 | NM_001171941 | yes |
| chr12 | 122324017 | 122329017 | NM_001171993 | yes |
| chr14 | 68084079 | 68089079 | NM_001172 | yes |
| chr12 | 58174028 | 58179028 | NM_001172695 | yes |
| chr1 | 29060952 | 29065952 | NM_001172828 | yes |
| chr1 | 29060633 | 29065633 | NM_001173128 | yes |
| chr12 | 53712912 | 53717912 | NM_001173466 | yes |
| chr2 | 220323034 | 220328034 | NM_001173476 | yes |
| chr10 | 73076510 | 73081510 | NM_001174098 | yes |
| chr19 | 1809736 | 1814736 | NM_001178002 | yes |
| chr12 | 57502696 | 57507696 | NM_001178078 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr12 | 57501589 | 57506589 | NM_001178079 | yes |
| chr10 | 104261219 | 104266219 | NM_001178133 | yes |
| chr12 | 56519486 | 56524486 | NM_001184796 | yes |
| chr3 | 14714106 | 14719106 | NM_001184957 | yes |
| chr22 | 20116864 | 20121864 | NM_001185024 | yes |
| chr1 | 161085362 | 161090362 | NM_001185092 | yes |
| chr1 | 161085407 | 161090407 | NM_001185093 | yes |
| chr1 | 161085408 | 161090408 | NM_001185094 | yes |
| chr9 | 140119518 | 140124518 | NM_001190228 | yes |
| chr5 | 37833429 | 37838429 | NM_001190468 | yes |
| chr15 | 40572287 | 40577287 | NM_001190479 | yes |
| chr20 | 30308401 | 30313401 | NM_001191 | yes |
| chr16 | 67593810 | 67598810 | NM_001191022 | yes |
| chr6 | 13572261 | 13577261 | NM_001193267 | yes |
| chr19 | 46146275 | 46151275 | NM_001193268 | yes |
| chr19 | 46144485 | 46149485 | NM_001193269 | yes |
| chr1 | 205088650 | 205093650 | NM_001193272 | yes |
| chr1 | 249150815 | 249155815 | NM_001193328 | yes |
| chr2 | 65213079 | 65218079 | NM_001193493 | yes |
| chr1 | 48460062 | 48465062 | NM_001194986 | yes |
| chr7 | 128503902 | 128508902 | NM_001195150 | yes |
| chr20 | 62336880 | 62341880 | NM_001195653 | yes |
| chr2 | 220405319 | 220410319 | NM_001195731 | yes |
| chr6 | 53407427 | 53412427 | NM_001197115 | yes |
| chr20 | 43988077 | 43993077 | NM_001197129 | yes |
| chr14 | 24801777 | 24806777 | NM_001198568 | yes |
| chr3 | 39231587 | 39236587 | NM_001198621 | yes |
| chr17 | 7459109 | 7464109 | NM_001198622 | yes |
| chr17 | 49241133 | 49246133 | NM_001198682 | yes |
| chr15 | 55698223 | 55703223 | NM_001198784 | yes |
| chr1 | 167187568 | 167192566 | NM_001198786 | yes |
| chr11 | 64946186 | 64951186 | NM_001198868 | yes |
| chr11 | 64946650 | 64951650 | NM_001198869 | yes |
| chr7 | 128500357 | 128505357 | NM_001198909 | yes |
| chr1 | 24739087 | 24744087 | NM_001199012 | yes |
| chr1 | 24737762 | 24742762 | NM_001199013 | yes |
| chr3 | 128877573 | 128882573 | NM_001199469 | yes |
| chr20 | 35231637 | 35236637 | NM_001199534 | yes |
| chr12 | 56543704 | 56548704 | NM_001199629 | yes |
| chr1 | 95580979 | 95585979 | NM_001199691 | yes |
| chr7 | 150752787 | 150757787 | NM_001199692 | yes |
| chr7 | 150757134 | 150762134 | NM_001199693 | yes |
| chr7 | 150757229 | 150762229 | NM_001199694 | yes |
| chr1 | 156673108 | 156678108 | NM_001199723 | yes |
| chr11 | 64779085 | 64784085 | NM_001199745 | yes |
| chr2 | 176991968 | 176996968 | NM_001199746 | yes |
| chr2 | 176991922 | 176996922 | NM_001199747 | yes |
| chr12 | 89916844 | 89921844 | NM_001199777 | yes |
| chr12 | 89917539 | 89922539 | NM_001199781 | yes |
| chr2 | 25013484 | 25018484 | NM_001199803 | yes |
| chr1 | 212206502 | 212211502 | NM_001199809 | yes |
| chr7 | 26329015 | 26334015 | NM_001199835 | yes |
| chr7 | 26401445 | 26406445 | NM_001199838 | yes |
| chr8 | 22547402 | 22552402 | NM_001199880 | yes |
| chr8 | 22547593 | 22552593 | NM_001199881 | yes |
| chr17 | 48169601 | 48174601 | NM_001199898 | yes |
| chr17 | 48170559 | 48175559 | NM_001199899 | yes |
| chr17 | 48170139 | 48175139 | NM_001199900 | yes |
| chr9 | 32570682 | 32575682 | NM_001199987 | yes |
| chr17 | 17397209 | 17402209 | NM_001199989 | yes |
| chr1 | 182756084 | 182761084 | NM_001200050 | yes |
| chr8 | 9006652 | 9011652 | NM_001201329 | yes |
| chr2 | 171782448 | 171787448 | NM_001201428 | yes |
| chr16 | 47175436 | 47180436 | NM_001201477 | yes |
| chr1 | 206783404 | 206788404 | NM_001201478 | yes |
| chr9 | 35094046 | 35099046 | NM_001201484 | yes |
| chr1 | 110879445 | 110884445 | NM_001201545 | yes |
| chr12 | 52414116 | 52419116 | NM_001202233 | yes |
| chr9 | 132401948 | 132406948 | NM_001202403 | yes |
| chr11 | 17370809 | 17375809 | NM_001202439 | yes |
| chr7 | 101456684 | 101461684 | NM_001202543 | yes |
| chr7 | 101456788 | 101461788 | NM_001202546 | yes |
| chr1 | 27112179 | 27117179 | NM_001202554 | yes |
| chr19 | 12248722 | 12253722 | NM_001203250 | yes |
| chr1 | 111171596 | 111176596 | NM_001204269 | yes |
| chr19 | 46847751 | 46852751 | NM_001204284 | yes |
| chr17 | 75082225 | 75087225 | NM_001204408 | yes |
| chr17 | 75082735 | 75087735 | NM_001204410 | yes |
| chr20 | 3798671 | 3803671 | NM_001204446 | yes |
| chr15 | 55698208 | 55703208 | NM_001204450 | yes |
| chr19 | 49974966 | 49979966 | NM_001204502 | yes |
| chr19 | 49975318 | 49980318 | NM_001204503 | yes |
| chr10 | 103537626 | 103542626 | NM_001206389 | yes |
| chr1 | 19809635 | 19814635 | NM_001206540 | yes |
| chr1 | 87167753 | 87172753 | NM_001206651 | yes |
| chr1 | 160066118 | 160071118 | NM_001206665 | yes |
| chr11 | 65476973 | 65481973 | NM_001206833 | yes |
| chr12 | 13246240 | 13251240 | NM_001206843 | yes |
| chr7 | 100228773 | 100233773 | NM_001206855 | yes |
| chr19 | 42634125 | 42639125 | NM_001207025 | yes |
| chr19 | 50177909 | 50182909 | NM_001207042 | yes |
| chr19 | 49147069 | 49152069 | NM_001217 | yes |
| chr6 | 36643987 | 36648987 | NM_001220778 | yes |
| chr4 | 110622129 | 110627129 | NM_001226 | yes |
| chr1 | 160157785 | 160162785 | NM_001231 | yes |
| chr20 | 33460266 | 33465266 | NM_001242393 | yes |
| chr1 | 110524887 | 110529887 | NM_001242673 | yes |
| chr12 | 52602139 | 52607139 | NM_001242696 | yes |
| chr12 | 56612985 | 56617985 | NM_001242826 | yes |
| chr11 | 47196176 | 47201176 | NM_001242832 | yes |
| chr1 | 205195559 | 205200559 | NM_001242925 | yes |
| chr6 | 20401410 | 20406410 | NM_001243076 | yes |
| chr6 | 37135422 | 37140422 | NM_001243186 | yes |
| chr17 | 19263551 | 19268551 | NM_001243473 | yes |
| chr12 | 51439582 | 51444582 | NM_001243689 | yes |
| chr11 | 119249936 | 119254936 | NM_001243759 | yes |
| chr1 | 10488304 | 10493304 | NM_001243768 | yes |
| chr12 | 54580278 | 54585278 | NM_001243787 | yes |
| chr12 | 54580241 | 54585241 | NM_001243789 | yes |
| chr20 | 62494081 | 62499081 | NM_001243891 | yes |
| chr3 | 50652062 | 50657062 | NM_001243925 | yes |
| chr3 | 50646793 | 50651793 | NM_001243926 | yes |
| chr12 | 6807509 | 6812509 | NM_001244014 | yes |
| chr12 | 6807096 | 6812096 | NM_001244015 | yes |
| chr14 | 69258131 | 69263131 | NM_001244698 | yes |
| chr14 | 69260460 | 69265460 | NM_001244701 | yes |
| chr9 | 115092806 | 115097806 | NM_001244898 | yes |
| chr3 | 49938570 | 49943570 | NM_001244937 | yes |
| chr6 | 74017438 | 74022438 | NM_001251874 | yes |
| chr1 | 200990328 | 200995328 | NM_001252100 | yes |
| chr5 | 57753466 | 57758466 | NM_001252226 | yes |
| chr17 | 73125390 | 73130390 | NM_001252377 | yes |
| chr1 | 154972606 | 154977606 | NM_001252406 | yes |
| chr1 | 155175272 | 155180272 | NM_001252607 | yes |
| chr7 | 137684347 | 137689347 | NM_001253775 | yes |
| chr1 | 114445045 | 114450045 | NM_001253852 | yes |
| chr1 | 114445246 | 114450246 | NM_001253853 | yes |
| chr4 | 154263301 | 154268301 | NM_001253861 | yes |
| chr11 | 75477278 | 75482278 | NM_001253891 | yes |
| chr7 | 130123516 | 130128516 | NM_001253901 | yes |
| chr7 | 130123688 | 130128688 | NM_001253902 | yes |
| chr11 | 60736613 | 60741613 | NM_001254750 | yes |
| chr17 | 40727234 | 40732234 | NM_001256014 | yes |
| chr17 | 40727349 | 40732349 | NM_001256015 | yes |
| chr19 | 30203952 | 30208952 | NM_001256046 | yes |
| chr19 | 30204196 | 30209196 | NM_001256047 | yes |
| chr1 | 46804350 | 46809350 | NM_001256127 | yes |
| chr11 | 102215605 | 102220605 | NM_001256163 | yes |
| chr16 | 29799534 | 29804534 | NM_001256269 | yes |
| chr16 | 29799789 | 29804789 | NM_001256270 | yes |
| chr1 | 146711791 | 146716791 | NM_001256336 | yes |
| chr1 | 54409499 | 54414499 | NM_001256409 | yes |
| chr22 | 19163518 | 19168518 | NM_001256534 | yes |
| chrX | 153623906 | 153628906 | NM_001256577 | yes |
| chr1 | 155143763 | 155148763 | NM_001256599 | yes |
| chr1 | 155144730 | 155149730 | NM_001256601 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr11 | 66244984 | 66249984 | NM_001256670 | yes |
| chr15 | 74282189 | 74287189 | NM_001256672 | yes |
| chr15 | 74284463 | 74289463 | NM_001256676 | yes |
| chr19 | 19246810 | 19251810 | NM_001256766 | yes |
| chr12 | 50464868 | 50469868 | NM_001256830 | yes |
| chr11 | 67118567 | 67123567 | NM_001256870 | yes |
| chr1 | 38155573 | 38160573 | NM_001256875 | yes |
| chr12 | 50503264 | 50508264 | NM_001257133 | yes |
| chr11 | 118659157 | 118664157 | NM_001257191 | yes |
| chr17 | 4611289 | 4616289 | NM_001257328 | yes |
| chr1 | 156093408 | 156098408 | NM_001257374 | yes |
| chr17 | 73994487 | 73999487 | NM_001258 | yes |
| chr16 | 22306196 | 22311196 | NM_001258033 | yes |
| chr20 | 50156758 | 50161758 | NM_001258296 | yes |
| chr11 | 44969259 | 44974259 | NM_001258320 | yes |
| chr11 | 44970357 | 44975357 | NM_001258321 | yes |
| chr11 | 44969955 | 44974955 | NM_001258323 | yes |
| chr19 | 1063422 | 1068422 | NM_001258328 | yes |
| chr17 | 48621950 | 48626950 | NM_001258372 | yes |
| chr11 | 72143228 | 72148228 | NM_001258392 | yes |
| chr5 | 139737287 | 139742287 | NM_001258426 | yes |
| chr19 | 35737059 | 35742059 | NM_001260489 | yes |
| chr9 | 130545805 | 130550805 | NM_001261 | yes |
| chr12 | 122324137 | 122329137 | NM_001261400 | yes |
| chr10 | 104152853 | 104157853 | NM_001261403 | yes |
| chr1 | 94310206 | 94315206 | NM_001261408 | yes |
| chr1 | 155021248 | 155026248 | NM_001261464 | yes |
| chr17 | 56403652 | 56408652 | NM_001261835 | yes |
| chr4 | 113555620 | 113560620 | NM_001267039 | yes |
| chr14 | 52116076 | 52121076 | NM_001267046 | yes |
| chr1 | 109654085 | 109659085 | NM_001267048 | yes |
| chr20 | 62336705 | 62341705 | NM_001267548 | yes |
| chr10 | 35413269 | 35418269 | NM_001267562 | yes |
| chr10 | 35481555 | 35486555 | NM_001267568 | yes |
| chr10 | 35482330 | 35487330 | NM_001267570 | yes |
| chr7 | 100447841 | 100452841 | NM_001267812 | yes |
| chr20 | 56098208 | 56103208 | NM_001269040 | yes |
| chr20 | 56097423 | 56102423 | NM_001269041 | yes |
| chr20 | 56097683 | 56102683 | NM_001269043 | yes |
| chr20 | 56097663 | 56102663 | NM_001269050 | yes |
| chr21 | 35881137 | 35886137 | NM_001270402 | yes |
| chr21 | 35881113 | 35886113 | NM_001270403 | yes |
| chr12 | 123752281 | 123757281 | NM_001270433 | yes |
| chr12 | 123750301 | 123755301 | NM_001270434 | yes |
| chr1 | 183602576 | 183607576 | NM_001270439 | yes |
| chr19 | 12943742 | 12948742 | NM_001270440 | yes |
| chr19 | 12942890 | 12947890 | NM_001270441 | yes |
| chr19 | 12938989 | 12943989 | NM_001270443 | yes |
| chr12 | 93961675 | 93966675 | NM_001270467 | yes |
| chr12 | 93962257 | 93967257 | NM_001270468 | yes |
| chr12 | 93962957 | 93967957 | NM_001270469 | yes |
| chr12 | 93963802 | 93968802 | NM_001270471 | yes |
| chr6 | 52147179 | 52152179 | NM_001270472 | yes |
| chr6 | 138185825 | 138190825 | NM_001270507 | yes |
| chr1 | 10487659 | 10492659 | NM_001270517 | yes |
| chr1 | 201082000 | 201087000 | NM_001270601 | yes |
| chr1 | 110571699 | 110576699 | NM_001270768 | yes |
| chr6 | 166794001 | 166799001 | NM_001270879 | yes |
| chr1 | 36612615 | 36617615 | NM_001270894 | yes |
| chr18 | 59990020 | 59995020 | NM_001270949 | yes |
| chr16 | 768642 | 773642 | NM_001271285 | yes |
| chr12 | 54716374 | 54721374 | NM_001271734 | yes |
| chr5 | 148927394 | 148932394 | NM_001271742 | yes |
| chr5 | 176728263 | 176733263 | NM_001271828 | yes |
| chr19 | 12033383 | 12038383 | NM_001271848 | yes |
| chr11 | 67273158 | 67278158 | NM_001271849 | yes |
| chr1 | 205323718 | 205328718 | NM_001271863 | yes |
| chr17 | 56030184 | 56035184 | NM_001271875 | yes |
| chr15 | 78421377 | 78426377 | NM_001271888 | yes |
| chr19 | 42827261 | 42832261 | NM_001271938 | yes |
| chr6 | 41700765 | 41705765 | NM_001271943 | yes |
| chr6 | 41699639 | 41704639 | NM_001271945 | yes |
| chr1 | 153955342 | 153960342 | NM_001272038 | yes |
| chr3 | 48512242 | 48517242 | NM_001272082 | yes |
| chr9 | 116353934 | 116358934 | NM_001276262 | yes |
| chr16 | 29814917 | 29819917 | NM_001276275 | yes |
| chr1 | 207223825 | 207228825 | NM_001276320 | yes |
| chr12 | 109122119 | 109127119 | NM_001276471 | yes |
| chr11 | 64876826 | 64881826 | NM_001277233 | yes |
| chr5 | 115175048 | 115180048 | NM_001277783 | yes |
| chr11 | 3874433 | 3879433 | NM_001277961 | yes |
| chr5 | 37832424 | 37837424 | NM_001278098 | yes |
| chr17 | 46045394 | 46050394 | NM_001278197 | yes |
| chr17 | 46045822 | 46050822 | NM_001278198 | yes |
| chr1 | 155291686 | 155296686 | NM_001278230 | yes |
| chr11 | 65147357 | 65152357 | NM_001278250 | yes |
| chr11 | 65148672 | 65153672 | NM_001278251 | yes |
| chr11 | 119209093 | 119214093 | NM_001278431 | yes |
| chr14 | 21535919 | 21540919 | NM_001278529 | yes |
| chr9 | 127531089 | 127536089 | NM_001278546 | yes |
| chr17 | 72854466 | 72859466 | NM_001278553 | yes |
| chr12 | 110885716 | 110890716 | NM_001278556 | yes |
| chr6 | 57084612 | 57089612 | NM_001278666 | yes |
| chr6 | 57083759 | 57088759 | NM_001278668 | yes |
| chr19 | 35627397 | 35632397 | NM_001278717 | yes |
| chr19 | 35628038 | 35633038 | NM_001278718 | yes |
| chr19 | 1266767 | 1271767 | NM_001280 | yes |
| chr7 | 142550276 | 142555276 | NM_001280794 | yes |
| chr11 | 61581175 | 61586175 | NM_001281501 | yes |
| chr11 | 61581376 | 61586376 | NM_001281502 | yes |
| chr1 | 26558144 | 26563144 | NM_001281517 | yes |
| chr1 | 32279152 | 32284152 | NM_001281987 | yes |
| chr17 | 28254746 | 28259746 | NM_001282129 | yes |
| chr11 | 119036922 | 119041922 | NM_001282143 | yes |
| chr19 | 45455342 | 45460342 | NM_001282176 | yes |
| chr14 | 21536531 | 21541531 | NM_001282211 | yes |
| chr17 | 46798030 | 46803030 | NM_001282275 | yes |
| chr17 | 46798554 | 46803554 | NM_001282276 | yes |
| chr7 | 150723009 | 150728009 | NM_001282291 | yes |
| chr11 | 119036543 | 119041543 | NM_001282358 | yes |
| chr2 | 209116682 | 209121682 | NM_001282386 | yes |
| chr2 | 209116527 | 209121527 | NM_001282387 | yes |
| chr16 | 3146818 | 3151818 | NM_001282415 | yes |
| chr11 | 64644685 | 64649685 | NM_001282444 | yes |
| chr11 | 64071199 | 64076199 | NM_001282450 | yes |
| chr11 | 64070500 | 64075500 | NM_001282451 | yes |
| chr6 | 57177103 | 57182103 | NM_001282488 | yes |
| chr17 | 72916858 | 72921858 | NM_001282489 | yes |
| chr19 | 11404315 | 11409315 | NM_001282509 | yes |
| chr20 | 49545250 | 49550250 | NM_001282531 | yes |
| chr17 | 55820190 | 55825190 | NM_001282544 | yes |
| chr1 | 28412648 | 28417648 | NM_001282560 | yes |
| chr3 | 50261620 | 50266620 | NM_001282619 | yes |
| chr11 | 11860470 | 11865470 | NM_001282659 | yes |
| chr9 | 128021573 | 128026573 | NM_001282679 | yes |
| chr1 | 171215110 | 171220110 | NM_001282693 | yes |
| chr8 | 80676210 | 80681210 | NM_001282851 | yes |
| chr8 | 126441951 | 126446951 | NM_001282985 | yes |
| chr1 | 159767801 | 159772801 | NM_001284217 | yes |
| chr15 | 34633016 | 34638016 | NM_001284292 | yes |
| chr15 | 40597674 | 40602674 | NM_001284297 | yes |
| chr8 | 10694909 | 10699909 | NM_001284356 | yes |
| chr17 | 1529169 | 1534169 | NM_001284498 | yes |
| chr20 | 48804620 | 48809620 | NM_001285878 | yes |
| chr11 | 62444089 | 62449089 | NM_001286077 | yes |
| chr6 | 155052012 | 155057012 | NM_001286188 | yes |
| chr6 | 212206395 | 212211395 | NM_001286229 | yes |
| chr1 | 157960563 | 157965563 | NM_001286349 | yes |
| chr1 | 114519513 | 114524513 | NM_001286352 | yes |
| chr14 | 24766560 | 24771560 | NM_001286367 | yes |
| chr1 | 161193229 | 161198229 | NM_001286373 | yes |
| chr15 | 91473299 | 91478299 | NM_001286451 | yes |
| chr6 | 3454293 | 3459293 | NM_001286456 | yes |
| chr21 | 47741313 | 47746313 | NM_001286476 | yes |
| chr21 | 47741271 | 47746271 | NM_001286477 | yes |
| chr6 | 44222808 | 44227808 | NM_001286509 | yes |

TABLE S1-continued

Constitutive CTCF peaks within a constitutive IN
across HCT116, Jurkat, K562 within 2.5 kb of TSS

| chr | start | stop | gene | loops to differential enhancers |
|---|---|---|---|---|
| chr6 | 44222589 | 44227589 | NM_001286510 | yes |
| chr6 | 44223127 | 44228127 | NM_001286511 | yes |
| chr6 | 35702309 | 35707309 | NM_001286574 | yes |
| chr16 | 29872109 | 29877109 | NM_001286585 | yes |
| chr6 | 36851140 | 36856140 | NM_001286635 | yes |
| chr6 | 43421870 | 43426870 | NM_001286655 | yes |
| chr6 | 43420862 | 43425862 | NM_001286656 | yes |
| chr9 | 132368663 | 132373663 | NM_001286796 | yes |
| chr2 | 220358577 | 220363577 | NM_001286811 | yes |
| chr19 | 18116477 | 18121477 | NM_001286826 | yes |
| chr9 | 124919687 | 124924687 | NM_001286828 | yes |
| chr12 | 49295393 | 49300393 | NM_001286957 | yes |
| chr19 | 18389966 | 18394966 | NM_001286968 | yes |
| chr6 | 43737222 | 43742222 | NM_001287044 | yes |
| chr15 | 74608382 | 74613382 | NM_001287181 | yes |
| chr8 | 71579182 | 71584182 | NM_001287260 | yes |
| chr20 | 3764919 | 3769919 | NM_001287516 | yes |
| chr20 | 3773886 | 3778886 | NM_001287519 | yes |
| chr10 | 104151367 | 104156367 | NM_001288724 | yes |
| chr19 | 46280377 | 46285377 | NM_001288765 | yes |
| chr16 | 31467094 | 31472094 | NM_001288767 | yes |
| chr8 | 145201048 | 145206048 | NM_001288814 | yes |
| chr19 | 6737193 | 6742193 | NM_001288962 | yes |
| chr3 | 138310725 | 138315725 | NM_001288964 | yes |
| chr17 | 48501019 | 48506019 | NM_001288968 | yes |
| chr19 | 19751976 | 19756976 | NM_001288998 | yes |
| chr1 | 25941459 | 25946459 | NM_001289010 | yes |
| chr14 | 23449351 | 23454351 | NM_001289097 | yes |
| chr19 | 11544061 | 11549061 | NM_001289102 | yes |
| chr17 | 7514882 | 7519882 | NM_001289114 | yes |
| chr5 | 133858840 | 133863840 | NM_001289984 | yes |
| chr4 | 76647206 | 76652206 | NM_001290049 | yes |
| chr19 | 4907605 | 4912605 | NM_001290051 | yes |
| chr19 | 4907879 | 4912879 | NM_001290052 | yes |
| chr3 | 50308050 | 50313050 | NM_001290062 | yes |
| chr14 | 24895992 | 24900992 | NM_001290256 | yes |
| chr14 | 24896641 | 24901641 | NM_001290257 | yes |
| chr16 | 89003945 | 89008945 | NM_001290330 | yes |
| chr11 | 1853040 | 1858040 | NM_001290332 | yes |
| chr1 | 225995336 | 226000336 | NM_001291163 | yes |
| chr1 | 41825103 | 41830103 | NM_001291281 | yes |
| chr19 | 14181321 | 14186321 | NM_001291291 | yes |
| chr19 | 47985021 | 47990021 | NM_001291296 | yes |
| chr19 | 15527432 | 15532432 | NM_001291478 | yes |
| chr1 | 113006663 | 113011663 | NM_001291880 | yes |
| chr5 | 176511373 | 176516373 | NM_001291980 | yes |
| chr6 | 134493534 | 134498534 | NM_001291995 | yes |
| chr2 | 170678941 | 170683941 | NM_001293186 | yes |
| chr1 | 32227164 | 32232164 | NM_001294335 | yes |
| chr5 | 41922854 | 41927854 | NM_001297437 | yes |
| chr19 | 7966165 | 7971165 | NM_001297555 | yes |
| chr19 | 45906967 | 45911967 | NM_001297590 | yes |
| chr1 | 27690857 | 27695857 | NM_001297609 | yes |
| chr1 | 205222829 | 205227829 | NM_001297613 | yes |
| chr11 | 2419218 | 2424218 | NM_001297658 | yes |
| chr11 | 2419748 | 2424748 | NM_001297659 | yes |
| chr1 | 51761133 | 51766133 | NM_001297666 | yes |
| chr1 | 183602682 | 183607682 | NM_001297669 | yes |
| chr1 | 10000481 | 10005481 | NM_001297778 | yes |
| chr1 | 10000986 | 10005986 | NM_001297779 | yes |
| chr1 | 45137780 | 45142780 | NM_001300746 | yes |
| chr12 | 49502183 | 49507183 | NM_001300750 | yes |
| chr1 | 172419533 | 172424533 | NM_001300760 | yes |
| chr11 | 62377737 | 62382737 | NM_001300793 | yes |
| chr19 | 1266765 | 1271765 | NM_001300815 | yes |
| chr12 | 53736077 | 53741077 | NM_001300837 | yes |
| chr1 | 150252443 | 150257443 | NM_001300838 | yes |
| chr1 | 150252632 | 150257632 | NM_001300841 | yes |
| chr12 | 69750990 | 69755990 | NM_001300950 | yes |
| chr5 | 140016512 | 140021512 | NM_001300980 | yes |
| chr7 | 44833735 | 44838735 | NM_001300981 | yes |
| chr15 | 75333110 | 75338110 | NM_001301104 | yes |
| chr12 | 108952739 | 108957739 | NM_001301140 | yes |
| chr15 | 45470905 | 45475905 | NM_001301171 | yes |
| chr15 | 40613757 | 40618757 | NM_001301268 | yes |
| chr2 | 159310765 | 159315765 | NM_001301684 | yes |
| chr17 | 38714765 | 38719765 | NM_001301716 | yes |
| chr17 | 38714146 | 38719146 | NM_001301718 | yes |
| chr16 | 31467675 | 31472675 | NM_001301820 | yes |
| chr12 | 7050165 | 7055165 | NM_001301834 | yes |
| chr12 | 7050101 | 7055101 | NM_001301836 | yes |
| chr12 | 7050480 | 7055480 | NM_001301837 | yes |
| chr20 | 39966993 | 39971993 | NM_001301860 | yes |
| chr19 | 11544103 | 11549103 | NM_001302453 | yes |
| chr19 | 11543480 | 11548480 | NM_001302454 | yes |
| chr7 | 100491254 | 100496254 | NM_001302622 | yes |
| chr19 | 45406770 | 45411778 | NM_001302689 | yes |
| chr19 | 45407158 | 45412158 | NM_001302690 | yes |
| chr11 | 65335430 | 65340430 | NM_001303024 | yes |
| chr1 | 38153767 | 38158767 | NM_001303030 | yes |
| chr1 | 145522391 | 145527391 | NM_001303040 | yes |
| chr7 | 100074402 | 100079402 | NM_001303043 | yes |
| chr2 | 27235122 | 27240122 | NM_001303050 | yes |
| chr1 | 202895272 | 202900272 | NM_001303051 | yes |
| chr1 | 156695731 | 156700731 | NM_001303095 | yes |
| chr2 | 220405885 | 220410885 | NM_001303098 | yes |
| chr1 | 202893900 | 202898900 | NM_001303109 | yes |
| chr12 | 56509504 | 56514504 | NM_001303124 | yes |
| chr12 | 56509844 | 56514844 | NM_001303125 | yes |
| chr3 | 150123622 | 150128622 | NM_001303264 | yes |
| chr17 | 73006259 | 73011259 | NM_001303265 | yes |
| chr17 | 7618578 | 7623578 | NM_001303270 | yes |
| chr17 | 65711449 | 65716449 | NM_001303272 | yes |
| chr1 | 78442389 | 78447389 | NM_001303433 | yes |
| chr7 | 1081709 | 1086709 | NM_001303473 | yes |
| chr19 | 39830599 | 39835599 | NM_001303614 | yes |
| chrX | 153624213 | 153629213 | NM_001303624 | yes |
| chrX | 153624338 | 153629338 | NM_001303626 | yes |
| chr1 | 156021116 | 156026116 | NM_001304342 | yes |
| chr2 | 113339514 | 113344514 | NM_001304353 | yes |
| chr2 | 113339949 | 113344949 | NM_001304354 | yes |
| chr6 | 44184742 | 44189742 | NM_001304462 | yes |
| chr1 | 203828213 | 203833213 | NM_001304464 | yes |
| chr16 | 19894456 | 19899456 | NM_001304771 | yes |
| chr16 | 788538 | 793538 | NM_001304799 | yes |
| chr12 | 49738200 | 49743200 | NM_001304944 | yes |
| chr6 | 41886385 | 41891385 | NM_001305455 | yes |
| chr6 | 41886181 | 41891181 | NM_001305456 | yes |
| chr17 | 56492443 | 56497443 | NM_001305544 | yes |
| chr11 | 64320573 | 64325573 | NM_001307985 | yes |
| chr18 | 44134232 | 44139232 | NM_001308013 | yes |
| chr3 | 196666811 | 196671811 | NM_001308036 | yes |
| chr3 | 195617155 | 195622155 | NM_001308046 | yes |
| chr5 | 133857566 | 133862566 | NM_001308143 | yes |
| chr5 | 157095988 | 157100988 | NM_001308165 | yes |
| chr8 | 145908697 | 145913697 | NM_001308208 | yes |
| chr1 | 78146612 | 78151612 | NM_001308237 | yes |
| chr1 | 94372654 | 94377654 | NM_001308253 | yes |
| chr18 | 43301588 | 43306588 | NM_001308278 | yes |
| chr16 | 57699657 | 57704657 | NM_001308360 | yes |
| chr19 | 35998912 | 36003912 | NM_001308380 | yes |
| chr19 | 50977503 | 50982503 | NM_001308429 | yes |
| chr21 | 44343208 | 44348208 | NM_001308491 | yes |
| chr1 | 202308594 | 202313594 | NM_001310326 | yes |
| chr16 | 31103820 | 31108820 | NM_001311311 | yes |
| chr5 | 76009368 | 76014368 | NM_001311313 | yes |
| chr1 | 113613292 | 113618292 | NM_001312686 | yes |
| chr2 | 178127359 | 178132359 | NM_001313902 | yes |
| chr6 | 36722686 | 36727686 | NM_001314018 | yes |
| chr10 | 6242340 | 6247340 | NM_001314063 | yes |
| chr21 | 47742302 | 47747302 | NM_001315529 | yes |
| chr3 | 52006542 | 52011542 | NM_001316331 | yes |
| chr1 | 54409481 | 54414481 | NM_001316935 | yes |
| chr1 | 10000985 | 10005985 | NM_001316973 | yes |
| chr6 | 150282610 | 150287610 | NM_001317089 | yes |
| chr1 | 78443368 | 78448368 | NM_001317099 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr1 | 78442342 | 78447342 | NM_001317100 | yes |
| chr1 | 36346296 | 36351296 | NM_001317122 | yes |
| chr3 | 48591856 | 48596856 | NM_001317134 | yes |
| chr3 | 48596113 | 48601113 | NM_001317136 | yes |
| chr19 | 857159 | 862159 | NM_001317335 | yes |
| chr6 | 13613059 | 13618059 | NM_001317724 | yes |
| chr9 | 116160900 | 116165900 | NM_001317745 | yes |
| chr8 | 98878749 | 98883749 | NM_001317748 | yes |
| chr8 | 71518194 | 71523194 | NM_001317804 | yes |
| chr8 | 71517426 | 71522426 | NM_001317805 | yes |
| chr8 | 23383808 | 23388808 | NM_001317812 | yes |
| chr8 | 124778179 | 124783179 | NM_001317917 | yes |
| chr20 | 30309302 | 30314302 | NM_001317920 | yes |
| chr9 | 131462283 | 131467283 | NM_001317926 | yes |
| chr2 | 46767196 | 46772196 | NM_001318063 | yes |
| chr9 | 33445131 | 33450131 | NM_001318144 | yes |
| chr9 | 124919598 | 124924598 | NM_001318195 | yes |
| chr7 | 26330165 | 26335165 | NM_001318199 | yes |
| chr4 | 40056024 | 40061024 | NM_001318359 | yes |
| chrX | 107016718 | 107021718 | NM_001318468 | yes |
| chr6 | 56817273 | 56822273 | NM_001318539 | yes |
| chr18 | 710164 | 715164 | NM_001318759 | yes |
| chr11 | 72522951 | 72527951 | NM_001318766 | yes |
| chr11 | 66185975 | 66190975 | NM_001318804 | yes |
| chr14 | 24096824 | 24101824 | NM_001318835 | yes |
| chr16 | 4362262 | 4367262 | NM_001318918 | yes |
| chr6 | 2997892 | 3002892 | NM_001318940 | yes |
| chr22 | 30659306 | 30664306 | NM_001319108 | yes |
| chr1 | 12674288 | 12679288 | NM_001319225 | yes |
| chr10 | 102818499 | 102823499 | NM_001319303 | yes |
| chr1 | 159748293 | 159753293 | NM_001319658 | yes |
| chr1 | 159748236 | 159753236 | NM_001319659 | yes |
| chr12 | 6980021 | 6985021 | NM_001319670 | yes |
| chr17 | 7755884 | 7760884 | NM_001319941 | yes |
| chr17 | 28658577 | 28663577 | NM_001319942 | yes |
| chr1 | 114445415 | 114450415 | NM_001319946 | yes |
| chr1 | 114444741 | 114449741 | NM_001319947 | yes |
| chr1 | 158967602 | 158972602 | NM_001320010 | yes |
| chr3 | 47514949 | 47519949 | NM_001320044 | yes |
| chr1 | 160065979 | 160070979 | NM_001320247 | yes |
| chr1 | 35322917 | 35327917 | NM_001320261 | yes |
| chr1 | 76079194 | 76084194 | NM_001320283 | yes |
| chr12 | 53898922 | 53903922 | NM_001320296 | yes |
| chr17 | 7255955 | 7260955 | NM_001320435 | yes |
| chr9 | 77639567 | 77644567 | NM_001320497 | yes |
| chr3 | 138308298 | 138313298 | NM_001320600 | yes |
| chr21 | 44525216 | 44530216 | NM_001320646 | yes |
| chr1 | 101699805 | 101704805 | NM_001320730 | yes |
| chr1 | 45954340 | 45959340 | NM_001320800 | yes |
| chr1 | 212001080 | 212006080 | NM_001320808 | yes |
| chr10 | 81317127 | 81322127 | NM_001320814 | yes |
| chr1 | 38453282 | 38458282 | NM_001320830 | yes |
| chr19 | 35643125 | 35648125 | NM_001320912 | yes |
| chr17 | 7758709 | 7763709 | NM_001320924 | yes |
| chr15 | 45692015 | 45697015 | NM_001321015 | yes |
| chr19 | 47536087 | 47541087 | NM_001321086 | yes |
| chr19 | 35757381 | 35762381 | NM_001321150 | yes |
| chr19 | 1064997 | 1069997 | NM_001321232 | yes |
| chr11 | 108090865 | 108095865 | NM_001321307 | yes |
| chr17 | 43207467 | 43212467 | NM_001321352 | yes |
| chr17 | 1529680 | 1534680 | NM_001321364 | yes |
| chr12 | 124066578 | 124071578 | NM_001321445 | yes |
| chr2 | 201372317 | 201377317 | NM_001321547 | yes |
| chr15 | 89087106 | 89092106 | NM_001321596 | yes |
| chr8 | 71313973 | 71318973 | NM_001321703 | yes |
| chr8 | 71313127 | 71318127 | NM_001321707 | yes |
| chr8 | 71313575 | 71318575 | NM_001321711 | yes |
| chr8 | 71312990 | 71317990 | NM_001321712 | yes |
| chr1 | 154931447 | 154936447 | NM_001321726 | yes |
| chr1 | 25662245 | 25667245 | NM_001321772 | yes |
| chr2 | 55275453 | 55280453 | NM_001321859 | yes |
| chr2 | 55275234 | 55280234 | NM_001321860 | yes |
| chr2 | 55274327 | 55279327 | NM_001321861 | yes |
| chr2 | 55273302 | 55278302 | NM_001321862 | yes |
| chr2 | 55271522 | 55276522 | NM_001321863 | yes |
| chr20 | 30307855 | 30312855 | NM_001322242 | yes |
| chr1 | 109630863 | 109635863 | NM_001322248 | yes |
| chr14 | 60629711 | 60634711 | NM_001322281 | yes |
| chr1 | 249117065 | 249122065 | NM_001322462 | yes |
| chr1 | 249117984 | 249122984 | NM_001322464 | yes |
| chr20 | 33541330 | 33546330 | NM_001322494 | yes |
| chr20 | 33540938 | 33545938 | NM_001322495 | yes |
| chr1 | 24737477 | 24742477 | NM_001322854 | yes |
| chr1 | 24739740 | 24744740 | NM_001322855 | yes |
| chr1 | 24740015 | 24745015 | NM_001322857 | yes |
| chr1 | 154912626 | 154917626 | NM_001323012 | yes |
| chr15 | 91475350 | 91480350 | NM_001323619 | yes |
| chr15 | 91475616 | 91480616 | NM_001323620 | yes |
| chr15 | 45692019 | 45697019 | NM_001323640 | yes |
| chr1 | 151040554 | 151045554 | NM_001323906 | yes |
| chr1 | 227913719 | 227918719 | NM_001323930 | yes |
| chr1 | 227913369 | 227918369 | NM_001323933 | yes |
| chr17 | 72560982 | 72565982 | NM_001324073 | yes |
| chr16 | 835883 | 840883 | NM_001324086 | yes |
| chr16 | 68025694 | 68030694 | NM_001324159 | yes |
| chr16 | 75654721 | 75659721 | NM_001324444 | yes |
| chr1 | 175710252 | 175715252 | NM_001328635 | yes |
| chr1 | 203828478 | 203833478 | NM_001328637 | yes |
| chr1 | 43994031 | 43999031 | NM_001329139 | yes |
| chr7 | 135240162 | 135245162 | NM_001329434 | yes |
| chr8 | 145700865 | 145705865 | NM_001329442 | yes |
| chr8 | 145701234 | 145706234 | NM_001329444 | yes |
| chr7 | 86847403 | 86852403 | NM_001329472 | yes |
| chr7 | 86847168 | 86852168 | NM_001329475 | yes |
| chr17 | 7758545 | 7763545 | NM_001330110 | yes |
| chr17 | 37884316 | 37889316 | NM_001330206 | yes |
| chr12 | 54066703 | 54071703 | NM_001330269 | yes |
| chr1 | 1281992 | 1286992 | NM_001330311 | yes |
| chr17 | 46657484 | 46662484 | NM_001330322 | yes |
| chr12 | 6872983 | 6877983 | NM_001330333 | yes |
| chr1 | 32714340 | 32719340 | NM_001330468 | yes |
| chr17 | 72730199 | 72735199 | NM_001330471 | yes |
| chr19 | 38823927 | 38828927 | NM_001330496 | yes |
| chr17 | 73849393 | 73854393 | NM_001330499 | yes |
| chr8 | 96034703 | 96039703 | NM_001330582 | yes |
| chr8 | 145685734 | 145690734 | NM_001330618 | yes |
| chr1 | 151168520 | 151173520 | NM_001330689 | yes |
| chr1 | 151224676 | 151229676 | NM_001330692 | yes |
| chr9 | 100682352 | 100687352 | NM_001330725 | yes |
| chr1 | 159793799 | 159798979 | NM_001330741 | yes |
| chr1 | 205223825 | 205228825 | NM_001331034 | yes |
| chr22 | 21984586 | 21989586 | NM_001331066 | yes |
| chr17 | 72361145 | 72366145 | NM_001331076 | yes |
| chr13 | 27842814 | 27847814 | NM_001331126 | yes |
| chr12 | 56322446 | 56327446 | NM_001345 | yes |
| chr11 | 62310738 | 62315738 | NM_001346445 | yes |
| chr11 | 62310659 | 62315659 | NM_001346446 | yes |
| chr17 | 66199770 | 66204770 | NM_001346471 | yes |
| chr6 | 109700442 | 109705442 | NM_001346500 | yes |
| chr17 | 1930906 | 1935906 | NM_001346574 | yes |
| chr19 | 39733217 | 39738217 | NM_001346937 | yes |
| chr11 | 118970285 | 118975285 | NM_001382 | yes |
| chr19 | 11589303 | 11594303 | NM_001420 | yes |
| chr6 | 52857678 | 52862678 | NM_001512 | yes |
| chr1 | 32080801 | 32085801 | NM_001525 | yes |
| chr17 | 38597176 | 38602176 | NM_001552 | yes |
| chr1 | 86043944 | 86048944 | NM_001554 | yes |
| chr11 | 67031405 | 67036405 | NM_001619 | yes |
| chr3 | 186328350 | 186333350 | NM_001622 | yes |
| chr1 | 161190918 | 161195918 | NM_001643 | yes |
| chr1 | 3859713 | 3864713 | NM_001665 | yes |
| chr11 | 117692959 | 117697959 | NM_001680 | yes |
| chr3 | 187461013 | 187466013 | NM_001706 | yes |
| chr12 | 92537173 | 92542173 | NM_001731 | yes |
| chr12 | 7242543 | 7247543 | NM_001733 | yes |
| chr21 | 36419095 | 36424095 | NM_001754 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr14 | 23586320 | 23591320 | NM_001805 | yes |
| chr20 | 3764837 | 3769837 | NM_001810 | yes |
| chr5 | 175841070 | 175846070 | NM_001834 | yes |
| chr1 | 40780439 | 40785439 | NM_001852 | yes |
| chr1 | 156672959 | 156677959 | NM_001878 | yes |
| chr17 | 61521222 | 61526222 | NM_001915 | yes |
| chr5 | 139723688 | 139728688 | NM_001945 | yes |
| chr6 | 20399637 | 20404637 | NM_001949 | yes |
| chr1 | 205599500 | 205604500 | NM_001973 | yes |
| chr12 | 56471309 | 56476309 | NM_001982 | yes |
| chr15 | 91425188 | 91430188 | NM_002005 | yes |
| chr1 | 171280822 | 171285822 | NM_002022 | yes |
| chr1 | 27996224 | 28001224 | NM_002038 | yes |
| chr17 | 73399289 | 73404289 | NM_002086 | yes |
| chr17 | 42419954 | 42424954 | NM_002087 | yes |
| chr7 | 26237913 | 26242913 | NM_002137 | yes |
| chr1 | 33349598 | 33354598 | NM_002143 | yes |
| chr17 | 46668603 | 46673603 | NM_002147 | yes |
| chr12 | 53488936 | 53493936 | NM_002178 | yes |
| chr1 | 59247285 | 59252285 | NM_002228 | yes |
| chr13 | 46753959 | 46758959 | NM_002298 | yes |
| chr12 | 120804483 | 120809483 | NM_002442 | yes |
| chr1 | 155175990 | 155180990 | NM_002455 | yes |
| chr8 | 128745815 | 128750815 | NM_002467 | yes |
| chr1 | 203052666 | 203057666 | NM_002479 | yes |
| chr5 | 141255475 | 141260475 | NM_002587 | yes |
| chr20 | 5104768 | 5109768 | NM_002592 | yes |
| chr7 | 100197382 | 100202382 | NM_002593 | yes |
| chr1 | 172410730 | 172415730 | NM_002642 | yes |
| chr20 | 39763661 | 39768661 | NM_002660 | yes |
| chr15 | 74284514 | 74289514 | NM_002675 | yes |
| chr17 | 37822206 | 37827206 | NM_002686 | yes |
| chr6 | 105848499 | 105853499 | NM_002726 | yes |
| chr19 | 14226059 | 14231059 | NM_002730 | yes |
| chr19 | 14541666 | 14546666 | NM_002741 | yes |
| chr19 | 11543966 | 11548966 | NM_002743 | yes |
| chr1 | 151224697 | 151229697 | NM_002810 | yes |
| chr20 | 25226206 | 25231206 | NM_002862 | yes |
| chr19 | 18312374 | 18317374 | NM_002866 | yes |
| chr1 | 153956353 | 153961353 | NM_002870 | yes |
| chr1 | 182571048 | 182576048 | NM_002928 | yes |
| chr1 | 153327830 | 153332830 | NM_002965 | yes |
| chr1 | 151964214 | 151969214 | NM_002966 | yes |
| chrX | 23798775 | 23803775 | NM_002970 | yes |
| chr19 | 51224105 | 51229105 | NM_002975 | yes |
| chr1 | 168543211 | 168548211 | NM_002995 | yes |
| chr7 | 37954025 | 37959025 | NM_003014 | yes |
| chr9 | 38066710 | 38071710 | NM_003028 | yes |
| chr2 | 65213995 | 65218995 | NM_003038 | yes |
| chr7 | 150754157 | 150759157 | NM_003040 | yes |
| chr1 | 27479121 | 27484121 | NM_003047 | yes |
| chr12 | 50476483 | 50481483 | NM_003076 | yes |
| chr9 | 139290389 | 139295389 | NM_003086 | yes |
| chr6 | 34722371 | 34727371 | NM_003093 | yes |
| chr1 | 168510735 | 168515735 | NM_003175 | yes |
| chr12 | 50132793 | 50137793 | NM_003217 | yes |
| chr11 | 1857733 | 1862733 | NM_003282 | yes |
| chr1 | 186341957 | 186346957 | NM_003292 | yes |
| chr11 | 2948150 | 2953150 | NM_003311 | yes |
| chr17 | 40167215 | 40172215 | NM_003315 | yes |
| chrX | 47050701 | 47055701 | NM_003334 | yes |
| chr3 | 48644598 | 48649598 | NM_003365 | yes |
| chr10 | 17267758 | 17272758 | NM_003380 | yes |
| chr12 | 49363141 | 49368141 | NM_003394 | yes |
| chr1 | 228133176 | 228138176 | NM_003395 | yes |
| chr11 | 107876908 | 107881908 | NM_003478 | yes |
| chr16 | 87900605 | 87905605 | NM_003486 | yes |
| chr6 | 27858463 | 27863463 | NM_003514 | yes |
| chr1 | 149811818 | 149816818 | NM_003516 | yes |
| chr1 | 149820128 | 149825128 | NM_003516_2 | yes |
| chr1 | 149856025 | 149861025 | NM_003517 | yes |
| chr6 | 27858703 | 27863703 | NM_003527 | yes |
| chr1 | 149855732 | 149860732 | NM_003528 | yes |
| chr1 | 149830225 | 149835225 | NM_003548 | yes |
| chr1 | 149801721 | 149806721 | NM_003548_2 | yes |
| chr1 | 150951999 | 150956999 | NM_003568 | yes |
| chr15 | 65501340 | 65506340 | NM_003613 | yes |
| chr17 | 40832132 | 40837132 | NM_003632 | yes |
| chr17 | 77810713 | 77815713 | NM_003655 | yes |
| chr3 | 5018597 | 5023597 | NM_003670 | yes |
| chr5 | 172754006 | 172759006 | NM_003714 | yes |
| chr9 | 140080554 | 140085554 | NM_003731 | yes |
| chr6 | 39194751 | 39199751 | NM_003740 | yes |
| chr16 | 11347539 | 11352539 | NM_003745 | yes |
| chr12 | 120905058 | 120910058 | NM_003769 | yes |
| chr17 | 39643616 | 39648616 | NM_003771 | yes |
| chr3 | 50357781 | 50362781 | NM_003773 | yes |
| chr12 | 89916083 | 89921083 | NM_003774 | yes |
| chr20 | 5104907 | 5109907 | NM_003818 | yes |
| chr19 | 48016015 | 48021015 | NM_003827 | yes |
| chr1 | 167520556 | 167525556 | NM_003851 | yes |
| chr12 | 93961098 | 93966098 | NM_003877 | yes |
| chr5 | 141013923 | 141018923 | NM_003883 | yes |
| chr10 | 72573204 | 72578204 | NM_003901 | yes |
| chr8 | 145699218 | 145704218 | NM_003923 | yes |
| chr17 | 76353660 | 76358660 | NM_003955 | yes |
| chr9 | 35789906 | 35794906 | NM_003995 | yes |
| chr6 | 41886465 | 41891465 | NM_004053 | yes |
| chr1 | 45263397 | 45268397 | NM_004073 | yes |
| chr12 | 56691675 | 56696675 | NM_004077 | yes |
| chrX | 106957791 | 106962791 | NM_004089 | yes |
| chr8 | 37885520 | 37890520 | NM_004095 | yes |
| chr20 | 30430920 | 30435920 | NM_004118 | yes |
| chr11 | 65653510 | 65658510 | NM_004214 | yes |
| chr11 | 57332680 | 57337680 | NM_004223 | yes |
| chr12 | 121085810 | 121090810 | NM_004276 | yes |
| chr1 | 9292363 | 9297363 | NM_004285 | yes |
| chr1 | 25254270 | 25259270 | NM_004350 | yes |
| chr12 | 120873393 | 120878393 | NM_004373 | yes |
| chr11 | 118659472 | 118664472 | NM_004397 | yes |
| chr5 | 172195703 | 172200703 | NM_004417 | yes |
| chr8 | 22548315 | 22553315 | NM_004430 | yes |
| chr9 | 131578279 | 131583279 | NM_004435 | yes |
| chr17 | 65819280 | 65824280 | NM_004459 | yes |
| chr1 | 47899189 | 47904189 | NM_004474 | yes |
| chr19 | 46365018 | 46370018 | NM_004497 | yes |
| chr6 | 44231025 | 44236025 | NM_004556 | yes |
| chr14 | 68064517 | 68069517 | NM_004569 | yes |
| chr14 | 24738333 | 24743333 | NM_004581 | yes |
| chr11 | 67156923 | 67161923 | NM_004584 | yes |
| chr19 | 46193074 | 46198074 | NM_004597 | yes |
| chr16 | 30100705 | 30105705 | NM_004608 | yes |
| chr11 | 75915074 | 75920074 | NM_004626 | yes |
| chr12 | 123754187 | 123759187 | NM_004642 | yes |
| chr16 | 67512589 | 67517589 | NM_004691 | yes |
| chr3 | 51973457 | 51978457 | NM_004704 | yes |
| chr15 | 55698074 | 55703074 | NM_004748 | yes |
| chr1 | 12675237 | 12680237 | NM_004753 | yes |
| chr1 | 52605266 | 52610266 | NM_004799 | yes |
| chr12 | 49243457 | 49248457 | NM_004818 | yes |
| chr19 | 46364048 | 46369048 | NM_004819 | yes |
| chr19 | 14140052 | 14145052 | NM_004843 | yes |
| chr19 | 50866587 | 50871587 | NM_004851 | yes |
| chr17 | 7515715 | 7520715 | NM_004860 | yes |
| chr19 | 18494270 | 18499270 | NM_004864 | yes |
| chr10 | 43902156 | 43907156 | NM_004966 | yes |
| chr1 | 160048860 | 160053860 | NM_004983 | yes |
| chr19 | 35627863 | 35632863 | NM_005031 | yes |
| chr1 | 151801848 | 151806848 | NM_005060 | yes |
| chr1 | 145505057 | 145510057 | NM_005105 | yes |
| chr3 | 38385751 | 38390751 | NM_005108 | yes |
| chr3 | 38204526 | 38209526 | NM_005109 | yes |
| chr17 | 60140143 | 60145143 | NM_005121 | yes |
| chr22 | 50961534 | 50966534 | NM_005138 | yes |
| chr1 | 113255450 | 113260450 | NM_005167 | yes |
| chr12 | 54067609 | 54072609 | NM_005176 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr11 | 64946804 | 64951804 | NM_005186 | yes |
| chr11 | 119074486 | 119079486 | NM_005188 | yes |
| chr17 | 77749477 | 77754477 | NM_005189 | yes |
| chr17 | 1357061 | 1362061 | NM_005206 | yes |
| chr22 | 21269214 | 21274214 | NM_005207 | yes |
| chr1 | 155033713 | 155038713 | NM_005227 | yes |
| chr1 | 92949933 | 92954933 | NM_005263 | yes |
| chr1 | 27716648 | 27721648 | NM_005281 | yes |
| chr19 | 35839945 | 35844945 | NM_005303 | yes |
| chr17 | 73773516 | 73778516 | NM_005324 | yes |
| chr19 | 16219990 | 16224990 | NM_005370 | yes |
| chr1 | 146641668 | 146646668 | NM_005399 | yes |
| chr12 | 49369736 | 49374736 | NM_005430 | yes |
| chr12 | 6859582 | 6864582 | NM_005439 | yes |
| chr5 | 141390120 | 141395120 | NM_005471 | yes |
| chr12 | 111841252 | 111846252 | NM_005475 | yes |
| chr19 | 6765023 | 6770023 | NM_005490 | yes |
| chr11 | 65623304 | 65628304 | NM_005507 | yes |
| chr1 | 26796402 | 26801402 | NM_005517 | yes |
| chr3 | 193851431 | 193856431 | NM_005524 | yes |
| chr1 | 152007011 | 152012011 | NM_005620 | yes |
| chr1 | 29506137 | 29511137 | NM_005626 | yes |
| chr2 | 231787441 | 231792441 | NM_005683 | yes |
| chr11 | 65360967 | 65365967 | NM_005714 | yes |
| chr10 | 104260012 | 104265012 | NM_005736 | yes |
| chr1 | 47653271 | 47658271 | NM_005764 | yes |
| chr12 | 7123342 | 7128342 | NM_005768 | yes |
| chr12 | 56613215 | 56618215 | NM_005785 | yes |
| chr3 | 183964259 | 183969259 | NM_005787 | yes |
| chr17 | 39842627 | 39847627 | NM_005801 | yes |
| chr7 | 100301176 | 100306176 | NM_005837 | yes |
| chr11 | 67273699 | 67278699 | NM_005851 | yes |
| chr3 | 136468745 | 136473745 | NM_005862 | yes |
| chr2 | 220297200 | 220302200 | NM_005876 | yes |
| chr17 | 43296792 | 43301792 | NM_005892 | yes |
| chr2 | 209117367 | 209122367 | NM_005896 | yes |
| chr2 | 85763601 | 85768601 | NM_005911 | yes |
| chr1 | 156468134 | 156473134 | NM_005920 | yes |
| chr3 | 196754187 | 196759187 | NM_005929 | yes |
| chr19 | 6277459 | 6282459 | NM_005934 | yes |
| chr1 | 38322792 | 38327792 | NM_005955 | yes |
| chr1 | 153535806 | 153540806 | NM_005978 | yes |
| chr1 | 153598215 | 153603215 | NM_005979 | yes |
| chr22 | 19163876 | 19168876 | NM_005984 | yes |
| chr20 | 48597013 | 48602013 | NM_005985 | yes |
| chr22 | 19741726 | 19746726 | NM_005992 | yes |
| chr21 | 47741536 | 47746536 | NM_006031 | yes |
| chr12 | 49522804 | 49527804 | NM_006082 | yes |
| chr14 | 24627922 | 24632922 | NM_006084 | yes |
| chr12 | 48149744 | 48154744 | NM_006105 | yes |
| chr1 | 27187133 | 27192133 | NM_006142 | yes |
| chr12 | 54687063 | 54692063 | NM_006163 | yes |
| chr2 | 201825924 | 201830924 | NM_006190 | yes |
| chr3 | 178863811 | 178868811 | NM_006218 | yes |
| chr12 | 49686409 | 49691409 | NM_006262 | yes |
| chr1 | 153598373 | 153603373 | NM_006271 | yes |
| chr2 | 112653691 | 112658691 | NM_006343 | yes |
| chr9 | 100742989 | 100747989 | NM_006401 | yes |
| chr19 | 42461028 | 42466028 | NM_006423 | yes |
| chr17 | 39965951 | 39970951 | NM_006455 | yes |
| chr17 | 43222184 | 43227184 | NM_006460 | yes |
| chr1 | 110088686 | 110093686 | NM_006496 | yes |
| chr17 | 1955893 | 1960893 | NM_006497 | yes |
| chr20 | 52197136 | 52202136 | NM_006526 | yes |
| chr14 | 50996876 | 51001876 | NM_006575 | yes |
| chr1 | 156644689 | 156649689 | NM_006617 | yes |
| chr11 | 72502250 | 72507250 | NM_006645 | yes |
| chr6 | 41745143 | 41750143 | NM_006653 | yes |
| chr19 | 45905812 | 45910812 | NM_006663 | yes |
| chr6 | 34357957 | 34362957 | NM_006703 | yes |
| chr11 | 118824508 | 118829508 | NM_006760 | yes |
| chr1 | 87791651 | 87796651 | NM_006769 | yes |
| chr11 | 65079789 | 65084789 | NM_006779 | yes |
| chr11 | 64643740 | 64648740 | NM_006795 | yes |
| chr19 | 48892310 | 48897310 | NM_006801 | yes |
| chr5 | 137087539 | 137092539 | NM_006805 | yes |
| chr12 | 124066576 | 124071576 | NM_006815 | yes |
| chr1 | 151029651 | 151034651 | NM_006818 | yes |
| chr1 | 79083567 | 79088567 | NM_006820 | yes |
| chr19 | 1602983 | 1607983 | NM_006830 | yes |
| chr11 | 65655375 | 65660375 | NM_006848 | yes |
| chr14 | 90860827 | 90865827 | NM_006888 | yes |
| chr12 | 8086392 | 8091392 | NM_006931 | yes |
| chr10 | 103540670 | 103545670 | NM_006993 | yes |
| chr11 | 130296388 | 130301388 | NM_007037 | yes |
| chr1 | 145713139 | 145718139 | NM_007053 | yes |
| chr6 | 35433678 | 35438678 | NM_007104 | yes |
| chr6 | 41700298 | 41705298 | NM_007162 | yes |
| chr1 | 112295690 | 112300690 | NM_007204 | yes |
| chr12 | 57608078 | 57613078 | NM_007224 | yes |
| chr17 | 47650798 | 47655798 | NM_007225 | yes |
| chr1 | 109286785 | 109291785 | NM_007269 | yes |
| chr7 | 26238331 | 26243331 | NM_007276 | yes |
| chr22 | 19947570 | 19952570 | NM_007310 | yes |
| chr1 | 161733534 | 161738534 | NM_007348 | yes |
| chr8 | 145548082 | 145553082 | NM_012079 | yes |
| chr1 | 150227638 | 150232638 | NM_012113 | yes |
| chr17 | 71305643 | 71310643 | NM_012121 | yes |
| chr15 | 43474966 | 43479966 | NM_012142 | yes |
| chr19 | 46140175 | 46145175 | NM_012155 | yes |
| chr5 | 41922856 | 41927856 | NM_012176 | yes |
| chr12 | 120737624 | 120742624 | NM_012240 | yes |
| chr6 | 13572359 | 13577359 | NM_012241 | yes |
| chr16 | 30454796 | 30459796 | NM_012248 | yes |
| chr2 | 46767367 | 46772367 | NM_012249 | yes |
| chr6 | 52439362 | 52444362 | NM_012288 | yes |
| chr19 | 1064665 | 1069665 | NM_012292 | yes |
| chr1 | 32571144 | 32576144 | NM_012316 | yes |
| chr10 | 28963924 | 28968924 | NM_012342 | yes |
| chr1 | 161085366 | 161090366 | NM_012394 | yes |
| chr7 | 44885225 | 44890225 | NM_012412 | yes |
| chr17 | 65370829 | 65375897 | NM_012417 | yes |
| chr6 | 74361237 | 74366237 | NM_012434 | yes |
| chr17 | 73849001 | 73854001 | NM_012478 | yes |
| chr11 | 67138706 | 67143706 | NM_013246 | yes |
| chr8 | 145632233 | 145637233 | NM_013291 | yes |
| chr12 | 110903732 | 110908732 | NM_013300 | yes |
| chr16 | 22215092 | 22220092 | NM_013302 | yes |
| chr11 | 64792380 | 64797380 | NM_013306 | yes |
| chr3 | 50646762 | 50651762 | NM_013324 | yes |
| chr17 | 897633 | 902633 | NM_013337 | yes |
| chr1 | 151146047 | 151151047 | NM_013353 | yes |
| chr9 | 140080557 | 140085557 | NM_013366 | yes |
| chr6 | 26594671 | 26599671 | NM_013375 | yes |
| chr6 | 41746000 | 41751000 | NM_013397 | yes |
| chr11 | 61582029 | 61587029 | NM_013402 | yes |
| chr8 | 145667312 | 145672312 | NM_013432 | yes |
| chr19 | 16293712 | 16298712 | NM_014077 | yes |
| chr7 | 73621587 | 73626587 | NM_014146 | yes |
| chr11 | 64882710 | 64887710 | NM_014205 | yes |
| chr1 | 156826212 | 156831212 | NM_014215 | yes |
| chr3 | 45633823 | 45638823 | NM_014240 | yes |
| chr12 | 6935038 | 6940038 | NM_014262 | yes |
| chr1 | 25662289 | 25667289 | NM_014313 | yes |
| chr12 | 109122826 | 109127826 | NM_014325 | yes |
| chr15 | 64336021 | 64341021 | NM_014326 | yes |
| chr11 | 35637235 | 35642235 | NM_014344 | yes |
| chr1 | 174966392 | 174971392 | NM_014412 | yes |
| chr19 | 47731951 | 47736951 | NM_014417 | yes |
| chr5 | 148756338 | 148761338 | NM_014443 | yes |
| chr6 | 47275183 | 47280183 | NM_014452 | yes |
| chr11 | 2441775 | 2446775 | NM_014555 | yes |
| chr1 | 40102848 | 40107848 | NM_014571 | yes |
| chr17 | 36505507 | 36510507 | NM_014598 | yes |
| chr19 | 48214101 | 48219101 | NM_014601 | yes |
| chr5 | 175872856 | 175877856 | NM_014613 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr1 | 153506217 | 153511217 | NM_014624 | yes |
| chr22 | 22304750 | 22309750 | NM_014634 | yes |
| chr2 | 219573068 | 219578068 | NM_014640 | yes |
| chr1 | 44409978 | 44414978 | NM_014652 | yes |
| chr1 | 31378980 | 31383980 | NM_014654 | yes |
| chr19 | 47850038 | 47855038 | NM_014681 | yes |
| chr3 | 183964945 | 183969945 | NM_014693 | yes |
| chr12 | 108952665 | 108957665 | NM_014706 | yes |
| chr19 | 36206421 | 36211421 | NM_014727 | yes |
| chr11 | 73017163 | 73022163 | NM_014786 | yes |
| chr11 | 72850643 | 72855643 | NM_014824 | yes |
| chr12 | 57397797 | 57402797 | NM_014830 | yes |
| chr1 | 153916654 | 153921654 | NM_014856 | yes |
| chr1 | 205194538 | 205199538 | NM_014858 | yes |
| chr1 | 212001614 | 212006614 | NM_014873 | yes |
| chr10 | 94048375 | 94053375 | NM_014912 | yes |
| chr6 | 52924100 | 52929100 | NM_014920 | yes |
| chr19 | 12946759 | 12951759 | NM_014975 | yes |
| chr7 | 129707849 | 129712849 | NM_014997 | yes |
| chr1 | 39872676 | 39877676 | NM_015038 | yes |
| chr1 | 10268264 | 10273264 | NM_015074 | yes |
| chr11 | 118474713 | 118479713 | NM_015157 | yes |
| chr8 | 67338763 | 67343763 | NM_015169 | yes |
| chr1 | 171452166 | 171457166 | NM_015172 | yes |
| chr11 | 111470615 | 111475615 | NM_015191 | yes |
| chr10 | 101767210 | 101772210 | NM_015221 | yes |
| chr5 | 133859298 | 133864298 | NM_015288 | yes |
| chr22 | 32338848 | 32343848 | NM_015372 | yes |
| chr9 | 139938176 | 139943176 | NM_015392 | yes |
| chr4 | 113556112 | 113561112 | NM_015454 | yes |
| chr10 | 102277095 | 102282095 | NM_015490 | yes |
| chr15 | 75491721 | 75496721 | NM_015492 | yes |
| chr2 | 171782536 | 171787536 | NM_015530 | yes |
| chr1 | 78145843 | 78150843 | NM_015534 | yes |
| chr1 | 156568779 | 156573779 | NM_015590 | yes |
| chr20 | 33678118 | 33683118 | NM_015638 | yes |
| chr19 | 46386928 | 46391928 | NM_015649 | yes |
| chr19 | 2473623 | 2478623 | NM_015675 | yes |
| chr19 | 48246293 | 48251293 | NM_015710 | yes |
| chr7 | 100491041 | 100496041 | NM_015831 | yes |
| chr1 | 26493888 | 26498888 | NM_015871 | yes |
| chr12 | 121016697 | 121021697 | NM_015918 | yes |
| chr17 | 7195376 | 7200376 | NM_015982 | yes |
| chr8 | 71578947 | 71583947 | NM_016027 | yes |
| chr11 | 66203819 | 66208819 | NM_016050 | yes |
| chr7 | 100885871 | 100890871 | NM_016068 | yes |
| chr19 | 12777965 | 12782965 | NM_016145 | yes |
| chr16 | 19893733 | 19898733 | NM_016235 | yes |
| chr1 | 202933904 | 202938904 | NM_016243 | yes |
| chr19 | 49337434 | 49342434 | NM_016246 | yes |
| chr6 | 17598018 | 17603018 | NM_016255 | yes |
| chr1 | 29060636 | 29065636 | NM_016258 | yes |
| chr10 | 76856748 | 76861748 | NM_016364 | yes |
| chr11 | 10560274 | 10565274 | NM_016422 | yes |
| chr2 | 97521256 | 97526256 | NM_016466 | yes |
| chr5 | 141336127 | 141341127 | NM_016580 | yes |
| chr17 | 40831345 | 40836345 | NM_016602 | yes |
| chr12 | 54376446 | 54381446 | NM_017409 | yes |
| chr11 | 64609541 | 64614541 | NM_017525 | yes |
| chr3 | 122397172 | 122402172 | NM_017554 | yes |
| chr17 | 33446131 | 33451131 | NM_017559 | yes |
| chr19 | 2048743 | 2053743 | NM_017572 | yes |
| chr1 | 154528620 | 154533620 | NM_017582 | yes |
| chr10 | 104675575 | 104680575 | NM_017649 | yes |
| chr2 | 97533235 | 97538235 | NM_017789 | yes |
| chr10 | 94048420 | 94053420 | NM_017824 | yes |
| chr1 | 36551953 | 36556953 | NM_017825 | yes |
| chr1 | 27111954 | 27116954 | NM_017837 | yes |
| chr8 | 95833018 | 95838018 | NM_017864 | yes |
| chr10 | 102293141 | 102298141 | NM_017902 | yes |
| chr14 | 55735521 | 55740521 | NM_017943 | yes |
| chr9 | 77565302 | 77570302 | NM_017998 | yes |
| chr5 | 150078169 | 150083169 | NM_018047 | yes |
| chr7 | 4920835 | 4925835 | NM_018059 | yes |
| chr1 | 201795788 | 201800788 | NM_018085 | yes |
| chr3 | 72895098 | 72900098 | NM_018130 | yes |
| chr19 | 14244940 | 14249940 | NM_018154 | yes |
| chr1 | 205323628 | 205328628 | NM_018203 | yes |
| chr1 | 65208278 | 65213278 | NM_018211 | yes |
| chr8 | 37704931 | 37709931 | NM_018310 | yes |
| chr17 | 48553661 | 48558661 | NM_018346 | yes |
| chr3 | 194390706 | 194395706 | NM_018385 | yes |
| chr4 | 113555651 | 113560651 | NM_018392 | yes |
| chr12 | 10824391 | 10829391 | NM_018423 | yes |
| chr1 | 11721650 | 11726650 | NM_018438 | yes |
| chr17 | 48472414 | 48477414 | NM_018509 | yes |
| chr17 | 207221922 | 207226922 | NM_018566 | yes |
| chr15 | 34632862 | 34637862 | NM_018648 | yes |
| chr15 | 90292040 | 90297040 | NM_018670 | yes |
| chr17 | 71186673 | 71191673 | NM_018714 | yes |
| chr1 | 207036654 | 207041654 | NM_018724 | yes |
| chr17 | 46679834 | 46684834 | NM_018952 | yes |
| chr12 | 54424332 | 54429332 | NM_018953 | yes |
| chr12 | 122229094 | 122234094 | NM_019034 | yes |
| chr10 | 74031177 | 74036177 | NM_019058 | yes |
| chr15 | 41219031 | 41224031 | NM_019074 | yes |
| chr19 | 42744236 | 42749236 | NM_019884 | yes |
| chr1 | 109630903 | 109635903 | NM_020141 | yes |
| chr12 | 57631975 | 57636975 | NM_020142 | yes |
| chr19 | 49942308 | 49947308 | NM_020309 | yes |
| chr22 | 38052237 | 38057237 | NM_020315 | yes |
| chr4 | 71551696 | 71556696 | NM_020368 | yes |
| chr17 | 37305402 | 37310402 | NM_020405 | yes |
| chr20 | 42813718 | 42818718 | NM_020433 | yes |
| chr1 | 24739745 | 24744745 | NM_020448 | yes |
| chr1 | 26124167 | 26129167 | NM_020451 | yes |
| chr1 | 154297776 | 154302776 | NM_020452 | yes |
| chr16 | 67873713 | 67878713 | NM_020457 | yes |
| chr14 | 35871460 | 35876460 | NM_020529 | yes |
| chr20 | 24970925 | 24975925 | NM_020531 | yes |
| chr17 | 73509164 | 73514164 | NM_020753 | yes |
| chr1 | 11536795 | 11541795 | NM_020780 | yes |
| chr15 | 74420243 | 74425243 | NM_020851 | yes |
| chr15 | 41184128 | 41189128 | NM_020857 | yes |
| chr17 | 7618172 | 7623172 | NM_020877 | yes |
| chr20 | 33541138 | 33546138 | NM_020884 | yes |
| chr1 | 33205012 | 33210012 | NM_020888 | yes |
| chr12 | 125397087 | 125402087 | NM_021009 | yes |
| chr12 | 56549545 | 56554545 | NM_021019 | yes |
| chr12 | 49486102 | 49491102 | NM_021044 | yes |
| chr11 | 1966002 | 1971002 | NM_021134 | yes |
| chr7 | 92074262 | 92079262 | NM_021167 | yes |
| chr19 | 38823943 | 38828943 | NM_021185 | yes |
| chr2 | 176962030 | 176967030 | NM_021193 | yes |
| chr1 | 211749599 | 211754599 | NM_021194 | yes |
| chr10 | 75399015 | 75404015 | NM_021245 | yes |
| chr20 | 44934637 | 44939637 | NM_021248 | yes |
| chr17 | 8019360 | 8024360 | NM_021628 | yes |
| chr2 | 12854498 | 12859498 | NM_021643 | yes |
| chr19 | 35627193 | 35632193 | NM_021902 | yes |
| chr6 | 35417638 | 35422638 | NM_021922 | yes |
| chr17 | 39966462 | 39971462 | NM_021939 | yes |
| chr19 | 35631654 | 35636654 | NM_022006 | yes |
| chr22 | 21994042 | 21999042 | NM_022044 | yes |
| chr6 | 35263095 | 35268095 | NM_022047 | yes |
| chr11 | 6702132 | 6707132 | NM_022061 | yes |
| chr11 | 125032059 | 125037059 | NM_022062 | yes |
| chr16 | 836122 | 841122 | NM_022092 | yes |
| chr1 | 40234520 | 40239520 | NM_022120 | yes |
| chr6 | 138426160 | 138431160 | NM_022121 | yes |
| chr1 | 179048612 | 179053612 | NM_022371 | yes |
| chr17 | 880498 | 885498 | NM_022463 | yes |
| chr3 | 178787156 | 178792156 | NM_022470 | yes |
| chr14 | 23524247 | 23529247 | NM_022478 | yes |
| chr2 | 74707700 | 74712700 | NM_022492 | yes |
| chr7 | 100284370 | 100289370 | NM_022574 | yes |

TABLE S1-continued

Constitutive CTCF peaks within a constitutive IN
across HCT116, Jurkat, K562 within 2.5 kb of TSS

| chr | start | stop | gene | loops to differential enhancers |
|---|---|---|---|---|
| chr12 | 54400390 | 54405390 | NM_022658 | yes |
| chr22 | 19129690 | 19134690 | NM_022719 | yes |
| chr11 | 62356609 | 62361609 | NM_022830 | yes |
| chr19 | 39901250 | 39906250 | NM_022835 | yes |
| chr5 | 176514051 | 176519051 | NM_022963 | yes |
| chr1 | 32799340 | 32804340 | NM_023009 | yes |
| chr1 | 53161538 | 53166538 | NM_023077 | yes |
| chr19 | 17413977 | 17418977 | NM_023937 | yes |
| chr16 | 762673 | 767673 | NM_024042 | yes |
| chr12 | 56615625 | 56620625 | NM_024068 | yes |
| chr7 | 99814371 | 99819371 | NM_024070 | yes |
| chr16 | 30438873 | 30443873 | NM_024096 | yes |
| chr1 | 43230416 | 43235416 | NM_024097 | yes |
| chr19 | 981828 | 986828 | NM_024100 | yes |
| chr12 | 102222145 | 102227145 | NM_024312 | yes |
| chr7 | 86846814 | 86851814 | NM_024315 | yes |
| chr2 | 232788613 | 232793613 | NM_024409 | yes |
| chr18 | 43649750 | 43654750 | NM_024430 | yes |
| chr16 | 29825028 | 29830028 | NM_024516 | yes |
| chr19 | 17411782 | 17416782 | NM_024527 | yes |
| chr1 | 193088588 | 193093588 | NM_024529 | yes |
| chr2 | 220405987 | 220410987 | NM_024536 | yes |
| chr1 | 151126605 | 151131605 | NM_024575 | yes |
| chr17 | 78963141 | 78968141 | NM_024591 | yes |
| chr8 | 9005720 | 9010720 | NM_024607 | yes |
| chr1 | 38271365 | 38276365 | NM_024640 | yes |
| chr16 | 30535410 | 30540410 | NM_024671 | yes |
| chr1 | 220861128 | 220866128 | NM_024709 | yes |
| chr17 | 40826548 | 40831548 | NM_024927 | yes |
| chr11 | 65625372 | 65630372 | NM_025128 | yes |
| chr3 | 196693242 | 196698242 | NM_025163 | yes |
| chr9 | 35113408 | 35118408 | NM_025182 | yes |
| chr8 | 126440063 | 126445063 | NM_025195 | yes |
| chr4 | 7067437 | 7072437 | NM_025196 | yes |
| chr3 | 52310159 | 52315159 | NM_025222 | yes |
| chr12 | 12712948 | 12717948 | NM_030640 | yes |
| chr1 | 249117654 | 249122654 | NM_030645 | yes |
| chr19 | 46316105 | 46321105 | NM_030785 | yes |
| chr11 | 75234099 | 75239099 | NM_030792 | yes |
| chr20 | 30537383 | 30542383 | NM_030815 | yes |
| chr15 | 73073626 | 73078626 | NM_031284 | yes |
| chr1 | 26603713 | 26608713 | NM_031286 | yes |
| chr3 | 46536985 | 46541985 | NM_031440 | yes |
| chr11 | 63971652 | 63976652 | NM_031471 | yes |
| chr19 | 54413491 | 54418491 | NM_031896 | yes |
| chr14 | 94593457 | 94598457 | NM_032036 | yes |
| chr1 | 202429371 | 202434371 | NM_032103 | yes |
| chr16 | 67698159 | 67703159 | NM_032140 | yes |
| chr5 | 125934107 | 125939107 | NM_032177 | yes |
| chr11 | 64105190 | 64110190 | NM_032251 | yes |
| chr1 | 27150701 | 27155701 | NM_032283 | yes |
| chr1 | 245130671 | 245135671 | NM_032328 | yes |
| chr19 | 12778017 | 12783017 | NM_032332 | yes |
| chr12 | 56319197 | 56324197 | NM_032345 | yes |
| chr17 | 46797382 | 46802382 | NM_032391 | yes |
| chr15 | 45720227 | 45725227 | NM_032413 | yes |
| chr10 | 98590212 | 98595212 | NM_032440 | yes |
| chr17 | 73898681 | 73903681 | NM_032478 | yes |
| chr1 | 40135210 | 40140210 | NM_032526 | yes |
| chr2 | 27502797 | 27507797 | NM_032546 | yes |
| chr19 | 914842 | 919842 | NM_032551 | yes |
| chr14 | 21507885 | 21512885 | NM_032572 | yes |
| chr16 | 4379725 | 4384725 | NM_032575 | yes |
| chr7 | 23051270 | 23056270 | NM_032581 | yes |
| chr17 | 48225378 | 48230378 | NM_032595 | yes |
| chr1 | 32710318 | 32715318 | NM_032648 | yes |
| chr8 | 145688349 | 145693349 | NM_032687 | yes |
| chr22 | 20847670 | 20852670 | NM_032775 | yes |
| chr2 | 74707857 | 74712857 | NM_032779 | yes |
| chr12 | 122061955 | 122066955 | NM_032790 | yes |
| chr6 | 150182980 | 150187980 | NM_032832 | yes |
| chr17 | 27945941 | 27950941 | NM_032854 | yes |
| chr15 | 85195074 | 85200074 | NM_032856 | yes |
| chr11 | 73085213 | 73090213 | NM_032871 | yes |
| chr12 | 53643376 | 53648376 | NM_032889 | yes |
| chr16 | 57494051 | 57499051 | NM_032940 | yes |
| chr3 | 196754186 | 196759186 | NM_033316 | yes |
| chr17 | 28254558 | 28259558 | NM_033389 | yes |
| chr11 | 109961587 | 109966587 | NM_033390 | yes |
| chr9 | 37901850 | 37906850 | NM_033412 | yes |
| chr15 | 40396139 | 40401139 | NM_033503 | yes |
| chr9 | 100952456 | 100957456 | NM_052820 | yes |
| chr22 | 37821005 | 37826005 | NM_052906 | yes |
| chr22 | 42320321 | 42325321 | NM_052945 | yes |
| chr8 | 11321776 | 11326776 | NM_053279 | yes |
| chr2 | 219855627 | 219860627 | NM_057093 | yes |
| chr1 | 55462117 | 55467117 | NM_057176 | yes |
| chr8 | 95904982 | 95909982 | NM_057749 | yes |
| chr1 | 32401488 | 32406488 | NM_080391 | yes |
| chr11 | 78126368 | 78131368 | NM_080491 | yes |
| chr12 | 7053240 | 7058240 | NM_080548 | yes |
| chr5 | 133745098 | 133750098 | NM_080656 | yes |
| chr20 | 631514 | 636514 | NM_080725 | yes |
| chr20 | 49250955 | 49255955 | NM_080829 | yes |
| chr1 | 160922089 | 160927089 | NM_080878 | yes |
| chr7 | 37023371 | 37028371 | NM_130442 | yes |
| chr17 | 38373074 | 38378074 | NM_133264 | yes |
| chr5 | 176235060 | 176240060 | NM_133369 | yes |
| chr17 | 43207400 | 43212400 | NM_133373 | yes |
| chr1 | 198123608 | 198128608 | NM_133494 | yes |
| chr15 | 41163987 | 41168987 | NM_133639 | yes |
| chr13 | 21274982 | 21279982 | NM_138284 | yes |
| chr1 | 154931758 | 154936758 | NM_138300 | yes |
| chr3 | 183945717 | 183950717 | NM_138345 | yes |
| chr15 | 45490873 | 45495873 | NM_138356 | yes |
| chr8 | 145978470 | 145983470 | NM_138367 | yes |
| chr11 | 65545562 | 65550562 | NM_138368 | yes |
| chr14 | 20771653 | 20776653 | NM_138376 | yes |
| chr8 | 145731919 | 145736919 | NM_138431 | yes |
| chr19 | 18043405 | 18048405 | NM_138442 | yes |
| chr14 | 24766166 | 24771166 | NM_138452 | yes |
| chr7 | 27050730 | 27055730 | NM_138463 | yes |
| chr1 | 75196340 | 75201340 | NM_138467 | yes |
| chr8 | 145687918 | 145692918 | NM_138496 | yes |
| chr6 | 126275361 | 126280361 | NM_138571 | yes |
| chr19 | 997918 | 1002918 | NM_138690 | yes |
| chr6 | 149885028 | 149890028 | NM_138785 | yes |
| chr19 | 1809775 | 1814775 | NM_138813 | yes |
| chr11 | 124629723 | 124634723 | NM_138961 | yes |
| chr5 | 5137943 | 5142943 | NM_139056 | yes |
| chr6 | 149864738 | 149869738 | NM_139126 | yes |
| chr19 | 35623678 | 35628678 | NM_139284 | yes |
| chr9 | 116204509 | 116209509 | NM_144488 | yes |
| chr9 | 116353700 | 116358700 | NM_144489 | yes |
| chr12 | 56658142 | 56663142 | NM_144576 | yes |
| chr19 | 48820832 | 48825832 | NM_144577 | yes |
| chr10 | 76993270 | 76998270 | NM_144589 | yes |
| chr18 | 44234496 | 44239496 | NM_144612 | yes |
| chr1 | 151040580 | 151045580 | NM_144618 | yes |
| chr17 | 27227589 | 27232589 | NM_144683 | yes |
| chr1 | 156887924 | 156892924 | NM_144702 | yes |
| chr19 | 35643172 | 35648172 | NM_144779 | yes |
| chr19 | 47161895 | 47166895 | NM_145056 | yes |
| chr1 | 33935732 | 33940732 | NM_145238 | yes |
| chr1 | 59009971 | 59014971 | NM_145243 | yes |
| chr2 | 11884222 | 11889222 | NM_145693 | yes |
| chr8 | 145689220 | 145694220 | NM_145754 | yes |
| chr11 | 34377055 | 34382055 | NM_145804 | yes |
| chr19 | 49173838 | 49178838 | NM_145807 | yes |
| chr18 | 12656238 | 12661238 | NM_147163 | yes |
| chr17 | 38518445 | 38523445 | NM_152222 | yes |
| chr11 | 73084905 | 73089905 | NM_152222 | yes |
| chr14 | 55736372 | 55741372 | NM_152231 | yes |
| chr10 | 98477779 | 98482779 | NM_152309 | yes |
| chr17 | 27918027 | 27923027 | NM_152345 | yes |
| chr19 | 40021007 | 40026007 | NM_152361 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr1 | 40994733 | 40999733 | NM_152373 | yes |
| chr2 | 170333506 | 170338506 | NM_152384 | yes |
| chr8 | 96034714 | 96039714 | NM_152416 | yes |
| chr9 | 77640846 | 77645846 | NM_152420 | yes |
| chr14 | 68166103 | 68171103 | NM_152443 | yes |
| chr1 | 95580394 | 95585394 | NM_152487 | yes |
| chr22 | 42093018 | 42098018 | NM_152513 | yes |
| chr2 | 230931215 | 230936215 | NM_152527 | yes |
| chr16 | 57123955 | 57128955 | NM_152727 | yes |
| chr19 | 1235490 | 1240490 | NM_152769 | yes |
| chr9 | 35094098 | 35099098 | NM_152850 | yes |
| chr2 | 178974651 | 178979651 | NM_152945 | yes |
| chr5 | 96476020 | 96481020 | NM_153234 | yes |
| chr1 | 45250926 | 45255926 | NM_153274 | yes |
| chrX | 47047699 | 47052699 | NM_153280 | yes |
| chr17 | 6944742 | 6949742 | NM_153357 | yes |
| chr15 | 34656895 | 34661895 | NM_153613 | yes |
| chr3 | 194404122 | 194409122 | NM_153690 | yes |
| chr4 | 141442812 | 141447812 | NM_153702 | yes |
| chr1 | 206969715 | 206974715 | NM_153758 | yes |
| chr2 | 170681518 | 170686518 | NM_172070 | yes |
| chr19 | 39756657 | 39761657 | NM_172138 | yes |
| chr19 | 39733146 | 39738146 | NM_172139 | yes |
| chr21 | 35733823 | 35738823 | NM_172201 | yes |
| chr18 | 3451272 | 3456272 | NM_173211 | yes |
| chr5 | 157168203 | 157173203 | NM_173491 | yes |
| chr10 | 134256214 | 134261214 | NM_173541 | yes |
| chr7 | 100079050 | 100084050 | NM_173564 | yes |
| chr11 | 63681816 | 63686816 | NM_173587 | yes |
| chr11 | 18745277 | 18750277 | NM_173588 | yes |
| chr12 | 56649643 | 56654643 | NM_173595 | yes |
| chr1 | 155143304 | 155148304 | NM_173852 | yes |
| chr12 | 122105060 | 122110060 | NM_173855 | yes |
| chr19 | 38891275 | 38896275 | NM_174905 | yes |
| chr8 | 145595204 | 145600204 | NM_174922 | yes |
| chr14 | 77605634 | 77610634 | NM_174976 | yes |
| chr19 | 50977234 | 50982234 | NM_175063 | yes |
| chr1 | 149856966 | 149861966 | NM_175065 | yes |
| chr12 | 50098697 | 50103697 | NM_175736 | yes |
| chr19 | 46269997 | 46274997 | NM_175875 | yes |
| chr7 | 106299134 | 106304134 | NM_175884 | yes |
| chr16 | 89005108 | 89010108 | NM_175931 | yes |
| chr19 | 1246052 | 1251052 | NM_177401 | yes |
| chr19 | 46192750 | 46197750 | NM_177542 | yes |
| chr20 | 33458161 | 33463161 | NM_178026 | yes |
| chr17 | 72917870 | 72922870 | NM_178160 | yes |
| chr17 | 27053332 | 27058332 | NM_178170 | yes |
| chr1 | 152746348 | 152751348 | NM_178354 | yes |
| chr1 | 152593079 | 152598079 | NM_178431 | yes |
| chr9 | 139962528 | 139967528 | NM_178448 | yes |
| chr17 | 1926139 | 1931139 | NM_178568 | yes |
| chr11 | 57225510 | 57230510 | NM_178570 | yes |
| chr5 | 67581752 | 67586752 | NM_181524 | yes |
| chr7 | 101458382 | 101463382 | NM_181552 | yes |
| chr10 | 35413885 | 35418885 | NM_181571 | yes |
| chr12 | 52398229 | 52403229 | NM_181711 | yes |
| chr17 | 6923869 | 6928869 | NM_181844 | yes |
| chr9 | 127536937 | 127541937 | NM_182487 | yes |
| chr2 | 11270679 | 11275679 | NM_182500 | yes |
| chr15 | 55579513 | 55584513 | NM_183235 | yes |
| chr14 | 74224501 | 74229501 | NM_194278 | yes |
| chr8 | 125382440 | 125387440 | NM_194291 | yes |
| chr3 | 39231577 | 39236577 | NM_194293 | yes |
| chr22 | 39926360 | 39931360 | NM_194326 | yes |
| chr12 | 56613253 | 56618253 | NM_194359 | yes |
| chr18 | 60380172 | 60385172 | NM_194449 | yes |
| chrX | 107016517 | 107021517 | NM_198057 | yes |
| chr1 | 85722855 | 85727855 | NM_198077 | yes |
| chr11 | 57333303 | 57338303 | NM_198183 | yes |
| chr12 | 121016701 | 121021701 | NM_198202 | yes |
| chr16 | 67916281 | 67921281 | NM_198443 | yes |
| chr1 | 204180720 | 204185720 | NM_198447 | yes |
| chr6 | 42844854 | 42849854 | NM_198486 | yes |
| chr8 | 86155216 | 86160216 | NM_198584 | yes |
| chr1 | 112295919 | 112300919 | NM_198926 | yes |
| chr9 | 140116587 | 140121587 | NM_199001 | yes |
| chr1 | 46803349 | 46808349 | NM_199044 | yes |
| chr5 | 37833093 | 37838093 | NM_199231 | yes |
| chr12 | 56323312 | 56328312 | NM_201444 | yes |
| chr2 | 85643554 | 85648554 | NM_201594 | yes |
| chr18 | 710017 | 715017 | NM_202758 | yes |
| chr9 | 131938040 | 131943040 | NM_203434 | yes |
| chr1 | 183619948 | 183624948 | NM_203454 | yes |
| chr17 | 73399290 | 73404290 | NM_203506 | yes |
| chr13 | 27841964 | 27846964 | NM_206827 | yes |
| chr19 | 7988551 | 7993551 | NM_206833 | yes |
| chr1 | 151412181 | 151417181 | NM_207171 | yes |
| chr17 | 73510109 | 73515109 | NM_207346 | yes |
| chr15 | 40630668 | 40635668 | NM_207380 | yes |
| chr19 | 14222500 | 14227500 | NM_207518 | yes |
| chr2 | 55273826 | 55278826 | NM_207521 | yes |
| chrX | 153626122 | 153631122 | NR_000011 | yes |
| chr19 | 17970897 | 17975897 | NR_000012 | yes |
| chr7 | 98868424 | 98873424 | NR_002147 | yes |
| chr1 | 155194825 | 155199825 | NR_002188 | yes |
| chr20 | 52489748 | 52494748 | NR_002189 | yes |
| chr11 | 2016605 | 2021605 | NR_002196 | yes |
| chr8 | 146217751 | 146222751 | NR_002807 | yes |
| chr12 | 7074269 | 7079269 | NR_003010 | yes |
| chr17 | 75082889 | 75087889 | NR_003013 | yes |
| chr1 | 109640315 | 109645315 | NR_003023 | yes |
| chr7 | 22893732 | 22898732 | NR_003075 | yes |
| chr20 | 43989309 | 43994309 | NR_003189 | yes |
| chr9 | 33621723 | 33626723 | NR_003573 | yes |
| chr16 | 2388423 | 2393423 | NR_003574 | yes |
| chr14 | 20792198 | 20797198 | NR_003693 | yes |
| chr19 | 51105720 | 51110720 | NR_004384 | yes |
| chr17 | 74555215 | 74560215 | NR_004395 | yes |
| chr17 | 74554690 | 74559690 | NR_004396 | yes |
| chr17 | 74552374 | 74557374 | NR_004397 | yes |
| chr16 | 29872655 | 29877655 | NR_015396 | yes |
| chr5 | 43039726 | 43044736 | NR_015447 | yes |
| chr7 | 5011116 | 5016116 | NR_015449 | yes |
| chr4 | 13546948 | 13551948 | NR_015450 | yes |
| chr1 | 22349184 | 22354184 | NR_023918 | yes |
| chr1 | 22349497 | 22354497 | NR_023919 | yes |
| chr6 | 150323780 | 150328780 | NR_024045 | yes |
| chr18 | 3591612 | 3596612 | NR_024101 | yes |
| chr1 | 151808445 | 151813445 | NR_024237 | yes |
| chr1 | 45767082 | 45772082 | NR_024270 | yes |
| chr9 | 35906980 | 35911980 | NR_024283 | yes |
| chr17 | 7816765 | 7821765 | NR_024349 | yes |
| chr16 | 29872504 | 29877504 | NR_024370 | yes |
| chr3 | 196666994 | 196671994 | NR_024388 | yes |
| chr6 | 52526699 | 52531699 | NR_024403 | yes |
| chr11 | 67082810 | 67087810 | NR_024469 | yes |
| chr20 | 61295473 | 61300473 | NR_024470 | yes |
| chr7 | 154717727 | 154722727 | NR_024476 | yes |
| chr3 | 194028093 | 194033093 | NR_024480 | yes |
| chr12 | 6860136 | 6865136 | NR_026581 | yes |
| chr12 | 110208792 | 110213792 | NR_026661 | yes |
| chr7 | 73146899 | 73151899 | NR_026690 | yes |
| chr6 | 170187669 | 170192669 | NR_026780 | yes |
| chr6 | 2985701 | 2990701 | NR_026856 | yes |
| chr16 | 2890252 | 2895252 | NR_026864 | yes |
| chr1 | 47897813 | 47902813 | NR_026878 | yes |
| chr6 | 87595109 | 87600109 | NR_026985 | yes |
| chr1 | 87592948 | 87597948 | NR_026988 | yes |
| chr15 | 78284067 | 78289067 | NR_026998 | yes |
| chr6 | 74017588 | 74022588 | NR_027005 | yes |
| chr1 | 204336347 | 204341347 | NR_027022 | yes |
| chr19 | 12200578 | 12205578 | NR_027049 | yes |
| chr15 | 74419119 | 74424119 | NR_027073 | yes |
| chr3 | 13689721 | 13694721 | NR_027103 | yes |
| chr5 | 173004137 | 173009137 | NR_027108 | yes |
| chr6 | 35702224 | 35707224 | NR_027117 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr11 | 45790483 | 45795483 | NR_027134 | yes |
| chr12 | 98907504 | 98912504 | NR_027157 | yes |
| chr22 | 46399996 | 46404996 | NR_027240 | yes |
| chr21 | 43526144 | 43531144 | NR_027243 | yes |
| chr2 | 43451850 | 43456850 | NR_027251 | yes |
| chr19 | 1267759 | 1272759 | NR_027271 | yes |
| chr4 | 40056319 | 40061319 | NR_027277 | yes |
| chr17 | 66192301 | 66197301 | NR_027283 | yes |
| chr12 | 52602214 | 52607214 | NR_027358 | yes |
| chr1 | 16969569 | 16974569 | NR_027504 | yes |
| chr6 | 26419119 | 26424119 | NR_027795 | yes |
| chr1 | 75196362 | 75201362 | NR_027962 | yes |
| chr17 | 2316230 | 2321230 | NR_028335 | yes |
| chr6 | 33548976 | 33553976 | NR_028361 | yes |
| chr17 | 73630175 | 73635175 | NR_028439 | yes |
| chr17 | 1417713 | 1422713 | NR_028514 | yes |
| chr22 | 46507066 | 46512066 | NR_029479 | yes |
| chr19 | 13944973 | 13949973 | NR_029495 | yes |
| chr19 | 13944673 | 13949673 | NR_029497 | yes |
| chr19 | 13944831 | 13949831 | NR_029501 | yes |
| chr7 | 130559069 | 130564069 | NR_029503 | yes |
| chr1 | 65521691 | 65526691 | NR_029516 | yes |
| chr7 | 130559798 | 130564798 | NR_029517 | yes |
| chr7 | 127845425 | 127850425 | NR_029596 | yes |
| chr15 | 89152556 | 89157556 | NR_029606 | yes |
| chr12 | 54383022 | 54388022 | NR_029617 | yes |
| chr12 | 62994966 | 62999966 | NR_029661 | yes |
| chr11 | 57406171 | 57411171 | NR_029673 | yes |
| chr3 | 52325824 | 52330824 | NR_029677 | yes |
| chr12 | 7070760 | 7075760 | NR_029682 | yes |
| chr17 | 56406179 | 56411179 | NR_029683 | yes |
| chr5 | 148805981 | 148810981 | NR_029684 | yes |
| chr5 | 148807709 | 148812709 | NR_029686 | yes |
| chr17 | 29884515 | 29889515 | NR_029710 | yes |
| chr17 | 6918520 | 6923520 | NR_029712 | yes |
| chr12 | 7070362 | 7075362 | NR_029779 | yes |
| chr11 | 64656411 | 64661411 | NR_029829 | yes |
| chr19 | 46139845 | 46144845 | NR_029886 | yes |
| chr12 | 54728500 | 54733500 | NR_029894 | yes |
| chr5 | 54463950 | 54468950 | NR_029960 | yes |
| chr17 | 6918841 | 6923841 | NR_030178 | yes |
| chr1 | 155162468 | 155167468 | NR_030281 | yes |
| chr7 | 5533048 | 5538048 | NR_030318 | yes |
| chr9 | 126162382 | 126167382 | NR_030332 | yes |
| chr10 | 98586021 | 98591021 | NR_030338 | yes |
| chr12 | 13066263 | 13071263 | NR_030345 | yes |
| chr20 | 49199823 | 49204823 | NR_030375 | yes |
| chr5 | 54464070 | 54469070 | NR_030387 | yes |
| chr11 | 2015561 | 2020561 | NR_030533 | yes |
| chr15 | 45722748 | 45727748 | NR_030599 | yes |
| chr1 | 94309888 | 94314888 | NR_030621 | yes |
| chr12 | 54425234 | 54430234 | NR_030753 | yes |
| chr1 | 117211871 | 117216871 | NR_031564 | yes |
| chr5 | 54465681 | 54470681 | NR_031572 | yes |
| chr3 | 47888545 | 47893545 | NR_031595 | yes |
| chr7 | 102043802 | 102048802 | NR_031669 | yes |
| chr22 | 20071081 | 20076081 | NR_031706 | yes |
| chr8 | 10680453 | 10685453 | NR_031711 | yes |
| chr11 | 61580212 | 61585212 | NR_031729 | yes |
| chr1 | 178509431 | 178514431 | NR_033186 | yes |
| chr17 | 46667154 | 46672154 | NR_033203 | yes |
| chr17 | 46670820 | 46675820 | NR_033205 | yes |
| chr9 | 130878513 | 130883513 | NR_033374 | yes |
| chr1 | 161065651 | 161070651 | NR_033385 | yes |
| chr1 | 59248323 | 59253323 | NR_034014 | yes |
| chr11 | 10560283 | 10565283 | NR_034093 | yes |
| chr5 | 43064573 | 43069573 | NR_034127 | yes |
| chr11 | 119249988 | 119254988 | NR_034160 | yes |
| chr1 | 31189119 | 31194119 | NR_034182 | yes |
| chr2 | 232575524 | 232580524 | NR_036052_2 | yes |
| chr9 | 130545697 | 130550697 | NR_036055 | yes |
| chr1 | 249118076 | 249123076 | NR_036070 | yes |
| chr2 | 178118238 | 178123238 | NR_036075 | yes |
| chr2 | 207645532 | 207650532 | NR_036077 | yes |
| chr2 | 207645458 | 207650458 | NR_036078 | yes |
| chr10 | 103358674 | 103363674 | NR_036114 | yes |
| chr10 | 103358754 | 103363754 | NR_036115 | yes |
| chr17 | 46799337 | 46804337 | NR_036150 | yes |
| chr19 | 18390387 | 18395387 | NR_036155 | yes |
| chr19 | 18494872 | 18499872 | NR_036156 | yes |
| chr19 | 42635165 | 42640165 | NR_036208 | yes |
| chr1 | 149819840 | 149824840 | NR_036461 | yes |
| chr19 | 13944603 | 13949603 | NR_036515 | yes |
| chr1 | 110879293 | 110884293 | NR_036595 | yes |
| chr6 | 42692814 | 42697814 | NR_037141 | yes |
| chr1 | 167187623 | 167192623 | NR_037163 | yes |
| chr22 | 20070769 | 20075769 | NR_037412 | yes |
| chr11 | 62325278 | 62330278 | NR_037427 | yes |
| chr10 | 118924785 | 118929785 | NR_037436 | yes |
| chr1 | 65521025 | 65526025 | NR_037443 | yes |
| chr17 | 73399650 | 73404650 | NR_037449 | yes |
| chr6 | 36587789 | 36592789 | NR_037491 | yes |
| chr6 | 33663405 | 33668405 | NR_037498 | yes |
| chr14 | 52115962 | 52120962 | NR_037676 | yes |
| chr17 | 33413848 | 33418848 | NR_037713 | yes |
| chr17 | 33446041 | 33451041 | NR_037714 | yes |
| chr17 | 6913236 | 6918236 | NR_037717 | yes |
| chr1 | 11897876 | 11902876 | NR_037806 | yes |
| chr3 | 5019146 | 5024146 | NR_037903 | yes |
| chr17 | 7462809 | 7467809 | NR_037926 | yes |
| chr17 | 74551346 | 74556346 | NR_038108 | yes |
| chr1 | 63780428 | 63785428 | NR_038252 | yes |
| chr12 | 93962674 | 93967674 | NR_038263 | yes |
| chr3 | 196727277 | 196732277 | NR_038285 | yes |
| chr4 | 79564648 | 79569648 | NR_038303 | yes |
| chr17 | 6920473 | 6925473 | NR_038310 | yes |
| chr19 | 42634281 | 42639281 | NR_038332 | yes |
| chr12 | 89410969 | 89415969 | NR_038385 | yes |
| chr17 | 56403799 | 56408799 | NR_038411 | yes |
| chr17 | 56404466 | 56409466 | NR_038413 | yes |
| chr14 | 75758607 | 75763607 | NR_038421 | yes |
| chr2 | 13144638 | 13149638 | NR_038434 | yes |
| chr19 | 47985039 | 47990039 | NR_038452 | yes |
| chr3 | 142643017 | 142648017 | NR_038455 | yes |
| chr4 | 87853502 | 87858502 | NR_038841 | yes |
| chr8 | 71518312 | 71523312 | NR_038881 | yes |
| chr21 | 36115622 | 36120622 | NR_038885 | yes |
| chr7 | 100199161 | 100204161 | NR_038910 | yes |
| chr11 | 65335384 | 65340384 | NR_038923 | yes |
| chr2 | 85763509 | 85768509 | NR_038942 | yes |
| chr1 | 51523009 | 51528009 | NR_039617 | yes |
| chr2 | 64750147 | 64755147 | NR_039633 | yes |
| chr3 | 48235554 | 48240554 | NR_039645 | yes |
| chr9 | 124879946 | 124884946 | NR_039690 | yes |
| chr11 | 61273568 | 61278568 | NR_039708 | yes |
| chr11 | 118778917 | 118783917 | NR_039713 | yes |
| chr14 | 74222950 | 74227950 | NR_039727 | yes |
| chr15 | 81287314 | 81292314 | NR_039739 | yes |
| chr17 | 80623683 | 80628683 | NR_039751 | yes |
| chr19 | 39897818 | 39902818 | NR_039755 | yes |
| chr19 | 45154502 | 45159502 | NR_039756 | yes |
| chr22 | 42316801 | 42321801 | NR_039760 | yes |
| chr9 | 130545612 | 130550612 | NR_039767 | yes |
| chr6 | 44219522 | 44224522 | NR_039790 | yes |
| chr9 | 130629274 | 130634274 | NR_039819 | yes |
| chr1 | 243506978 | 243511978 | NR_039824 | yes |
| chr1 | 3874792 | 3879792 | NR_039835 | yes |
| chr15 | 89152655 | 89157655 | NR_039867 | yes |
| chr17 | 73778188 | 73783188 | NR_039892 | yes |
| chr22 | 19948776 | 19953776 | NR_039918 | yes |
| chr22 | 46506946 | 46511946 | NR_039920 | yes |
| chr4 | 110352473 | 110357473 | NR_039978 | yes |
| chr16 | 4301290 | 4306290 | NR_039999 | yes |
| chr2 | 177499802 | 177504802 | NR_040001 | yes |
| chr2 | 202020015 | 202025015 | NR_040030 | yes |
| chr19 | 47162235 | 47167235 | NR_040041 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr19 | 47161121 | 47166121 | NR_040042 | yes |
| chr2 | 11269802 | 11274802 | NR_040080 | yes |
| chr17 | 6913153 | 6918153 | NR_040089 | yes |
| chr15 | 73072676 | 73077676 | NR_040107 | yes |
| chr8 | 67338712 | 67343712 | NR_040434 | yes |
| chr14 | 23282601 | 23287601 | NR_040448 | yes |
| chr16 | 48387096 | 48392096 | NR_040677 | yes |
| chr1 | 155021141 | 155026141 | NR_040772 | yes |
| chr1 | 155033967 | 155038967 | NR_040773 | yes |
| chr22 | 45018799 | 45023799 | NR_044991 | yes |
| chr12 | 51439600 | 51444600 | NR_045017 | yes |
| chr17 | 42296494 | 42301494 | NR_045058 | yes |
| chr5 | 131743965 | 131748965 | NR_045116 | yes |
| chr6 | 150182134 | 150187134 | NR_045126 | yes |
| chr19 | 14245464 | 14250464 | NR_045214 | yes |
| chr2 | 136575261 | 136580261 | NR_045486 | yes |
| chr11 | 75477192 | 75482192 | NR_046090 | yes |
| chr1 | 98512749 | 98517749 | NR_046105 | yes |
| chr12 | 92532989 | 92537989 | NR_046159 | yes |
| chr12 | 92534107 | 92539107 | NR_046160 | yes |
| chr16 | 89230291 | 89235291 | NR_046200 | yes |
| chr2 | 209117457 | 209122457 | NR_046452 | yes |
| chr1 | 110750109 | 110755109 | NR_046546 | yes |
| chr1 | 201796187 | 201801187 | NR_046696 | yes |
| chr3 | 52321249 | 52326249 | NR_046719 | yes |
| chr1 | 119909069 | 119914069 | NR_046780 | yes |
| chr7 | 5717592 | 5722592 | NR_046834 | yes |
| chr1 | 47642422 | 47647422 | NR_047498 | yes |
| chr12 | 54376803 | 54381803 | NR_047506 | yes |
| chr16 | 3079982 | 3084982 | NR_047572 | yes |
| chr3 | 45548537 | 45553537 | NR_048543 | yes |
| chr6 | 138186870 | 138191870 | NR_049793 | yes |
| chr1 | 161194476 | 161199476 | NR_049819 | yes |
| chr12 | 125397593 | 125402593 | NR_049820 | yes |
| chr8 | 81151124 | 81156124 | NR_049894 | yes |
| chr12 | 123754363 | 123759363 | NR_073007 | yes |
| chr12 | 123753149 | 123758149 | NR_073008 | yes |
| chr11 | 64214029 | 64219029 | NR_073177 | yes |
| chr3 | 46596388 | 46601388 | NR_073385 | yes |
| chr14 | 36537133 | 36542133 | NR_073454 | yes |
| chr17 | 37821734 | 37826734 | NR_073461 | yes |
| chr17 | 40825608 | 40830608 | NR_073574 | yes |
| chr17 | 38181398 | 38186398 | NR_102369 | yes |
| chr20 | 61434439 | 61439439 | NR_102430 | yes |
| chr14 | 24503121 | 24508121 | NR_102689 | yes |
| chr5 | 43064625 | 43069625 | NR_102752 | yes |
| chr5 | 37838040 | 37843040 | NR_103441 | yes |
| chr6 | 52439500 | 52444500 | NR_103446 | yes |
| chr6 | 52439596 | 52444596 | NR_103447 | yes |
| chr1 | 151988254 | 151993254 | NR_103561 | yes |
| chr17 | 47648926 | 47653926 | NR_103773 | yes |
| chr1 | 113613224 | 113618224 | NR_103777 | yes |
| chr1 | 101699584 | 101704584 | NR_104626 | yes |
| chr5 | 43065041 | 43070041 | NR_104651 | yes |
| chr3 | 50262368 | 50267368 | NR_106714 | yes |
| chr19 | 14181673 | 14186673 | NR_106715 | yes |
| chr1 | 63790155 | 63795155 | NR_106716 | yes |
| chr21 | 45027370 | 45032370 | NR_106718 | yes |
| chr19 | 45937412 | 45942412 | NR_106736 | yes |
| chr1 | 51523190 | 51528190 | NR_106754 | yes |
| chr11 | 47198788 | 47203788 | NR_106803 | yes |
| chr19 | 6734289 | 6739289 | NR_106849 | yes |
| chr2 | 238417074 | 238422074 | NR_106869 | yes |
| chr22 | 30400538 | 30405538 | NR_106876 | yes |
| chr3 | 48584954 | 48589954 | NR_106881 | yes |
| chr8 | 145538478 | 145543478 | NR_106907 | yes |
| chr9 | 33465433 | 33470433 | NR_106910 | yes |
| chr17 | 38347349 | 38352349 | NR_106927 | yes |
| chr3 | 50308167 | 50313167 | NR_106932 | yes |
| chr15 | 75130548 | 75135548 | NR_106942 | yes |
| chr17 | 38180162 | 38185162 | NR_106944 | yes |
| chr6 | 35435785 | 35440785 | NR_106961 | yes |
| chr11 | 64106876 | 64111876 | NR_106977 | yes |
| chr14 | 72981028 | 72986028 | NR_106994 | yes |
| chr17 | 75082999 | 75087999 | NR_106997 | yes |
| chr11 | 1898775 | 1903775 | NR_107001 | yes |
| chr12 | 123846890 | 123851890 | NR_107039 | yes |
| chr10 | 17269484 | 17274484 | NR_108061 | yes |
| chr8 | 128410144 | 128415144 | NR_109834 | yes |
| chr20 | 39764140 | 39769140 | NR_109889 | yes |
| chr20 | 43076697 | 43081697 | NR_109893 | yes |
| chr5 | 5137667 | 5142667 | NR_109915 | yes |
| chr14 | 23396318 | 23401318 | NR_110002 | yes |
| chr20 | 49545021 | 49550021 | NR_110007 | yes |
| chr12 | 124066374 | 124071374 | NR_110049 | yes |
| chr2 | 179275886 | 179280886 | NR_110204 | yes |
| chr2 | 65088265 | 65093265 | NR_110224 | yes |
| chr14 | 24027806 | 24032806 | NR_110555 | yes |
| chr2 | 177499982 | 177504982 | NR_110599 | yes |
| chr19 | 56575550 | 56580550 | NR_110741 | yes |
| chr17 | 63094430 | 63099430 | NR_110801 | yes |
| chr17 | 76354029 | 76359029 | NR_110845 | yes |
| chr17 | 76354583 | 76359583 | NR_110846 | yes |
| chr16 | 4375841 | 4380841 | NR_110901 | yes |
| chr16 | 47175479 | 47180479 | NR_110903 | yes |
| chr1 | 245131671 | 245136671 | NR_111907 | yes |
| chr8 | 128743713 | 128748713 | NR_117101 | yes |
| chr16 | 87810254 | 87815254 | NR_120309 | yes |
| chr15 | 45568920 | 45573920 | NR_120335 | yes |
| chr15 | 68128717 | 68133717 | NR_120345 | yes |
| chr12 | 52476030 | 52481030 | NR_120438 | yes |
| chr12 | 10900333 | 10905333 | NR_120463 | yes |
| chr11 | 78138382 | 78143382 | NR_120564 | yes |
| chr11 | 124629827 | 124634827 | NR_120579 | yes |
| chr11 | 66245220 | 66250220 | NR_120586 | yes |
| chr8 | 144361370 | 144366370 | NR_120682 | yes |
| chr9 | 77565381 | 77570381 | NR_121183 | yes |
| chr4 | 40306702 | 40311702 | NR_121641 | yes |
| chr10 | 118926066 | 118931066 | NR_121650 | yes |
| chr1 | 46912876 | 46917876 | NR_121680 | yes |
| chr12 | 62994714 | 62999714 | NR_121682 | yes |
| chr7 | 91761377 | 91766377 | NR_122109 | yes |
| chr16 | 3106871 | 3111871 | NR_123723 | yes |
| chr3 | 178863261 | 178868261 | NR_125401 | yes |
| chr8 | 80677877 | 80682877 | NR_125410 | yes |
| chr8 | 10695036 | 10700036 | NR_125432 | yes |
| chr20 | 48806106 | 48811106 | NR_125739 | yes |
| chr11 | 125032005 | 125037005 | NR_125759 | yes |
| chr1 | 85084214 | 85089214 | NR_125761 | yes |
| chr6 | 1603266 | 1608266 | NR_125804 | yes |
| chr6 | 44039889 | 44044889 | NR_125864 | yes |
| chr1 | 95697038 | 95702038 | NR_125948 | yes |
| chr1 | 26791528 | 26796528 | NR_125952 | yes |
| chr1 | 112295631 | 112300631 | NR_125963 | yes |
| chr1 | 47900489 | 47905489 | NR_126355 | yes |
| chr17 | 73994740 | 73999740 | NR_130467_2 | yes |
| chr10 | 102898523 | 102903523 | NR_130724 | yes |
| chr19 | 46142252 | 46147252 | NR_130728 | yes |
| chr5 | 139534404 | 139539404 | NR_130738 | yes |
| chr8 | 130689985 | 130694985 | NR_130917 | yes |
| chr15 | 85194977 | 85199977 | NR_130944 | yes |
| chr14 | 50569261 | 50574261 | NR_131171 | yes |
| chr11 | 2020196 | 2025196 | NR_131224 | yes |
| chr20 | 30306810 | 30311810 | NR_131907 | yes |
| chr7 | 22764739 | 22769739 | NR_131935 | yes |
| chr9 | 132478485 | 132483485 | NR_132102 | yes |
| chr19 | 48269597 | 48274597 | NR_132382 | yes |
| chr1 | 9239763 | 9244763 | NR_132738 | yes |
| chr1 | 9239897 | 9244897 | NR_132742 | yes |
| chr1 | 39978038 | 39983038 | NR_132962 | yes |
| chr11 | 1968061 | 1973061 | NR_132974 | yes |
| chr6 | 74225661 | 74230661 | NR_132980_2 | yes |
| chr16 | 14393645 | 14398645 | NR_132983 | yes |
| chr16 | 14393862 | 14398862 | NR_132984 | yes |
| chr11 | 64658421 | 64663421 | NR_133638 | yes |
| chr21 | 44558702 | 44563702 | NR_133677 | yes |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr20 | 30307633 | 30312633 | NR_134257 | yes |
| chr5 | 10519696 | 10524696 | NR_134289 | yes |
| chr8 | 145594148 | 145599148 | NR_134307 | yes |
| chr9 | 35113469 | 35118469 | NR_134455 | yes |
| chr16 | 30438621 | 30443621 | NR_134471 | yes |
| chr6 | 150253149 | 150258149 | NR_134598 | yes |
| chr6 | 26567052 | 26572052 | NR_134611 | yes |
| chr6 | 33599022 | 33604022 | NR_134628 | yes |
| chr19 | 51286967 | 51291967 | NR_134883 | yes |
| chr19 | 18313040 | 18318040 | NR_134910 | yes |
| chr3 | 195584775 | 195589775 | NR_134939 | yes |
| chr12 | 47698682 | 47703682 | NR_135024 | yes |
| chr12 | 7069908 | 7074908 | NR_135032 | yes |
| chr12 | 92537361 | 92542361 | NR_135036 | yes |
| chr1 | 91314695 | 91319695 | NR_135038 | yes |
| chr12 | 122498696 | 122503696 | NR_135044 | yes |
| chr10 | 102823556 | 102828556 | NR_135068 | yes |
| chr12 | 6996022 | 7001022 | NR_135083 | yes |
| chr14 | 91161177 | 91166177 | NR_135190 | yes |
| chr14 | 90981053 | 90986053 | NR_135274 | yes |
| chr3 | 72710900 | 72715900 | NR_135531 | yes |
| chr2 | 101765622 | 101770622 | NR_135594 | yes |
| chr1 | 212000479 | 212005479 | NR_135818 | yes |
| chr1 | 212000688 | 212005688 | NR_135819 | yes |
| chr1 | 212001803 | 212006803 | NR_135820 | yes |
| chr15 | 41196507 | 41201507 | NR_135836 | yes |
| chr1 | 87167676 | 87172676 | NR_135837 | yes |
| chr10 | 98589715 | 98594715 | NR_135921 | yes |
| chr2 | 64748789 | 64753789 | NR_136167 | yes |
| chr6 | 16758869 | 16763869 | NR_136240 | yes |
| chr17 | 7484897 | 7489897 | NR_136401 | yes |
| chr11 | 2321779 | 2326779 | NR_138249 | yes |
| chr6 | 36643836 | 36648836 | NR_144384 | yes |
| chr17 | 40704320 | 40709320 | NR_144402 | yes |
| chr17 | 48276540 | 48281500 | NM_000088 | no |
| chr16 | 67462536 | 67467536 | NM_000196 | no |
| chr17 | 45328708 | 45333708 | NM_000212 | no |
| chr4 | 100482735 | 100487735 | NM_000253 | no |
| chr11 | 76836810 | 76841810 | NM_000260 | no |
| chr3 | 38688663 | 38693663 | NM_000335 | no |
| chr16 | 56896619 | 56901619 | NM_000339 | no |
| chr20 | 23027801 | 23032801 | NM_000361 | no |
| chr12 | 48296314 | 48301314 | NM_000376 | no |
| chr1 | 21833351 | 21838351 | NM_000478 | no |
| chr7 | 45958371 | 45963371 | NM_000598 | no |
| chr8 | 18065112 | 18070112 | NM_000662 | no |
| chr5 | 159341240 | 159346240 | NM_000679 | no |
| chr11 | 15092646 | 15097646 | NM_000728 | no |
| chr11 | 62686512 | 62691512 | NM_000738 | no |
| chr11 | 46405658 | 46410658 | NM_000741 | no |
| chr5 | 174868663 | 174873663 | NM_000794 | no |
| chr10 | 74854232 | 74859232 | NM_000917 | no |
| chr21 | 45717417 | 45722417 | NM_001002021 | no |
| chr2 | 96801675 | 96806675 | NM_001002036 | no |
| chr7 | 150943249 | 150948249 | NM_001003801 | no |
| chr2 | 71015275 | 71020275 | NM_001004311 | no |
| chr1 | 242159885 | 242164885 | NM_001004343 | no |
| chr11 | 4658445 | 4663445 | NM_001004751 | no |
| chr17 | 57406553 | 57411553 | NM_001005404 | no |
| chr6 | 130337014 | 130342014 | NM_001007102 | no |
| chr20 | 23584110 | 23589110 | NM_001008693 | no |
| chr8 | 30239517 | 30244517 | NM_001008710 | no |
| chr10 | 106111022 | 106116022 | NM_001008723 | no |
| chr19 | 9692709 | 9697709 | NM_001008727 | no |
| chr2 | 158181725 | 158186725 | NM_001009959 | no |
| chr10 | 21783713 | 21788713 | NM_001010911 | no |
| chr20 | 45310624 | 45315624 | NM_001011554 | no |
| chr3 | 118751176 | 118756176 | NM_001015885 | no |
| chr4 | 38782111 | 38787111 | NM_001017388 | no |
| chr22 | 41937993 | 41942993 | NM_001018050 | no |
| chr8 | 56984640 | 56989640 | NM_001023 | no |
| chr1 | 6301752 | 6306752 | NM_001024598 | no |
| chr19 | 43030161 | 43035161 | NM_001024912 | no |
| chr12 | 50014697 | 50019697 | NM_001031698 | no |
| chr4 | 159091702 | 159096702 | NM_001031700 | no |
| chr3 | 9288869 | 9293869 | NM_001033117 | no |
| chr11 | 14991332 | 14996332 | NM_001033952 | no |
| chr2 | 10260363 | 10265363 | NM_001034 | no |
| chr12 | 51816094 | 51821094 | NM_001039960 | no |
| chr1 | 212779470 | 212784470 | NM_001040619 | no |
| chr19 | 41100641 | 41105641 | NM_001042544 | no |
| chr19 | 41104777 | 41109777 | NM_001042545 | no |
| chr19 | 45346893 | 45351893 | NM_001042724 | no |
| chr2 | 219132615 | 219137615 | NM_001077399 | no |
| chr19 | 51520931 | 51525931 | NM_001077500 | no |
| chr8 | 133069127 | 133074127 | NM_001080399 | no |
| chr14 | 75328037 | 75333037 | NM_001080408 | no |
| chr7 | 1541518 | 1546518 | NM_001080453 | no |
| chr2 | 85105869 | 85110869 | NM_001080824 | no |
| chr16 | 3505485 | 3510485 | NM_001083600 | no |
| chr2 | 219132432 | 219137432 | NM_001087 | no |
| chr17 | 74461130 | 74466130 | NM_001088 | no |
| chr6 | 35106687 | 35111687 | NM_001093728 | no |
| chr14 | 21154432 | 21159432 | NM_001097577 | no |
| chr11 | 60521840 | 60526840 | NM_001098835 | no |
| chr2 | 70778647 | 70783647 | NM_001099691 | no |
| chr22 | 24638610 | 24643610 | NM_001099781 | no |
| chr16 | 30933396 | 30938396 | NM_001099784 | no |
| chr19 | 18696995 | 18701995 | NM_001100418 | no |
| chr12 | 109824024 | 109829024 | NM_001101421 | no |
| chr16 | 30668340 | 30673340 | NM_001105079 | no |
| chr7 | 75828711 | 75833711 | NM_001110199 | no |
| chr15 | 89784694 | 89789694 | NM_001113378 | no |
| chr11 | 76836816 | 76841816 | NM_001127180 | no |
| chr22 | 18558260 | 18563260 | NM_001127649 | no |
| chr11 | 47427546 | 47432546 | NM_001128225 | no |
| chr8 | 22222262 | 22227262 | NM_001128431 | no |
| chr3 | 51702691 | 51707691 | NM_001129884 | no |
| chr10 | 99329698 | 99334698 | NM_001129981 | no |
| chr17 | 36828687 | 36833687 | NM_001130677 | no |
| chr4 | 122870409 | 122875409 | NM_001130698 | no |
| chr7 | 129012984 | 129017984 | NM_001130722 | no |
| chr7 | 129005464 | 129010464 | NM_001130723 | no |
| chr3 | 71775769 | 71780769 | NM_001134650 | no |
| chr4 | 100482714 | 100487714 | NM_001134665 | no |
| chr8 | 22222550 | 22227550 | NM_001135153 | no |
| chr17 | 19646425 | 19651425 | NM_001135167 | no |
| chr17 | 19646272 | 19651272 | NM_001135168 | no |
| chr2 | 88749553 | 88754553 | NM_001135649 | no |
| chr8 | 20038217 | 20043217 | NM_001135691 | no |
| chr1 | 15476528 | 15481528 | NM_001136216 | no |
| chr1 | 15477729 | 15482729 | NM_001136218 | no |
| chr11 | 118013684 | 118018684 | NM_001142349 | no |
| chr11 | 27720100 | 27725100 | NM_001143808 | no |
| chr11 | 27719947 | 27724947 | NM_001143812 | no |
| chr11 | 27719535 | 27724535 | NM_001143813 | no |
| chr11 | 72351004 | 72356004 | NM_001143839 | no |
| chr5 | 142075135 | 142080135 | NM_001144934 | no |
| chr12 | 56099186 | 56104186 | NM_001144996 | no |
| chr11 | 43961606 | 43966606 | NM_001145033 | no |
| chr9 | 133811955 | 133816955 | NM_001145106 | no |
| chr9 | 114359635 | 114364635 | NM_001146108 | no |
| chr21 | 40757192 | 40762192 | NM_001146218 | no |
| chr16 | 8619726 | 8624726 | NM_001146336 | no |
| chr17 | 40994100 | 40999100 | NM_001158 | no |
| chr5 | 173041166 | 173046166 | NM_001159651 | no |
| chr3 | 38688664 | 38693664 | NM_001160160 | no |
| chr15 | 44953376 | 44958376 | NM_001160227 | no |
| chr16 | 18993109 | 18998109 | NM_001160364 | no |
| chr19 | 51842878 | 51847878 | NM_001163922 | no |
| chr2 | 10260195 | 10265195 | NM_001165931 | no |
| chr17 | 48346267 | 48351267 | NM_001168215 | no |
| chr3 | 119960642 | 119965642 | NM_001168271 | no |
| chr6 | 12288029 | 12293029 | NM_001168319 | no |
| chr3 | 137829822 | 137834822 | NM_001170538 | no |
| chr3 | 51531518 | 51536518 | NM_001171904 | no |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr10 | 73569140 | 73574140 | NM_001171935 | no |
| chr7 | 116162563 | 116167563 | NM_001172895 | no |
| chr7 | 116163847 | 116168847 | NM_001172896 | no |
| chr7 | 116163912 | 116168912 | NM_001172897 | no |
| chr9 | 117265236 | 117270236 | NM_001173425 | no |
| chr20 | 46128101 | 46133101 | NM_001174087 | no |
| chr17 | 26938711 | 26943711 | NM_001174103 | no |
| chr12 | 51982520 | 51987520 | NM_001177984 | no |
| chr12 | 859589 | 864589 | NM_001184985 | no |
| chr2 | 234157717 | 234162717 | NM_001190266 | no |
| chr10 | 106032387 | 106037387 | NM_001191014 | no |
| chr12 | 113571544 | 113576544 | NM_001193520 | no |
| chr12 | 113571059 | 113576059 | NM_001193521 | no |
| chr16 | 58032777 | 58037777 | NM_001195302 | no |
| chr11 | 74949450 | 74954450 | NM_001195528 | no |
| chr17 | 74862298 | 74867298 | NM_001199172 | no |
| chr9 | 117441869 | 117446869 | NM_001199233 | no |
| chr22 | 18558186 | 18563186 | NM_001199319 | no |
| chr19 | 45752016 | 45757016 | NM_001199867 | no |
| chr16 | 71915593 | 71920593 | NM_001201552 | no |
| chr16 | 71914944 | 71919944 | NM_001201553 | no |
| chr4 | 155469085 | 155474085 | NM_001201564 | no |
| chr5 | 172568945 | 172573945 | NM_001205 | no |
| chr2 | 219260561 | 219265561 | NM_001206878 | no |
| chr9 | 34587638 | 34592638 | NM_001207011 | no |
| chr22 | 31476346 | 31481346 | NM_001207017 | no |
| chr22 | 31478482 | 31483482 | NM_001207018 | no |
| chr18 | 30047947 | 30052947 | NM_001242409 | no |
| chr3 | 51702790 | 51707790 | NM_001243725 | no |
| chr11 | 120104849 | 120109849 | NM_001244682 | no |
| chr5 | 39422835 | 39427835 | NM_001244871 | no |
| chr15 | 51198369 | 51203369 | NM_001252127 | no |
| chr2 | 27068657 | 27073657 | NM_001253723 | no |
| chr2 | 27068792 | 27073792 | NM_001253724 | no |
| chr2 | 31359092 | 31364092 | NM_001253826 | no |
| chr18 | 20712028 | 20717028 | NM_001256438 | no |
| chr2 | 128403328 | 128408328 | NM_001256542 | no |
| chr5 | 73934749 | 73939749 | NM_001256574 | no |
| chr12 | 121645164 | 121650164 | NM_001256796 | no |
| chr1 | 2123714 | 2128714 | NM_001256945 | no |
| chr12 | 51816401 | 51821401 | NM_001258403 | no |
| chr7 | 23747445 | 23752445 | NM_001260504 | no |
| chr7 | 23747286 | 23752286 | NM_001260505 | no |
| chr17 | 79978285 | 79983285 | NM_001271006 | no |
| chr5 | 1006577 | 1011577 | NM_001271082 | no |
| chr10 | 32633646 | 32638646 | NM_001272004 | no |
| chr10 | 32633476 | 32638476 | NM_001272019 | no |
| chr9 | 139375711 | 139380711 | NM_001276418 | no |
| chr19 | 42298022 | 42303022 | NM_001277163 | no |
| chr2 | 72372491 | 72377491 | NM_001277742 | no |
| chr19 | 17389954 | 17394954 | NM_001278443 | no |
| chr22 | 24817065 | 24822065 | NM_001278500 | no |
| chr6 | 159460885 | 159465885 | NM_001278733 | no |
| chr17 | 47782813 | 47787813 | NM_001278784 | no |
| chr17 | 15163406 | 15168406 | NM_001281455 | no |
| chr16 | 30931876 | 30936876 | NM_001282351 | no |
| chr9 | 137977014 | 137982014 | NM_001282611 | no |
| chr9 | 137976606 | 137981606 | NM_001282612 | no |
| chr2 | 10970111 | 10975111 | NM_001282704 | no |
| chr2 | 10975603 | 10980603 | NM_001282705 | no |
| chr22 | 31157740 | 31162740 | NM_001282740 | no |
| chr22 | 41938110 | 41943110 | NM_001282884 | no |
| chr2 | 232648593 | 232653593 | NM_001282950 | no |
| chr9 | 135283083 | 135288083 | NM_001282957 | no |
| chr2 | 97168622 | 97173622 | NM_001285485 | no |
| chr19 | 33790970 | 33795970 | NM_001285829 | no |
| chr21 | 30462075 | 30467075 | NM_001286619 | no |
| chr9 | 132379992 | 132384992 | NM_001286797 | no |
| chr9 | 132385932 | 132390932 | NM_001286798 | no |
| chr9 | 132386223 | 132391223 | NM_001286799 | no |
| chr16 | 8617507 | 8622507 | NM_001290095 | no |
| chr19 | 42210004 | 42215004 | NM_001291484 | no |
| chr22 | 22897674 | 22902674 | NM_001291715 | no |
| chr22 | 22899268 | 22904268 | NM_001291717 | no |
| chr5 | 73933348 | 73938348 | NM_001292004 | no |
| chr11 | 69059105 | 69064105 | NM_001293291 | no |
| chr15 | 81069184 | 81074184 | NM_001293298 | no |
| chr3 | 46247332 | 46252332 | NM_001295 | no |
| chr4 | 8268992 | 8273992 | NM_001297559 | no |
| chr1 | 244813850 | 244818850 | NM_001297746 | no |
| chr11 | 58936403 | 58941403 | NM_001300727 | no |
| chr16 | 18992756 | 18997756 | NM_001300732 | no |
| chr1 | 234347457 | 234352457 | NM_001300845 | no |
| chr11 | 66821789 | 66826789 | NM_001300886 | no |
| chr11 | 107433961 | 107438961 | NM_001301010 | no |
| chr5 | 148518510 | 148523510 | NM_001301015 | no |
| chr19 | 41768455 | 41773455 | NM_001301016 | no |
| chr15 | 45026060 | 45031060 | NM_001301144 | no |
| chr15 | 78110742 | 78115742 | NM_001301186 | no |
| chr15 | 78110174 | 78115174 | NM_001301187 | no |
| chr15 | 78109944 | 78114944 | NM_001301189 | no |
| chr15 | 78109366 | 78114366 | NM_001301191 | no |
| chr15 | 78076856 | 78081856 | NM_001301195 | no |
| chr12 | 113570904 | 113575904 | NM_001301202 | no |
| chr17 | 41558785 | 41563785 | NM_001302623 | no |
| chr9 | 100171802 | 100176802 | NM_001302884 | no |
| chr18 | 3245028 | 3250028 | NM_001303047 | no |
| chr18 | 3244980 | 3249980 | NM_001303048 | no |
| chr3 | 73480647 | 73485647 | NM_001303142 | no |
| chr22 | 39265839 | 39270839 | NM_001303494 | no |
| chr2 | 158181321 | 158186321 | NM_001304344 | no |
| chr2 | 158179960 | 158184960 | NM_001304346 | no |
| chr20 | 1162819 | 1167819 | NM_001304748 | no |
| chr20 | 1163577 | 1168577 | NM_001304749 | no |
| chr11 | 122730519 | 122735519 | NM_001304782 | no |
| chr4 | 5050744 | 5055744 | NM_001306082 | no |
| chr5 | 118321415 | 118326415 | NM_001308081 | no |
| chr2 | 70778270 | 70783270 | NM_001308158 | no |
| chr3 | 155521576 | 155526576 | NM_001308229 | no |
| chr10 | 129702825 | 129707825 | NM_001316676 | no |
| chr19 | 59028426 | 59033426 | NM_001316978 | no |
| chr19 | 59028876 | 59033876 | NM_001316979 | no |
| chr8 | 23101605 | 23106605 | NM_001317899 | no |
| chr20 | 50416562 | 50421562 | NM_001318031 | no |
| chr22 | 22895847 | 22900847 | NM_001318126 | no |
| chr10 | 28589495 | 28594495 | NM_001318170 | no |
| chr16 | 71915575 | 71920575 | NM_001318238 | no |
| chr16 | 71911879 | 71916879 | NM_001318239 | no |
| chr4 | 128649033 | 128654033 | NM_001318467 | no |
| chr1 | 15477707 | 15482707 | NM_001319665 | no |
| chrX | 15516400 | 15521400 | NM_001320866 | no |
| chr19 | 41767764 | 41772764 | NM_001321208 | no |
| chr17 | 35730428 | 35735428 | NM_001321399 | no |
| chr9 | 4982586 | 4987586 | NM_001322194 | no |
| chr9 | 4982730 | 4987730 | NM_001322196 | no |
| chr17 | 41558733 | 41563733 | NM_001322216 | no |
| chr5 | 178155203 | 178160203 | NM_001324339 | no |
| chr14 | 23338426 | 23343426 | NM_001329226 | no |
| chr1 | 233083777 | 233088777 | NM_001329452 | no |
| chr5 | 90676690 | 90681690 | NM_001329672 | no |
| chr16 | 83999737 | 84004737 | NM_001329748 | no |
| chr2 | 70526677 | 70531677 | NM_001329752 | no |
| chr2 | 70526715 | 70531715 | NM_001329753 | no |
| chr2 | 70526720 | 70531720 | NM_001329755 | no |
| chr14 | 76445865 | 76450865 | NM_001329938 | no |
| chr14 | 76446854 | 76451854 | NM_001329939 | no |
| chr11 | 47427551 | 47432551 | NM_001330245 | no |
| chr16 | 19176656 | 19181656 | NM_001330509 | no |
| chr17 | 79978294 | 79983294 | NM_001330536 | no |
| chr16 | 58031003 | 58036003 | NM_001330568 | no |
| chr12 | 64236033 | 64241033 | NM_001346201 | no |
| chr6 | 130338289 | 130343289 | NM_001346550 | no |
| chr6 | 130337705 | 130342705 | NM_001346551 | no |
| chr15 | 51571959 | 51576959 | NM_001347251 | no |
| chr4 | 55092756 | 55097756 | NM_001347827 | no |
| chr4 | 55096749 | 55101749 | NM_001347829 | no |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr4 | 55097627 | 55102627 | NM_001347830 | no |
| chr5 | 111752513 | 111757513 | NM_001347887 | no |
| chr8 | 28556490 | 28561490 | NM_001440 | no |
| chr8 | 82190218 | 82195218 | NM_001444 | no |
| chr3 | 49708935 | 49713935 | NM_001640 | no |
| chr4 | 75308315 | 75313315 | NM_001657 | no |
| chr4 | 75478091 | 75483091 | NM_001657_2 | no |
| chr5 | 78405104 | 78410104 | NM_001713 | no |
| chr16 | 71390116 | 71395116 | NM_001740 | no |
| chr7 | 116162339 | 116167339 | NM_001753 | no |
| chr9 | 34587235 | 34592235 | NM_001842 | no |
| chr16 | 21311957 | 21316957 | NM_001888 | no |
| chr2 | 10440530 | 10445530 | NM_002149 | no |
| chr2 | 219922738 | 219927738 | NM_002181 | no |
| chr2 | 11049563 | 11054563 | NM_002236 | no |
| chr11 | 8282925 | 8287925 | NM_002315 | no |
| chr11 | 46937673 | 46942673 | NM_002334 | no |
| chr11 | 61973640 | 61978640 | NM_002407 | no |
| chr19 | 42256928 | 42261928 | NM_002483 | no |
| chr17 | 3817460 | 3822460 | NM_002558 | no |
| chr1 | 2341510 | 2346510 | NM_002617 | no |
| chr20 | 52822002 | 52827002 | NM_002623 | no |
| chr19 | 51520782 | 51525782 | NM_002776 | no |
| chr11 | 119596935 | 119601935 | NM_002855 | no |
| chr17 | 32687752 | 32692752 | NM_002981 | no |
| chr8 | 134581683 | 134586683 | NM_003033 | no |
| chr6 | 50783939 | 50788939 | NM_003221 | no |
| chr15 | 39870780 | 39875780 | NM_003246 | no |
| chr4 | 38803912 | 38808912 | NM_003263 | no |
| chr17 | 34133959 | 34138959 | NM_003487 | no |
| chr8 | 23019043 | 23024043 | NM_003840 | no |
| chr2 | 86113657 | 86118657 | NM_003896 | no |
| chr6 | 158400388 | 158405388 | NM_003898 | no |
| chr22 | 23520052 | 23525052 | NM_004327 | no |
| chr6 | 75913123 | 75918123 | NM_004370 | no |
| chrX | 68046340 | 68051340 | NM_004429 | no |
| chr3 | 184277087 | 184282087 | NM_004443 | no |
| chr9 | 4982745 | 4987745 | NM_004972 | no |
| chr20 | 48096681 | 48101681 | NM_004975 | no |
| chr17 | 48070088 | 48075088 | NM_005220 | no |
| chr10 | 120964697 | 120969697 | NM_005308 | no |
| chr10 | 93390358 | 93395358 | NM_005398 | no |
| chr17 | 54668560 | 54673560 | NM_005450 | no |
| chr17 | 40910712 | 40915712 | NM_005854 | no |
| chr3 | 40348673 | 40353673 | NM_005875 | no |
| chr9 | 36166889 | 36171889 | NM_005893 | no |
| chr6 | 137111156 | 137116156 | NM_005923 | no |
| chr10 | 111983262 | 111988262 | NM_005962 | no |
| chr2 | 232392682 | 232397682 | NM_006056 | no |
| chr4 | 38855938 | 38860938 | NM_006068 | no |
| chr11 | 76811386 | 76816386 | NM_006189 | no |
| chr19 | 18630437 | 18635437 | NM_006532 | no |
| chr16 | 24264374 | 24269374 | NM_006539 | no |
| chr9 | 92217427 | 92222427 | NM_006705 | no |
| chr2 | 118569755 | 118574755 | NM_006773 | no |
| chr22 | 31474782 | 31479782 | NM_006932 | no |
| chr19 | 41767579 | 41772579 | NM_007040 | no |
| chr5 | 95295275 | 95300275 | NM_012081 | no |
| chr6 | 3847100 | 3852100 | NM_012135 | no |
| chr11 | 33561377 | 33566377 | NM_012194 | no |
| chr9 | 114359211 | 114364211 | NM_012212 | no |
| chr12 | 50014903 | 50019903 | NM_012272 | no |
| chr10 | 71208726 | 71213726 | NM_012339 | no |
| chr20 | 4700000 | 4705000 | NM_012409 | no |
| chr16 | 69342787 | 69347787 | NM_013245 | no |
| chr6 | 16126817 | 16131817 | NM_013262 | no |
| chr19 | 40929432 | 40934432 | NM_013376 | no |
| chr8 | 53319939 | 53324939 | NM_014682 | no |
| chr9 | 139375007 | 139380007 | NM_014866 | no |
| chr4 | 99914288 | 99919288 | NM_015143 | no |
| chr14 | 103056496 | 103061496 | NM_015156 | no |
| chr11 | 58937312 | 58942312 | NM_015177 | no |
| chr17 | 5971434 | 5976434 | NM_015253 | no |
| chr5 | 173470107 | 173475107 | NM_015980 | no |
| chr5 | 149666903 | 149671903 | NM_015981 | no |
| chr16 | 19177035 | 19182035 | NM_016524 | no |
| chr5 | 33933991 | 33938991 | NM_016568 | no |
| chr4 | 159091218 | 159096218 | NM_016613 | no |
| chr21 | 26977301 | 26982301 | NM_017446 | no |
| chr14 | 76042440 | 76047440 | NM_017791 | no |
| chr1 | 245315787 | 245320787 | NM_018012 | no |
| chr20 | 1162617 | 1167617 | NM_018354 | no |
| chr12 | 68617071 | 68622071 | NM_018402 | no |
| chr19 | 4789228 | 4794228 | NM_018708 | no |
| chr3 | 56833495 | 56838495 | NM_019555 | no |
| chr20 | 54821288 | 54826288 | NM_019888 | no |
| chr2 | 27068469 | 27073469 | NM_020134 | no |
| chr3 | 52476601 | 52481601 | NM_020163 | no |
| chr7 | 105514531 | 105519531 | NM_020725 | no |
| chr6 | 40552703 | 40557703 | NM_020737 | no |
| chr6 | 44278563 | 44283563 | NM_020745 | no |
| chr16 | 58031262 | 58036262 | NM_020807 | no |
| chr20 | 22562601 | 22567601 | NM_021784 | no |
| chr20 | 43371988 | 43376988 | NM_022358 | no |
| chr12 | 118811858 | 118816858 | NM_022491 | no |
| chr6 | 119397312 | 119402312 | NM_024581 | no |
| chr15 | 101456920 | 101461920 | NM_024652 | no |
| chr9 | 27527350 | 27532350 | NM_024761 | no |
| chr3 | 133646156 | 133651156 | NM_025041 | no |
| chr1 | 208415165 | 208420165 | NM_025179 | no |
| chr19 | 41033895 | 41038895 | NM_025213 | no |
| chr20 | 31592884 | 31597884 | NM_025227 | no |
| chr17 | 41833656 | 41838656 | NM_025237 | no |
| chr19 | 10809612 | 10814612 | NM_031209 | no |
| chr2 | 85358083 | 85363083 | NM_031283 | no |
| chr1 | 6482348 | 6487348 | NM_031475 | no |
| chr12 | 57846574 | 57851574 | NM_031479 | no |
| chr11 | 94797541 | 94802541 | NM_032102 | no |
| chr19 | 11667551 | 11672551 | NM_032377 | no |
| chr1 | 20957448 | 20962448 | NM_032409 | no |
| chr17 | 72207196 | 72212196 | NM_032646 | no |
| chr3 | 133811739 | 133816739 | NM_032843 | no |
| chr11 | 12305947 | 12310947 | NM_032867 | no |
| chr9 | 116915325 | 116920325 | NM_032888 | no |
| chr5 | 141991226 | 141996226 | NM_033137 | no |
| chr22 | 20305128 | 20310128 | NM_033257 | no |
| chr11 | 69453373 | 69458373 | NM_053056 | no |
| chr6 | 159463684 | 159468684 | NM_054114 | no |
| chr19 | 10044728 | 10049728 | NM_058164 | no |
| chr12 | 55245799 | 55250799 | NM_058173 | no |
| chr22 | 46370508 | 46375508 | NM_058238 | no |
| chr22 | 31501073 | 31506073 | NM_080430 | no |
| chr20 | 31589739 | 31594739 | NM_080675 | no |
| chr20 | 44255885 | 44260885 | NM_080753 | no |
| chr10 | 111964863 | 111969863 | NM_130439 | no |
| chr19 | 3583069 | 3588069 | NM_133261 | no |
| chr4 | 1899853 | 1904853 | NM_133334 | no |
| chr2 | 10441326 | 10446326 | NM_134421 | no |
| chr20 | 23417822 | 23422822 | NM_138283 | no |
| chr14 | 105442194 | 105447194 | NM_138420 | no |
| chr6 | 151644166 | 151649166 | NM_144497 | no |
| chr12 | 8972568 | 8977568 | NM_144670 | no |
| chr19 | 41765801 | 41770881 | NM_144732 | no |
| chr17 | 79978678 | 79983678 | NM_144999 | no |
| chr10 | 71387503 | 71392503 | NM_145306 | no |
| chr19 | 51520454 | 51525454 | NM_145888 | no |
| chr20 | 44257407 | 44262407 | NM_147198 | no |
| chr22 | 37953971 | 37958971 | NM_152243 | no |
| chr8 | 23098650 | 23103650 | NM_152272 | no |
| chr4 | 100482325 | 100487325 | NM_152292 | no |
| chr11 | 100555907 | 100560907 | NM_152432 | no |
| chr21 | 40813628 | 40818628 | NM_152505 | no |
| chr9 | 139375447 | 139380447 | NM_152571 | no |
| chr17 | 48349288 | 48354288 | NM_153229 | no |
| chr17 | 15161661 | 15166661 | NM_153322 | no |
| chr20 | 22563601 | 22568601 | NM_153675 | no |

TABLE S1-continued

Constitutive CTCF peaks within a constitutive IN across HCT116, Jurkat, K562 within 2.5 kb of TSS

| chr | start | stop | gene | loops to differential enhancers |
|---|---|---|---|---|
| chr11 | 27720680 | 27725680 | NM_170733 | no |
| chr11 | 27718714 | 27723714 | NM_170734 | no |
| chr10 | 103597111 | 103602111 | NM_173194 | no |
| chr9 | 138232595 | 138237595 | NM_173520 | no |
| chr3 | 137831951 | 137836951 | NM_173543 | no |
| chr19 | 51758464 | 51763464 | NM_173635 | no |
| chr5 | 118321800 | 118326800 | NM_173666 | no |
| chr9 | 126115946 | 126120946 | NM_173689 | no |
| chr7 | 150145218 | 150150218 | NM_175571 | no |
| chr20 | 31365158 | 31370158 | NM_175850 | no |
| chr17 | 79916557 | 79921557 | NM_178493 | no |
| chr19 | 52640691 | 52645691 | NM_178523 | no |
| chr6 | 47747275 | 47752275 | NM_181744 | no |
| chr20 | 31237283 | 31242283 | NM_182584 | no |
| chr14 | 21154436 | 21159436 | NM_194431 | no |
| chr19 | 660733 | 665733 | NM_194460 | no |
| chr5 | 153567795 | 153572795 | NM_198321 | no |
| chr16 | 85143614 | 85148614 | NM_198491 | no |
| chr22 | 36016901 | 36021901 | NM_203377 | no |
| chr2 | 33169869 | 33174869 | NM_206943 | no |
| chr22 | 39707416 | 39712416 | NR_000028 | no |
| chr8 | 56983960 | 56988960 | NR_002437 | no |
| chr14 | 101121105 | 101126105 | NR_024096 | no |
| chr17 | 48247337 | 48252337 | NR_024192 | no |
| chr15 | 37176234 | 37181234 | NR_024264 | no |
| chr12 | 121407595 | 121412595 | NR_024345 | no |
| chr16 | 30932090 | 30937090 | NR_024348 | no |
| chr11 | 122071317 | 122076317 | NR_024430 | no |
| chr17 | 40910775 | 40915775 | NR_024461 | no |
| chr16 | 21309670 | 21314670 | NR_026675 | no |
| chr9 | 100156473 | 100161473 | NR_026847 | no |
| chr19 | 33791263 | 33796263 | NR_026887 | no |
| chr17 | 72206960 | 72211960 | NR_026914 | no |
| chr22 | 31315795 | 31320795 | NR_026920 | no |
| chr1 | 24524230 | 24529230 | NR_027087 | no |
| chr1 | 15476460 | 15481460 | NR_027136 | no |
| chr22 | 22899250 | 22904250 | NR_027426 | no |
| chr5 | 111752780 | 111757780 | NR_027706 | no |
| chr2 | 219863930 | 219868930 | NR_029867 | no |
| chr10 | 21783070 | 21788070 | NR_031736 | no |
| chr15 | 93336214 | 93341214 | NR_033769 | no |
| chr1 | 20752787 | 20757787 | NR_033887 | no |
| chr3 | 40348689 | 40353689 | NR_033965 | no |
| chr12 | 127356736 | 127361736 | NR_033970 | no |
| chr2 | 219920972 | 219925972 | NR_036081 | no |
| chr1 | 23187219 | 23192219 | NR_036214 | no |
| chr15 | 79041879 | 79046879 | NR_036495 | no |
| chr12 | 111371906 | 111376906 | NR_036513 | no |
| chr7 | 99575885 | 99580885 | NR_036679 | no |
| chr4 | 99916038 | 99921038 | NR_037455 | no |
| chr17 | 79280548 | 79285548 | NR_038080 | no |
| chr2 | 86039753 | 86044753 | NR_038888 | no |
| chr1 | 19207269 | 19212269 | NR_039844 | no |
| chr1 | 235673625 | 235678625 | NR_039973_2 | no |
| chr2 | 219864437 | 219869437 | NR_046086 | no |
| chr16 | 66439927 | 66444927 | NR_046242 | no |
| chr12 | 9783515 | 9788515 | NR_046448 | no |
| chr21 | 30742321 | 30747321 | NR_046564 | no |
| chr3 | 156162225 | 156167225 | NR_046618 | no |
| chr5 | 142245975 | 142250975 | NR_046680 | no |
| chr13 | 31374843 | 31379843 | NR_047012 | no |
| chr11 | 4205882 | 4210882 | NR_047550 | no |
| chr2 | 182816468 | 182821468 | NR_048567 | no |
| chr22 | 23225947 | 23230947 | NR_049835 | no |
| chr3 | 185483192 | 185488192 | NR_049838_2 | no |
| chr3 | 51703143 | 51708143 | NR_103462 | no |
| chr4 | 41882128 | 41887128 | NR_104143 | no |
| chr10 | 32633792 | 32638792 | NR_104163 | no |
| chr14 | 77250567 | 77255567 | NR_104183 | no |
| chr12 | 54148318 | 54153318 | NR_104332 | no |
| chr2 | 97171346 | 97176346 | NR_104346 | no |
| chr1 | 20957672 | 20962672 | NR_106732 | no |
| chr17 | 47363316 | 47368316 | NR_106745 | no |
| chr2 | 218762851 | 218767851 | NR_106867 | no |
| chr12 | 121879655 | 121884655 | NR_106957 | no |
| chr10 | 106110833 | 106115833 | NR_108036 | no |
| chr20 | 21548162 | 21553162 | NR_109880 | no |
| chr5 | 79376988 | 79381988 | NR_109930 | no |
| chr16 | 66507805 | 66512805 | NR_109960 | no |
| chr12 | 103939072 | 103944072 | NR_110103 | no |
| chr12 | 106095481 | 106100481 | NR_110108 | no |
| chr12 | 106098052 | 106103052 | NR_110110 | no |
| chr2 | 71173241 | 71178241 | NR_110273 | no |
| chr11 | 94881203 | 94886203 | NR_110303 | no |
| chr7 | 55320828 | 55325828 | NR_110426 | no |
| chr14 | 76043431 | 76048431 | NR_110552 | no |
| chr2 | 86113903 | 86118903 | NR_110569 | no |
| chr16 | 5663751 | 5668751 | NR_110902 | no |
| chr15 | 77949893 | 77954893 | NR_120361 | no |
| chr11 | 119597793 | 119602793 | NR_120587 | no |
| chr4 | 40316002 | 40321002 | NR_121640 | no |
| chr3 | 138660362 | 138665362 | NR_121649 | no |
| chr11 | 45390448 | 45395448 | NR_122071 | no |
| chr12 | 8831773 | 8836773 | NR_123740 | no |
| chr19 | 46578387 | 46583387 | NR_125344 | no |
| chr10 | 90689941 | 90694941 | NR_125373 | no |
| chr11 | 130729505 | 130734505 | NR_125383 | no |
| chr8 | 134896239 | 134901239 | NR_125424 | no |
| chr12 | 4382850 | 4387850 | NR_125790 | no |
| chr8 | 28556481 | 28561481 | NR_126027 | no |
| chr11 | 72279200 | 72284200 | NR_126364 | no |
| chr13 | 76448522 | 76453522 | NR_126373 | no |
| chr17 | 67228653 | 67233653 | NR_130736 | no |
| chr5 | 95295205 | 95300205 | NR_130776 | no |
| chr11 | 43588356 | 43593356 | NR_131246 | no |
| chr2 | 192552407 | 192557407 | NR_131917 | no |
| chr20 | 43372368 | 43377368 | NR_132377 | no |
| chr15 | 89902310 | 89907310 | NR_133001 | no |
| chr11 | 100556186 | 100561186 | NR_133571 | no |
| chr11 | 47426327 | 47431327 | NR_134854 | no |
| chr19 | 11311804 | 11316804 | NR_134909 | no |
| chr11 | 94471021 | 94476021 | NR_135093 | no |
| chr15 | 101456988 | 101461988 | NR_135827 | no |
| chr20 | 55150119 | 55155119 | NR_136537 | no |
| chr1 | 233084088 | 233089088 | NR_138027 | no |

Example 2—MYC Enhancer-Docking Site

Figure 1B:
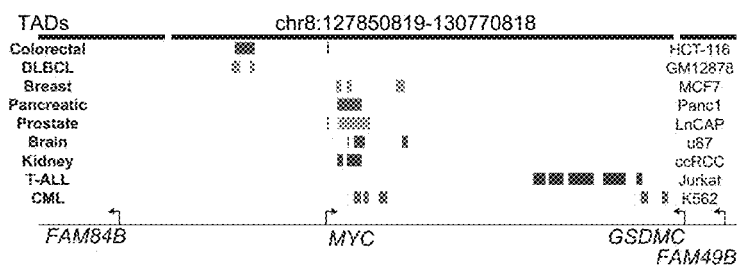
Figure 7A:
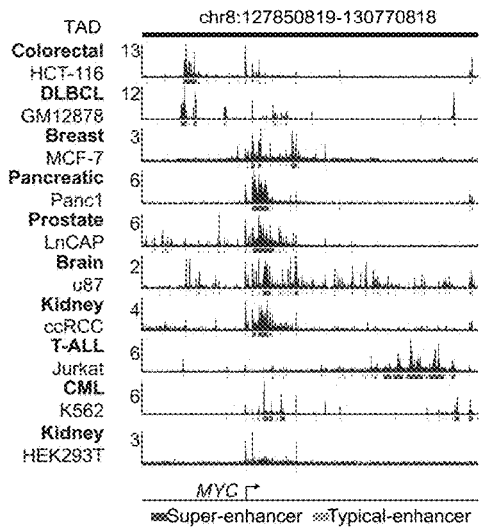
FIGS. 7A-7E.
Figure 7B:
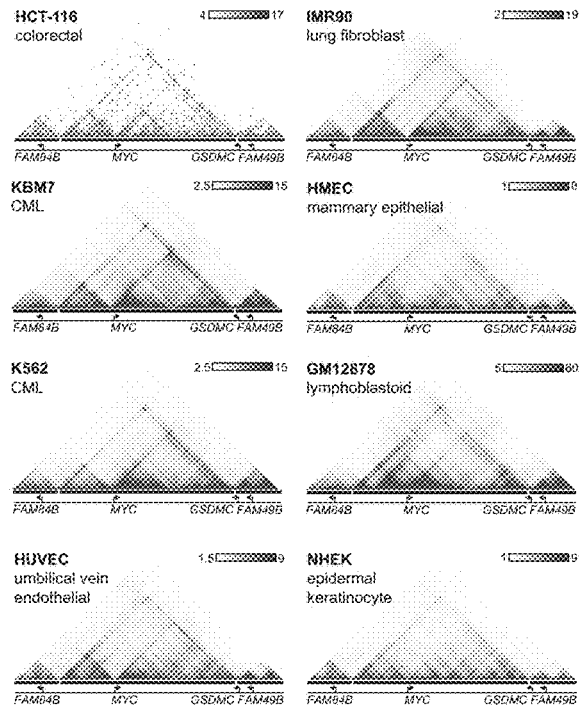
Figure 7C:
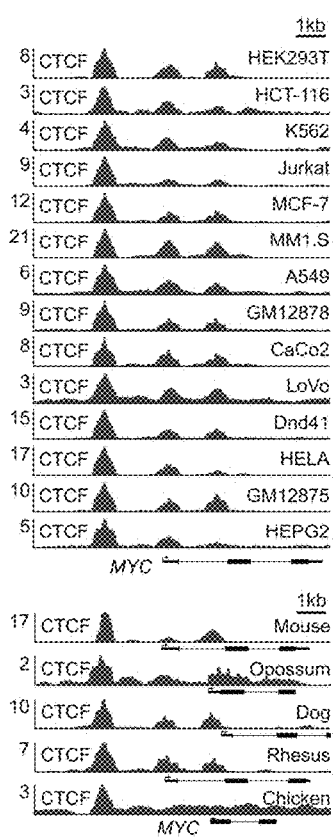

Previous studies have established that tumor cells acquire tumor-specific super-enhancers at various sites throughout the MYC locus (FIG. 1B, 7A) (Bradner et al., 2017; Chapuy et al., 2013; Gabay et al., 2014; Groschel et al., 2014; Herranz et al., 2014; Hnisz et al., 2013; Lin et al., 2016; Lovén et al., 2013; Parker et al., 2013; Zhang et al., 2015), but the mechanisms by which these diverse enhancer structures control MYC are not clear. To gain insights into the potential role of DNA loop structures in gene control at the MYC locus, we generated cohesin HiChIP data for HCT-116 cells and collected published DNA interaction data for three other cancer cell types for comparison (FIG. 1C)(Hnisz et al., 2016a; Pope et al., 2014). Among the DNA loop structures observed in these datasets, a large DNA loop was evident, spanning 2.8 Mb, that connects CTCF sites encompassing the MYC gene. The DNA anchor sites of this 2.8 Mb DNA loop occur at the boundaries of a TAD found in all cells (FIG. 7B). The MYC TAD encompasses a region previously described as a "gene desert" because this large span of DNA contains no other annotated protein-coding genes (Montavon and Duboule, 2012; Ovcharenko et al., 2005).

Figure 1C:
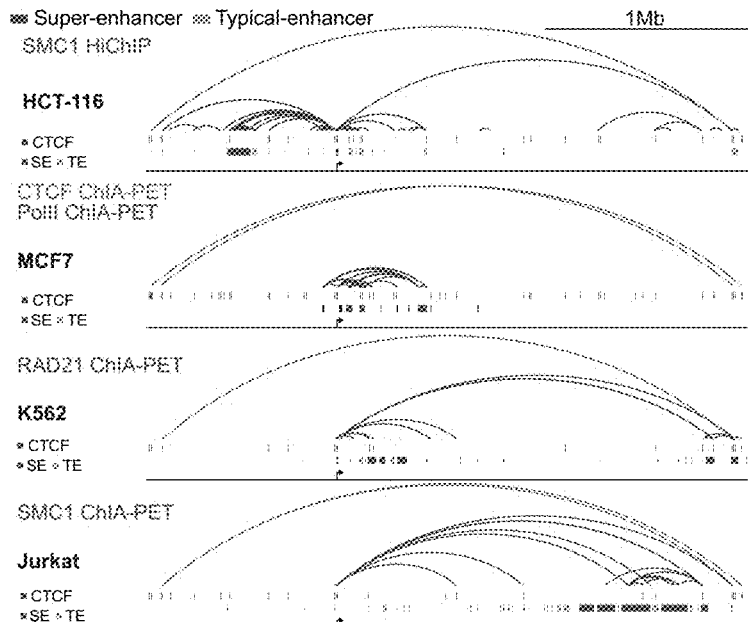

While all cells examined appear to share the TAD-spanning 2.8 Mb loop encompassing MYC, the loop structures within the neighborhood were found to be markedly different among the tumor types. The internal loops were dominated by interactions between a MYC promoter-proximal CTCF site and diverse cell specific super-enhancers (FIG. 1C). The major differences between these internal structures in the different tumor cells involved the different positions of the tumor-specific super-enhancer elements. Examination of Hi-C data for a broader spectrum of tumor cell types suggests that tumor cells generally have DNA contacts between the MYC promoter-proximal site and other sites within the 2.8 Mb MYC TAD (FIG. 7B).

Figure 1D:
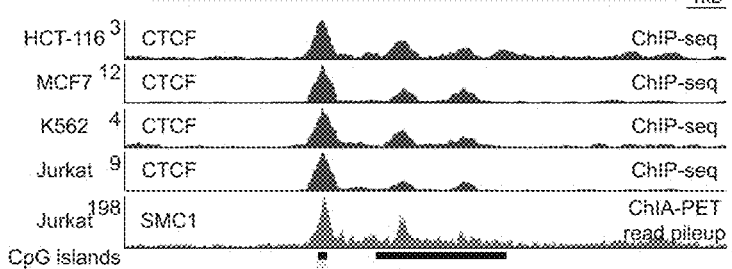
Figure 1E:
Figure 7D:
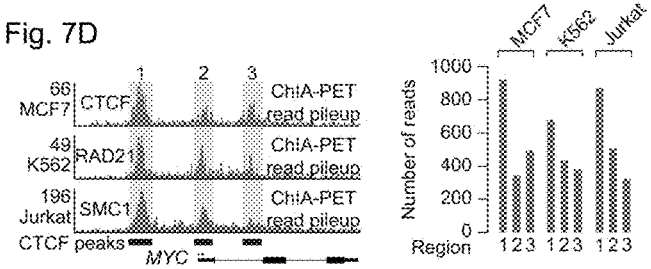
Figure 7E:
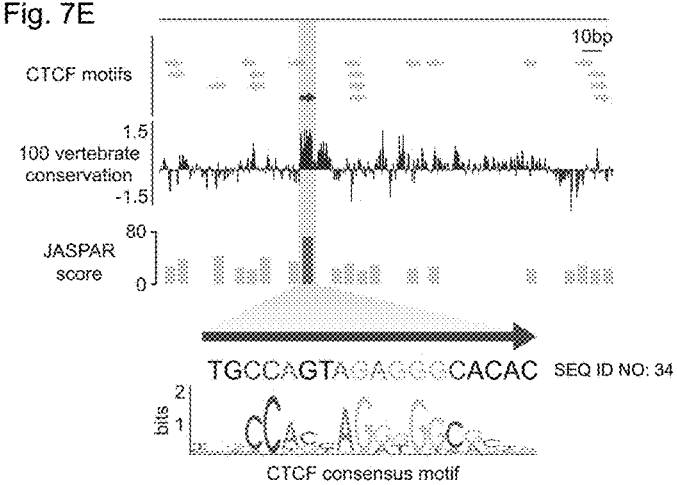

Further examination of the MYC promoter-proximal region revealed three constitutive CTCF binding sites (FIG. 1D). All three sites were found to be occupied by CTCF in a wide variety of normal cells and tumor cells, and this binding pattern is shared across species (FIG. 1C). Previous studies have examined the role of CTCF binding at all three sites (Filippova et al., 1996; Gombert et al., 2003; Klenova et al., 1993, 2001; Rubio et al., 2008). The two sites located within the MYC gene have been shown to play roles in MYC transcript start site selection and in promoter-proximal pausing of RNA polymerase II (Filippova et al., 1996; Klenova et al., 2001). The CTCF binding site located 2 kb upstream of the major transcript start site, has been reported to be an insulator element (Gombert et al., 2003). The DNA interaction data described here, however, suggests that this upstream site dominates connections with distal enhancer elements, as the majority of reads in the DNA interaction data are associated with this site in all tumor cells examined (FIG. 1D, FIG. 7D). The −2 kb CTCF binding site contains a number of putative CTCF binding motifs; one of these most closely matches the canonical CTCF motif in the JASPAR database (Sandelin, 2004) and occurs within a highly conserved sequence (FIG. 1E, FIG. 7E). These features, the presence of CTCF sites in tumor super-enhancers and the ability of two CTCF-bound sites to be brought together through CTCF homodimerization (Saldana-Meyer et al., 2014; Yusufzai et al., 2004), led us to further study the possibility that the −2 kb site has an enhancer-docking function critical to MYC expression (FIG. 2A).

Figure 8A:
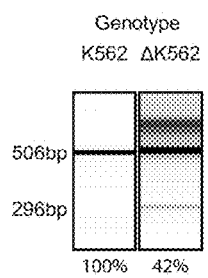
FIGS. 8A-8E.

To determine whether the putative enhancer-docking site plays a functional role in MYC expression through DNA loop formation, we used the CRISPR/Cas9 system to delete a 210 bp segment centered on this site in the Chronic Myeloid Leukemia (CML) cell line K562 (FIG. 2B). Cells were virally transduced with constructs carrying Cas9 and doxycycline dependent gRNA expression cassettes, selected for the presence of the constructs, induced for gRNA expression, and harvested. Genotyping of the AK562 cells indicated that the putative enhancer-docking site was altered in approximately half of the alleles in the cell population (FIG. 8A). CTCF occupancy, measured in the total AK562 cell population by ChIP-seq, was reduced by approximately 2-fold at the site, while other sites, such as the comparable CTCF-bound region of the MYCL promoter, were unaffected (FIG. 2B). There was an approximately 2-fold reduction in MYC mRNA levels in the AK562 cells, indicating that the putative enhancer loop-anchor is necessary for the high levels of MYC expression normally produced by these cancer cells (FIG. 2C).

Figure 8B:
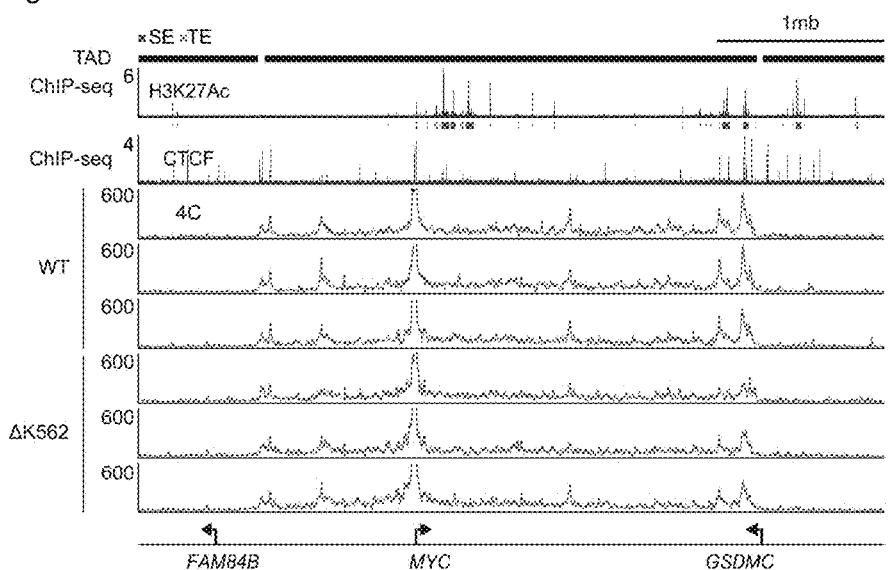

If the putative MYC enhancer-docking site contributes to looping interactions with distal enhancers, then the loss of this site in AK562 cells should cause a decrease in DNA interactions between the MYC promoter and the distal super-enhancers located nearly 2 Mb away in the downstream portion of the insulated neighborhood. We used chromosome conformation capture combined with high-throughput sequencing (4C-seq) to compare the interactions in K562 and AK562 cells (FIG. 2D, FIG. 8B). In wild-type cells, the 4C-seq data indicated that the putative enhancer-docking site interacts predominantly with the two distal super-enhancers (FIG. 2D) and that interactions between the enhancer-docking site and other DNA sites terminates at the TAD boundaries (FIG. 8B), indicating that the 2.8 Mb CTCF-CTCF loop has the properties expected of an insulated neighborhood (Dowen et al., 2014; Hnisz et al., 2016b). The results also showed that there was decreased interaction between the putative docking site and the distal super-enhancers in AK562 cells (FIG. 2D, FIG. 8B). This indicates that the CTCF site in the MYC promoter is important for optimal interaction with these distal enhancers and supports the idea that this CTCF site functions as an enhancer-docking site.

Figure 8C:
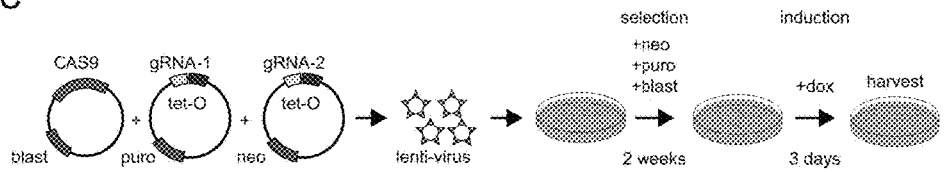
Figure 8D:
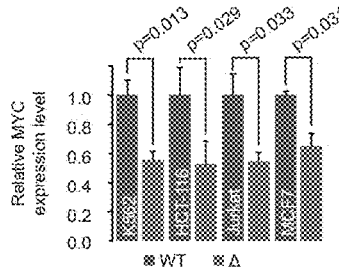
Figure 8E:
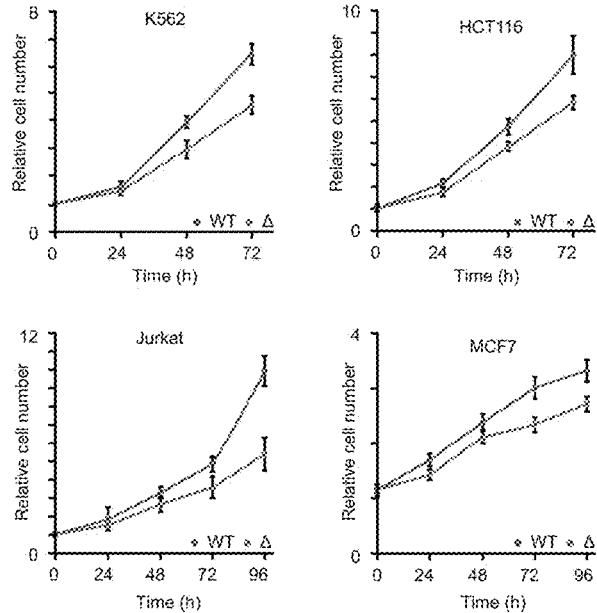

If the MYC enhancer-docking site functions similarly across a variety of tumor cells, then deletion of the site in various tumor cells should consistently cause reduced MYC expression. Indeed, when the CRISPR/Cas9 system was used to delete the 210 bp segment in colorectal cancer cells (HCT-116), acute T-cell leukemia cells (Jurkat) and breast cancer cells (MCF7), we consistently observed a reduction in MYC transcripts (FIG. 8C, D). The reduced expression of MYC in all these tumor types was accompanied by reduced cell proliferation in culture (FIG. 8E). These results suggest that MYC expression is similarly dependent on the MYC enhancer-docking site in multiple tumor cell types.

Importance of CTCF Motif Sequence in Enhancer-Docking Site

Figure 9A:
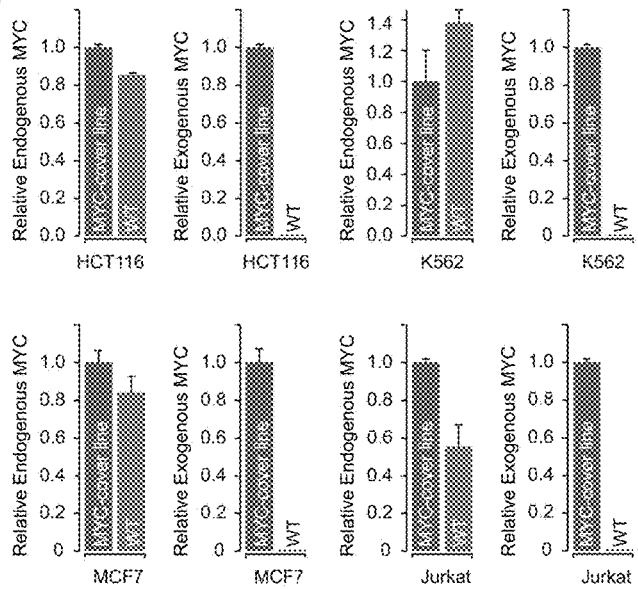
(FIG. 9A) qPCR measuring the mRNA levels of endogenous and exogenous MYC in parental (wild type) HCT-116 K562, MCF7 and Jurkat cells and in HCT-116 and K562 cells expressing exogenous MYC.Endogenous and exogenous MYC were detected using primers directed against the 3' UTR of the MYC mRNA and the MYC-tdTomato junction respectively.

The enhancer-docking site contains multiple putative CTCF motifs, of which one stood out in terms of conservation and JASPAR score (FIG. 1E, 7E). To ascertain whether this CTCF binding site contributes to optimal MYC expression, small perturbations of the site were generated in both alleles of the tumor cell lines K562, HCT-116, Jurkat and MCF7 using CRISPR/Cas9 (FIG. 3A, B). Previous experiments were conducted on cell populations where the cells could survive reduced MYC levels if they suffered alteration of only one allele. In contrast, these CTCF binding site deletion experiments were conducted in cells with an exogenous MYC gene driven by a pGK promoter to allow cells to continue to proliferate if CTCF motif deletion is lethal (FIG. 9A). Sequence differences in the 3' UTR allowed discrimination between the endogenous and exogenous MYC mRNAs. RNA analysis revealed that the CTCF binding site mutations in the MYC enhancer docking site caused a 70-80% reduction of endogenous MYC mRNA in K562, HCT-116, Jurkat and MCF7 cells (FIG. 3C). These results demonstrate that optimal expression of MYC in a spectrum of tumor cells is highly dependent upon the CTCF binding site sequence in the enhancer-docking site.

Loss of MYC Expression Upon Methylation of Enhancer-Docking Site

Figure 4A:
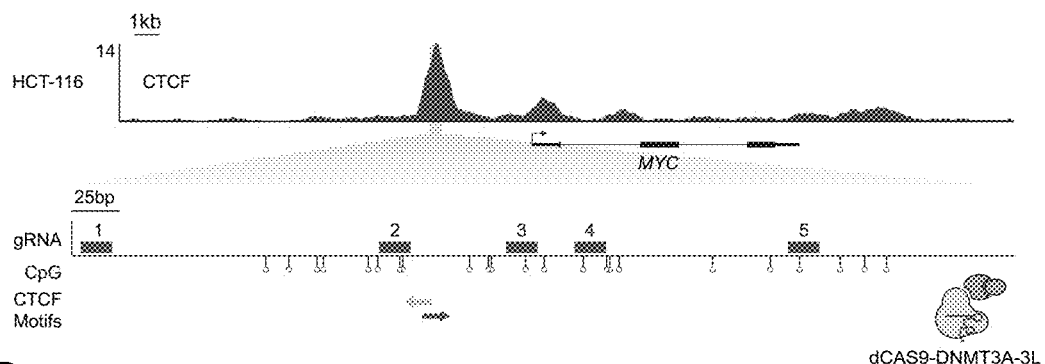
FIGS. 4A-4D. dCas9-mediated methylation of the enhancer-docking site reduces MYC expression in tumor cells.
Figure 4B:
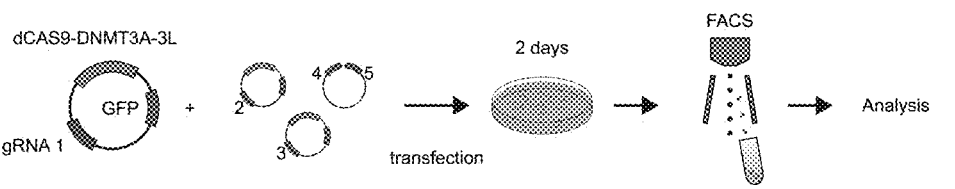
Figure 4C:
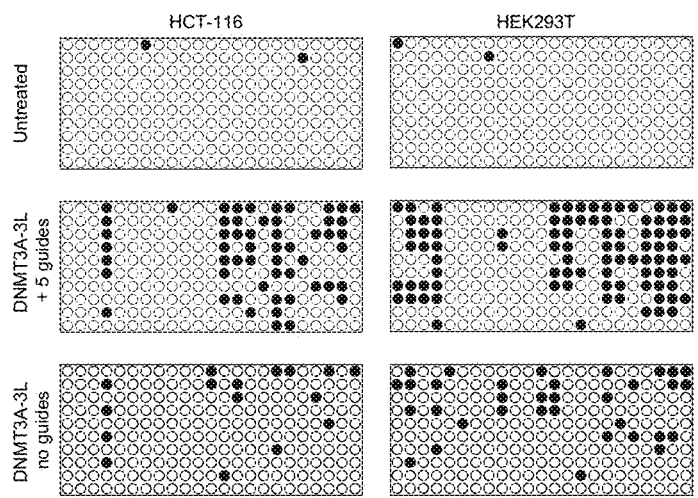
Figure 4D:
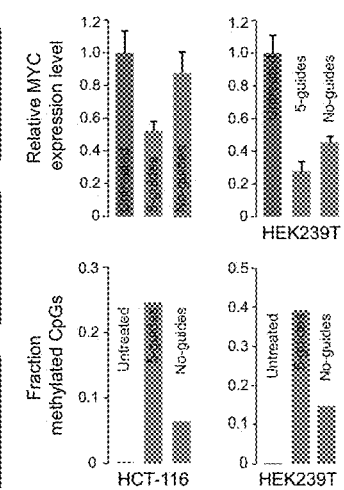
Figure 10A:
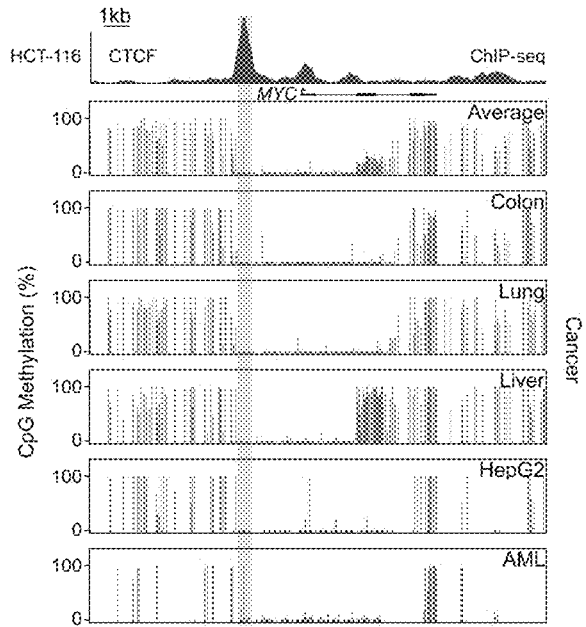
FIGS. 10A-10B. The common CTCF enhancer docking site is hypomethylated in a swathe of cancer and normal cells. Percentage of methylation of CpG's at the MYC locus in (FIG. 10A) cander cancer and (FIG. 10B) normal cells. Percent methylation of each CpG in the region is represented as a blue dot. HCT-116 CTCF ChIP-seq signal is shown in purple for reference. ChIP-seq read counts are shown in reads per million sequenced reads per basepair. Whole genome bisulfite sequencing data for a panel of healthy cells. The whole MYC gene body and the surrounding region, with the common CTCF enhancer docking site highlighted in yellow is depicted. Data from ENCODE, (Barabe et al., 2016; Ziller et al., 2013).
Figure 10B:
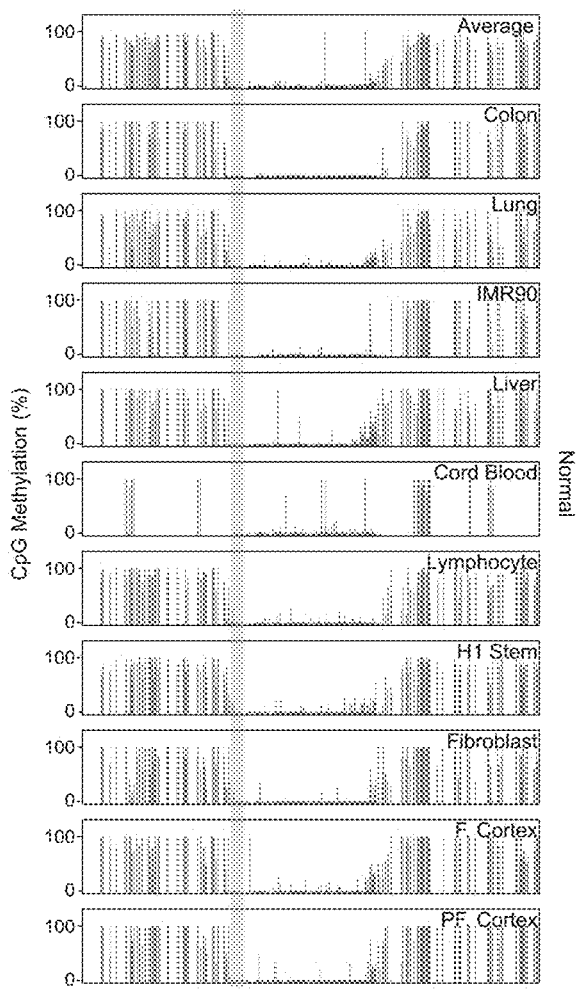
Figure 11:
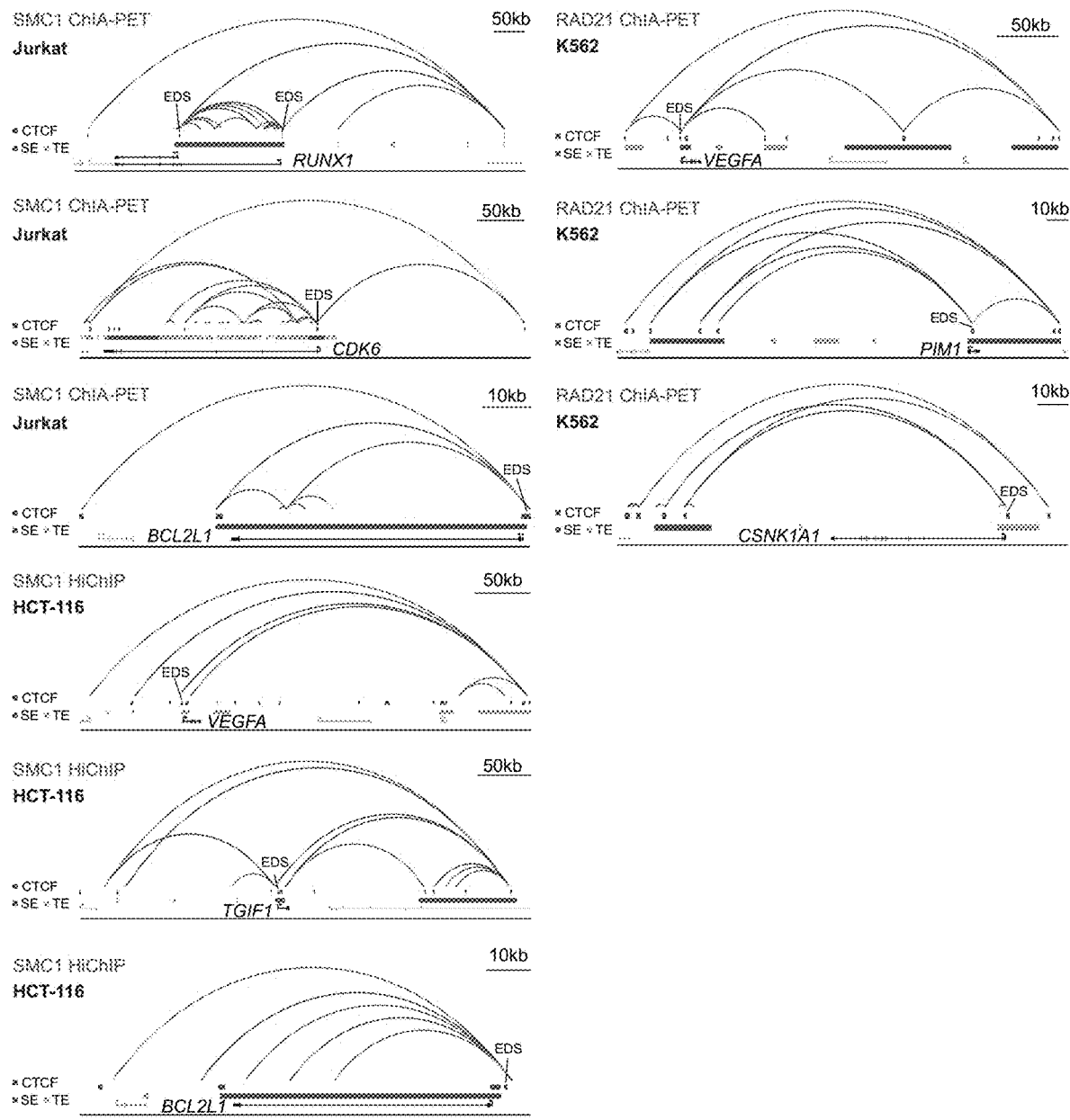
FIG. 11. Displays of example loci with enhancer-docking sites. ChIA-PET or HiChIP data is indicated in purple arcs with the insulated neighborhood spanning interaction in blue. CTCF ChIP-seq peaks are indicated in purple rectangles, typical enhancers are indicated in grey rectangles and super-enhancers are indicated in red rectangles. ChIA-PET data used is indicated in purple lettering. EDS=enhancer-docking site.
Figure 12A:
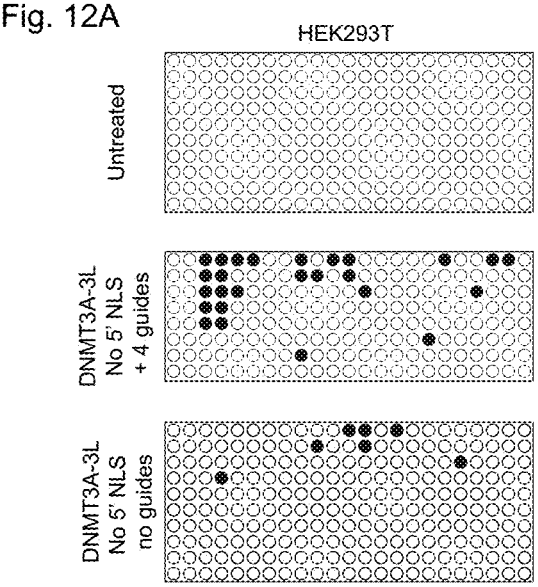
FIGS. 12A-12B. Targeted methylation of the MYC CTCF enhancer loop anchor using dCas(-DNMT3A without the 5' NLS in HEK293T cells.
Figure 12B:
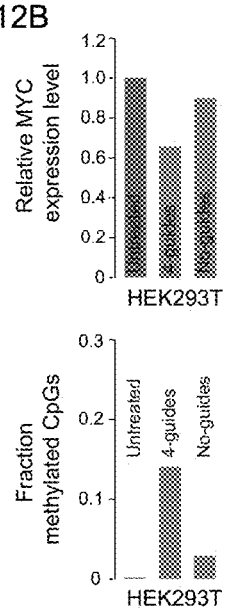

CTCF binding is abrogated when its sequence motif is methylated (Bell and Felsenfeld, 2000; Maurano et al., 2015), and the MYC enhancer-docking site occurs within a CpG island that is consistently hypomethylated in different tumor types (FIG. 10A). The recent development of tools that permit site-specific DNA methylation (Flavahan et al., 2016; Hark et al., 2000; Liu et al., 2016) suggested a means to disrupt MYC expression by methylation of the enhancer-docking site. To achieve targeted methylation, we created a construct to express a dCas9 fusion protein consisting of the catalytic domain of DNMT3A and the interacting domain of DNMT3L. This dCas9-DNMT3A-3L protein was targeted to the MYC enhancer-docking site using multiple guide RNAs that span the region (FIG. 4A, B). The targeting of dCas9-DNMT3A-3L resulted in robust local DNA methylation (FIG. 4C) and a 50-70% reduction in mRNA levels in HCT-116 and HEK293T cells (FIG. 4D). These results demonstrate that epigenetic editing of the enhancer-docking site can reduce MYC expression in multiple cell types.

MYC Enhancer-Docking Site in Normal Development and Differentiation

Figure 5A:
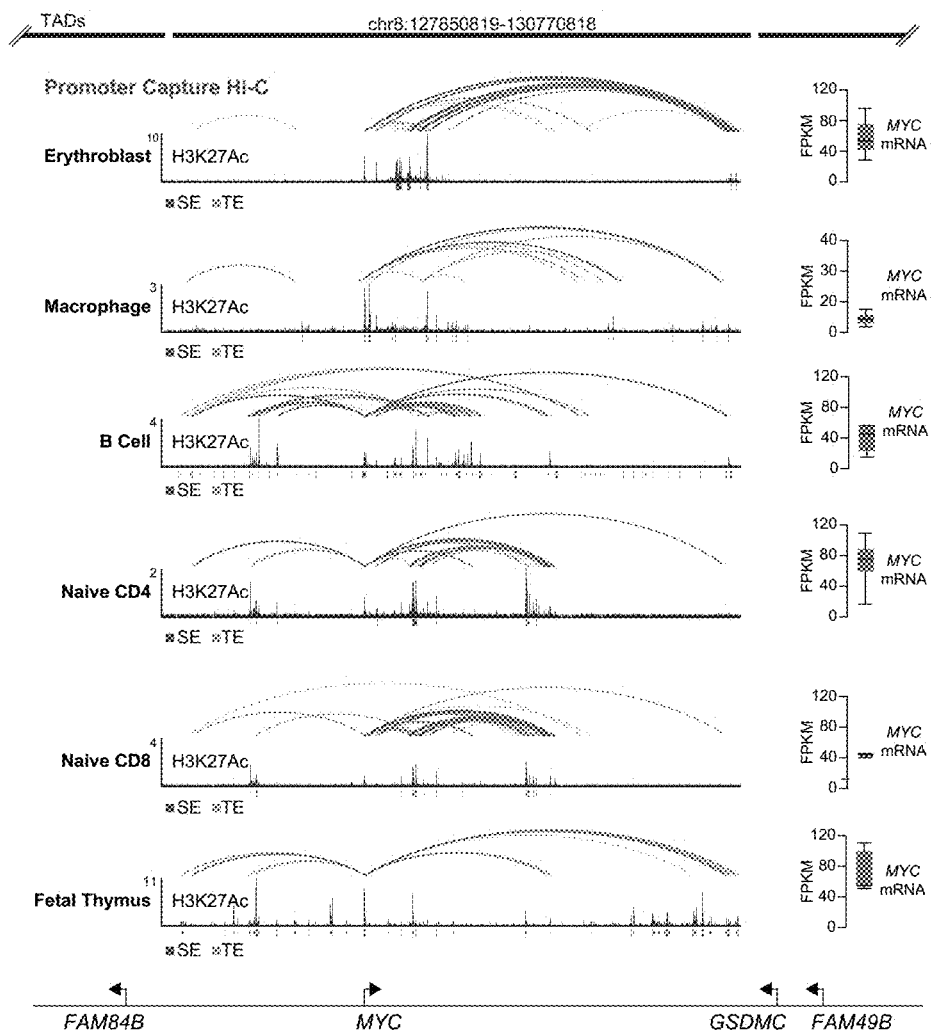
FIGS. 5A-5B. MYC-proximal enhancer docking site is used during development and differentiation.
Figure 5B:
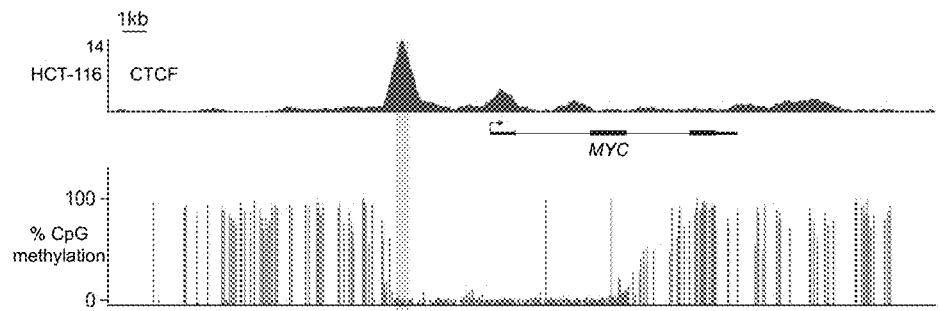

It seems unlikely that the MYC enhancer-docking site would have evolved to facilitate the development of diverse cancers, so we explored the possibility that this site might typically be employed during normal development and differentiation, when MYC expression contributes to normal cellular proliferation and different cell-type specific transcription factors establish the different cell states. Examination of enhancer and promoter-capture Hi-C data in a variety of normal cell types that express MYC (Javierre et al., 2016) revealed that cell-type specific enhancers do indeed loop to the MYC enhancer-docking site (FIG. 5A). The enhancer-docking site is hypomethylated in a broad spectrum of cell and tissue types (FIG. 5B, FIG. 10A,B), which would allow for CTCF binding at these sites. These results indicate that the MYC enhancer-docking site is used during normal development by cell-type specific enhancers to facilitate MYC expression and cellular proliferation. The levels of MYC transcripts in these normal cells, however, are considerably less than those found in tumor cells, where high levels of MYC expression produce oncogenic effects.

Enhancer-Docking Sites at Additional Genes with Prominent Roles in Cancer

Figure 6A:
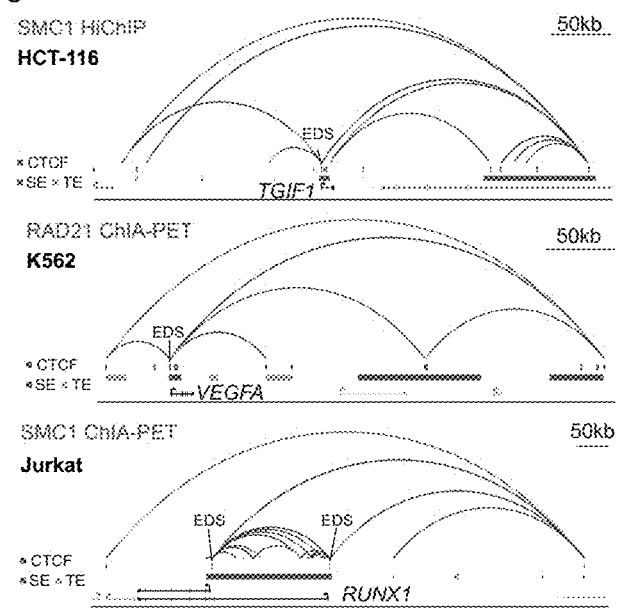
FIGS. 6A-6B. Enhancer-docking sites at additional genes with prominent roles in cancer.
Figure 6B:
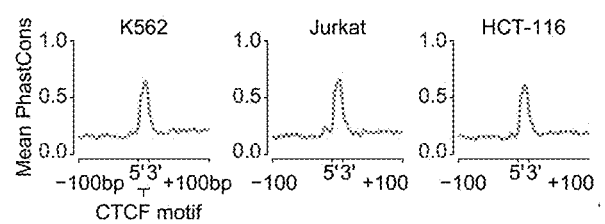

Our initial analysis of putative enhancer-docking sites suggested that additional cancer-associated genes may be regulated in a manner similar to MYC (FIG. 1A). That analysis identified genes within insulated neighborhoods that have CTCF-bound sites at their promoters and that are expressed in multiple cell types. Among these genes were cancer associated genes such as VEGFA and RUNX1, but also developmentally active genes such as TGIF1 (FIG. 6A). These enhancer-docking sites tend to have sequence motifs that are highly conserved (FIG. 6B). These results show that multiple cancer-associated genes possess conserved enhancer-docking sites with properties similar to that described for MYC.

Discussion

We describe here a class of human genes that utilize CTCF-CTCF interactions to connect different cell-type specific enhancers with a single promoter-proximal element that functions as a docking site for those enhancers. These CTCF-mediated enhancer-promoter interactions are generally nested within larger CTCF-mediated loops that function as insulated neighborhoods. At these genes with CTCF-mediated enhancer docking, the enhancers are often bound by CTCF in a cell-type specific fashion whereas the promoter-proximal enhancer-docking sites tend to be constitutively bound by CTCF.

The proto-oncogene MYC, which is controlled by different cell-type specific enhancers during development, is a prominent oncogene and an example of a gene regulated in this fashion. Many different human cancer cells acquire super-enhancers within the ~3 MB MYC TAD/insulated neighborhood and we show here that these exploit a CTCF-mediated enhancer-docking mechanism to express MYC at oncogenic levels. Because tumor super-enhancers can encompass genomic regions as large as 200 kb, and CTCF occupies sites that occur on average every 10 kb, there is considerable opportunity for super-enhancers to adventitiously contain a CTCF-bound site, which in turn could serve to interact with an enhancer-docking site.

Additional genes with roles in cancer employ this CTCF-mediated enhancer-docking mechanism to engender interactions with tumor-specific enhancers. For example, at CSNK1A1, a drug target in AML tumor cells (Järås et al., 2014), VEGFA, which is upregulated in many cancers (Goel and Mercurio, 2013), and RUNX1, a well-defined oncogene in AML (Deltcheva and Nimmo, 2017; Ito et al., 2015), the evidence indicates that super-enhancers in these cancer cells use a CTCF enhancer-docking site to interact with the oncogene. Thus, a CTCF-dependent enhancer-docking mechanism, which presumably facilitates interaction with different cell-specific enhancers during development, is exploited by cancer cells to dysregulate expression of prominent oncogenes.

MYC dysregulation is a hallmark of cancer (Bradner et al., 2017). The c-Myc TF is an attractive target for cancer therapy because of the role that excessive c-Myc levels play in a broad spectrum of aggressive cancers (Felsher and Bishop, 1999; Jain et al., 2002; Soucek et al., 2008, 2013), but direct pharmacologic inhibition of MYC remains an elusive challenge in drug discovery (Bradner et al., 2017). The MYC enhancer-docking site, and presumably those of other oncogenes, can be repressed by dCas9-DNMT-mediated DNA methylation. Oncogene enhancer-docking sites may thus represent a common vulnerability in multiple human cancers.

Materials and Methods:

Star Methods

Experimental Model and Subject Details

Cell Lines

K562 (female), MCF7 (female), HCT-116 (male), Jurkat (male) and HEK293T cells were purchased from ATCC (CCL-243, HTB-22, CCL-247, TIB-152, CRL-3216) and propagated according to ATCC guidelines in RPMI-1640 with GlutaMax (Life Technologies 61870-127) or DMEM, high glucose, pyruvate (Life Technologies 11995-073), supplemented with 10% fetal bovine serum (Sigma). Cells were maintained at 37° C. and 5% CO2.

Method Details

CRISPR/Cas9 Genome Editing

Genome editing was performed using CRISPR/Cas9 essentially as described (Ran et al., 2013; Shalem et al., 2014). The genomic sequences complementary to all guide RNAs are listed in Table S2

TABLE S2

| FIG. 3 sequences gRNAs in pAW21 and pAW22 | |
|---|---|
| 210-Δ.1 | ACCGCCTGTCCTTCCCCCGC (SEQ ID NO: 6) |
| 210-Δ.2 | TTGGTTGCTCCCCGCGTTTG (SEQ ID NO: 7) |
| 4C primers Fwd | AGAGAGGCAGTCTGGTCATG (SEQ ID NO: 9) |
| Rev | CCAGTGTCTTGCTTTCAAAT (SEQ ID NO: 10) |

TABLE S2-continued

FIG. 4 sequences
gRNA for CTCF motif deletion

| | |
|---|---|
| MYC_CTCF | ATGATCTCTGCTGCCAGTAG (SEQ ID NO: 8) |

Primers for detection of endogenous MYC

| | |
|---|---|
| FWD | AACCTCACAACCTTGGCTGA (SEQ ID NO: 11) |
| REV | TTCTTTTATGCCCAAAGTCCAA (SEQ ID NO: 12) |

Primers for detection of exogenous MYC

| | |
|---|---|
| FWD | TGATCCTAGCAGAAGCACAGG (SEQ ID NO: 13) |
| REV | TGGACGAGCTGTTACAAGAGC (SEQ ID NO: 14) |

Primers for detection of GAPDH

| | |
|---|---|
| FWD | TGCACCACCAACTGCTTAGC (SEQ ID NO: 15) |
| REV | GGCATGGACTGTGGTCATGAG (SEQ ID NO: 16) |

FIG. 5 sequences
sgRNAs in pJS-DNMT3A-3L and pLentiGuide Puro

| |
|---|
| GCCTGGATGTCAACGAGGGC (SEQ ID NO: 1) |
| GCGGGTGCTGCCCAGAGAGG (SEQ ID NO: 2) |
| GCAAAATCCAGCATAGCGAT (SEQ ID NO: 3) |
| CTATTCAACCGCATAAGAGA (SEQ ID NO: 4) |
| CGCTGAGCTGCAAACTCAAC (SEQ ID NO: 5) |

Primers for Bisulfite PCR

| | |
|---|---|
| FWD | AAGGAGGTGGYTGGAAAYTT (SEQ ID NO: 17) |
| REV | TCCCTCCACCACCTCCAAAA (SEQ ID NO: 18) |

Figure 9B:
(FIG. 9B) Sequencing of mutant alleles in the selected MCF7 clone with mutated enhancer docking site. The CRISPR targeted region was amplified, fragmented and sequenced to identify the composition and frequency of mutant alleles. The 6 most common mutant alleles are displayed.

FIG. 9 sequences
Primers for genotyping

| | |
|---|---|
| FWD | TCTGAACCACTTTTTCCTCCA (SEQ ID NO: 19) |
| REV | ACTGGCAGCAGAGATCATCG (SEQ ID NO: 20) |

For generation of Myc-cover clones, target-specific oligonucleotides were cloned into the pX330 plasmid which carries a U6 promoter, chimeric guide RNA, and a codon-optimized version of Cas9. pX330 was a kind gift of F. Zhang (Cong et al., 2013) (Addgene: 42230). For the generation of Myc-cover line clones, 2 million cells were transfected with 10 ug of DNA with 50 uL of 1mg/ml PEI and sorted for presence of GFP after 2 days. Individual cells were then propagated in to clonal lines.

For the 210-4 experiments (FIG. 3), target specific oligonucleotides were cloned into a plasmid containing the chimeric RNA, a doxycycline inducible H1 promoter, TetR, and a selectable marker (pAW 21 Addgene 85673 or pAW 22 Addgene 85674). Three separate viruses were produced containing pAW21::up guide, pAW22::down guide, and pLentiCas9-blast (Addgene: 52962, a kind gift of F. Zhang (Sanjana et al., 2014)). Stable cell lines were generated (see section on virus production and cell line generation) and then genome editing was induced by the addition of doxycycline (Sigma Aldrich D9891) at 1 ug/mL. Cells were induced for 72 hours and every 24 hours fresh doxycycline was spiked in.

Virus Production and Generation of Cell Lines

For virus production, HEK293T cells grown to 50-75% confluency on a 15 cm dish and then transfected with 15 μg plasmid of interest, 11.25 μg psPAX (Addgene 12260), and 3.75 μg pMD2.G (Addgene 12259). psPAX and pMD2.G were kind gifts of Didier Trono. After 12 hours, media was replaced. Viral supernatant was collected 24 hours after media replacement (36 hrs post transfection) and fresh media was added. Viral supernatant was collected again 48 hours after the media replacement (60 hours post transfection). Viral supernatant was cleared of cells by either centrifugation at 500×g for 10 minutes or filtration through a 0.45-micron filter. The virus was concentrated with Lenti-X concentrator (Clonetech 631231) per manufacturers' instruction. Concentrated virus was resuspended in either DMEM or RPMI (depending on the cell line being infected) and added to 5 million cells in the presence of polybrene (Millipore TR-1003) at 8 ug/mL. After 24 hours, viral media was removed and fresh media containing drug was added. Drug concentrations are as follows: Puromycin (Thermo A1113802) (2 ug/mL), Geneticin (Thermo 10131027) (800 ug/mL), Blasticidin (Invivogen ant-b1-1) (10 ug/mL). Cells were selected until all cells on non-transduced plates died. The viral plasmid containing pGK-MYC-tdTomato was deposited on Addgene (Plasmid #85675).

RNA Isolation and Quantitative RT-PCR

RNA was isolated using the RNeasy, RNeasy plus or AllPrep kit (QIAGEN 74004, 80204) and reverse transcribed using oligo-dT primers (Promega C1101) and SuperScript III reverse transcriptase (Thermo 18080093) according to the manufacturers' instructions. Quantitative real-time PCR was performed on a 7000 AB Detection System using Taqman probes for MYC (Hs00153408_m1) and GAPDH (Hs02758991_g1) in conjunction with Taqman 2× master mix (Thermo 4304437). For detection of endogenous MYC only in experiments utilizing the MYC cover, primers specific to the endogenous copy of MYC (Table S2) were designed against a MYC 3' UTR region not present in the cover construct and qPCR was conducted with SYBR green PCR master mix (Thermo 4309155).

ChIP-Seq

ChIP was performed as described in (Lee et al., 2006) with a few adaptations.

30 million K562 cells were crosslinked for 10 min at room temperature by the addition of one-tenth of the volume of 11% formaldehyde solution (11% formaldehyde, 50 mM HEPES pH 7.3, 100 mM NaCl, 1 mM EDTA pH 8.0, 0.5 mM EGTA pH 8.0) to the growth media followed by 5 min quenching with 125 mM glycine. Cells were washed twice with PBS, then the supernatant was aspirated and the cell pellet was flash frozen at −80° C. 100 μl of Protein G Dynabeads (Thermo 10003D) were blocked with 0.5% BSA (w/v) in PBS. Magnetic beads were bound with 40 μl of anti-CTCF antibody (Millipore 07-729). Nuclei were isolated as previously described (Lee et al., 2006), and sonicated in lysis buffer (20 mM Tris-HCl pH 8.0, 150 mM NaCl, 2 mM EDTA pH8.0, 0.1% SDS, and 1% Triton X-100) on a Misonix 3000 sonicator for 5 cycles at 30 s each on ice (18-21 W) with 60 s on ice between cycles. Sonicated lysates were cleared once by centrifugation and incubated overnight at 4° C. with magnetic beads bound with antibody to enrich for DNA fragments bound by the indicated factor. Beads were washed with wash buffer A (50 mM HEPES-KOH pH7.9, 140 mM NaCl, 1 mM EDTA pH 8.0, 0.1% Na-Deoxycholate, 1% Triton X-100, 0.1% SDS), B (50 mM HEPES-KOH pH7.9, 500 mM NaCl, 1 mM EDTA pH 8.0, 0.1% Na-Deoxycholate, 1% Triton X-100, 0.1% SDS), C (20 mM Tris-HCl pH8.0, 250 mMLiCl, 1 mM EDTA pH 8.0, 0.5% Na-Deoxycholate, 0.5% IGEPAL C-630 0.1% SDS) and D (TE with 50 mM NaCl) sequentially. DNA was eluted in elution buffer (50 mM Tris-HCL pH 8.0, 10 mM EDTA, 1% SDS). Cross-links were reversed overnight at 65° C. RNA and protein were digested using RNase A and Proteinase K, respectively and DNA was purified with phenol chloroform extraction and ethanol precipitation. Purified ChIP DNA was used to prepare Illumina multiplexed sequencing libraries. Libraries for Illumina sequencing were prepared following the Illumina TruSeq DNA Sample Preparation v2 kit. Amplified libraries were size-selected using a 2% gel cassette in the Pippin Prep system from Sage Science set to capture fragments between 200 and 400 bp. Libraries were quantified by qPCR using the KAPA Biosystems Illumina Library Quantification kit according to kit protocols. Libraries were sequenced on the Illumina HiSeq 2500 for 40 bases in single read mode.

4C-seq

A modified version of 4C-seq (van de Werken et al., 2012a, 2012b) was developed. The major change was the ligation is performed in intact nuclei (in situ). This change was incorporated because previous work has noted that in situ ligation dramatically decreases the rate of chimeric ligations and background interactions (Nagano et al., 2015; Rao et al., 2014).

Approximately 5 million K562 cells were resuspended in 5 mL 10% FBS/PBS. 5 mL of 4% formaldehyde in 10% FBS/PBS was added and cells were cross-linked for 10 minutes while rotating at room temperature. Glycine was added to a final concentration of 0.125 M and cells were centrifuged at 300×g for 5 minutes. Cells were washed twice with PBS, transferred to an eppendorf tube, snap frozen and stored at −80. Pellets were gently resuspended in Hi-C lysis buffer (10 mM Tris-HCl pH 8, 10 mM NaCl, 0.2% Igepal) with 1× protease inhibitors (Roche, 11697498001). Cells were incubated on ice for 30 minutes then washed once with 500 uL of ice-cold Hi-C lysis buffer with no protease inhibitors. Pellets were resuspended in 50 uL of 0.5% SDS and incubated at 62° C. for 7 minutes. 145 uL of water and 25 uL of 10% Triton X-100 were added and tubes incubated at 37° C. for 15 minutes. 25 uL of 10× New England Biolabs CutSmart buffer and 200 units of NlaIII (NEB R0125L) enzyme were added and the chromatin was digested for four hours at 37 degrees in a thermomixer at 500 RPM. 200 additional units of NlaIII was spiked in and digest continued for 12 hours. Then, 200 additional units of NlaIII was spiked in and digest continued for four more hours. Restriction enzyme was inactivated by heating to 62° C. for 20 minutes while shaking at 500 rpm. Proximity ligation was performed in a total of 1200 uL with 2000 units of T4 DNA ligase (NEB M0202M) for six hours at room temperature. After ligation samples were spun down for 5 minutes at 2500 g and resuspended in 300 uL 10 mM Tris-HCl, 1% SDS and 0.5 mM NaCl with 1000 units of Proteinase K. Samples were reversed cross-linked overnight at 68° C.

Samples were then phenol-chloroform extracted and ethanol precipitated and the second digestion was performed overnight in 450 uL with 50 units of CviQI (NEB R0639L). Samples were phenol-chloroform extracted and ethanol precipitated and the second ligation was performed in 14 mL total with 6700 units of T4 DNA ligase (NEB 0202M) at 16° C. overnight. Samples were ethanol precipitated, resuspended in 500 uL Qiagen EB buffer, and purified with a Qiagen PCR kit.

The concentration was measured with a Nanodrop and PCR amplification was performed with 16 50 uL PCR reactions using Roche Expand Long Template polymerase (Roche 11759060001). Reaction conditions are as follows: 11.2 uL Roche Expand Long Template Polymerase, 80 uL of 10× Roche Buffer 1, 16 uL of 10 mM dNTPs (Promega PAU1515), 112 uL of 10 uM forward primer, 112 uL of 10 uM reverse primer (Table S2), 200 ng template, and milli-q water till 800 uL total. Reactions were mixed and then distributed into 16 50 uL reactions for amplification. Cycling conditions were a "Touchdown PCR" based on reports that this decreases non-specific amplification of 4C libraries (Ghavi-Helm et al., 2014). The conditions are: 2' 94° C., 10" 94° C., 1' 63° C., 3' 68° C., repeat steps 2-4 but decrease annealing temperature by one degree, until 53° C. is reached at which point reaction is cycled an additional 15 times at 53° C., after 25 total cycles are performed the reaction is held for 5' at 68° C. and then 4° C. Libraries were cleaned-up using a Roche PCR purification kit (Roche 11732676001) using 4 columns per library. Reactions were then further purified with Ampure XP beads (Agencourt A63882) with a 1:1 ratio of bead solution to library following the manufactures instructions. Samples were then quantified with Qubit and the KAPA Biosystems Illumina Library Quantification kit according to kit protocols. Libraries were sequenced on the Illumina HiSeq 2500 for 40 bases in single read mode.

HiChIP

HiChIP was performed essentially as described (Mumbach et al., 2016). 10 million HCT116 cells were crosslinked for 10 min at room temperature by the addition of one-tenth of the volume of 11% formaldehyde solution (11% formaldehyde, 50 mM HEPES pH 7.3, 100 mM NaCl, 1 mM EDTA pH 8.0, 0.5 mM EGTA pH 8.0) to the growth media followed by 5 min quenching with 125 mM glycine. Cells were washed twice with PBS, then the supernatant was aspirated and the cell pellet was flash frozen in liquid nitrogen. Frozen crosslinked cells were stored at −80° C.

The crosslinked pellets were thawed on ice, resuspended in 500 µL of ice-cold Hi-C Lysis Buffer (10 mM Tris-HCl pH 8.0, 10 mM NaCl, 0.2% NP-40 with protease inhibitors), and rotated at 4° C. for 30 minutes. Nuclei were spun down at 2500 rcf for 5 minutes at 4° C., and washed once with 500 µL of ice-cold Hi-C Lysis Buffer. Supernatant was removed, and the pellet was resuspended in 100 µL of 0.5% SDS. Nuclei were incubated at 62° C. for 7 minutes, and SDS was quenched by addition of 285 µL of H$_2$O and 50 µL of 10% Triton X-100 for 15 minutes at 37° C. After the addition of 50 µL of 10×NEB Buffer 2 and 400 U of MboI restriction enzyme (NEB, R0147), chromatin was digested overnight at 37° C. The following day, the MboI enzyme was inactivated by incubating the nuclei at 62° C. for 20 minutes.

To fill in the restriction fragment overhangs and mark the DNA ends with biotin, the following was added: 37.5 µL 0.4 mM biotin-ATP (19524-016, Invitrogen) 1.5 µL of 10 mM dCTP (N0441S, NEB), 1.5 µL of 10 mM dTTP (N0443S, NEB), 1.5 µL of 10 mM dGTP (N0442S, NEB), 10 µL of 5 U/µL DNA Polymerase I, Large (Klenow) Fragment (NEB, M0210), and the tubes were incubated at 37° C. for 1 hour with rotation. Next, the following mix was added for the proximity ligation step: 150 µL of 10×NEB T4 DNA ligase buffer with 10 mM ATP (NEB, B0202), 125 µL 10% Triton X-100, 3 µL 50 mg/mL BSA, 10 µL 400 U/µL T4 DNA Ligase (NEB, M0202), 660 µL H2O, and the nuclei suspension was incubated at room temperature for 6 hours with rotation. Nuclei were pelleted at 2500 rcf for 5 minutes and supernatant was removed.

Pellets were resuspended in 880 µL in Nuclear Lysis Buffer (50 mM Tris-HCl pH 7.5, 10 mM EDTA, 1% SDS with protease inhibitors), and the lysates were sonicated on a Covaris 5220 instrument using the following parameters: Fill Level 10, Duty Cycle 5, PIP 140, Cycles/Burst 200, for 4 minutes. Sonicated lysates were spun down at 16100 rcf for 15 minutes at 4° C., and the supernatant was transferred to a fresh tube. The supernatant was split into two Eppendorf tubes (about 400 µL of lysate in each), and 800 µL of ChIP dilution buffer (0.01% SDS, 1.1% Triton X-100, 1.2 mM EDTA, 16.7 mM Tris pH 7.5, 167 mM NaCl) was added to each tube. 60 µL of Protein G beads (Life Technologies) were washed in ChIP dilution buffer, resuspended in 100 µL ChIP dilution buffer and 50 µL were added to each of the two tubes of lysates. Tubes were then rotated for 1 hour at 4° C. to preclear the lysates. Dynabeads were separated on a magnetic stand, and the supernatant was moved to a fresh tube. 3.5 µg of SMC1A antibody (Bethyl A300-055A) were added to each tube, and tubes were incubated at 4° C. overnight with rotation. The next day, 60 µL of Protein G beads were washed ChIP Dilution Buffer, resuspended in 100 µL ChIP Dilution Buffer, and 50 µL was added to each sample tube. Samples were then incubated for 2 hours at 4° C. with rotation. Beads were washed twice with Low Salt Wash Buffer (0.1% SDS, 1% Triton X-100, 2 mM EDTA, 20 mM Tris-HCl pH 7.5, 150 mM NaCl), twice with High Salt Wash Buffer (0.1% SDS, 1% Triton X-100, 2 mM EDTA, 20 mM Tris-HCl pH 7.5, 500 mM NaCl), twice with LiCl buffer (10 mM Tris pH 7.5, 250 mM LiCl, 1% NP-40, 1% Sodium-deoxycholate, 1 mM EDTA). Beads were then resuspended in 100 µL of DNA Elution Buffer (50 mM NaHCO$_3$, 1% SDS), incubated for 10 minutes at room temperature with rotation and 3 minutes at 37° C. with shaking. Beads were separated on a magnetic stand, and supernatant was transferred to a fresh tube. Beads were then mixed with another 100 µL of DNA Elution Buffer, incubated for 10 minutes at room temperature with rotation and 3 minutes at 37° C. with shaking. Beads were separated on a magnetic stand, and supernatant was combined with the previous round of supernatant. 10 µL of Proteinase K (20 mg/ml) was added to each sample and samples were incubated at 55° C. for 45 minutes with shaking. Temperature was then increased to 67° C., and samples were incubated for 1.5 hours with shaking. Samples were purified on a Zymo column (Zymo Research).

Fragmentation of the ChIP DNA was performed using the Tn5 transposase (Illumina). First, 5 µL of Streptavidin M-280 magnetic beads were washed with Tween Wash Buffer (5 mM Tris-HCl pH 7.5, 0.5 mM EDTA, 1 M NaCl, 0.05% Tween-20), resuspended in 10 µL of Binding Buffer (10 mM, Tris-HCl pH 7.5, 1 mM EDTA, 2 M NaCl), and added to the samples. Samples were then rotated for 15 minutes at room temperature. Beads were separated on a magnet, and supernatant was discarded. Beads were washed twice with 500 µL of Tween Wash Buffer and incubated at 55° C. for 2 minutes shaking. Beads were then washed with 100 µL of 1×TD Buffer (Nextera DNA sample preparation kit, FC-121-1030, Illumina), and tagmented using the Nextera DNA sample preparation kit (FC-121-1030, Illumina). 0.5 µL TDE1 enzyme was used to tagment 10 ng of ChIP DNA (quantified after the previous Zymo column purification). Tagmentation was performed for 10 minutes at 55° C. with shaking. Beads were then separated on a magnet, and supernatant was discarded. Beads were washed with 50 mM EDTA at 50° C. for 30 minutes, and twice with 50 mM EDTA at 50° C. for 3 minutes. Beads were then washed twice in Tween Wash Buffer at 55° C. for 2 minutes, and once with 10 mM Tris for 1 minute at room temperature. The tagmented library still bound to the beads was amplified by 12 cycles of PCR using the Nextera DNA sample preparation kit. The library was then purified on a Zymo column, size-selected (300-700 bp) using AMPure beads (Agencourt) per manufacturers' instructions, and sequenced 100× 100 on an Illumina Hi-Seq 2500.

Targeted Methylation and Bisulfite Sequencing.

To perform targeted methylation, HCT-116 cells or HEK293T were transfected with a dCas9-DNMT3A-3L construct with or without guides. To generate the dCas9-DNMT3A-3L construct, dCas9 was isolated from pSQL1658 (Addgene: 51023) by PCR. Cas9 was removed from pX330-Cas9 (Addgene: 42230) by AgeI and EcoRI restriction digest. dCas9 was inserted into pX330 to create pX330-dCas9. DNMT3A-3L carrier plasmid was a generous gift from the Jeltsch lab (Siddique et al., 2013). DNMT3A-3L was cloned into pX330-dCas9 using PmeI and AscI sites to create pX330-dCas9-DNMT3A-3L (no guides). Guide RNAs were added to pX330-dCas9-DNMT3A-3L by digesting pX330-dCas9-DNMT3A-3L with BbsI followed by ligation of annealed oligos (Table S2) to create pX330-dCas9-DNMT3A-3L-guide with three different guides. An additional plasmid containing two guides, lentiGuide-Puro-double_guide, was also generated. Double guide containing gBlock (individual guide sequences Table S2) was cloned into lentiGuide-Puro (Addgene: 52963) as described (Vidigal and Ventura, 2015) to create lentiGuide-Puro-double_guide. Two hundred fifty thousand HCT-116 or HEK293T cells were transfected with either 750 ng of pX330-dCas9-DNMT3A-3L (no guides) (Addgene: 85701), 250 ng lentiGuide-Puro, and 5 uL of 1mg/ml PEI, or 250 ng of pX330-dCas9-DNMT3A-3L-guide1, 250 ng of pX330-dCas9-DNMT3A-3L-guide2, 250 ng of pX330-dCas9-DNMT3A-3L-guide3, 250 ng lentiGuide-Puro-double_guide, and 5 uL of 1mg/ml PEI, and harvested after two days. HCT-116 cells were harvested and sorted for GFP presence after two days, HEK293T cells were harvested without cell sorting.

To detect methylation, 2 ug of gDNA from HCT-116 or HEK293T cells transfected with dCas9-DNMT3A-3L or dCas9-DNMT3A-3L plus guides were bisulfite converted using the EpiTect Bisulfite Kit (QIAGEN 59104). Converted gDNA was eluted in 20 uL H2O. Converted gDNA was PCR amplified with EpiMark® Hot Start Taq DNA Polymerase (NEB M0490) using 3 uL of converted gDNA as template and locus specific primers (Table S2). PCR was carried out as follows: 95° C. for 30 sec; 95° C. for 20 sec; 52° C. for 30 sec; 68° C. for 30 sec; repeat steps 2-4 45×; 68° C. for 5 min; Hold 4° C. Resultant amplicons were cleaned up using QIAquick PCR Purification Kit (QIAGEN 28106) and eluted in 20 ul H2O. Clean amplicons (3 uL) were subcloned using the pGEM-T Easy vector system (Promega A1360) and transformed into DH5a competent cells. Individual colonies were then picked, and colony PCR was carried out using GoTaq Green Master Mix (Promega M712) with the same primers originally used for the converted gDNA amplification. Colony PCR was carried out as follows: 95° C. for 2 min; 95° C. for 45 sec; 51° C. for 45 sec; 72° C. for 45 sec; repeat steps 2-4 29×; 72° C. 5 min; Hold 4° C. Resultant amplicons were then Sanger sequenced, and CpG methylation was detected as CpG sequences that were not converted to TpG. All converted DNA analyzed had >95% bisulfite conversion rate.

Hi-C Visualization

Hi-C datasets were visualized using the 3D Genome browser at http://www.3dgenome.org.

Visualization of ChIA-PET Interactions on the WashU Genome Browser

The output of origami was visualized in the WashU genome browser by converting the output of origami into a WashU compatible format using origami-conversion.

Topologically Associating Domain (TAD) Calls

TAD calls were taken from the TAD calls in (Dixon et al., 2012) from the H1 human embryonic cell line.

Quantification and Statistical Analysis

ChIP-Seq Data Analysis

ChIP-Seq datasets were generated for this study as well as collated from previous studies (Table S3), and were aligned using Bowtie (version 0.12.2) (44) to the human genome (build hg19, GRCh37) with parameter-k 1-m 1-n 2. We used the MACS version 1.4.2 (model-based analysis of ChIP-seq) (45) peak finding algorithm to identify regions of ChIP-seq enrichment over input DNA control with the parameter "--no-model--keep-dup=auto". A p-value threshold of enrichment of 1e-09 was used. UCSC Genome Browser tracks were generated using MACS wiggle outputs with parameters "-w-S-space=50". The browser snapshots of the ChIP-Seq binding profiles displayed throughout the study use read per kilobase per million mapped reads dimension (rpm/bp) on the y-axis.

TABLE S3

Datasets and their reference numbers used in this study

ChIP-seq

| Origin | Factor | GEO |
|---|---|---|
| HCT-116 | H3K27Ac | GSM945853 |
| HCT-116 | Input | GSM749774 |
| GM12878 | H3K27Ac | GSM733771 |
| GM12878 | Input | GSM733742 |
| MCF-7 | H3K27Ac | GSM946850 |
| MCF-7 | Input | GSM945859 |
| Panc1 | H3K27Ac | GSM818826 |
| Panc1 | Input | GSM818828 |
| LnCAP | H3K27Ac | GSM686937 |
| LnCAP | Input | GSM686947 |
| u87 | H3K27Ac | GSM894065 |
| u87 | Input | GSM894096 |
| ccRCC | H3K27Ac | GSM1960256 |
| ccRCC | Input | GSM1960260 |
| Jurkat | H3K27Ac | GSM1224780 |
| Jurkat | Input | GSM569086 |
| K562 | H3K27Ac | GSM733656 |
| K562 | Input | GSM733780 |
| HEK293T | H3K27Ac | GSE92879 |
| HEK293T | Input | GSM1910999 |
| GM12878 | CTCF | GSM749706 |
| Jurkat | CTCF | GSM1689152 |
| K562 | CTCF | GSE92879 |
| K562 | Input | GSE92879 |
| ΔK562 | CTCF | GSE92879 |
| HEK293T | CTCF | GSM749668 |
| HCT-116 | CTCF | GSM1010903 |
| MCF7 | CTCF | GSM1022658 |
| MCF7 | Input | GSM945859 |
| Dnd41 | CTCF | GSM1003464 |
| GP5D | CTCF | GSM1240813 |
| LoVo | CTCF | GSM1239390 |
| HeLa | CTCF | GSM749729 |
| HeLa | Input | SRX1097060 |
| Caco2 | CTCF | GSM749748 |
| GM12878 | CTCF | GSM749706 |
| GM12875 | CTCF | GSM749764 |
| A549 | CTCF | GSM1003606 |
| HepG2 | CTCF | GSM803486 |
| MM1.S | CTCF | GSM1070125 |
| Mouse | CTCF | GSM747536 |
| Opossum | CTCF | E-MTAB-437 |
| Dog | CTCF | E-MTAB-437 |
| Rhesus | CTCF | E-MTAB-437 |
| Chicken | CTCF | GSE51846 |

DNA interaction data

| Origin | Factor | Technique | GEO |
|---|---|---|---|
| MCF7 | PolII | ChIA-PET | GSE33664 |
| MCF7 | CTCF | ChIA-PET | GSM970215 |
| K562 | RAD21 | ChIA-PET | GSM1436264 |
| Jurkat | SMC1 | ChIA-PET | GSE68977 |
| HCT-116 | SMC1 | HiChIP | GSE92879 |

Identification of Enhancers and Super-Enhancers

Enhancers and super-enhancers were identified using H3K27Ac ChIP-seq data as previously described (Hnisz et al., 2013). Briefly, enhancers were defined as H3K27Ac ChIP-Seq peaks identified using MACS. To identify super-enhancers, the H3K27Ac ChIP-Seq peaks (i.e. enhancers) were stitched together if they were within 12.5 kb, and the stitched enhancers were ranked by their ChIP-seq read signal of H3K27Ac, using the ROSE algorithm (https://bitbucket.org/young_computation/rose) (Lovén et al., 2013). ROSE separates super-enhancers from typical enhancers by identifying an inflection point of H3K27ac signal vs. enhancer rank (Hnisz et al., 2013; Lovén et al., 2013).

| Super-enhancers across cancer types and their H3K27Ac ChIP-seq densities | | | | | | |
|---|---|---|---|---|---|---|
| Chrom | start | stop | from | H3K27Ac | input | /input |
| chr8 | 128901634 | 128963789 | Brain-u87 | 46516.8 | 10547.7 | 4.410136 |
| chr8 | 129165089 | 129210112 | Brain-u87 | 33222.47 | 7550.357 | 4.400119 |
| chr8 | 128795447 | 128824370 | Breast-MCF7 | 29790.69 | 8491.793 | 3.508174 |
| chr8 | 128860824 | 128884150 | Breast-MCF7 | 31550.75 | 9038.825 | 3.490581 |
| chr8 | 129147244 | 129191727 | Breast-MCF7 | 48980.23 | 13696.32 | 3.576161 |
| chr8 | 128901900 | 128941452 | CML-K562 | 54601.54 | 5758.771 | 9.481456 |
| chr8 | 129046437 | 129091141 | CML-K562 | 66448.03 | 6437.376 | 10.32222 |
| chr8 | 130564436 | 130604313 | CML-K562 | 54930.57 | 7141.971 | 7.691234 |
| chr8 | 130690815 | 130723494 | CML-K562 | 44322.53 | 5202.497 | 8.519472 |
| chr8 | 128957467 | 128984610 | CML-K562 | 29181.44 | 4166.451 | 7.003909 |
| chr8 | 128744519 | 128756323 | Colorectal-HCT116 | 40916.21 | 1541.602 | 26.54135 |
| chr8 | 128208736 | 128320580 | Colorectal-HCT116 | 190906.5 | 18756.24 | 10.17829 |
| chr8 | 128190704 | 128239822 | DLBCL-GM12878 | 115388 | 3281.082 | 35.16766 |
| chr8 | 128298980 | 128321170 | DLBCL-GM12878 | 61690.42 | 1835.113 | 33.61669 |

| Super-enhancers across cancer types and their H3K27Ac ChIP-seq densities | | | | | | |
|---|---|---|---|---|---|---|
| Chrom | start | stop | from | H3K27Ac | input | /input |
| chr8 | 129594445 | 129618316 | Liver-HEPG2 | 62107.57 | 23615.58 | 2.62994 |
| chr8 | 128805716 | 128945203 | Pancreatic-panc1 | 231869.2 | 13627.88 | 17.01433 |
| chr8 | 128805846 | 128836987 | PrimaryKidney-ccRCCII | 15523.79 | 3512.705 | 4.419326 |
| chr8 | 128857246 | 128942648 | PrimaryKidney-ccRCCII | 65699.76 | 13698.48 | 4.796135 |
| chr8 | 128746055 | 128755790 | Prostate-LnCAP | 25723.76 | 1478.747 | 17.39566 |
| chr8 | 128810486 | 128990391 | Prostate-LnCAP | 189655.9 | 24664.98 | 7.689278 |
| chr8 | 129942458 | 130013116 | T-ALL-Jurkat | 43984.61 | 8478.96 | 5.1875 |
| chr8 | 130030058 | 130115864 | T-ALL-Jurkat | 81018.03 | 11266.33 | 7.191165 |
| chr8 | 130148897 | 130290103 | T-ALL-Jurkat | 190811.7 | 19359.34 | 9.856309 |
| chr8 | 130345866 | 130473031 | T-ALL-Jurkat | 156082.3 | 16048.22 | 9.725832 |
| chr8 | 130540472 | 130572787 | T-ALL-Jurkat | 31678.39 | 4262.349 | 7.432146 |

4C Analysis

The 4C-seq samples were first processed by removing their associated read primer sequences from the 5' end of each FASTQ read. To improve mapping efficiency of the trimmed reads by making the read longer, the restriction enzyme digest site was kept on the trimmed read. After trimming the reads, the reads were mapped using bowtie with options -k1-m1 against the hg19 genome assembly. All unmapped or repetitively mapping reads were discarded from further analysis. The hg19 genome was then "digested" in silico according to the restriction enzyme pair used for that sample to identify all the fragments that could be generated by a 4C experiment given a restriction enzyme pair. All mapped reads were assigned to their corresponding fragment based on where they mapped to the genome. The digestion of a sample in a 4C experiment creates a series of "blind" and "non-blind" fragments as described (van de Werken et al., 2012b). In a perfect experiment, we should have only observed reads at non-blind fragments, and reads at blind fragments exhibit a much higher experimental variability than non-blind fragments, so we only used the reads from non-blind fragments for further analysis. To normalize the distribution of different samples, we quantile normalized all non-blind fragments in each sample together. If no reads were detected at a non-blind fragment for a given sample when reads were detected in at least one other sample, we assigned a "0" to that non-blind fragment for the sample(s) missing reads. After normalization, we then smoothed the normalized profile of each sample using a 10 kb running mean at 1000 bp steps across the genome. After smoothing, for each condition we combined the replicates of a condition by taking the mean signal of each bin across all replicates of the condition.

HiChIP Data Analysis

The HiChIP samples were processed by removing their associated read primer sequences from the 5' end of each FASTQ read. Read pairs were separated and separate reads were mapped using bowtie with options -k 1-m 1 against the hg19 genome assembly. Al unmapped or repetitively mapping read were discarded from further analysis. The hg19 genome was then divided in 50 kb bins and reads were joined back together in pairs (Paired End Tag PET). For every pair of bins the number of PETS joining them was then calculated. These data were then further analyzed by the ORIGAMI pipeline to identify significant bin to bin interaction pairs.

ChIA-PET Data Analysis and ORIGAMI Description

We development a new software pipeline and analytical method called origami to process ChIA-PET. The software and releases can be found at https://github.com/younglab/origami using version alpha20160828. Each ChIA-PET data sets was processed as follows: the reads were first trimmed and aligned using origami-alignment, which trims the ChIA-PET linker if present and aligns trimmed PETs. PETs not having a linker were discarded from further analysis. Each end of a PET with a linker sequence were separately mapped to the hg19 genome assembly using bowtie with the following options: -v 1-k 1-m 1. After alignment, the separated PETs were re-paired in the final BAM output. After repairing, all duplicated PETs within the data were removed, since these were believed to be PCR duplicates. Peaks were called on the re-paired ChIA-PET reads using MACS1 v1.4.2 with the following parameters: --nolambda-nomodel-p 1e-9. The ChIA-PET data analyzed with their corresponding linker sequence can be found in Table S4.

TABLE S4

Rad21 ChIA-PET interactions identified using the Mango pipeline within chr8:127100000-131525000

| Anchor 1 | | | Anchor 2 | | | Origami Posterior |
|---|---|---|---|---|---|---|
| chr | start | end | chr | start | end | score |
| chr8 | 100023513 | 100026504 | chr8 | 135844278 | 135845179 | 0 |
| chr8 | 101552284 | 101554003 | chr8 | 146227224 | 146228981 | 0 |
| chr8 | 101575720 | 101577906 | chr8 | 144804210 | 144805137 | 0 |
| chr8 | 101776000 | 101776619 | chr8 | 129201051 | 129204117 | 0 |
| chr8 | 101993048 | 101993904 | chr8 | 144613630 | 144615202 | 0.044 |
| chr8 | 102138237 | 102139789 | chr8 | 130572932 | 130573977 | 0 |
| chr8 | 102148782 | 102152241 | chr8 | 144648850 | 144650112 | 0.045 |
| chr8 | 102215344 | 102218586 | chr8 | 131662983 | 131664104 | 0 |
| chr8 | 103079364 | 103080681 | chr8 | 143528588 | 143529404 | 0.001 |
| chr8 | 103579789 | 103581463 | chr8 | 130690599 | 130698597 | 0 |
| chr8 | 103754509 | 103755759 | chr8 | 139779408 | 139780700 | 0 |
| chr8 | 103822007 | 103824271 | chr8 | 129074007 | 129074657 | 0.069 |
| chr8 | 103874149 | 103877683 | chr8 | 143556624 | 143557688 | 0 |
| chr8 | 10405232 | 10406385 | chr8 | 130458049 | 130460184 | 0 |
| chr8 | 10447038 | 10451285 | chr8 | 145687898 | 145694087 | 0 |
| chr8 | 10548811 | 10549484 | chr8 | 142440979 | 142442237 | 0 |
| chr8 | 106103943 | 106106051 | chr8 | 130708318 | 130711352 | 0.001 |
| chr8 | 106328459 | 106332780 | chr8 | 145747174 | 145749210 | 0 |
| chr8 | 107603518 | 107604902 | chr8 | 130690599 | 130698597 | 0.078 |
| chr8 | 11266584 | 11268410 | chr8 | 144976258 | 144977630 | 0 |
| chr8 | 11424252 | 11425502 | chr8 | 144818191 | 144819803 | 0 |
| chr8 | 116439654 | 116440634 | chr8 | 130586622 | 130588918 | 0.071 |
| chr8 | 11758993 | 11760861 | chr8 | 144814755 | 144816677 | 0 |
| chr8 | 117635580 | 117636837 | chr8 | 146124945 | 146128287 | 0 |
| chr8 | 123687920 | 123688890 | chr8 | 128863351 | 128864822 | 0 |
| chr8 | 123689226 | 123691973 | chr8 | 142396269 | 142398926 | 0 |
| chr8 | 123701700 | 123702600 | chr8 | 145668976 | 145670660 | 0 |
| chr8 | 124048990 | 124051516 | chr8 | 131539617 | 131541377 | 0 |
| chr8 | 124052796 | 124055142 | chr8 | 142309091 | 142310265 | 0 |
| chr8 | 124166473 | 124167842 | chr8 | 130690599 | 130698597 | 0 |
| chr8 | 124427965 | 124430186 | chr8 | 144512427 | 144514351 | 0 |

TABLE S4-continued

Rad21 ChIA-PET interactions identified using the Mango pipeline within chr8:127100000-131525000

| Anchor 1 | | | Anchor 2 | | | Origami Posterior score |
|---|---|---|---|---|---|---|
| chr | start | end | chr | start | end | |
| chr8 | 124775023 | 124781216 | chr8 | 135898207 | 135899420 | 0 |
| chr8 | 124933901 | 124936146 | chr8 | 131687123 | 131688649 | 0.059 |
| chr8 | 124933901 | 124936146 | chr8 | 135643306 | 135644060 | 0 |
| chr8 | 124936563 | 124937824 | chr8 | 130568321 | 130570573 | 0 |
| chr8 | 125049074 | 125050755 | chr8 | 144766236 | 144767123 | 0 |
| chr8 | 125576122 | 125577245 | chr8 | 127821728 | 127822652 | 0 |
| chr8 | 125900120 | 125901746 | chr8 | 127312430 | 127314227 | 0 |
| chr8 | 125968009 | 125969031 | chr8 | 141645298 | 141648346 | 0 |
| chr8 | 12611291 | 12611897 | chr8 | 144678737 | 144680359 | 0 |
| chr8 | 126438288 | 126439362 | chr8 | 146029960 | 146030748 | 0 |
| chr8 | 126440793 | 126445829 | chr8 | 128585179 | 128586353 | 0 |
| chr8 | 126440793 | 126445829 | chr8 | 145022340 | 145027313 | 0 |
| chr8 | 126714207 | 126715689 | chr8 | 127395261 | 127396692 | 0 |
| chr8 | 126714207 | 126715689 | chr8 | 127821728 | 127822652 | 0 |
| chr8 | 126714207 | 126715689 | chr8 | 127836281 | 127837654 | 0 |
| chr8 | 126741377 | 126742014 | chr8 | 127395261 | 127396692 | 0 |
| chr8 | 126923847 | 126924704 | chr8 | 127312430 | 127314227 | 0 |
| chr8 | 126923847 | 126924704 | chr8 | 127395261 | 127396692 | 0 |
| chr8 | 12697849 | 12699125 | chr8 | 143807971 | 143809086 | 0 |
| chr8 | 127312430 | 127314227 | chr8 | 127314423 | 127315266 | 1 |
| chr8 | 127312430 | 127314227 | chr8 | 127395261 | 127396692 | 1 |
| chr8 | 127312430 | 127314227 | chr8 | 127821728 | 127822652 | 0.803 |
| chr8 | 127314423 | 127315266 | chr8 | 127395261 | 127396692 | 0.034 |
| chr8 | 127836281 | 127837654 | chr8 | 128190325 | 128191348 | 0 |
| chr8 | 127836281 | 127837654 | chr8 | 128745001 | 128752294 | 0 |
| chr8 | 127836281 | 127837654 | chr8 | 129201051 | 129204117 | 0 |
| chr8 | 127881465 | 127882077 | chr8 | 127888216 | 127890235 | 0 |
| chr8 | 127881465 | 127882077 | chr8 | 128755105 | 128756028 | 0.022 |
| chr8 | 127888216 | 127890235 | chr8 | 130598258 | 130600266 | 0 |
| chr8 | 127888216 | 127890235 | chr8 | 130690599 | 130698597 | 0.439 |
| chr8 | 127888216 | 127890235 | chr8 | 130708318 | 130711352 | 0 |
| chr8 | 128190325 | 128191348 | chr8 | 128412665 | 128413632 | 0 |
| chr8 | 128190325 | 128191348 | chr8 | 130698611 | 130700895 | 0 |
| chr8 | 128190325 | 128191348 | chr8 | 130708318 | 130711352 | 0 |
| chr8 | 128412665 | 128413632 | chr8 | 128772026 | 128773570 | 0 |
| chr8 | 128412665 | 128413632 | chr8 | 130546973 | 130552572 | 0 |
| chr8 | 128412665 | 128413632 | chr8 | 130737602 | 130739686 | 0 |
| chr8 | 128585179 | 128586353 | chr8 | 128737215 | 128739057 | 0.001 |
| chr8 | 128585179 | 128586353 | chr8 | 128740727 | 128741574 | 0.001 |
| chr8 | 128585179 | 128586353 | chr8 | 128745001 | 128752294 | 0 |
| chr8 | 128585179 | 128586353 | chr8 | 129060227 | 129063805 | 0.033 |
| chr8 | 128585179 | 128586353 | chr8 | 129870968 | 129871979 | 0 |
| chr8 | 128585179 | 128586353 | chr8 | 130546973 | 130552572 | 0 |
| chr8 | 128737215 | 128739057 | chr8 | 128739537 | 128740494 | 1 |
| chr8 | 128737215 | 128739057 | chr8 | 128740727 | 128741574 | 0.942 |
| chr8 | 128737215 | 128739057 | chr8 | 128745001 | 128752294 | 0.999 |
| chr8 | 128737215 | 128739057 | chr8 | 129201051 | 129204117 | 0 |
| chr8 | 128737215 | 128739057 | chr8 | 129209019 | 129210639 | 0 |
| chr8 | 128737215 | 128739057 | chr8 | 129323874 | 129325067 | 0.021 |
| chr8 | 128737215 | 128739057 | chr8 | 129665003 | 129666346 | 0.82 |
| chr8 | 128737215 | 128739057 | chr8 | 129870968 | 129871979 | 0 |
| chr8 | 128737215 | 128739057 | chr8 | 130690599 | 130698597 | 0.04 |
| chr8 | 128737215 | 128739057 | chr8 | 130698611 | 130700895 | 0 |
| chr8 | 128737215 | 128739057 | chr8 | 130737602 | 130739686 | 0 |
| chr8 | 128737215 | 128739057 | chr8 | 145022340 | 145027313 | 0 |
| chr8 | 128739537 | 128740494 | chr8 | 128740727 | 128741574 | 0 |
| chr8 | 128739537 | 128740494 | chr8 | 128745001 | 128752294 | 0.073 |
| chr8 | 128739537 | 128740494 | chr8 | 128772026 | 128773570 | 0 |
| chr8 | 128739537 | 128740494 | chr8 | 129201051 | 129204117 | 0 |
| chr8 | 128739537 | 128740494 | chr8 | 130690599 | 130698597 | 0 |
| chr8 | 128740727 | 128741574 | chr8 | 128745001 | 128752294 | 1 |
| chr8 | 128740727 | 128741574 | chr8 | 130605506 | 130606759 | 0 |
| chr8 | 128752908 | 128753569 | chr8 | 128752908 | 128753569 | 0.976 |
| chr8 | 128745001 | 128752294 | chr8 | 128772026 | 128773570 | 0.985 |
| chr8 | 128745001 | 128752294 | chr8 | 128812838 | 128813544 | 0 |
| chr8 | 128745001 | 128752294 | chr8 | 128830032 | 128831239 | 1 |
| chr8 | 128745001 | 128752294 | chr8 | 128863351 | 128864822 | 0.022 |
| chr8 | 128745001 | 128752294 | chr8 | 128871531 | 128872830 | 0.762 |
| chr8 | 128745001 | 128752294 | chr8 | 128906465 | 128907622 | 0.96 |
| chr8 | 128745001 | 128752294 | chr8 | 128910320 | 128912382 | 0.248 |
| chr8 | 128745001 | 128752294 | chr8 | 128922538 | 128924783 | 0.959 |
| chr8 | 128745001 | 128752294 | chr8 | 128926524 | 128927220 | 0 |
| chr8 | 128745001 | 128752294 | chr8 | 128971685 | 128973318 | 0.224 |
| chr8 | 128745001 | 128752294 | chr8 | 128973335 | 128974261 | 0.039 |
| chr8 | 128745001 | 128752294 | chr8 | 128979417 | 128982624 | 0.021 |
| chr8 | 128745001 | 128752294 | chr8 | 128982695 | 128983816 | 0.03 |
| chr8 | 128745001 | 128752294 | chr8 | 129005065 | 129006002 | 0.284 |
| chr8 | 128745001 | 128752294 | chr8 | 129056676 | 129058361 | 0.019 |
| chr8 | 128745001 | 128752294 | chr8 | 129179729 | 129180447 | 0 |
| chr8 | 128745001 | 128752294 | chr8 | 129188678 | 129190475 | 0 |
| chr8 | 128745001 | 128752294 | chr8 | 129196702 | 129197452 | 0.03 |
| chr8 | 128745001 | 128752294 | chr8 | 129201051 | 129204117 | 1 |
| chr8 | 128745001 | 128752294 | chr8 | 129205265 | 129206000 | 0 |
| chr8 | 128745001 | 128752294 | chr8 | 129209019 | 129210639 | 0.033 |
| chr8 | 128745001 | 128752294 | chr8 | 129334525 | 129335739 | 0.993 |
| chr8 | 128745001 | 128752294 | chr8 | 129665003 | 129666346 | 0.04 |
| chr8 | 128745001 | 128752294 | chr8 | 129870968 | 129871979 | 0 |
| chr8 | 128745001 | 128752294 | chr8 | 130046989 | 130047842 | 0 |
| chr8 | 128745001 | 128752294 | chr8 | 130545778 | 130546819 | 0.044 |
| chr8 | 128745001 | 128752294 | chr8 | 130546973 | 130552572 | 0.329 |
| chr8 | 128745001 | 128752294 | chr8 | 130593151 | 130597089 | 0 |
| chr8 | 128745001 | 128752294 | chr8 | 130598258 | 130600266 | 1 |
| chr8 | 128745001 | 128752294 | chr8 | 130690599 | 130698597 | 0.799 |
| chr8 | 128745001 | 128752294 | chr8 | 130698611 | 130700895 | 0.375 |
| chr8 | 128745001 | 128752294 | chr8 | 130708318 | 130711352 | 0.976 |
| chr8 | 128745001 | 128752294 | chr8 | 130737602 | 130739686 | 0.033 |
| chr8 | 128745001 | 128752294 | chr8 | 140642655 | 140643943 | 0 |
| chr8 | 128752908 | 128753569 | chr8 | 128979417 | 128982624 | 0 |
| chr8 | 128752908 | 128753569 | chr8 | 129201051 | 129204117 | 0 |
| chr8 | 128755105 | 128756028 | chr8 | 128772026 | 128773570 | 0 |
| chr8 | 128755105 | 128756028 | chr8 | 128922538 | 128924783 | 0.027 |
| chr8 | 128755105 | 128756028 | chr8 | 128926524 | 128927220 | 0 |
| chr8 | 128755105 | 128756028 | chr8 | 128982695 | 128983816 | 0 |
| chr8 | 128772026 | 128773570 | chr8 | 128830032 | 128831239 | 0.022 |
| chr8 | 128772026 | 128773570 | chr8 | 129060227 | 129063805 | 0 |
| chr8 | 128772026 | 128773570 | chr8 | 129334525 | 129335739 | 0 |
| chr8 | 128812838 | 128813544 | chr8 | 128973335 | 128974261 | 0 |
| chr8 | 128830032 | 128831239 | chr8 | 128906465 | 128907622 | 0 |
| chr8 | 128830032 | 128831239 | chr8 | 128979417 | 128982624 | 0 |
| chr8 | 128830032 | 128831239 | chr8 | 129209019 | 129210639 | 0 |
| chr8 | 128830032 | 128831239 | chr8 | 130690599 | 130698597 | 0.452 |
| chr8 | 128863351 | 128864822 | chr8 | 129201051 | 129204117 | 0 |
| chr8 | 128871531 | 128872830 | chr8 | 128906465 | 128907622 | 0 |
| chr8 | 128871531 | 128872830 | chr8 | 128922538 | 128924783 | 0 |
| chr8 | 128871531 | 128872830 | chr8 | 130546973 | 130552572 | 0 |
| chr8 | 128871531 | 128872830 | chr8 | 130598258 | 130600266 | 0 |
| chr8 | 128896096 | 128897209 | chr8 | 128910320 | 128912382 | 0.012 |
| chr8 | 128896096 | 128897209 | chr8 | 128971685 | 128973318 | 0 |
| chr8 | 128896096 | 128897209 | chr8 | 129665003 | 129666346 | 0 |
| chr8 | 128906465 | 128907622 | chr8 | 128910320 | 128912382 | 0.001 |
| chr8 | 128906465 | 128907622 | chr8 | 128971685 | 128973318 | 0 |
| chr8 | 128906465 | 128907622 | chr8 | 129056676 | 129058361 | 0.001 |
| chr8 | 128906465 | 128907622 | chr8 | 129334525 | 129335739 | 0 |
| chr8 | 12890957 | 12892199 | chr8 | 131354943 | 131355849 | 0 |
| chr8 | 128910320 | 128912382 | chr8 | 128922538 | 128924783 | 0.167 |
| chr8 | 128910320 | 128912382 | chr8 | 128926524 | 128927220 | 0.013 |
| chr8 | 128910320 | 128912382 | chr8 | 128961565 | 128962391 | 0 |
| chr8 | 128910320 | 128912382 | chr8 | 128971685 | 128973318 | 0 |
| chr8 | 128910320 | 128912382 | chr8 | 128979417 | 128982624 | 0 |
| chr8 | 128910320 | 128912382 | chr8 | 129060227 | 129063805 | 0.814 |
| chr8 | 128910320 | 128912382 | chr8 | 130546973 | 130552572 | 0 |
| chr8 | 128910320 | 128912382 | chr8 | 130568321 | 130570573 | 0.027 |
| chr8 | 128922538 | 128924783 | chr8 | 128926524 | 128927220 | 0.974 |
| chr8 | 128922538 | 128924783 | chr8 | 128971685 | 128973318 | 0 |
| chr8 | 128922538 | 128924783 | chr8 | 129005065 | 129006002 | 0 |
| chr8 | 128922538 | 128924783 | chr8 | 129060227 | 129063805 | 0 |
| chr8 | 128922538 | 128924783 | chr8 | 129209019 | 129210639 | 0 |
| chr8 | 128922538 | 128924783 | chr8 | 129334525 | 129335739 | 0.028 |
| chr8 | 128926524 | 128927220 | chr8 | 128979417 | 128982624 | 0 |
| chr8 | 128926524 | 128927220 | chr8 | 129026412 | 129027434 | 0 |
| chr8 | 128926524 | 128927220 | chr8 | 129077563 | 129078732 | 0 |
| chr8 | 128958204 | 128958790 | chr8 | 128971685 | 128973318 | 0 |
| chr8 | 128961565 | 128962391 | chr8 | 128971685 | 128973318 | 0 |
| chr8 | 128971685 | 128973318 | chr8 | 128973335 | 128974261 | 1 |

TABLE S4-continued

Rad21 ChIA-PET interactions identified using the Mango pipeline within chr8:127100000-131525000

| Anchor 1 | | | Anchor 2 | | | Origami Posterior score |
|---|---|---|---|---|---|---|
| chr | start | end | chr | start | end | |
| chr8 | 128971685 | 128973318 | chr8 | 128979417 | 128982624 | 0 |
| chr8 | 128971685 | 128973318 | chr8 | 129056676 | 129058361 | 0 |
| chr8 | 128971685 | 128973318 | chr8 | 129060227 | 129063805 | 0.224 |
| chr8 | 128971685 | 128973318 | chr8 | 129209019 | 129210639 | 0 |
| chr8 | 128973335 | 128974261 | chr8 | 128979417 | 128982624 | 0.006 |
| chr8 | 128973335 | 128974261 | chr8 | 128982695 | 128983816 | 0.01 |
| chr8 | 128973335 | 128974261 | chr8 | 130708318 | 130711352 | 0 |
| chr8 | 128979417 | 128982624 | chr8 | 128982695 | 128983816 | 1 |
| chr8 | 128979417 | 128982624 | chr8 | 128989794 | 128990535 | 0 |
| chr8 | 128979417 | 128982624 | chr8 | 129026412 | 129027434 | 0 |
| chr8 | 128979417 | 128982624 | chr8 | 129056676 | 129058361 | 0.019 |
| chr8 | 128979417 | 128982624 | chr8 | 129058652 | 129059360 | 0 |
| chr8 | 128979417 | 128982624 | chr8 | 129060227 | 129063805 | 0 |
| chr8 | 128979417 | 128982624 | chr8 | 129089447 | 129090574 | 0 |
| chr8 | 128979417 | 128982624 | chr8 | 129201051 | 129204117 | 0.021 |
| chr8 | 128982695 | 128983816 | chr8 | 128988702 | 128989721 | 0 |
| chr8 | 128982695 | 128983816 | chr8 | 128989794 | 128990535 | 0 |
| chr8 | 128982695 | 128983816 | chr8 | 129026412 | 129027434 | 0 |
| chr8 | 128982695 | 128983816 | chr8 | 129056676 | 129058361 | 0 |
| chr8 | 128982695 | 128983816 | chr8 | 129060227 | 129063805 | 0 |
| chr8 | 128988702 | 128989721 | chr8 | 128989794 | 128990535 | 0.163 |
| chr8 | 128988702 | 128989721 | chr8 | 129060227 | 129063805 | 0 |
| chr8 | 128988702 | 128989721 | chr8 | 130698611 | 130700895 | 0 |
| chr8 | 128988702 | 128989721 | chr8 | 145800376 | 145801377 | 0 |
| chr8 | 128989794 | 128990535 | chr8 | 129060227 | 129063805 | 0 |
| chr8 | 128989794 | 128990535 | chr8 | 130598258 | 130600266 | 0.001 |
| chr8 | 129026412 | 129027434 | chr8 | 129060227 | 129063805 | 0.237 |
| chr8 | 129026412 | 129027434 | chr8 | 135702207 | 135704374 | 0 |
| chr8 | 129056676 | 129058361 | chr8 | 129058652 | 129059360 | 1 |
| chr8 | 129056676 | 129058361 | chr8 | 129060227 | 129063805 | 0.992 |
| chr8 | 129056676 | 129058361 | chr8 | 129074007 | 129074657 | 0 |
| chr8 | 129056676 | 129058361 | chr8 | 129188678 | 129190475 | 0 |
| chr8 | 129056676 | 129058361 | chr8 | 129201051 | 129204117 | 0.021 |
| chr8 | 129058652 | 129059360 | chr8 | 129060227 | 129063805 | 0.246 |
| chr8 | 129060227 | 129063805 | chr8 | 129074007 | 129074657 | 0 |
| chr8 | 129060227 | 129063805 | chr8 | 129188678 | 129190475 | 0 |
| chr8 | 129060227 | 129063805 | chr8 | 129201051 | 129204117 | 0 |
| chr8 | 129060227 | 129063805 | chr8 | 130546973 | 130552572 | 0 |
| chr8 | 129074007 | 129074657 | chr8 | 129077563 | 129078732 | 0.001 |
| chr8 | 129074007 | 129074657 | chr8 | 129188678 | 129190475 | 0.016 |
| chr8 | 129077563 | 129078732 | chr8 | 129201051 | 129204117 | 0 |
| chr8 | 129139733 | 129140369 | chr8 | 129200156 | 129200875 | 0 |
| chr8 | 129139733 | 129140369 | chr8 | 129201051 | 129204117 | 0 |
| chr8 | 129179729 | 129180447 | chr8 | 129201051 | 129204117 | 0 |
| chr8 | 129179729 | 129180447 | chr8 | 129209019 | 129210639 | 0 |
| chr8 | 129188678 | 129190475 | chr8 | 129196702 | 129197452 | 0 |
| chr8 | 129188678 | 129190475 | chr8 | 129334525 | 129335739 | 0 |
| chr8 | 129188678 | 129190475 | chr8 | 129439950 | 129441386 | 0 |
| chr8 | 129188678 | 129190475 | chr8 | 130708318 | 130711352 | 0 |
| chr8 | 129196702 | 129197452 | chr8 | 129200156 | 129200875 | 0 |
| chr8 | 129196702 | 129197452 | chr8 | 129201051 | 129204117 | 0.051 |
| chr8 | 129200156 | 129200875 | chr8 | 129201051 | 129204117 | 0.998 |
| chr8 | 129200156 | 129200875 | chr8 | 129205265 | 129206000 | 0 |
| chr8 | 129201051 | 129204117 | chr8 | 129205265 | 129206000 | 1 |
| chr8 | 129201051 | 129204117 | chr8 | 129209019 | 129210639 | 1 |
| chr8 | 129201051 | 129204117 | chr8 | 130598258 | 130600266 | 0 |
| chr8 | 129201051 | 129204117 | chr8 | 130698611 | 130700895 | 0.045 |
| chr8 | 129205265 | 129206000 | chr8 | 129209019 | 129210639 | 0.002 |
| chr8 | 129209019 | 129210639 | chr8 | 129334525 | 129335739 | 0 |
| chr8 | 129209019 | 129210639 | chr8 | 129439950 | 129441386 | 0 |
| chr8 | 129209019 | 129210639 | chr8 | 129870968 | 129871979 | 0 |
| chr8 | 129209019 | 129210639 | chr8 | 130546973 | 130552572 | 0.432 |
| chr8 | 129209019 | 129210639 | chr8 | 130690599 | 130698597 | 0 |
| chr8 | 129209019 | 129210639 | chr8 | 130708318 | 130711352 | 0 |
| chr8 | 129323874 | 129325067 | chr8 | 129870968 | 129871979 | 0 |
| chr8 | 129439950 | 129441386 | chr8 | 130568321 | 130570573 | 0.043 |
| chr8 | 129439950 | 129441386 | chr8 | 130593151 | 130597089 | 0 |
| chr8 | 129439950 | 129441386 | chr8 | 130708318 | 130711352 | 0 |
| chr8 | 129665003 | 129666346 | chr8 | 130698611 | 130700895 | 0.36 |
| chr8 | 130046989 | 130047842 | chr8 | 130593151 | 130597089 | 0 |
| chr8 | 130046989 | 130047842 | chr8 | 130708318 | 130711352 | 0.036 |
| chr8 | 130046989 | 130047842 | chr8 | 131026525 | 131029774 | 0 |
| chr8 | 130315457 | 130316173 | chr8 | 130458049 | 130460184 | 0.001 |
| chr8 | 130315457 | 130316173 | chr8 | 130545778 | 130546819 | 0 |
| chr8 | 130315457 | 130316173 | chr8 | 130546973 | 130552572 | 0.252 |
| chr8 | 130315457 | 130316173 | chr8 | 130568321 | 130570573 | 0.001 |
| chr8 | 130315457 | 130316173 | chr8 | 130690599 | 130698597 | 0 |
| chr8 | 130458049 | 130460184 | chr8 | 130593151 | 130597089 | 0.016 |
| chr8 | 130458049 | 130460184 | chr8 | 130690599 | 130698597 | 0 |
| chr8 | 130492020 | 130493130 | chr8 | 130708318 | 130711352 | 0 |
| chr8 | 130545778 | 130546819 | chr8 | 130546973 | 130552572 | 1 |
| chr8 | 130545778 | 130546819 | chr8 | 130568321 | 130570573 | 0 |
| chr8 | 130545778 | 130546819 | chr8 | 130593151 | 130597089 | 0 |
| chr8 | 130545778 | 130546819 | chr8 | 130690599 | 130698597 | 0 |
| chr8 | 130546973 | 130552572 | chr8 | 130568321 | 130570573 | 0.011 |
| chr8 | 130546973 | 130552572 | chr8 | 130585224 | 130586153 | 0.717 |
| chr8 | 130546973 | 130552572 | chr8 | 130586622 | 130588918 | 0 |
| chr8 | 130546973 | 130552572 | chr8 | 130593151 | 130597089 | 0.988 |
| chr8 | 130546973 | 130552572 | chr8 | 130598258 | 130600266 | 0.708 |
| chr8 | 130546973 | 130552572 | chr8 | 130690599 | 130698597 | 1 |
| chr8 | 130546973 | 130552572 | chr8 | 130704200 | 130705767 | 0.017 |
| chr8 | 130546973 | 130552572 | chr8 | 130708318 | 130711352 | 0.018 |
| chr8 | 130546973 | 130552572 | chr8 | 130737602 | 130739686 | 0.026 |
| chr8 | 130568321 | 130570573 | chr8 | 130572932 | 130573977 | 0.037 |
| chr8 | 130568321 | 130570573 | chr8 | 130586622 | 130588918 | 0.156 |
| chr8 | 130568321 | 130570573 | chr8 | 130593151 | 130597089 | 1 |
| chr8 | 130568321 | 130570573 | chr8 | 130597106 | 130598041 | 0 |
| chr8 | 130568321 | 130570573 | chr8 | 130690599 | 130698597 | 0.23 |
| chr8 | 130568321 | 130570573 | chr8 | 130737602 | 130739686 | 0.022 |
| chr8 | 130572932 | 130573977 | chr8 | 130586622 | 130588918 | 0 |
| chr8 | 130572932 | 130573977 | chr8 | 130593151 | 130597089 | 0 |
| chr8 | 130572932 | 130573977 | chr8 | 130598258 | 130600266 | 0 |
| chr8 | 130583755 | 130584650 | chr8 | 130585224 | 130586153 | 0 |
| chr8 | 130583755 | 130584650 | chr8 | 130593151 | 130597089 | 0.857 |
| chr8 | 130583755 | 130584650 | chr8 | 130605506 | 130606759 | 0 |
| chr8 | 130585224 | 130586153 | chr8 | 130586622 | 130588918 | 0.554 |
| chr8 | 130585224 | 130586153 | chr8 | 130593151 | 130597089 | 0 |
| chr8 | 130585224 | 130586153 | chr8 | 130690599 | 130698597 | 0.022 |
| chr8 | 130586622 | 130588918 | chr8 | 130593151 | 130597089 | 0.065 |
| chr8 | 130586622 | 130588918 | chr8 | 130598258 | 130600266 | 0 |
| chr8 | 130586622 | 130588918 | chr8 | 130603392 | 130604269 | 0 |
| chr8 | 130586622 | 130588918 | chr8 | 130690599 | 130698597 | 0.236 |
| chr8 | 130586622 | 130588918 | chr8 | 130698611 | 130700895 | 0 |
| chr8 | 130586622 | 130588918 | chr8 | 142396269 | 142398926 | 0 |
| chr8 | 130593151 | 130597089 | chr8 | 130597106 | 130598041 | 0.089 |
| chr8 | 130593151 | 130597089 | chr8 | 130598258 | 130600266 | 1 |
| chr8 | 130593151 | 130597089 | chr8 | 130603392 | 130604269 | 0 |
| chr8 | 130593151 | 130597089 | chr8 | 130690599 | 130698597 | 0.674 |
| chr8 | 130593151 | 130597089 | chr8 | 130698611 | 130700895 | 0.014 |
| chr8 | 130597106 | 130598041 | chr8 | 130598258 | 130600266 | 1 |
| chr8 | 130597106 | 130598041 | chr8 | 130603392 | 130604269 | 0.004 |
| chr8 | 130597106 | 130598041 | chr8 | 130690599 | 130698597 | 0 |
| chr8 | 130598258 | 130600266 | chr8 | 130603392 | 130604269 | 0.004 |
| chr8 | 130598258 | 130600266 | chr8 | 130605506 | 130606759 | 0.004 |
| chr8 | 130598258 | 130600266 | chr8 | 130690599 | 130698597 | 0.214 |
| chr8 | 130598258 | 130600266 | chr8 | 130698611 | 130700895 | 0 |
| chr8 | 130598258 | 130600266 | chr8 | 130704200 | 130705767 | 0 |
| chr8 | 130598258 | 130600266 | chr8 | 130737602 | 130739686 | 0 |
| chr8 | 130603392 | 130604269 | chr8 | 130605506 | 130606759 | 0.009 |
| chr8 | 130603392 | 130604269 | chr8 | 130690599 | 130698597 | 0.804 |
| chr8 | 130603392 | 130604269 | chr8 | 130698611 | 130700895 | 0 |
| chr8 | 130605506 | 130606759 | chr8 | 130690599 | 130698597 | 1 |
| chr8 | 130605506 | 130606759 | chr8 | 130708318 | 130711352 | 0.015 |
| chr8 | 130605506 | 130606759 | chr8 | 130737602 | 130739686 | 0.329 |
| chr8 | 130690599 | 130698597 | chr8 | 130698611 | 130700895 | 1 |
| chr8 | 130690599 | 130698597 | chr8 | 130704200 | 130705767 | 0.11 |
| chr8 | 130690599 | 130698597 | chr8 | 130708318 | 130711352 | 0.996 |
| chr8 | 130690599 | 130698597 | chr8 | 130737602 | 130739686 | 0.999 |
| chr8 | 130690599 | 130698597 | chr8 | 130831818 | 130832877 | 0 |
| chr8 | 130698611 | 130700895 | chr8 | 130704200 | 130705767 | 0.371 |
| chr8 | 130698611 | 130700895 | chr8 | 130708318 | 130711352 | 0.15 |
| chr8 | 130698611 | 130700895 | chr8 | 130737602 | 130739686 | 0.264 |
| chr8 | 130708318 | 130711352 | chr8 | 130737602 | 130739686 | 0.028 |
| chr8 | 130708318 | 130711352 | chr8 | 130837988 | 130839275 | 0 |

TABLE S4-continued

Rad21 ChIA-PET interactions identified using the Mango pipeline within chr8:127100000-131525000

| Anchor 1 | | | Anchor 2 | | | Origami Posterior score |
|---|---|---|---|---|---|---|
| chr | start | end | chr | start | end | |
| chr8 | 130708318 | 130711352 | chr8 | 142188957 | 142189899 | 0 |
| chr8 | 130737602 | 130739686 | chr8 | 130831818 | 130832877 | 0 |
| chr8 | 130737602 | 130739686 | chr8 | 130903346 | 130904813 | 0 |
| chr8 | 130831818 | 130832877 | chr8 | 130837988 | 130839275 | 0.505 |
| chr8 | 130831818 | 130832877 | chr8 | 131004713 | 131005540 | 0.022 |
| chr8 | 130831818 | 130832877 | chr8 | 131026525 | 131029774 | 0 |
| chr8 | 130837988 | 130839275 | chr8 | 130903346 | 130904813 | 0.301 |
| chr8 | 130837988 | 130839275 | chr8 | 130949614 | 130953044 | 0 |
| chr8 | 130837988 | 130839275 | chr8 | 131026525 | 131029774 | 0 |
| chr8 | 130837988 | 130839275 | chr8 | 131106374 | 131107715 | 0.014 |
| chr8 | 130837988 | 130839275 | chr8 | 131141341 | 131142646 | 0 |
| chr8 | 130903346 | 130904813 | chr8 | 130949614 | 130953044 | 0 |
| chr8 | 130903346 | 130904813 | chr8 | 131026525 | 131029774 | 0.03 |
| chr8 | 130903346 | 130904813 | chr8 | 131054195 | 131055145 | 0.024 |
| chr8 | 130903346 | 130904813 | chr8 | 131106374 | 131107715 | 0.02 |
| chr8 | 130949614 | 130953044 | chr8 | 131004713 | 131005540 | 0 |
| chr8 | 130949614 | 130953044 | chr8 | 131012082 | 131012745 | 0 |
| chr8 | 130949614 | 130953044 | chr8 | 131026525 | 131029774 | 1 |
| chr8 | 130949614 | 130953044 | chr8 | 131106374 | 131107715 | 0.275 |
| chr8 | 130949614 | 130953044 | chr8 | 131141341 | 131142646 | 0 |
| chr8 | 130949614 | 130953044 | chr8 | 131314549 | 131315329 | 0 |
| chr8 | 131004713 | 131005540 | chr8 | 131012082 | 131012745 | 0 |
| chr8 | 131004713 | 131005540 | chr8 | 131026525 | 131029774 | 0 |
| chr8 | 131004713 | 131005540 | chr8 | 131106374 | 131107715 | 0.179 |
| chr8 | 131004713 | 131005540 | chr8 | 131687123 | 131688649 | 0 |
| chr8 | 131012082 | 131012745 | chr8 | 131026525 | 131029774 | 0 |
| chr8 | 131026525 | 131029774 | chr8 | 131106374 | 131107715 | 0.741 |
| chr8 | 131026525 | 131029774 | chr8 | 131108342 | 131109153 | 0 |
| chr8 | 131054195 | 131055145 | chr8 | 131108342 | 131109153 | 0 |
| chr8 | 131106374 | 131107715 | chr8 | 131108342 | 131109153 | 0.992 |
| chr8 | 131108342 | 131109153 | chr8 | 131141341 | 131142646 | 0 |
| chr8 | 131141341 | 131142646 | chr8 | 131218754 | 131220917 | 0 |
| chr8 | 131141341 | 131142646 | chr8 | 131428415 | 131429483 | 0.016 |
| chr8 | 131141341 | 131142646 | chr8 | 131539617 | 131541377 | 0 |
| chr8 | 131141341 | 131142646 | chr8 | 131687123 | 131688649 | 0.033 |
| chr8 | 131217475 | 131218635 | chr8 | 131218754 | 131220917 | 1 |
| chr8 | 131217475 | 131218635 | chr8 | 131662983 | 131664104 | 0 |
| chr8 | 131217475 | 131218635 | chr8 | 131687123 | 131688649 | 0 |
| chr8 | 131217475 | 131218635 | chr8 | 131814715 | 131815599 | 0.008 |
| chr8 | 131217475 | 131218635 | chr8 | 141368515 | 141369409 | 0 |
| chr8 | 131218754 | 131220917 | chr8 | 131221892 | 131222566 | 1 |
| chr8 | 131218754 | 131220917 | chr8 | 131314549 | 131315329 | 0.001 |
| chr8 | 131218754 | 131220917 | chr8 | 131354943 | 131355849 | 0.014 |
| chr8 | 131218754 | 131220917 | chr8 | 131428415 | 131429483 | 0 |
| chr8 | 131218754 | 131220917 | chr8 | 131539617 | 131541377 | 0.023 |
| chr8 | 131218754 | 131220917 | chr8 | 131662983 | 131664104 | 0.02 |
| chr8 | 131218754 | 131220917 | chr8 | 131685699 | 131686905 | 0.023 |
| chr8 | 131218754 | 131220917 | chr8 | 131687123 | 131688649 | 0 |
| chr8 | 131218754 | 131220917 | chr8 | 131761459 | 131762640 | 0 |
| chr8 | 131324383 | 131326133 | chr8 | 131354943 | 131355849 | 0 |
| chr8 | 131324383 | 131326133 | chr8 | 131368061 | 131368807 | 0 |
| chr8 | 131324383 | 131326133 | chr8 | 131449242 | 131450570 | 0.024 |
| chr8 | 131324383 | 131326133 | chr8 | 131687123 | 131688649 | 0 |
| chr8 | 131354943 | 131355849 | chr8 | 131368061 | 131368807 | 0 |
| chr8 | 131354943 | 131355849 | chr8 | 131428415 | 131429483 | 0 |
| chr8 | 131449242 | 131450570 | chr8 | 131685699 | 131686905 | 0 |
| chr8 | 131449242 | 131450570 | chr8 | 131687123 | 131688649 | 0 |
| chr8 | 17721821 | 17722593 | chr8 | 141839832 | 141842447 | 0 |
| chr8 | 17766122 | 17766760 | chr8 | 145633535 | 145635801 | 0.058 |
| chr8 | 19980680 | 19981998 | chr8 | 130593151 | 130597089 | 0 |
| chr8 | 20233066 | 20234571 | chr8 | 134897905 | 134898841 | 0.08 |
| chr8 | 20233066 | 20234571 | chr8 | 144065140 | 144066265 | 0 |
| chr8 | 20238005 | 20238898 | chr8 | 145050444 | 145052169 | 0 |
| chr8 | 21775364 | 21780955 | chr8 | 128745001 | 128752294 | 0 |
| chr8 | 21775364 | 21780955 | chr8 | 144482902 | 144484922 | 0 |
| chr8 | 22021266 | 22023560 | chr8 | 145595825 | 145599141 | 0 |
| chr8 | 22223857 | 22226191 | chr8 | 141645298 | 141648346 | 0 |
| chr8 | 2241050 | 2242195 | chr8 | 130568321 | 130570573 | 0 |
| chr8 | 22431393 | 22432637 | chr8 | 128745001 | 128752294 | 0 |
| chr8 | 22446101 | 22447372 | chr8 | 130737602 | 130739686 | 0 |
| chr8 | 22479429 | 22481441 | chr8 | 135490147 | 135491713 | 0 |
| chr8 | 22479429 | 22481441 | chr8 | 141677746 | 141679430 | 0 |
| chr8 | 22479429 | 22481441 | chr8 | 144698944 | 144700284 | 0 |
| chr8 | 22612812 | 22615737 | chr8 | 139947975 | 139948942 | 0 |
| chr8 | 22758225 | 22759650 | chr8 | 129201051 | 129204117 | 0 |
| chr8 | 22759967 | 22760950 | chr8 | 145687898 | 145694087 | 0 |
| chr8 | 22774357 | 22777284 | chr8 | 128737215 | 128739057 | 0 |
| chr8 | 23152772 | 23154664 | chr8 | 135732055 | 135733214 | 0 |
| chr8 | 23152772 | 23154664 | chr8 | 145742678 | 145744490 | 0 |
| chr8 | 23327688 | 23328475 | chr8 | 141520657 | 141522552 | 0 |
| chr8 | 23350728 | 23352514 | chr8 | 130586622 | 130588918 | 0 |
| chr8 | 24748840 | 24750060 | chr8 | 130690599 | 130698597 | 0 |
| chr8 | 26183546 | 26186302 | chr8 | 131368061 | 131368807 | 0 |
| chr8 | 26239804 | 26241164 | chr8 | 144512427 | 144514351 | 0 |
| chr8 | 26511309 | 26512178 | chr8 | 142085213 | 142086393 | 0 |
| chr8 | 27168515 | 27169605 | chr8 | 145149363 | 145151859 | 0 |
| chr8 | 27221014 | 27222090 | chr8 | 141677746 | 141679430 | 0 |
| chr8 | 27283202 | 27284503 | chr8 | 127312430 | 127314227 | 0 |
| chr8 | 27283202 | 27284503 | chr8 | 130593151 | 130597089 | 0 |
| chr8 | 27339112 | 27340519 | chr8 | 144922768 | 144924012 | 0 |
| chr8 | 28587092 | 28589233 | chr8 | 142010917 | 142013275 | 0 |
| chr8 | 28749559 | 28750678 | chr8 | 144128912 | 144130455 | 0 |
| chr8 | 29197205 | 29199759 | chr8 | 134897905 | 134898841 | 0.061 |
| chr8 | 29504636 | 29505351 | chr8 | 144896213 | 144898507 | 0 |
| chr8 | 30457638 | 30459196 | chr8 | 145595825 | 145599141 | 0 |
| chr8 | 30523919 | 30525218 | chr8 | 142085213 | 142086393 | 0.076 |
| chr8 | 30600783 | 30603338 | chr8 | 142396269 | 142398926 | 0.067 |
| chr8 | 31109302 | 31110357 | chr8 | 135917363 | 135919042 | 0.001 |
| chr8 | 37250368 | 37251410 | chr8 | 145595825 | 145599141 | 0 |
| chr8 | 37593419 | 37595400 | chr8 | 128922538 | 128924783 | 0 |
| chr8 | 37641933 | 37642550 | chr8 | 144128912 | 144130455 | 0 |
| chr8 | 37756439 | 37758610 | chr8 | 134467563 | 134468527 | 0 |
| chr8 | 37772855 | 37774422 | chr8 | 130690599 | 130698597 | 0 |
| chr8 | 37923256 | 37925824 | chr8 | 139779408 | 139780700 | 0 |
| chr8 | 38041196 | 38042674 | chr8 | 143626502 | 143627671 | 0.001 |
| chr8 | 38143794 | 38144883 | chr8 | 131662983 | 131664104 | 0 |
| chr8 | 38237603 | 38238986 | chr8 | 142182810 | 142185945 | 0 |
| chr8 | 38650278 | 38651134 | chr8 | 130698611 | 130700895 | 0.058 |
| chr8 | 38758123 | 38759985 | chr8 | 144635158 | 144636621 | 0 |
| chr8 | 41399857 | 41401097 | chr8 | 140642655 | 140643943 | 0 |
| chr8 | 43092906 | 43097258 | chr8 | 130546973 | 130552572 | 0 |
| chr8 | 43092906 | 43097258 | chr8 | 132816043 | 132817267 | 0 |
| chr8 | 43092906 | 43097258 | chr8 | 139779408 | 139780700 | 0 |
| chr8 | 43092906 | 43097258 | chr8 | 142393692 | 142395621 | 0 |
| chr8 | 43092906 | 43097258 | chr8 | 145156628 | 145157340 | 0 |
| chr8 | 48091681 | 48092511 | chr8 | 130949614 | 130953044 | 0 |
| chr8 | 49230259 | 49232309 | chr8 | 141473789 | 141479154 | 0 |
| chr8 | 49426773 | 49427489 | chr8 | 130737602 | 130739686 | 0 |
| chr8 | 53024556 | 53025728 | chr8 | 144512427 | 144514351 | 0 |
| chr8 | 54720136 | 54723135 | chr8 | 144465150 | 144466745 | 0 |
| chr8 | 54720136 | 54723135 | chr8 | 145022340 | 145027313 | 0 |
| chr8 | 54922363 | 54923759 | chr8 | 143807971 | 143809086 | 0 |
| chr8 | 55077613 | 55079504 | chr8 | 144065140 | 144066265 | 0 |
| chr8 | 55081419 | 55082697 | chr8 | 128772026 | 128773570 | 0.139 |
| chr8 | 56491886 | 56493220 | chr8 | 128830032 | 128831239 | 0 |
| chr8 | 57154084 | 57155164 | chr8 | 142318117 | 142319018 | 0 |
| chr8 | 59613344 | 59615285 | chr8 | 133887320 | 133888571 | 0 |
| chr8 | 61047831 | 61049604 | chr8 | 144360266 | 144362998 | 0.001 |
| chr8 | 61145216 | 61146452 | chr8 | 128772026 | 128773570 | 0 |
| chr8 | 61308455 | 61310413 | chr8 | 145638041 | 145639295 | 0 |
| chr8 | 61385388 | 61386460 | chr8 | 128745001 | 128752294 | 0.001 |
| chr8 | 61526023 | 61526989 | chr8 | 130603392 | 130604269 | 0.043 |
| chr8 | 62156131 | 62157133 | chr8 | 143946196 | 143947130 | 0 |
| chr8 | 62694046 | 62694993 | chr8 | 130568321 | 130570573 | 0 |
| chr8 | 65294292 | 65295369 | chr8 | 143554594 | 143555736 | 0 |
| chr8 | 6697727 | 6698956 | chr8 | 134220900 | 134224092 | 0 |
| chr8 | 67333464 | 67334660 | chr8 | 145566424 | 145567522 | 0 |
| chr8 | 67340514 | 67343200 | chr8 | 133063885 | 133064792 | 0.067 |
| chr8 | 67340514 | 67343200 | chr8 | 145056104 | 145057625 | 0 |
| chr8 | 67524845 | 67525961 | chr8 | 130698611 | 130700895 | 0 |
| chr8 | 67600719 | 67601821 | chr8 | 141645298 | 141648346 | 0 |
| chr8 | 68250221 | 68253790 | chr8 | 144372705 | 144375080 | 0.052 |
| chr8 | 68401676 | 68404310 | chr8 | 141473789 | 141479154 | 0 |
| chr8 | 68401676 | 68404310 | chr8 | 145022340 | 145027313 | 0 |

TABLE S4-continued

Rad21 ChIA-PET interactions identified using the Mango pipeline within chr8:127100000-131525000

| Anchor 1 | | | Anchor 2 | | | Origami Posterior |
|---|---|---|---|---|---|---|
| chr | start | end | chr | start | end | score |
| chr8 | 73231621 | 73232880 | chr8 | 141842667 | 141843643 | 0 |
| chr8 | 73906671 | 73907562 | chr8 | 145638041 | 145639295 | 0.039 |
| chr8 | 80705725 | 80706386 | chr8 | 142238036 | 142239233 | 0.001 |
| chr8 | 80732159 | 80732950 | chr8 | 129089447 | 129090574 | 0.053 |
| chr8 | 82146964 | 82148288 | chr8 | 129060227 | 129063805 | 0 |
| chr8 | 86131810 | 86134006 | chr8 | 134214242 | 134216129 | 0 |
| chr8 | 8869186 | 8870222 | chr8 | 131539617 | 131541377 | 0.055 |
| chr8 | 90730005 | 90731033 | chr8 | 131687123 | 131688649 | 0 |
| chr8 | 91012042 | 91015686 | chr8 | 145687898 | 145694087 | 0 |
| chr8 | 91236869 | 91238022 | chr8 | 130708318 | 130711352 | 0 |
| chr8 | 91657631 | 91659214 | chr8 | 128979417 | 128982624 | 0 |
| chr8 | 91959973 | 91961433 | chr8 | 145180815 | 145182187 | 0 |
| chr8 | 9486458 | 9487251 | chr8 | 141403217 | 141404903 | 0.063 |
| chr8 | 95916524 | 95918435 | chr8 | 131814715 | 131815599 | 0.06 |
| chr8 | 95961343 | 95962069 | chr8 | 128745001 | 128752294 | 0 |
| chr8 | 96279779 | 96283324 | chr8 | 145156628 | 145157340 | 0 |
| chr8 | 97787468 | 97788663 | chr8 | 142440979 | 142442237 | 0 |
| chr8 | 9898778 | 9899915 | chr8 | 146011931 | 146013790 | 0 |
| chr8 | 99568655 | 99571429 | chr8 | 131218754 | 131220917 | 0 |
| chr8 | 99717328 | 99719182 | chr8 | 130546973 | 130552572 | 0 |
| chr8 | 99902376 | 99903468 | chr8 | 131217475 | 131218635 | 0.037 |

We developed a novel analytical method to analyze ChIA-PET data that used a two-component Bayesian mixture model to accurately identify in vivo interactions from the ChIA-PET data by accurately estimating the difference between the biological signal and technical and biological noise by controlling for error within the ChIA-PET protocol and linear genomic distance. We defined an in vivo interaction as two regions of the genome brought together in the nucleus longer than expected at random given the linear genomic distance between those two region. Our intuition was that true in vivo interactions would follow one distribution where experimental noise would arise from a separate distribution, and these two groups could be learned from the data using a mixture model. After alignment, we defined a set of putative contacts where a putative contact was any two MACS1 peaks linked together by at least one mapped PET. The PET count for a putative interaction was the total number of unique PETs mapped at both ends of the putative contact. All putative contacts and their PET count were used in the estimation. We estimated the distributions two-component mixture model (described more below) from these putative contacts using origami-analysis. We specifically designed the model to have the second mixture component represent the distribution of the in vivo interactions, and we tested whether the estimated group means (described below) were significantly different to validate that model found at least two different groups. After the estimation of each component, for each putative contact we estimate the posterior probability of whether the putative contact was within the distribution of the second component. If this posterior probability was greater than 0.9, we called this putative contact an in vivo interaction. We used this threshold because it was a good balance between what be believed to be a high true positive rate while minimizing the false positive rate in each sample analyzed (although we believe that are a few in vivo interactions below this threshold as well). In general, we often displayed all putative contacts within the MYC TAD by this posterior probability, eliminating the need for a specific cutoff threshold.

For the analytical model, we wanted to build a model that was able to estimate and control for noise arising from the ChIA-PET protocol and linear genomic distance. The linear genomic distance is a potential source of noise in the data because regions of the genome closer together in linear genomic distance are on average more likely to have more frequent interactions by chance than regions of the genome farther away from each other, as observed in Hi-C data. We assume that these two sources of noise are independent Poisson processes from each other (since we are measuring the interaction frequency through PET counts), which appears to be a valid assumption in practice (Phanstiel et al., 2015). With this in mind, the parameters within the model were as follows:

$P_i$—the count of DNA mapped sequences/reads measured at position i, where $i \in \{1 .. N\}$ and N is the total number of positions measured $Z_i$—a latent variable having a value of either 0 or 1 measuring whether the measurement in $P_i$ came from a technical artifact (0) or in vivo biology (1)

$G_{ij}$—a latent variable, where $j \in \{0, 1\}$, measuring the number of counts observed for sample i if were part of component j $B_{ij}$—a latent variable measuring the number of counts observed for sample i if were part of component j as a function of the bias due to the genomic distance that sample i spans in the genome (where the distance is assumed to be a constant $d_i$ for that sample i)

$R_{ij}$—a latent variable measuring sum of the two independent processes $G_{ij}$ and $B_{ij}$ for sample i if were part of component j $\lambda_j$—a parameter describing the mean of latent variable $G_{.j}$ for all samples, and we guarantee that $\lambda_1 > \lambda_0$ to maintain identifiability of each component $v_j(d)$—a parameter describing the mean of the latent variable $B_{.j}$ at distance d $w_{ij}$—a parameter describing the binomial probability that sample I is part of component j $a_i, b_i$—a set of constants on the prior distribution of $w_{i1}$ it to adjust our prior belief in sample i based on our understanding of the biology we have already validated in lab More specifically, the model is parametrized as follows:

$$\lambda_j \sim \text{Gamma}(1, 1)$$

$$w_{i1} \sim \text{Beta}(a_i, b_i)$$

$$G_j \mid \lambda_j \sim \text{Poisson}(\lambda_j)$$

$$B_{ij} \mid v_j, d_i \sim \text{Poisson}(v_j \mid d_i)$$

$$R_{ij} = G_{ij} + B_{ij} \mid \lambda_j, v_j, d_i \sim \text{Poisson}(\lambda_j + v_j \mid d_i)$$

$$P_i \mid R_{ij}, \lambda_j, v_j, d_i = \sum_{j \in \{0,1\}} w_{ij} * R_j$$

$$P_i \mid Z_i = z_i, \lambda_{z_i}, v_{z_i}, d_i \sim \text{Poisson}(\lambda_j + v_j \mid d_i)$$

$$w_{i1} \mid Z_i = z_i, P_i \sim \text{Beta}(a_i + z_i, b_i + (1 - z_i))$$

And $$w_{i0} = 1 - w_{i1}.$$

The distribution of the parameters and hyperparameters were simulated by Markov Chain Monte Carlo (MCMC) using either Gibbs sampling or the Metropolis-Hastings algorithm as appropriate. To speed up the simulation between $G_{\cdot j}$ and $B_{ij}$, the $G_{\cdot j}$ parameter is updated first. Then the $B_{ij}$ parameters is updated using the difference between the PETs for $G_{\cdot j}$ and the number of PETs observed for each contact according to the component they are assigned to in that iteration. Additionally, the mean of $G_0$ is enforced to be less than the mean of $G_1$, although in practice the mean of $G_1$ was always strictly greater than the mean of $G_0$ during the MCMC run so this was never a problem.

The parameter $v_j(d)$ is the mean of the Poisson process estimating the biological bias from the linear genomic distance between the two ends of the putative contact as a function of this distance. To simplify processing, we estimated this function at each iterative using a smoothed cubic spline regression for putative contacts within group j. This approximation worked well by generating trends consistent with the power-law decay observed in Hi-C data sets.

The priors $a_{\cdot i}$ and $b_{\cdot i}$ are set to be minimally informative as possible. The $a_{\cdot i}$ hyperparameter is the frequency of the number of contacts sharing one of the same anchors that have a strictly lower measured PET count than the putative contact i. The $b_{\cdot i}$ hyperparamer is set to be the frequency of putative contacts sharing the same anchor that have strictly higher number of observed PETs linking the anchors plus the ratio of the multiplication of the depth of reads at both anchors of the putative contact divided by the median depth across all putative contacts floored at 0. We found setting the priors with a non-informative Beta distribution (i.e., Beta (1,1)) would also generally call the same in vivo interactions but call many more interactions from the putative contacts, where we believed many more of these were artifacts. Hence, we found this minimally informative prior to be more useful for us biologically.

Each run of origami-analysis was for 1,000 iterations with a 100 step burn-in period. We chose this number of iterations because the model tended to converge fairly quickly given the complexity of these ChIA-PET data sets. The output of origami is the estimated posterior probability that the putative contact arose from the distribution estimated for the second mixture component, which is assumed to model in vivo interactions within the ChIA-PET experiment. Accordingly, putative contact with a posterior probability closer to 1 are believed to be more likely to be in vivo interactions.

CTCF Motif Analysis

CTCF motifs were called in the human and mouse genomes (using hg19 and mm9 assemblies, respectively) using fimo (Grant et al., 2011). The CTCF motif from the JASPAR CORE 2014 database was used. The fimo p-value threshold was set to 1e-2 and the max-stored-scores parameter set to 100000000. To rank the importance of individual CTCF motifs, the motifs within the targeted CTCF peak upstream of MYC were ranked by their score within the score column in the GFF output of fimo.

Identification of Genes with a Putative Enhancer Docking Site

Genes with a putative enhancer docking site were identified by filtering the list of all 26,801 annotated genes down to those which occurred within a constitutive insulated neighborhood, had a constitutive CTCF site within 2.5 kb of the TSS, and exhibited differential enhancer usage across the cell lines HCT-116, Jurkat, and K562. Constitutive insulated neighborhoods were identified as follows. First, CTCF binding sites and cohesin binding sites were identified in HCT-116, Jurkat, and K562 cells. Cohesin ChIA-PET in the three cell types were processed with the Oragami pipeline as described below, and two CTCF bound sites that are connected by a cohesin ChIA-PET interaction were annotated as CTCF-CTCF/cohesin interactions in each cell type (i.e. insulated neighborhoods). Insulated neighborhoods were scored as constitutive across two cell types if they had a reciprocal overlap of at least 80% of the length of the interaction. The ChIA-PET datasets are likely not saturated, suggesting that not every interaction found within a cell will be potentially represented in the dataset. Therefore, we defined constitutive insulated neighborhoods as the set of insulated neighborhoods from all three cell types that were found overlapping in at least two of the three cell types. Conserved CTCF sites at gene's TSSs were defined as those sites that occur within 2.5 kb of the TSS and overlap by at least 1 bp across all 3 cell types. A gene was considered to use differential enhancers if in one of the cell types there was an enhancer present within the confines of the gene's constitutive insulated neighborhood that was not present in at least one of the other two cell types. Applying these three filters results in 1,725 genes that may utilize an enhancer docking site.

Data and Software Availability

ORIGAMI: https://github.com/younglab/origami using version alpha20160828.

The ChIP-seq data have been deposited in the Gene Expression Omnibus (GEO) under ID code GSE92879

The HiChIP data have been deposited in the Gene Expression Omnibus (GEO) under ID codes GSE92881

The 4C-seq data have been deposited in the the Gene Expression Omnibus (GEO) under ID code GSE92880

Software and Algorithms

| | | |
|---|---|---|
| Origami | This study/Weintraub et al | https://github.com/younglab/origami |
| ROSE | Whyte et al | https://bitbucket.org/young_computation/rose |
| 4C Fourfold | This study | https://github.com/younglab/fourfold |
| BISMARK | Krueger et al. | https://github.com/FelixKrueger/Bismark |
| Bowtie | Langmead et al., 2009 | http://bowtiebio.sourceforge.net/index.shtml |
| Samtools | Li et al., 2009 | http://samtools.sourceforge.net |
| MACS | Zhang et al., 2008 | http://liulab.dfci.harvard.edu/MACS/index.html |
| BEDTools | Quinlan et al., 2010 | http://bedtools.readthedocs.io |
| UCSC Genome Browser | Kent et al., 2002 | http://genome.ucsc.edu/cgibin/hgGateway |
| WASHU EpiGenome browser | Zhou et al., 2011 | http://epigenomegateway.wustl.edu/ |
| 3D Genome viewer | Wang et al., 2017 | http://www.3dgenome.org |
| Kallisto | Bray et al., 2016 | https://pachterlab.github.io/kallisto/ |

REFERENCES

Allen, B. L., and Taatjes, D. J. (2015). The Mediator complex: a central integrator of transcription. Nat. Rev. Mol. Cell Biol. 16, 155-166.

N. Ahmadiyeh et al., 8q24 prostate, breast, and colon cancer risk loci show tissue-specific long-range interaction with MYC. 107 (2010), doi:10.1073/pnas.0910668107/-/DCSupplemental.www.pnas.org/cgi/doi/10.1073/pnas.0910668107.

Anders, L., Guenther, M. G., Qi, J., Fan, Z. P., Marineau, J. J., Rahl, P. B., Lovén, J., Sigova, A. A., Smith, W. B., Lee, T. I., et al. (2014). Genome-wide localization of small molecules. Nat. Biotechnol. 32, 92-96.

Barabé, F., Gil, L., Celton, M., Bergeron, A., Lamontagne, V., Rogues, É., Lagacé, K., Forest, A., Johnson, R., Pecheux, L., et al. (2016). Modeling human MLL-AF9 translocated acute myeloid leukemia from single donors reveals RET as a potential therapeutic target. Leukemia 1166-1176.

Becket, E., Chopra, S., Duymich, C. E., Lin, J. J., You, J. S., Pandiyan, K., Nichols, P. W., Siegmund, K. D., Charlet, J., Weisenberger, D. J., et al. (2016). Identification of DNA methylation-independent epigenetic events underlying clear cell renal cell carcinoma. Cancer Res. 76, 1954-1964.

Bell, A. C., and Felsenfeld, G. (2000). Methylation of a CTCF-dependent boundary controls imprinted expression of the Igf2 gene. Nature 405, 482-485. E. M. J. J. Berns et al., c-MYC Amplification is a better prognostic factor than HER2/neu amplification in primary breast cancer. Cancer Res. 52, 1107-1113 (1992).

Bernstein, B. E., Stamatoyannopoulos, J. A., Costello, J. F., Ren, B., Milosavljevic, A., Meissner, A., Kellis, M., Marra, M. A., Beaudet, A. L., Ecker, J. R., et al. (2010). The NIH Roadmap Epigenomics Mapping Consortium. Nat. Biotechnol. 28, 1045-1048.

Bonev, B., and Cavalli, G. (2016). Organization and function of the 3D genome. Nat. Rev. Genet. 17,661-678.

Bradner, J. E., Hnisz, D., and Young, R. A. (2017). Transcriptional Addiction in Cancer. Cell 168,629-643.

Buecker, C., and Wysocka, J. (2012). Enhancers as information integration hubs in development: Lessons from genomics. Trends Genet. 28, 276-284.

Bulger, M., and Groudine, M. (2011). Functional and mechanistic diversity of distal transcription enhancers. Cell 144, 327-339.

Chapuy, B., McKeown, M. R., Lin, C. Y., Monti, S., Roemer, M. G. M., Qi, J., Rahl, P. B., Sun, H. H., Yeda, K. T., Doench, J. G., et al. (2013). Discovery and characterization of super-enhancer-associated dependencies in diffuse large B cell lymphoma. Cancer Cell 24, 777-790.

Cong, L., Ran, F. A., Cox, D., Lin, S., Barrett®, R., Habib, N., Hsu, P. D., Wu, X., Jiang, W., Marraffini, L. A., et al. (2013). Multiplex genome engineering using CRISPR/Cas systems. Science (80-.). 339, 819-823.

Cuddapah, S., Jothi, R., Schones, D. E., Roh, T. Y., Cui, K., and Zhao, K. (2009). Global analysis of the insulator binding protein CTCF in chromatin barrier regions reveals demarcation of active and repressive domains. Genome Res. 19, 24-32.

C. V. Dang, MYC on the path to cancer. Cell. 149, 22-35 (2012).

Dekker, J., and Mirny, L. (2016). The 3D genome as moderator of chromosomal communication. Cell 164, 1110-1121.

Deltcheva, E., and Nimmo, R. (2017). RUNX transcription factors at the interface of stem cells and cancer. 1755-1768.

Deng, W., Lee, J., Wang, H., Miller, J., Reik, A., Gregory, P. D., Dean, A., and Blobel, G. A. (2012). Controlling long-range genomic interactions at a native locus by targeted tethering of a looping factor. Cell 149, 1233-1244.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dixon, J. R., Gorkin, D. U., and Ren, B. (2016). Chromatin Domains: The Unit of Chromosome Organization. Mol. Cell 62, 668-680.

Dowen, J. M., Fan, Z. P., Hnisz, D., Ren, G., Abraham, B. J., Zhang, L. N., Weintraub, A. S., Schuijers, J., Lee, T. I., Zhao, K., et al. (2014). Control of Cell Identity Genes Occurs in Insulated Neighborhoods in Mammalian Chromosomes. Cell 159,374-387.

Encode Consortium (2012). An integrated encyclopedia of DNA elements in the human genome. Nature 489, 57-74.

Felsher, D. W., and Bishop, J. M. (1999). Reversible tumorigenesis by MYC in hematopoietic lineages. Mol. Cell 4, 199-207.

Filippova, G. N., Fagerlie, S., Klenova, E. M., Myers, C., Dehner, Y., Goodwin, G., Neiman, P. E., Collins, S. J., and Lobanenkov, V. V (1996). An exceptionally conserved transcriptional repressor, CTCF, employs different combinations of zinc fingers to bind diverged promoter sequences of avian and mammalian c-myc oncogenes. Mol. Cell. Biol. 16, 2802-2813.

Flavahan, W. A., Drier, Y., Liau, B. B., Gillespie, S. M., Venteicher, A. S., Stemmer-Rachamimov, A. O., Suva, M. L., and Bernstein, B. E. (2016). Insulator dysfunction and oncogene activation in IDH mutant gliomas. Nature 529, 110-114.

Franke, M., Ibrahim, D. M., Andrey, G., Schwarzer, W., Heinrich, V., Schopflin, R., Kraft, K., Kempfer, R., Jerkovie, I., Chan, W.-L., et al. (2016). Formation of new chromatin domains determines pathogenicity of genomic duplications. Nature 538, 265-269.

Fraser, J., Ferrai, C., Chiariello, A. M., Schueler, M., Rito, T., Laudanno, G., Barbieri, M., Moore, B. L., Kraemer, D. C., Aitken, S., et al. (2015). Hierarchical folding and reorganization of chromosomes are linked to transcriptional changes in cellular differentiation. Mol Syst Biol 11, 1-14.

Frietze, S., Wang, R., Yao, L., Tak, Y. G., Ye, Z., Gaddis, M., Witt, H., Farnham, P. J., and Jin, V. X. (2012). Cell type-specific binding patterns reveal that TCF7L2 can be tethered to the genome by association with GATA3. Genome Biol. 13, R52.

Gabay, M., Li, Y., and Felsher, D. W. (2014). MYC activation is a hallmark of cancer initiation and maintenance. Cold Spring Harb. Perspect. Med. 4, 1-14.

Gertz, J., Savic, D., Varley, K. E., Partridge, E. C., Safi, A., Jain, P., Cooper, G. M., Reddy, T. E., Crawford, G. E., and Myers, R. M. (2013). Distinct properties of cell-type-specific and shared transcription factor binding sites. Mol. Cell 52, 25-36.

Ghavi-Helm, Y., Klein, F. A., Pakozdi, T., Ciglar, L., Noordermeer, D., Huber, W., and Furlong, E. E. M. (2014). Enhancer loops appear stable during development and are associated with paused polymerase. Nature 512, 96-9100.

Gibcus, J. H., and Dekker, J. (2013). The hierarchy of the 3D genome. Mol. Cell 49, 773-782.

Goel, H. L., and Mercurio, A. M. (2013). VEGF targets the tumour cell. Nat. Rev. Cancer 13, 871-882.

Gombert, W. M., Farris, S. D., Rubio, E. D., Morey-Rosler, K. M., Schubach, W. H., and Krumm, A. (2003). The c-myc insulator element and matrix attachment regions define the c-myc chromosomal domain. Mol. Cell. Biol. 23, 9338-9348.

Gorkin, D. U., Leung, D., and Ren, B. (2014). The 3D genome in transcriptional regulation and pluripotency. Cell Stem Cell 14, 762-775.

Grant, C. E., Bailey, T. L., and Noble, W. S. (2011). FIMO: Scanning for occurrences of a given motif. Bioinformatics 27, 1017-1018.

Groschel, S., Sanders, M. A., Hoogenboezem, R., De Wit, E., Bouwman, B. A. M., Erpelinck, C., Van Der Velden, V. H. J., Havermans, M., Avellino, R., Van Lom, K., et al. (2014). A single oncogenic enhancer rearrangement causes concomitant EVI1 and GATA2 deregulation in Leukemia. Cell 157, 369-381.

M. A. Grotzer et al., MYC Messenger RNA Expression Predicts Survival Outcome in Childhood Primitive Neuroectodermal Tumor/Medulloblastoma MYC Messenger RNA Expression Predicts Survival Outcome in Childhood Primitive Neuroectodermal Tumor /. 7, 2425-2433 (2001).

Guo, Y., Xu, Q., Canzio, D., Shou, J., Li, J., Gorkin, D. U., Jung, I., Wu, H., Zhai, Y., Tang, Y., et al. (2015). CRISPR Inversion of CTCF Sites Alters Genome Topology and Enhancer/Promoter Function. Cell 162, 900-910.

O. Hallikas et al., Genome-wide Prediction of Mammalian Enhancers Based on Analysis of Transcription-Factor Binding Affinity. Cell. 124, 47-59 (2006).

Handoko, L., Xu, H., Li, G., Ngan, C. Y., Chew, E., Schnapp, M., Lee, C. W. H., Ye, C., Ping, J. L. H., Mulawadi, F., et al. (2011). CTCF-mediated functional chromatin interactome in pluripotent cells. Nat. Genet. 43, 630-638.

Hark, A. T., Schoenherr, C. J., Katz, D. J., Ingram, R. S., Levorse, J. M., and Tilghman, S. M. (2000). CTCF mediates methylation-sensitive enhancer-blocking activity at the H19/Igf2 locus. Nature 405, 486-489.

Heard, E., and Bickmore, W. (2007). The ins and outs of gene regulation and chromosome territory organisation. Curr. Opin. Cell Biol. 19, 311-316.

Heidari, N., Phanstiel, D. H., He, C. C. C., Grubert, F., Jahanbani, F., Kasowski, M., Zhang, M. Q., Snyder, M. P., Jahanbanian, F., Kasowski, M., et al. (2014). Genome-wide map of regulatory interactions in the human genome. Genome Res. 24, 1905-1917.

Herranz, D., Ambesi-Impiombato, A., Palomero, T., Schnell, S. A., B elver, L., Wendorff, A. A., Xu, L., Castillo-Martin, M., Llobet-Navas, D., Cordon-Cardo, C., et al. (2014). A NOTCH1-driven MYC enhancer promotes T cell development, transformation and acute lymphoblastic leukemia. Nat. Med. 20, 1130-1137.

Hnisz, D., Abraham, B. J., Lee, T. I., Lau, A., Saint-André, V., Sigova, A. A., Hoke, H. A., and Young, R. A. (2013). Super-enhancers in the control of cell identity and disease. Cell 155, 934-947.

Hnisz, D., Weintraub, A. S., Day, D. S., Valton, A.-L., Bak, R. O., Li, C. H., Goldmann, J., Lajoie, B. R., Fan, Z. P., Sigova, A. A., et al. (2016). Activation of proto-oncogenes by disruption of chromosome neighborhoods. Science (80-.). 351, 1454-1458.

Ito, Y., Bae, S.-C., and Chuang, L. S. H. (2015). The RUNX family: developmental regulators in cancer. Nat. Rev. Cancer 15, 81-95.

Jain, M., Arvanitis, C., Chu, K., Dewey, W., Leonhardt, E., Trinh, M., Sundberg, C. D., Bishop, J. M., and Felsher, D. W. (2002). Sustained Loss of a Neoplastic Phenotype by Brief Inactivation of MYC. Science (80-.). 297, 102-104.

Järås, M., Miller, P. G., Chu, L. P., Puram, R. V., Fink, E. C., Schneider, R. K., Al-Shahrour, F., Pella, P., Breyfogle, L. J., Hartwell, K. A., et al. (2014). Csnk1a1 inhibition has p53-dependent therapeutic efficacy in acute myeloid leukemia. J. Exp. Med. 211, 605-612.

Javierre, B. M., Sewitz, S., Cairns, J., Wingett, S. W., V??rnai, C., Thiecke, M. J., Freire-Pritchett, P., Spivakov, M., Fraser, P., Burren, O. S., et al. (2016). Lineage-Specific Genome Architecture Links Enhancers and Non-coding Disease Variants to Target Gene Promoters. Cell 167, 1369-1384.e19.

Jeronimo, C., Langelier, M. F., Bataille, A. R., Pascal, J. M., Pugh, B. F., and Robert, F. (2016). Tail and Kinase Modules Differently Regulate Core Mediator Recruitment and Function In Vivo. Mol. Cell 64, 455-466.

Ji, X., Dadon, D. B., Powell, B. E., Fan, Z. P., Borges-Rivera, D., Shachar, S., Weintraub, A. S., Hnisz, D., Pegoraro, G., Lee, T. I., et al. (2016). 3D Chromosome Regulatory Landscape of Human Pluripotent Cells. Cell Stem Cell 18, 262-275.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kim, T. H., Abdullaev, Z. K., Smith, A. D., Ching, K. A., Loukinov, D. I., Green, R. D. D., Zhang, M. Q., Lobanenkov, V. V., and Ren, B. (2007). Analysis of the Vertebrate Insulator Protein CTCF-Binding Sites in the Human Genome. Cell 128, 1231-1245.

Klenova, E. M., Nicolas, R. H., Paterson, H. F., Came, A. F., Heath, C. M., Goodwin, G. H., Neiman, P. E., and Lobanenkov, V. V (1993). CTCF, a conserved nuclear factor required for optimal transcriptional activity of the chicken c-myc gene, is an 11-Zn-finger protein differentially expressed in multiple forms. Mol. Cell. Biol. 13, 7612-7624.

Klenova, E. M., Chernukhin, I. V, El-Kady, A., Lee, R. E., Pugachev a, E. M., Loukinov, D. I., Goodwin, G. H., Delgado, D., Filippova, G. N., Leon, J., et al. (2001). Functional phosphorylation sites in the C-terminal region of the multivalent multifunctional transcriptional factor CTCF. Mol. Cell. Biol. 2/, 2221-2234.

de Laat, W., and Duboule, D. (2013). Topology of mammalian developmental enhancers and their regulatory landscapes. Nature 502, 499-506.

A. Lavenu, S. Pournin, C. Babinet, D. Morello, The cis-acting elements known to regulate c-MYC expression ex vivo are not sufficient for correct transcription in vivo. Oncogene. 9,527-536 (1994).

Lee, J., Krivega, I., Dale, R. K., and Dean, A. (2017). The LDB1 Complex Co-opts CTCF for Erythroid Lineage-Specific Long-Range Enhancer Interactions. Cell Rep. 19, 2490-2502.

Lee, T., Johnston, S., and Young, R. (2006). Chromatin immunoprecipitation and microarray-based analysis of protein location. Nat. Protoc. /, 729-748.

Li, G., Ruan, X., Auerbach, R. K., Sandhu, K. S., Zheng, M., Wang, P., Poh, H. M., Goh, Y., Lim, J., Zhang, J., et al. (2012). Extensive promoter-centered chromatin interactions provide a topological basis for transcription regulation. Cell 148, 84-98.

Lin, C. Y., Lovén, J., Rahl, P. B., Paranal, R. M., Burge, C. B., Bradner, J. E., Lee, T. I., and Young, R. A. (2012). Transcriptional amplification in tumor cells with elevated c-Myc. Cell 151, 56-67.

Lin, C. Y., Erkek, S., Tong, Y., Yin, L., Federation, A. J., Zapatka, M., Haldipur, P., Kawauchi, D., Risch, T., Warnatz, H.-J., et al. (2016). Active medulloblastoma enhancers reveal subgroup-specific cellular origins. Nature 530, 57-62.

Liu, X. S., Wu, H., Ji, X., Stelzer, Y., Wu, X., Czauderna, S., Shu, J., Dadon, D., Young, R. A., and Jaenisch, R. (2016). Editing DNA Methylation in the Mammalian Genome. Cell 167,233-247.

Lovén, J., Hoke, H. A., Lin, C. Y., Lau, A., Orlando, D. A., Vakoc, C. R., Bradner, J. E., Lee, T. I., and Young, R. A. (2013). Selective inhibition of tumor oncogenes by disruption of super-enhancers. Cell 153,320-334.

Lupiáñez, D. G., Kraft, K., Heinrich, V., Krawitz, P., Brancati, F., Klopocki, E., Horn, D., Kayserili, H., Opitz, J. M., Laxova, R., et al. (2015). Disruptions of topological chromatin domains cause pathogenic rewiring of gene-enhancer interactions. Cell 161, 1012-1025.

Malik, S., and Roeder, R. G. (2010). The metazoan Mediator co-activator complex as an integrative hub for transcriptional regulation. Nat. Rev. Genet.11, 761-772.

Malik, S., and Roeder, R. G. (2016). Mediator: A Drawbridge across the Enhancer-Promoter Divide. Mol. Cell 64, 433-434.

Maurano, M. T., Wang, H., John, S., Shafer, A., Canfield, T., Lee, K., and Stamatoyannopoulos, J. A. (2015). Role of DNA Methylation in Modulating Transcription Factor Occupancy. Cell Rep. 12, 1184-1195.

Merkenschlager, M., and Nora, E. P. (2016). CTCF and Cohesin in Genome Folding and Transcriptional Gene Regulation. Annu. Rev. Genomics Hum. Genet. 17, 17-43.

Montavon, T., and Duboule, D. (2012). Landscapes and archipelagos: Spatial organization of gene regulation in vertebrates. Trends Cell Biol. 22,347-354.

Muerdter, F., and Stark, A. (2016). Gene Regulation: Activation through Space. Curr. Biol. 26, R895-R898.

Müller, H. P., Sogo, J., and Schaffner, W. (1989). An enhancer stimulates transcription in Trans when attached to the promoter via a protein bridge. Cell 58, 767-777.

Mumbach, M. R., Rubin, A. J., Flynn, R. A., Dai, C., Khavari, P. A., Greenleaf, W. J., and Chang, H. Y. (2016). HiChIP: efficient and sensitive analysis of protein-directed genome architecture. Nat. Methods 13, 919-922.

Nagano, T., Varnai, C., Schoenfelder, S., Javierre, B.-M., Wingett, S., and Fraser, P. (2015). Comparison of Hi-C results using in-solution versus in-nucleus ligation. Genome Biol. 16, 175.

Narendra, V., Rocha, P. P., An, D., Raviram, R., Skok, J. A., Mazzoni, E. O., and Reinberg, D. (2015). Transcription. CTCF establishes discrete functional chromatin domains at the Hox clusters during differentiation. Science 347, 1017-1021.

C. E. Nesbit, J. M. Tersak, E. V Prochownik, MYC oncogenes and human neoplastic disease. Oncogene. 18, 3004-3016 (1999).

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Ovcharenko, I., Loots, G. G., Nobrega, M. A., Hardison, R. C., Miller, W., and Stubbs, L. (2005). Evolution and functional classification of vertebrate gene deserts. Genome Res. 15, 137-145.

Parelho, V., Hadjur, S., Spivakov, M., Leleu, M., Sauer, S., Gregson, H. C., Jarmuz, A., Canzonetta, C., Webster, Z., Nesterova, T., et al. (2008). Cohesins Functionally Associate with CTCF on Mammalian Chromosome Arms. Cell 132,422-433.

Parker, S. C. J., Stitzel, M. L., Taylor, D. L., Orozco, J. M., Erdos, M. R., Akiyama, J. A., van Bueren, K. L., Chines, P. S., Narisu, N., Black, B. L., et al. (2013). Chromatin stretch enhancer states drive cell-specific gene regulation and harbor human disease risk variants. Proc. Natl. Acad. Sci. 110, 17921-17926.

Petrenko, N., Jin, Y., Wong, K. H., and Struhl, K. (2016). Mediator Undergoes a Compositional Change during Transcriptional Activation. Mol. Cell 64, 443-454.

Phanstiel, D. H., Boyle, A. P., Heidari, N., and Snyder, M. P. (2015). Mango: A bias-correcting ChIA-PET analysis pipeline. Bioinformatics 31, 3092-3098.

Phillips-Cremins, J. E., Sauria, M. E., Sanyal, A., Gerasimova, T. I., Lajoie, B. R., Bell, J. S., Ong, C.-T. T., Hookway, T. A., Guo, C., Sun, Y., et al. (2013). Architectural protein subclasses shape 3D organization of genomes during lineage commitment. Cell 153, 1281-1295.

Pombo, A., and Dillon, N. (2015). Three-dimensional genome architecture: players and mechanisms. Nat. Rev. Mol. Cell Biol. 16, 245-257.

M. M. Pomerantz et al., The 8q24 cancer risk variant rs6983267 shows long-range interaction with MYC in colorectal cancer. Nat. Genet. 41,882-884 (2009).

Pope, B. D., Ryba, T., Dileep, V., Yue, F., Wu, W., Denas, O., Vera, D. L., Wang, Y., Hansen, R. S., Canfield, T. K., et al. (2014). Topologically associating domains are stable units of replication-timing regulation. Nature 515, 402-405.

Ran, F. A., Hsu, P. D., Wright, J., Agarwala, V., Scott, D. A., and Zhang, F. (2013). Genome engineering using the CRISPR-Cas9 system. Nat. Protoc. 8, 2281-2308.

P. H. Rao et al., Chromosomal and gene amplification in diffuse large B-cell lymphoma. Blood. 92,234-240 (1998).

Rao, S. S. P., Huntley, M. H., Durand, N. C., Stamenova, E. K., Bochkov, I. D., Robinson, J. T., Sanborn, A. L., Machol, I., Omer, A. D., Lander, E. S., et al. (2014). A 3D map of the human genome at kilobase resolution reveals principles of chromatin looping. Cell 159, 1665-1680.

Rubio, E. D., Reiss, D. J., Welcsh, P. L., Disteche, C. M., Filippova, G. N., Baliga, N. S., Aebersold, R., Ranish, J. A., and Krumm, A. (2008). CTCF physically links cohesin to chromatin. Proc. Natl. Acad. Sci. U.S.A 105, 8309-8314.

Saldana-Meyer, R., Gonzalez-Buendia, E., Guerrero, G., Narendra, V., Bonasio, R., Recillas-Targa, F., and Reinberg, D. (2014). CTCF regulates the human p53 gene through direct interaction with its natural antisense transcript, Wrap53. Genes Dev. 28, 723-734.

Sandelin, A. (2004). JASPAR: an open-access database for eukaryotic transcription factor binding profiles. Nucleic Acids Res. 32, 91D-94.

Sanjana, N. E., Shalem, O., and Zhang, F. (2014). Improved vectors and genome-wide libraries for CRISPR screening. Nat. Methods 11, 783-784.

Schmidt, D., Schwalie, P. C., Wilson, M. D., Ballester, B., Gonalves, A., Kutter, C., Brown, G. D., Marshall, A., Flicek, P., and Odom, D. T. (2012). Waves of retrotransposon expansion remodel genome organization and CTCF binding in multiple mammalian lineages. Cell 148,335-348.

Schmidt, S. V, Krebs, W., Ulas, T., Xue, J., BaBler, K., Gunther, P., Hardt, A.-L., Schultze, H., Sander, J., Klee, K., et al. (2016). The transcriptional regulator network of human inflammatory macrophages is defined by open chromatin. Cell Res. 26, 1-20.

Shalem, O., Sanjana, N. E., Hartenian, E., Shi, X., Scott, D. a, Mikkelsen, T. S., Heckl, D., Ebert, B. L., Root, D. E., Doench, J. G., et al. (2014). Genome-scale CRISPR-Cas9 knockout screening in human cells. Science 343, 84-87.

Siddique et al, Targeted methylation and gene silencing of VEGF-A in human cells by using a designed Dnmt3a-Dnmt3L single-chain fusion protein with increased DNA methylation activity. J Mol Biol. 2013 Feb. 8; 425(3): 479-91.

J. Sotelo et al., Long-range enhancers on 8q24 regulate c-MYC. Proc. Natl. Acad. Sci. 107, 3001-3005 (2010).

Soucek, L., Whitfield, J., Martins, C. P., Finch, A. J., Murphy, D. J., Sodir, N. M., Karnezis, A. N., Swigart, L. B., Nasi, S., and Evan, G. I. (2008). Modelling Myc inhibition as a cancer therapy. Nature 455, 679-683.

Soucek, L., Whitfield, J. R., Sodir, N. M., Mas so-Valles, D., Serrano, E., Karnezis, A. N., Swigart, L. B., and Evan, G. I. (2013). Inhibition of Myc family proteins eradicates KRas-driven lung cancer in mice. Genes Dev. 27,504-513.

Spitz, F. (2016). Gene regulation at a distance: From remote enhancers to 3D regulatory ensembles. Semin. Cell Dev. Biol. 57, 57-67.

Splinter, E., Heath, H., Kooren, J., Palstra, R. J., Klous, P., Grosveld, F., Galjart, N., and De Laat, W. (2006). CTCF mediates long-range chromatin looping and local histone modification in the ??-globin locus. Genes Dev. 20, 2349-2354.

Stadler, M. B., Murr, R., Burger, L., Ivanek, R., Lienert, F., Scholer, A., van Nimwegen, E., Wirbelauer, C., Oakeley, E. J., Gaidatzis, D., et al. (2011). DNA-binding factors shape the mouse methylome at distal regulatory regions. Nature 480, 490-495.

Tang, Z., Luo, O. J., Li, X., Zheng, M., Zhu, J. J., Szalaj, P., Trzaskoma, P., Magalska, A., Wlodarczyk, J., Ruszczycki, B., et al. (2015). CTCF-mediated human 3D genome architecture reveals chromatin topology for transcription. Cell 163, 1611-1627.

Tolhuis, B., Palstra, R. J., Splinter, E., Grosveld, F., and De Laat, W. (2002). Looping and interaction between hypersensitive sites in the active (3-globin locus. Mol. Cell 10, 1453-1465.

S. Tuupanen et al., The common colorectal cancer predisposition SNP rs6983267 at chromosome 8q24 confers potential to enhanced Wnt signaling. Nat. Genet. 41, 885-890 (2009).

Y. Wang et al., CDK7-Dependent Transcriptional Addiction in Triple-Negative Breast Cancer. Cell. 163,174-186 (2015).

Wang, D., Garcia-Bassets, I., Benner, C., Li, W., Su, X., Zhou, Y., Qiu, J., Liu, W., Kaikkonen, M. U., Ohgi, K. a, et al. (2011). Reprogramming transcription by distinct classes of enhancers functionally defined by eRNA. Nature 474, 390-394.

Wang, H., Maurano, M. T., Qu, H., Varley, K. E., Gertz, J., Pauli, F., Lee, K., Canfield, T., Weaver, M., Sandstrom, R., et al. (2012). Widespread plasticity in CTCF occupancy linked to DNA methylation. Genome Res. 22, 1680-1688.

Wendt, K. S., Yoshida, K., Itoh, T., Bando, M., Koch, B., Schirghuber, E., Tsutsumi, S., Nagae, G., Ishihara, K., Mishiro, T., et al. (2008). Cohesin mediates transcriptional insulation by CCCTC-binding factor. Nature 451, 796-801.

I. Wierstra, J. Alves, The c-MYC Promoter: Still MysterY and Challenge. Adv. Cancer Res. 99,113-333 (2008).

J. B. Wright, S. J. Brown, M. D. Cole, Upregulation of c-MYC in cis through a Large Chromatin Loop Linked to a Cancer Risk-Associated Single-Nucleotide Polymorphism in Colorectal Cancer Cells. Mol. Cell. Biol. 30, 1411-1420 (2010).

van de Werken, H. J. G., De Vree, P. J. P., Splinter, E., Holwerda, S. J. B., Klous, P., De Wit, E., and De Laat, W. (2012a). 4C technology: Protocols and data analysis (Elsevier Inc.).

van de Werken, H. J. G., Landan, G., Holwerda, S. J. B., Hoichman, M., Klous, P., Chachik, R., Splinter, E., Valdes-Quezada, C., Oz, Y., Bouwman, B. A. M., et al. (2012b). Robust 4C-seq data analysis to screen for regulatory DNA interactions. Nat Methods 9, 969-972.

de Wit, E., Vos, E. S. M., Holwerda, S. J. B., Valdes-Quezada, C., Verstegen, M. J. A. M., Teunissen, H., Splinter, E., Wijchers, P. J., Krijger, P. H. L., and de Laat, W. (2015). CTCF Binding Polarity Determines Chromatin Looping. Mol. Cell 60, 676-684.

J.-F. Xiang et al., Human colorectal cancer-specific CCAT1-L lncRNA regulates long-range chromatin interactions at the MYC locus. Cell Res. 24,513-531 (2014).

Xu, J., Shao, Z., Glass, K., Bauer, D. E., Pinello, L., Van Handel, B., Hou, S., Stamatoyannopoulos, J. A., Mikkola, H. K. A., Yuan, G. C., et al. (2012). Combinatorial Assembly of Developmental Stage-Specific Enhancers Controls Gene Expression Programs during Human Erythropoiesis. Dev. Cell 23, 796-811.

Yan, J., Enge, M., Whitington, T., Dave, K., Liu, J., Sur, I., Schmierer, B., Jolma, A., Kivioja, T., Taipale, M., et al. (2013). Transcription factor binding in human cells occurs in dense clusters formed around cohesin anchor sites. Cell 154, 801-813.

G. S. Yochum, R. Cleland, R. H. Goodman, A Genome-Wide Screen for—Catenin Binding Sites Identifies a Downstream Enhancer Element That Controls c-MYC Gene Expression. Mol. Cell. Biol. 28, 7368-7379 (2008).

Yusufzai, T. M., Tagami, H., Nakatani, Y., and Felsenfeld, G. (2004). CTCF tethers an insulator to subnuclear sites, suggesting shared insulator mechanisms across species. Mol. Cell 13,291-298.

Zhang, X., Choi, P. S., Francis, J. M., Imielinski, M., Watanabe, H., Cherniack, A. D., and Meyerson, M. (2015). Identification of focally amplified lineage-specific super-enhancers in human epithelial cancers. Nat. Genet. 48, 1-8.

Ziller, M. J., Gu, H., Müller, F., Donaghey, J., Tsai, L. T.-Y., Kohlbacher, O., De Jager, P. L., Rosen, E. D., Bennett, D. A., Bernstein, B. E., et al. (2013). Charting a dynamic DNA methylation landscape of the human genome. Nature 500, 477-481.

The invention claimed is:

1. A method for methylating a promoter region CTCF binding site of a gene in a cell comprising introducing into the cell:
   (a) a fusion protein comprising a catalytically inactive Cas9 operably linked to at least one DNA methyltransferase, or a nucleic acid encoding the fusion protein; and
   (b) a nucleic acid comprising one or more guide sequences homologous to a sequence, wherein the sequence is (i) in the promoter region CTCF binding site or (ii) within a region of 100, 200, 300, 400, 500, 600, 700, 800, 900 or 1000 nucleotides upstream or downstream of the promoter region CTCF binding site, thereby methylating the promoter region CTCF binding site.

2. The method of claim 1, wherein the gene is an oncogene.

3. The method of claim 1, wherein the gene is selected from the group consisting of MYC, TGIF1, VEGFAI, RUNX1, CDK6, BCL2L1, PIM1, and CSNK1A1.

4. The method of claim 1, wherein the gene is MYC.

5. The method of claim 1, wherein the at least one DNA methyltransferase is selected from the group consisting of DNA (cytosine-5)-methyltransferase 3A (DMNT3A) or a portion thereof, DMNT3L or a portion thereof, and a combination thereof.

6. The method of claim 1, wherein the fusion protein comprises dCas9 operably linked to DNMT3A-L, with or without a 5'NLS.

7. The method of claim 1, wherein the sequence is in the promoter region CTCF binding site.

8. The method of claim 1, wherein the sequence is within a region 100, 200, 300, 400, 500, 600, 700, 800, 900 or 1000 nucleotides upstream or downstream of the promoter region CTCF binding site.

9. The method of claim 1, comprising introducing into the cell the nucleic acid encoding the fusion protein.

10. A method of decreasing expression of a gene having a promoter region CTCF binding site in a cell, comprising introducing into the cell:
    (a) a fusion protein comprising a catalytically inactive Cas9 operably linked to at least one DNA methyltransferase, or a nucleic acid encoding the fusion protein; and
    (b) a nucleic acid comprising one or more guide sequences homologous to a sequence wherein the sequence is (i) in the promoter region CTCF binding site or (ii) within a region of 100, 200, 300, 400, 500, 600, 700, 800, 900 or 1000 nucleotides upstream or downstream of the promoter region CTCF binding site, thereby decreasing expression of the gene,
    wherein expression of the gene is decreased compared to expression of the gene in a cell not introduced with (a) and (b).

11. The method of claim 10, wherein the introducing decreases binding of a CTCF protein to the promoter region CTCF binding site, wherein decreased binding is compared to binding of a CTCF protein to the promoter region CTCF binding site in the cell not introduced with (a) and (b).

12. The method of claim 10, wherein the introducing increases the degree of methylation of the promoter region CTCF binding site, wherein the increased degree of methylation is compared to the degree of methylation of the promoter region CTCF binding site in the cell not introduced with (a) and (b).

13. The method of claim 10, wherein the gene is an oncogene.

14. The method of claim 10, wherein the gene is selected from the group consisting of MYC, TGIF1, VEGFAI, RUNX1, CDK6, BCL2L1, PIM1, and CSNK1A1.

15. The method of claim 10, wherein the gene is MYC.

16. The method of claim 10, wherein the at least one DNA methyltransferase is selected from the group consisting of DMNT3A or a portion thereof, DMNT3L or a portion thereof, and a combination thereof.

17. The method of claim 10, wherein the fusion protein comprises dCas9 operably linked to DNMT3A-L, with or without a 5'NLS.

18. The method of claim 10, wherein the sequence is in the promoter region CTCF binding site.

19. The method of claim 10, wherein the sequence is within a region 100, 200, 300, 400, 500, 600, 700, 800, 900 or 1000 nucleotides upstream or downstream of the promoter region CTCF binding site.

20. The method of claim 10, comprising introducing into the cell the nucleic acid encoding the fusion protein.

* * * * *

SEQUENCE LISTING

```
Sequence total quantity: 43
SEQ ID NO: 1              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 1
gcctggatgt caacgagggc                                                       20

SEQ ID NO: 2              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 2
gcgggtgctg cccagagagg                                                       20

SEQ ID NO: 3              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 3
gcaaaatcca gcatagcgat                                                       20

SEQ ID NO: 4              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 4
ctattcaacc gcataagaga                                                       20

SEQ ID NO: 5              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 5
cgctgagctg caaactcaac                                                       20

SEQ ID NO: 6              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 6
accgcctgtc cttcccccgc                                                       20

SEQ ID NO: 7              moltype = DNA   length = 20
FEATURE                   Location/Qualifiers
misc_feature              1..20
                          note = target sequence
source                    1..20
                          mol_type = other DNA
                          organism = synthetic construct
SEQUENCE: 7
ttggttgctc cccgcgtttg                                                       20

SEQ ID NO: 8              moltype = DNA   length = 20
FEATURE                   Location/Qualifiers
misc_feature              1..20
                          note = target sequence
source                    1..20
                          mol_type = other DNA
                          organism = synthetic construct
```

```
SEQUENCE: 8
atgatctctg ctgccagtag                                                    20

SEQ ID NO: 9              moltype = DNA  length = 20
FEATURE                   Location/Qualifiers
misc_feature              1..20
                          note = primer
source                    1..20
                          mol_type = other DNA
                          organism = synthetic construct
SEQUENCE: 9
agagaggcag tctggtcatg                                                    20

SEQ ID NO: 10             moltype = DNA  length = 20
FEATURE                   Location/Qualifiers
misc_feature              1..20
                          note = primer
source                    1..20
                          mol_type = other DNA
                          organism = synthetic construct
SEQUENCE: 10
ccagtgtctt gctttcaaat                                                    20

SEQ ID NO: 11             moltype = DNA  length = 20
FEATURE                   Location/Qualifiers
misc_feature              1..20
                          note = primer
source                    1..20
                          mol_type = other DNA
                          organism = synthetic construct
SEQUENCE: 11
aacctcacaa ccttggctga                                                    20

SEQ ID NO: 12             moltype = DNA  length = 22
FEATURE                   Location/Qualifiers
misc_feature              1..22
                          note = primer
source                    1..22
                          mol_type = other DNA
                          organism = synthetic construct
SEQUENCE: 12
ttcttttatg cccaaagtcc aa                                                 22

SEQ ID NO: 13             moltype = DNA  length = 21
FEATURE                   Location/Qualifiers
misc_feature              1..21
                          note = primer
source                    1..21
                          mol_type = other DNA
                          organism = synthetic construct
SEQUENCE: 13
tgatcctagc agaagcacag g                                                  21

SEQ ID NO: 14             moltype = DNA  length = 21
FEATURE                   Location/Qualifiers
misc_feature              1..21
                          note = primer
source                    1..21
                          mol_type = other DNA
                          organism = synthetic construct
SEQUENCE: 14
tggacgagct gttacaagag c                                                  21

SEQ ID NO: 15             moltype = DNA  length = 20
FEATURE                   Location/Qualifiers
misc_feature              1..20
                          note = primer
source                    1..20
                          mol_type = other DNA
                          organism = synthetic construct
SEQUENCE: 15
tgcaccacca actgcttagc                                                    20

SEQ ID NO: 16             moltype = DNA  length = 21
FEATURE                   Location/Qualifiers
misc_feature              1..21
                          note = primer
source                    1..21
                          mol_type = other DNA
```

-continued

```
                         organism = synthetic construct
SEQUENCE: 16
ggcatggact gtggtcatga g                                          21

SEQ ID NO: 17            moltype = DNA  length = 20
FEATURE                  Location/Qualifiers
misc_feature             1..20
                         note = primer
source                   1..20
                         mol_type = other DNA
                         organism = synthetic construct
SEQUENCE: 17
aaggaggtgg ytggaaaytt                                            20

SEQ ID NO: 18            moltype = DNA  length = 20
FEATURE                  Location/Qualifiers
misc_feature             1..20
                         note = primer
source                   1..20
                         mol_type = other DNA
                         organism = synthetic construct
SEQUENCE: 18
tccctccacc acctccaaaa                                            20

SEQ ID NO: 19            moltype = DNA  length = 21
FEATURE                  Location/Qualifiers
misc_feature             1..21
                         note = primer
source                   1..21
                         mol_type = other DNA
                         organism = synthetic construct
SEQUENCE: 19
tctgaaccac ttttcctcc a                                           21

SEQ ID NO: 20            moltype = DNA  length = 20
FEATURE                  Location/Qualifiers
misc_feature             1..20
                         note = primer
source                   1..20
                         mol_type = other DNA
                         organism = synthetic construct
SEQUENCE: 20
actggcagca gagatcatcg                                            20

SEQ ID NO: 21            moltype = DNA  length = 14
FEATURE                  Location/Qualifiers
source                   1..14
                         mol_type = other DNA
                         organism = Homo sapiens
SEQUENCE: 21
ccgcgnggng gcag                                                  14

SEQ ID NO: 22            moltype = DNA  length = 56
FEATURE                  Location/Qualifiers
source                   1..56
                         mol_type = other DNA
                         organism = Homo sapiens
SEQUENCE: 22
tgacatccag gcgcgatgat ctctgctgcc agtagagggc acacttactt tactttt    56

SEQ ID NO: 23            moltype = DNA  length = 45
FEATURE                  Location/Qualifiers
source                   1..45
                         mol_type = other DNA
                         organism = Homo sapiens
SEQUENCE: 23
tgacatccag gcgcgatgat ctctgctgca cacttacttt acttt                 45

SEQ ID NO: 24            moltype = DNA  length = 43
FEATURE                  Location/Qualifiers
source                   1..43
                         mol_type = other DNA
                         organism = Homo sapiens
SEQUENCE: 24
tgacatccag gcgcgatgat agagggcaca cttactttac ttt                   43

SEQ ID NO: 25            moltype = DNA  length = 43
FEATURE                  Location/Qualifiers
source                   1..43
```

-continued

```
                              mol_type = other DNA
                              organism = Homo sapiens
SEQUENCE: 25
tgacatccag gcgcgatgat ctctgctgcc cttactttac ttt             43

SEQ ID NO: 26                 moltype = DNA  length = 43
FEATURE                       Location/Qualifiers
source                        1..43
                              mol_type = other DNA
                              organism = Homo sapiens
SEQUENCE: 26
tgacatccag gcgcgatgat ctctgctgcc cttactttac ttt             43

SEQ ID NO: 27                 moltype = DNA  length = 56
FEATURE                       Location/Qualifiers
source                        1..56
                              mol_type = other DNA
                              organism = Homo sapiens
SEQUENCE: 27
tgacatccag gcgcgatgat ctctgctgcc agtagagggc acacttactt tacttt   56

SEQ ID NO: 28                 moltype = DNA  length = 51
FEATURE                       Location/Qualifiers
source                        1..51
                              mol_type = other DNA
                              organism = Homo sapiens
SEQUENCE: 28
tgacatccag gcgcgatgat ctctgctgca gtatcacact tactttactt t        51

SEQ ID NO: 29                 moltype = DNA  length = 56
FEATURE                       Location/Qualifiers
source                        1..56
                              mol_type = other DNA
                              organism = Homo sapiens
SEQUENCE: 29
tgacatccag gcgcgatgat ctctgctgcc agtagagggc acacttactt tacttt   56

SEQ ID NO: 30                 moltype = DNA  length = 38
FEATURE                       Location/Qualifiers
source                        1..38
                              mol_type = other DNA
                              organism = Homo sapiens
SEQUENCE: 30
aggaaagtaa agtgtaccta aaagaaagtg tacctcta                   38

SEQ ID NO: 31                 moltype = DNA  length = 56
FEATURE                       Location/Qualifiers
misc_feature                  1..56
                              note = Insertion sequence
source                        1..56
                              mol_type = other DNA
                              organism = synthetic construct
SEQUENCE: 31
tgacatccag gcgcgatgat ctctgctgcc agtagagggc acacttactt tacttt   56

SEQ ID NO: 32                 moltype = DNA  length = 55
FEATURE                       Location/Qualifiers
source                        1..55
                              mol_type = other DNA
                              organism = Homo sapiens
SEQUENCE: 32
tgacatccag gcgcgatgat ctctgctgca gtagagggca cacttacttt acttt    55

SEQ ID NO: 33                 moltype = DNA  length = 10
FEATURE                       Location/Qualifiers
misc_feature                  1..10
                              note = Insertion sequence
source                        1..10
                              mol_type = other DNA
                              organism = synthetic construct
SEQUENCE: 33
ctttccctta                                                  10

SEQ ID NO: 34                 moltype = DNA  length = 18
FEATURE                       Location/Qualifiers
source                        1..18
                              mol_type = other DNA
                              organism = Homo sapiens
SEQUENCE: 34
```

-continued

```
tgccagtaga gggcacac                                                   18

SEQ ID NO: 36          moltype = DNA   length = 58
FEATURE                Location/Qualifiers
source                 1..58
                       mol_type = other DNA
                       organism = Homo sapiens
SEQUENCE: 35
wttgacatcc aggcgcgatg atctctgctg ccagtagagg gcacacttac tttacttt       58

SEQ ID NO: 36          moltype = DNA   length = 56
FEATURE                Location/Qualifiers
source                 1..56
                       mol_type = other DNA
                       organism = Homo sapiens
SEQUENCE: 36
tgacatccag gcgcgatgat ctctgctgcc agtagagggc acacttactt tacttt         56

SEQ ID NO: 37          moltype = DNA   length = 56
FEATURE                Location/Qualifiers
source                 1..56
                       mol_type = other DNA
                       organism = Homo sapiens
SEQUENCE: 37
tgacatccag gcgcgatgat ctctgctgcc agtagagggc acacttactt tacttt         56

SEQ ID NO: 38          moltype = DNA   length = 93
FEATURE                Location/Qualifiers
source                 1..93
                       mol_type = other DNA
                       organism = Homo sapiens
SEQUENCE: 38
tgacatccag gcgcgatgat ctctgctgcc agaggaaagt aaagtgtacc taaaagaaag     60
tgtacctcta agagggcaca cttactttac ttt                                  93

SEQ ID NO: 39          moltype = DNA   length = 65
FEATURE                Location/Qualifiers
source                 1..65
                       mol_type = other DNA
                       organism = Homo sapiens
SEQUENCE: 39
tgacatccag gcgcgatgat ctctgctgca gtactttccc ttagagggca cacttacttt     60
acttt                                                                 65

SEQ ID NO: 40          moltype = DNA   length = 53
FEATURE                Location/Qualifiers
source                 1..53
                       mol_type = other DNA
                       organism = Homo sapiens
SEQUENCE: 40
tgacatccag gcgcgatgat ctctgctgct agagggcaca cttactttac ttt            53

SEQ ID NO: 41          moltype = DNA   length = 39
FEATURE                Location/Qualifiers
source                 1..39
                       mol_type = other DNA
                       organism = Homo sapiens
SEQUENCE: 41
tgacatccag gcgcgatgat ctctgctgcc agctactttt                           39

SEQ ID NO: 42          moltype = DNA   length = 24
FEATURE                Location/Qualifiers
source                 1..24
                       mol_type = other DNA
                       organism = Homo sapiens
SEQUENCE: 42
tgacattcac acttacttta cttt                                            24

SEQ ID NO: 43          moltype = DNA   length = 72
FEATURE                Location/Qualifiers
source                 1..72
                       mol_type = other DNA
                       organism = Homo sapiens
SEQUENCE: 43
tgacatccag gcgcgcccag agaggggggcg gagggaaaga cgctttgcag caaaatccag    60
catagcgatt gg                                                         72
```